US011286473B2

(12) United States Patent
Dong et al.

(10) Patent No.: US 11,286,473 B2
(45) Date of Patent: Mar. 29, 2022

(54) BOTULINUM NEUROTOXIN AND ITS DERIVATIVES

(71) Applicants: Children's Medical Center Corporation, Boston, MA (US); Paul Stenmark, Stockholm (SE)

(72) Inventors: Min Dong, Weatogue, CT (US); Sicai Zhang, Boston, MA (US); Paul Stenmark, Stockholm (SE)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/315,698

(22) PCT Filed: Jul. 7, 2017

(86) PCT No.: PCT/US2017/041255
§ 371 (c)(1),
(2) Date: Jan. 7, 2019

(87) PCT Pub. No.: WO2018/009903
PCT Pub. Date: Jan. 11, 2018

(65) Prior Publication Data

US 2019/0136216 A1  May 9, 2019
US 2020/0224185 A9  Jul. 16, 2020

Related U.S. Application Data

(60) Provisional application No. 62/360,239, filed on Jul. 8, 2016.

(51) Int. Cl.
| C12N 9/52 | (2006.01) |
| C07K 14/33 | (2006.01) |
| A61K 9/00 | (2006.01) |
| A61K 38/00 | (2006.01) |

(52) U.S. Cl.
CPC .............. *C12N 9/52* (2013.01); *A61K 9/0019* (2013.01); *C07K 14/33* (2013.01); *C12Y 304/24069* (2013.01); *A61K 38/00* (2013.01); *C07K 2319/01* (2013.01); *C07K 2319/035* (2013.01); *C07K 2319/21* (2013.01); *C07K 2319/22* (2013.01); *C07K 2319/23* (2013.01); *C07K 2319/24* (2013.01); *C07K 2319/41* (2013.01); *C07K 2319/42* (2013.01); *C07K 2319/43* (2013.01); *C07K 2319/50* (2013.01); *C07K 2319/55* (2013.01); *Y02A 50/30* (2018.01)

(58) Field of Classification Search
None
See application file for complete search history.

(56) References Cited

U.S. PATENT DOCUMENTS

| 9,598,685 | B2 * | 3/2017 | Dong | A61P 25/04 |
| 9,920,310 | B2 * | 3/2018 | Anderson | A61P 1/04 |
| 10,190,110 | B2 * | 1/2019 | Dong | C12Y 304/24069 |
| 10,266,816 | B2 * | 4/2019 | Rummel | A61P 27/02 |
| 10,501,731 | B2 * | 12/2019 | Steward | A61P 27/16 |
| 10,647,750 | B2 * | 5/2020 | Anderson | A61P 25/16 |
| 10,648,045 | B2 * | 5/2020 | Kwan | A61P 1/04 |
| 10,704,035 | B2 * | 7/2020 | Collier | C12N 9/50 |
| 2015/0166972 | A1 * | 6/2015 | Dong | C12Y 304/24069 435/220 |
| 2015/0253326 | A1 * | 9/2015 | Chapman | G01N 33/542 506/10 |
| 2017/0226496 | A1 * | 8/2017 | Dong | A61P 13/00 |
| 2018/0073089 | A1 * | 3/2018 | Kwan | A61P 5/00 |
| 2018/0080016 | A1 * | 3/2018 | Dong | C12N 15/1055 |
| 2019/0136216 | A1 * | 5/2019 | Dong | A61P 13/10 |
| 2019/0185524 | A1 * | 6/2019 | Dong | C12Y 304/24069 |
| 2019/0219575 | A1 * | 7/2019 | Gray | C07K 16/1282 |
| 2019/0256834 | A1 * | 8/2019 | Dong | A61P 21/02 |
| 2019/0300869 | A1 * | 10/2019 | Dong | A61P 25/08 |
| 2019/0364907 | A1 | 12/2019 | Gill et al. | |
| 2020/0224185 | A9 * | 7/2020 | Dong | A61P 1/00 |
| 2020/0255481 | A1 * | 8/2020 | Dong | C07K 14/33 |

FOREIGN PATENT DOCUMENTS

| WO | WO 2009/014854 A1 | 1/2009 | |
| WO | WO 2012/041761 A2 | 4/2012 | |
| WO | WO 2013/180799 A1 | 12/2013 | |
| WO | WO-2013180799 A1 * | 12/2013 | ............ A61P 25/14 |
| WO | WO-2016154534 A1 * | 9/2016 | ............ C07K 14/33 |
| WO | WO 2018/009903 A2 | 1/2018 | |
| WO | WO-2018073370 A1 * | 4/2018 | ............... C12Q 1/37 |
| WO | WO 2019/067815 A2 | 4/2019 | |
| WO | WO-2019152380 A1 * | 8/2019 | ............ C07K 14/33 |
| WO | WO-2019243376 A1 * | 12/2019 | ......... A61K 38/4893 |
| WO | WO-2020065336 A1 * | 4/2020 | ............ A61K 38/48 |
| WO | WO-2020065338 A1 * | 4/2020 | ........... A61K 47/183 |

OTHER PUBLICATIONS

Kukreja et al, Biochimica et Biophysica Acta 2007, 1774:213-222. available online: Nov. 17, 2006 (Year: 2006).*
Webb et al, Vaccine. 2009. 27:4490-4497. available online:May 28, 2009 (Year: 2009).*
Zhou et al, Biochemistry, 1995, 34/46:15175-15181 (Year: 1995).*
GenBank Submission; NIH/NCBI, Accession No. BAQ12790. Putative botulinum neurotoxin [Clostridium botulinum]. Feb. 21, 2015. 2 pages.
Hill et al., Genetic diversity within the botulinum neurotoxin-producing bacteria and their neurotoxins. Toxicon. Dec. 1, 2015;107(Pt A):2-8.
PCT/US2020/028742, dated Feb. 12, 2021, International Search Report and Written Opinion.

(Continued)

*Primary Examiner* — Nita M. Minnifield
(74) *Attorney, Agent, or Firm* — Wolf, Greenfield & Sacks, P.C.

(57) ABSTRACT

Provided herein are Clostridial *Botulinum* neurotoxin (BoNT) polypeptides of a novel serotype (BoNT/X) and methods of making and using the BoNT polypeptides, e.g., in therapeutic applications.

15 Claims, 21 Drawing Sheets
Specification includes a Sequence Listing.

(56) References Cited

OTHER PUBLICATIONS

Contreras et al., A neurotoxin that specifically targets Anopheles mosquitoes. Nat Commun. Jun. 28, 2019;10(1):2869.
Hansbauer et al., Detection, differentiation, and identification of botulinum neurotoxin serotypes C, CD, D, and DC by highly specific immunoassays and mass spectrometry. Analyst. Sep. 21, 2016;141(18):5281-97.
Kakinuma et al., The first case of type B infant botulism in Japan. Acta Paediatr Jpn. Oct. 1996;38(5):541-3.
Webb et al., Engineering of Botulinum Neurotoxins for Biomedical Applications. Toxins (Basel). Jun. 6, 2018;10(6):231.
Binz et al., Arg(362) and Tyr(365) of the botulinum neurotoxin type a light chain are involved in transition state stabilization. Biochemistry. Feb. 12, 2002;41(6):1717-23. doi: 10.1021/bi0157969.

\* cited by examiner

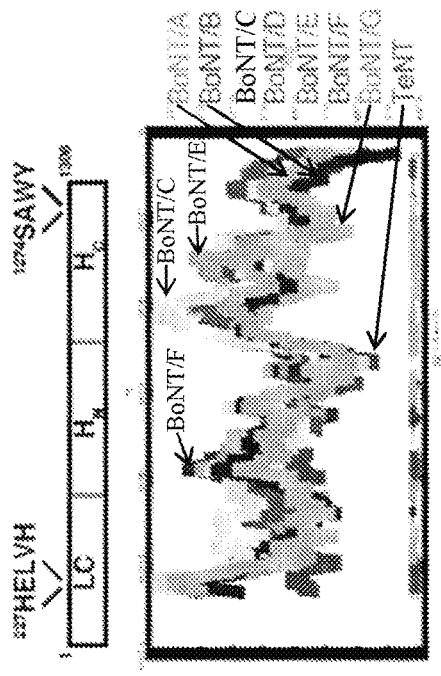
FIG. 1A
FIG. 1B
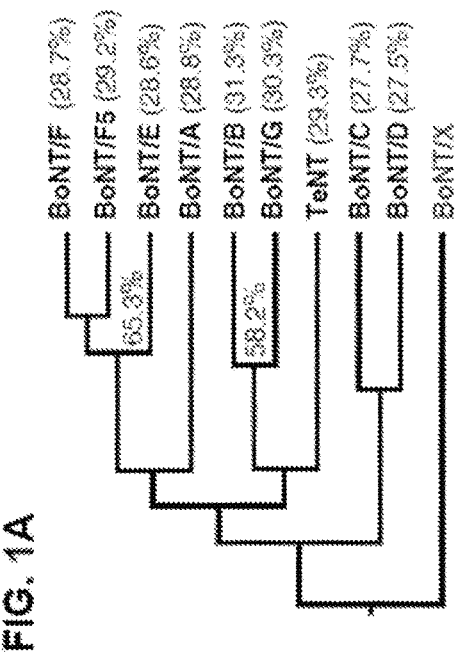
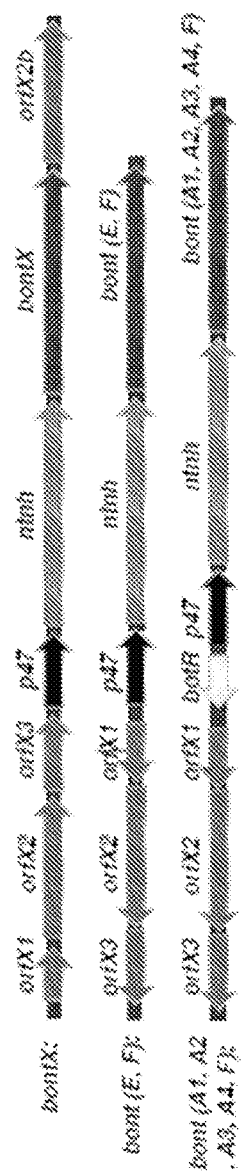
FIG. 1C

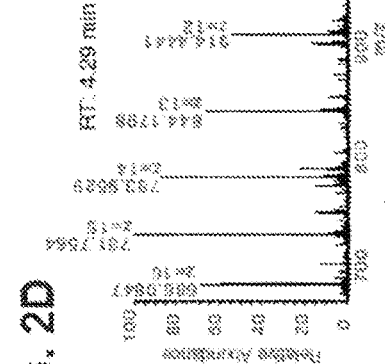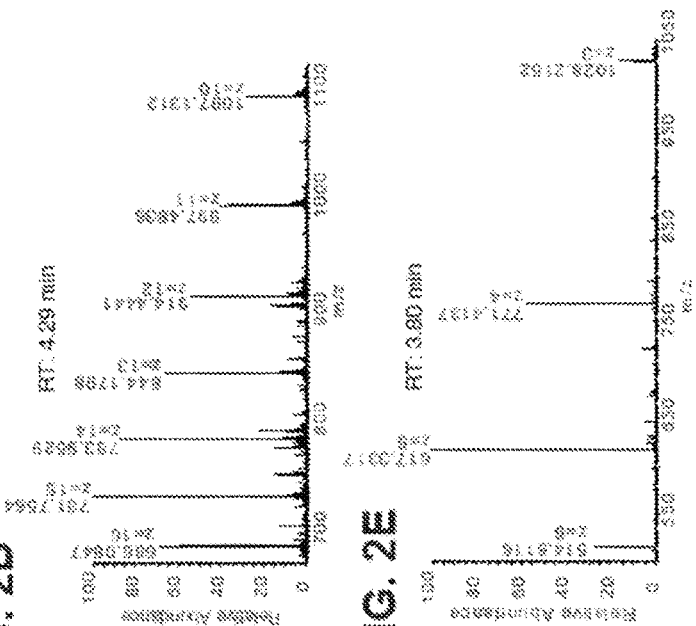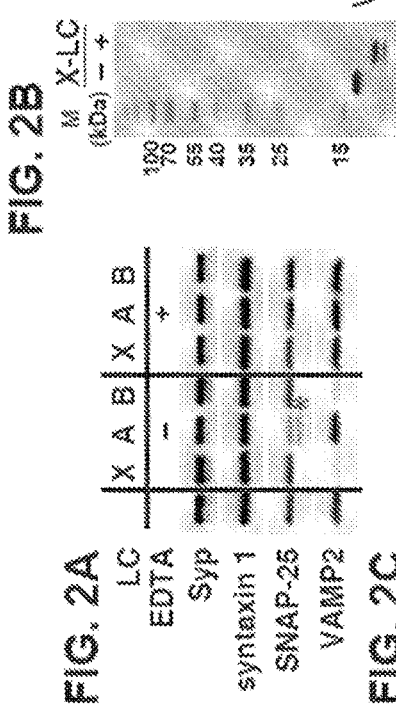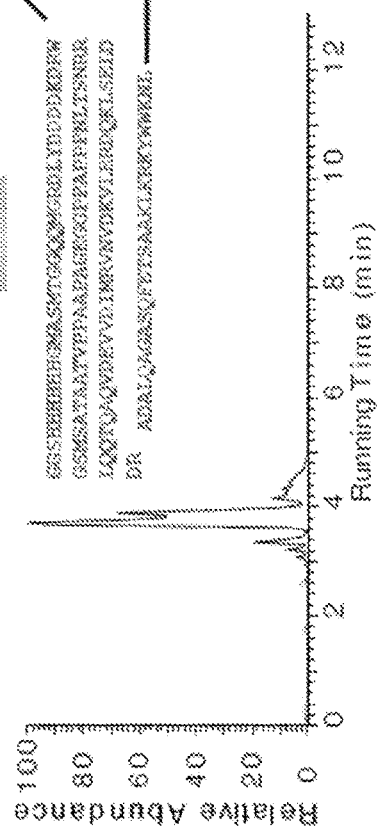
FIG. 2A FIG. 2B FIG. 2C FIG. 2D FIG. 2E

FIG. 2F

```
                    F  D      X           B  G
VAMP2    33 QQTQA VDKVYDIMR PVDKVLERDQKLSELDDRADALQ AGASQFETSAAKLKR 86
VAMP1    33 QQTQA QVEEVVDIMR VNVDKVLERDQKLSELIDDRADALQ AGASQFETSAAKLKR 88
VAMP3    20 QQTQA QVDEVVDIMR VNVDKVLERDQKLSELIDDRADALQ AGASQFETSAAKLKR 88
VAMP4    34 KHVQ KQVDEVVDIMR VNVQENITRVIERILAKADQ SESLSDNATAFSNR SKQLRR 107
VAMP5     7 ERCQQQM EVTEIRMNNFQVRKVLERGVVLAEZLQQK SDQLLIMS STPNKTYTQMLAQ 69
VAMP7   127 TETQAQ VDELKGIMVTQNVIDLVAQRGERLELLIDKTENL VDSSVT FKTTSRNLAR 180
VAMP8    14 RNLQSE VRGVKNIMTQNVERILARGEMIDHIRNKTEDLEAZKSHPFTTSQKVAR 67
Sec22b  136 GSINTELQEVQRIMVANIEEVLQRSEALSAIDSKAANTLSSLSKYRQDAKYLNM 187
Ykt6    140 SKVQARLDETKIILHNTMESILERGEKILDDIVSE RVLGTQSKAFYKTAR ----- 189
```

FIG. 2G

| | X-LC | − | − | + | + |
|---|---|---|---|---|---|
| | VAMP1 | − | + | − | + |
| | actin | | | | |
| | VAMP1 | | | | |

| | X-LC | − | − | + | + |
|---|---|---|---|---|---|
| | VAMP7 | − | + | − | + |
| | actin | | | | |
| | VAMP7 | | | | |

| | X-LC | − | − | + | + |
|---|---|---|---|---|---|
| | Sec22b | − | + | − | + |
| | actin | | | | |
| | Sec22b | | | | |

| | X-LC | − | − | + | + |
|---|---|---|---|---|---|
| | VAMP3 | − | + | − | + |
| | actin | | | | |
| | VAMP3 | | | | |

| | X-LC | − | − | + | + |
|---|---|---|---|---|---|
| | VAMP8 | − | + | − | + |
| | actin | | | | |
| | VAMP8 | | | | |

| | X-LC | − | − | + | + |
|---|---|---|---|---|---|
| | Ykt6 | − | + | − | + |
| | actin | | | | |
| | Ykt6 | | | | |

FIG. 2H Ykt6  FIG. 2I VAMP2  VAMP4  VAMP5

LC − 0 0 8 min                LC − 0 0 8 − 0 0 8 − 0 0 8 min

FIG. 2J

| | X | A | B | X | A | B |
|---|---|---|---|---|---|---|
| EDTA | − | | | + | | |
| LC | | | | | | |
| Syt | | | | | | |
| Sec22b | | | | | | |
| VAMP4 | | | | | | |

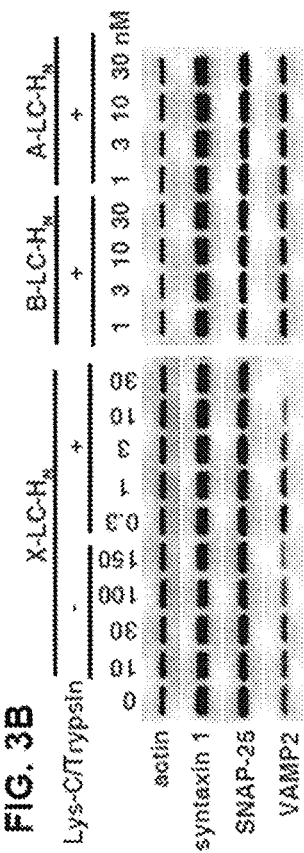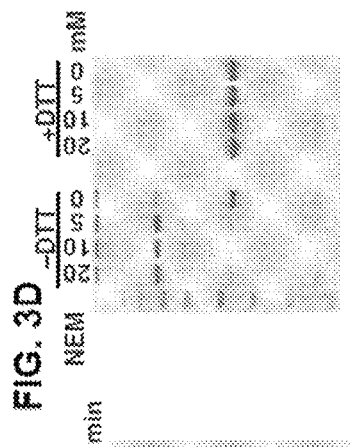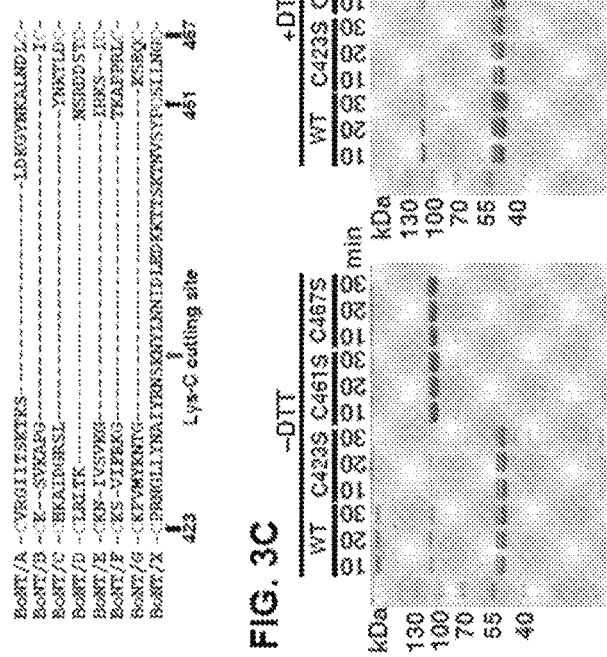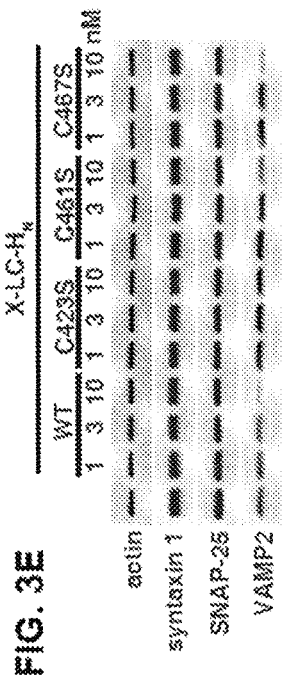

MSPILGYWKIKGLVQPTRLLLEYLEEKYEEHLYERDEGDK
WRNKKFELGLEFPNLPYYIDGDVKLTQSMAIIRYIADKHN
MLGGCPKERAEISMLEGAVLDIRYGVSRIAYSKDFETLKV
DFLSKLPEMLKMFEDRLCHKTYLNGDHVTHPDFMLYDAL
DVVLYMDPMCLDAFPKLVCFKKRIEAIPQIDKYLKSSKYIA
WPLQGWQATFGGGDHPPKSDLVPRGS|QQTQAQVDEV
VDIMRVNVDKVLERDQKLSELDDR|ADALQAGASQFETSA
AKLKR|

↑　　　　　　　　↑
　　　　　　VAMP2 (33-66)　　VAMP2 (67-86)

MSPILGYWKIKGLVQPTRLLLEYLEEKYEEHLYERDEGDK
WRNKKFELGLEFPNLPYYIDGDVKLTQSMAIIRYIADKHN
MLGGCPKERAEISMLEGAVLDIRYGVSRIAYSKDFETLKV
DFLSKLPEMLKMFEDRLCHKTYLNGDHVTHPDFMLYDAL
DVVLYMDPMCLDAFPKLVCFKKRIEAIPQIDKYLKSSKYIA
WPLQGWQATFGGGDHPPKSDLVPRGSQQTQAQVDEV
VDIMRVNVDKVLERDQKLSELDDR

FIG. 9

FIG. 12A GD1a Binding

FIG. 12B GT1b Binding

FIG. 12C GD1b Binding

FIG. 12D GM1 Binding

FIG. 12E Ganglioside binding by BoNT/X

FIG. 12F Ganglioside binding by BoNT/A

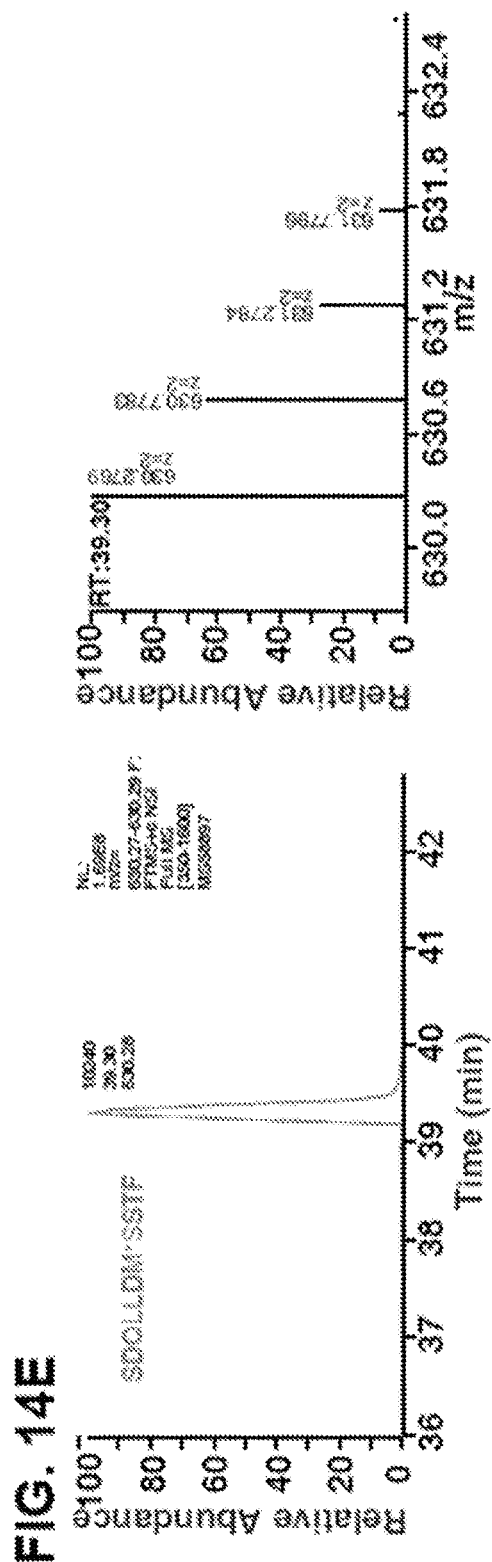

BOTULINUM NEUROTOXIN AND ITS DERIVATIVES

RELATED APPLICATIONS

This application is a national stage filing under 35 U.S.C. § 371 of international application number PCT/US2017/041255, filed Jul. 7, 2017, which claims the benefit under 35 U.S.C. § 119(e) of U.S. provisional application No. 62/360,239, filed Jul. 8, 2016, each of which is incorporated by reference herein in its entirety.

GOVERNMENT SUPPORT

This invention was made with government support under R01NS080833 awarded by the National Institutes of Health. The government has certain rights in the invention.

BACKGROUND

Clostridial *Botulinum* neurotoxins (BoNTs) are among the most dangerous potential bioterrorism agents and are also used clinically to treat a growing list of medical conditions. There are seven serotypes of BoNTs (BoNT/A-G) known to date. In recent years, BoNTs have been widely used to treat a growing list of medical conditions: local injections of minute amount of toxins can attenuate neuronal activity in targeted regions, which can be beneficial in many medical conditions as well as for cosmetic purposes. As the application of BoNTs grows, limitations and adverse effects have been reported. The major limitation is the generation of neutralizing antibodies in patients, which renders future treatment ineffective. Termination of BoNT usage often leaves patients with no other effective ways to treat/relieve their disorders. Adverse effects associated with BoNT use range from transient non-serious events such as ptosis and diplopia to life-threatening events even death. The limitations and adverse effects of BoNTs are largely correlated with dose. There are considerable interests in developing novel BoNT types as therapeutic toxins. No new BoNT types have been recognized for the past 45 years.

SUMMARY

The present disclosure is based, at least in part, on the identification of a novel BoNT serotype, BoNT/X, from searching genomic database of Clostridium *Botulinum* strains. BoNT/X the lowest sequence identity with other BoNTs and it is not recognized by antisera raised against known BoNT types. BoNT/X cleaves SNARE proteins, like other BoNTs.

However, BoNT/X also cleave several SNARE proteins that other BoNTs cannot cleave, e.g., VAMP4, VAMP5, and Ykt6. Compositions and methods for treating diseases using BoNT/X are provided. Also provided herein are methods of making BoNT/X.

Accordingly, some aspects of the present disclosure provide isolated Clostridial *Botulinum* neurotoxin (BoNT) polypeptides comprising the amino acid sequence of SEQ ID NO: 1.

Some aspects of the present disclosure provide isolated BoNT polypeptides comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 1. In some embodiments, the isolated BoNT polypeptide consists of the amino acid sequence of SEQ ID NO: 1.

Some aspects of the present disclosure provide isolated BoNT polypeptides comprising the amino acid sequence of SEQ ID NO: 2. Some aspects of the present disclosure provide isolated BoNT polypeptides an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 2. In some embodiments, the isolated BoNT polypeptide consists of the amino acid sequence of SEQ ID NO: 2.

Some aspects of the present disclosure provide isolated BoNT polypeptides comprising the amino acid sequence of SEQ ID NO: 3. Some aspects of the present disclosure provide isolated BoNT polypeptides an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 3. In some embodiments, the isolated BoNT polypeptide consists of the amino acid sequence of SEQ ID NO: 3.

Some aspects of the present disclosure provide modified BoNT polypeptides comprising one or more substitution mutation(s) in a position corresponding to C461, C467, and C1240 of SEQ ID NO: 1. In some embodiments, the substitution mutation(s) corresponds to C461S, C461A, C467S, C467A, C1240S, C1240A, C461S/C1240S, C416S/C1240A, C461A/C1240S, C461A/C1240A, C467S/C1240S, C461S/C1240A, C467A/C1240S, or C467A/C1240A in SEQ ID NO: 1.

In some embodiments, the modified BoNT polypeptide comprises the amino acid sequence of any one of SEQ ID NO: 4-17. In some embodiments, the modified BoNT polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any of SEQ ID NOs: 4-17, wherein the polypeptide does not have the amino acid sequence of SEQ ID NO: 1. In some embodiments, the modified BoNT polypeptide consists of the amino acid sequence of any one of SEQ ID NOs: 4-17.

Some aspects of the present disclosure provide modified BoNT polypeptides comprising a single substitution mutation in a position corresponding to C461 or C467 of SEQ ID NO: 2.

In some embodiments, the substitution mutation corresponds to C461S, C461A, C467S, C467A, C1240S, C1240A, C461S/C1240S, C416S/C1240A, C461A/C1240S, C461A/C1240A, C467S/C1240S, C461S/C1240A, C467A/C1240S, or C467A/C1240A in SEQ ID NO: 2.

In some embodiments, the modified BoNT polypeptide comprises the amino acid sequence of any one of SEQ ID NOs: 18-21. In some embodiments, the modified BoNT polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any of SEQ ID NOs: 18-21, wherein the polypeptide does not have the amino acid sequence of SEQ ID NO: 2. In some embodiments, the modified BoNT polypeptide consists of the amino acid sequence of any one of SEQ ID NOs: 18-21.

Some aspects of the present disclosure provide chimeric BoNT polypeptides comprising the amino acid sequence of any one of SEQ ID NOs: 22-24. In some embodiments, the chimeric BoNT polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 22-24, wherein the polypeptide does not have the amino acid sequence of SEQ ID NO: 1 or SEQ ID NO: 2. In some embodiments, the chimeric BoNT polypeptide consists of the amino acid sequence of any one of SEQ ID NOs: 22-24.

In some embodiments, the chimeric BoNT polypeptide further comprises a single substitution mutation in a position corresponding to C461 or C467 of in SEQ ID NO: 2.

In some embodiments, the chimeric BoNT polypeptide comprises the amino acid sequence of any one of SEQ ID NOs: 25-30. In some embodiments, the chimeric BoNT polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 25-30. In some embodiments, the chimeric BoNT polypeptide consists of the amino acid sequence of any one of SEQ ID NOs: 25-30.

In some embodiments, the BoNT polypeptide enters a cell. In some embodiments, the BoNT polypeptide cleaves a SNARE protein in the cell. In some embodiments, the SNARE protein is selected from the group consisting of: SNAP-25, VAMP1, VAMP2, VAMP3, VAMP4, VAMP5, Ykt6, and syntaxin 1.

In some embodiments, the SNARE protein is VAMP1. In some embodiments, the BoNT cleaves between amino acid residues corresponding to R66 and A67 of SEQ ID NO: 39.

In some embodiments, the SNARE protein is VAMP2. In some embodiments, the BoNT cleaves between amino acid residues corresponding to R66 and A67 of SEQ ID NO: 40.

In some embodiments, the SNARE protein is VAMP3. In some embodiments, the BoNT cleaves between amino acid residues corresponding to R66 and A67 of SEQ ID NO: 41.

In some embodiments, the SNARE protein is VAMP4. In some embodiments, the BoNT cleaves between amino acid residues corresponding to K87 and S88 of SEQ ID NO: 42.

In some embodiments, the SNARE protein is VAMP5. In some embodiments, the BoNT cleaves between amino acid residues corresponding to R40 and S41 of SEQ ID NO: 43.

In some embodiments, the SNARE protein is Ykt6. In some embodiments, the BoNT cleaves between amino acid residues corresponding to K173 and S174 of SEQ ID NO: 44.

In some embodiments, the BoNT polypeptide has increased stability compared to its corresponding wild type BoNT polypeptide.

In some embodiments, the cell is a secretory cell. In some embodiments, the cell is a neuronal cell. In some embodiments, the cell is an immune cell. In some embodiments, the BoNT polypeptide suppresses neuronal activity. In some embodiments, the BoNT polypeptide induces flaccid paralysis. In some embodiments, the cell is a cultured cell. In some embodiments, the cell is in vivo. In some embodiments, the cell is from a mammal. In some embodiments, the mammal is a human. In some embodiments, mammal is a rodent. In some embodiments, the rodent is a mice. In some embodiments, the rodent is a rat.

In some embodiments, the BoNT polypeptide does not cross react with an antibody against BoNT serotype A, B, C, D, E, F, or G.

Other aspects of the present disclosure provide nucleic acid molecules comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identity to the BoNT polypeptide described herein. Nucleic acid vectors comprising such nucleic acid molecules are provided. Cells comprising the nucleic acid molecules or the nucleic acid vectors described herein are provided. In some embodiments, such cells express the BoNT polypeptide described herein.

Methods of producing the BoNT polypeptide of the present disclosure are provided. Such methods comprise the steps of culturing the cell expressing the BoNT polypeptides under conditions wherein said BoNT polypeptide is produced. In some embodiments, the methods further comprise recovering the BoNT polypeptide from the culture.

Other aspects of the present disclosure provide modified BoNT polypeptides comprising: (a) a protease domain; (b) a modified linker region; and (c) a translocation domain; wherein (a), (b), and (c) are from BoNT serotype X, and wherein the modified linker region comprises one single substitution mutation in a position corresponding to C461 or C467 of SEQ ID NO: 1.

In some embodiments, the modified BoNT polypeptide further comprises: (d) a receptor binding domain.

In some embodiments, modified linker region comprises a substitution mutation corresponding to C461S or C461A in SEQ ID NO: 1. In some embodiments, the modified linker region comprises a substitution mutation corresponding to C467S or C467A in SEQ ID NO: 1.

In some embodiments, the receptor binding domain is from BoNT/X. In some embodiments, the receptor binding domain is modified. In some embodiments, the receptor binding domain comprises a substitution mutation corresponding to C1240S or C1240A in SEQ ID NO: 1.

In some embodiments, the receptor binding domain is from a serotype selected from the group consisting of A, B, C, D, E, F, and G.

In some embodiments, the modified BoNT polypeptide enters a cell. In some embodiments, the modified BoNT polypeptide cleaves SNARE proteins in the cell. In some embodiments, the SNARE protein is selected from the group consisting of: SNAP-25, VAMP1, VAMP2, VAMP3, VAMP4, VAMP5, Ykt6, and syntaxin 1.

In some embodiments, the SNARE protein is VAMP1. In some embodiments, the BoNT cleaves between amino acid residues corresponding to R66 and A67 of SEQ ID NO: 39.

In some embodiments, the SNARE protein is VAMP2. In some embodiments, the BoNT cleaves between amino acid residues corresponding to R66 and A67 of SEQ ID NO: 40.

In some embodiments, the SNARE protein is VAMP3. In some embodiments, the BoNT cleaves between amino acid residues corresponding to R66 and A67 of SEQ ID NO: 41.

In some embodiments, the SNARE protein is VAMP4. In some embodiments, the BoNT cleaves between amino acid residues corresponding to K87 and S88 of SEQ ID NO: 42.

In some embodiments, the SNARE protein is VAMP5. In some embodiments, the BoNT cleaves between amino acid residues corresponding to R40 and S41 of SEQ ID NO: 43.

In some embodiments, the SNARE protein is Ykt6. In some embodiments, the BoNT cleaves between amino acid residues corresponding to K173 and S174 of SEQ ID NO: 44.

In some embodiments, the BoNT polypeptide has increased stability compared to its corresponding wild type BoNT polypeptide.

In some embodiments, the cell is a secretory cell. In some embodiments, the cell is a neuronal cell. In some embodiments, the cell is an immune cell. In some embodiments, the BoNT polypeptide suppresses neuronal activity. In some embodiments, the BoNT polypeptide induces flaccid paralysis. In some embodiments, the cell is a cultured cell. In some embodiments, the cell is in vivo. In some embodiments, the cell is from a mammal. In some embodiments, the mammal is a human. In some embodiments, mammal is a rodent. In some embodiments, the rodent is a mice. In some embodiments, the rodent is a rat.

In some embodiments, the BoNT polypeptide does not cross react with an antibody against BoNT serotype A, B, C, D, E, F, or G.

In some embodiments, the modified linker region comprises an artificial linker. In some embodiments, the artificial linker contains a cleavage site of a protease. In some embodiments, the protease is selected from the group consisting of Thrombin, TEV, PreScission (3C protease), Factor Xa, MMP-12, MMP-13, MMP-17, MMP-20, Granzyme-B, and Enterokinase. In some embodiments, the linker comprises the amino acid sequence of any of SEQ ID NOs: 50-60).

Other aspects of the present disclosure provide nucleic acid molecules comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identity to the BoNT polypeptide described herein. Nucleic acid vectors comprising such nucleic acid molecules are provided. Cells comprising the nucleic acid molecules or the nucleic acid vectors described herein are provided. In some embodiments, such cells expressed the BoNT polypeptide described herein.

Methods of producing the BoNT polypeptide of the present disclosure are provided. Such methods comprise the steps of culturing the cell expressing the BoNT polypeptides under conditions wherein said BoNT polypeptide is produced. In some embodiments, the methods further comprise recovering the BoNT polypeptide from the culture.

Other aspects of the present disclosure provide modified BoNT polypeptides comprising one or more substitution mutation(s) in positions corresponding to R360, Y363, H227, E228, or H231 in SEQ ID NO: 1. In some embodiments, the one or more substitution mutation corresponds to R360A/Y363F, H227Y, E228Q, or H231Y in SEQ ID NO: 1.

In some embodiments, the modified BoNT polypeptide comprises the amino acid sequence of any one of SEQ ID NOs: 31-38. In some embodiments, the modified BoNT polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any of SEQ ID NOs: 31-38, wherein the polypeptide does not have the amino acid sequence of SEQ ID NO: 1 or SEQ ID NO: 2.

In some embodiments, the modified BoNT polypeptide consists of the amino acid sequence of any one of SEQ ID NOs: 31-38.

Other aspects of the present disclosure provide modified BoNT/X polypeptide comprising: a) an inactive protease domain; b) a linker region; and c) a translocation domain. In some embodiments, the modified BoNT/X further comprises a receptor binding domain.

In some embodiments, the inactive protease domain comprises one or more substitution mutations in positions corresponding to R360, Y363, H227, E228, or H231 of SEQ ID NO: 1. In some embodiments, the one or more substitution mutations correspond to R360A/Y363F, H227Y, E228Q, or H231Y of SEQ ID NO: 1.

In some embodiments, the modified BoNT polypeptide enters a cell. In some embodiments, the modified BoNT polypeptide does not cleave a SNARE protein.

In some embodiments, the modified BoNT/X polypeptide further comprises a modification in the linker region of (b). In some embodiments, the modification in the linker region comprises one single substitution mutation in a position corresponding to C461 or C467 of SEQ ID NO: 1. In some embodiments, the single substitution mutation corresponds to C461A, C461S, C467A, or C467S in SEQ ID NO: 1. In some embodiments, the modified BoNT/X polypeptide further comprises a modification in the receptor binding domain of (d).

In some embodiments, the modification in the receptor binding domain comprises a substitution mutation in a position corresponding to C1240 of SEQ ID NO: 1.

Other aspects of the present disclosure provide nucleic acid molecules comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identity to the BoNT polypeptide described herein. Nucleic acid vectors comprising such nucleic acid molecules are provided. Cells comprising the nucleic acid molecules or the nucleic acid vectors described herein are provided. In some embodiments, such cells expresses the BoNT polypeptide described herein.

Methods of producing the BoNT polypeptide of the present disclosure are provided. Such methods comprise the steps of culturing the cell expressing the BoNT polypeptides under conditions wherein said BoNT polypeptide is produced. In some embodiments, the methods further comprise recovering the BoNT polypeptide from the culture.

Further provided herein are use of the modified BoNT polypeptide described herein as a delivery vehicle to deliver therapeutics into neurons.

Some aspects of the present disclosure provide chimeric molecules comprising a first portion linked to a second portion, wherein the first portion is a modified BoNT polypeptide described herein.

In some embodiments, the first portion and the second portion are linked covalently. In some embodiments, the first portion and the second portion are linked non-covalently.

In some embodiments, wherein the second portion is selected from the group consisting of a small molecule, a nucleic acid, a short polypeptide and a protein. In some embodiments, the second portion is a bioactive molecule. In some embodiments, the second portion is a non-polypeptide drug. In some embodiments, the second portion is a therapeutic polypeptide.

Other aspects of the present disclosure provide nucleic acid molecules comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identity to the chimeric BoNT polypeptide described herein. Nucleic acid vectors comprising such nucleic acid molecules are provided. Cells comprising the nucleic acid molecules or the nucleic acid vectors described herein are provided. In some embodiments, such cells expresses the chimeric BoNT polypeptide described herein.

Methods of producing the chimeric BoNT polypeptide of the present disclosure are provided. Such methods comprise the steps of culturing the cell expressing the chimeric BoNT polypeptides under conditions wherein said chimeric BoNT polypeptide is produced. In some embodiments, the methods further comprise recovering the chimeric BoNT polypeptide from the culture.

Other aspects of the present disclosure provide pharmaceutical compositions comprising the BoNT polypeptides described herein.

In some embodiments, the pharmaceutical composition further comprises a pharmaceutically acceptable excipient.

Kit comprising such pharmaceutical compositions and directions for therapeutic administration of the pharmaceutical composition are also provided.

Some aspects of the present disclosure provide methods of treating a condition, comprising administering a therapeutically effective amount of the BoNT polypeptide, the chimeric molecule, or the pharmaceutical composition described herein to a subject to treat the condition.

In some embodiments, the condition is associated with overactive neurons or glands. In some embodiments, the condition is selected from the group consisting of, spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions, secretory disorders, pain from muscle spasms, headache pain, dermatological or aesthetic/cosmetic conditions, and obesity/reduced appetite.

In some embodiments, the condition is not associated with unwanted neuronal activity. In some embodiments, the condition is selected from the group consisting of: psoriasis, allergy, haemophagocytic lymphohistiocytosis, and alcoholic pancreatic diseases.

In some embodiments, the administering is via injection to where unwanted neuronal activity is present.

Yet other aspects of the present disclosure provide methods of producing a Clostridial *Botulinum* neurotoxin (BoNT) polypeptide, the method comprising:

(i) obtaining a first BoNT fragment comprising a light chain (LC) and a N-terminal domain of a heavy chain ($H_N$), wherein the first BoNT fragment comprises a C-terminal LPXTGG (SEQ ID NO: 60) motif;

(ii) obtaining a second BoNT fragment comprising a C-terminal domain of the heavy chain ($H_C$); wherein the second BoNT fragment comprise a specific protease cleavage site at its N-terminus;

(iii) cleaving the second BoNT fragment with a specific protease, wherein the cleavage results in a free Glycine residue at the N-terminus; and (iv) contacting the first BoNT fragment and the second BoNT fragment in the presence of a transpeptidase, thereby ligating the first BoNT fragment and the second BoNT fragment to form a ligated BoNT.

In some embodiments, the first BoNT fragment further comprises an affinity tag. In some embodiments, the affinity tag is fused to the first BoNT fragment at the N-terminus. In some embodiments, the affinity tag is fused to the first BoNT fragment at the C-terminus. In some embodiments, the affinity tag is selected from the group consisting of: His6, GST, Avi, Strep, S, MBP, Sumo, FLAG, HA, Myc, SBP, E, Calmodulin, Softag 1, Softag 3, TC, V5, VSV, Xpress, Halo, and Fc.

In some embodiments, the second BoNT fragment further comprises an affinity tag. In some embodiments, the affinity tag is fused to the first BoNT fragment at the N-terminus. In some embodiments, the affinity tag is fused to the second BoNT fragment at the C-terminus. In some embodiments, the affinity tag is selected from the group consisting of: His6, GST, Avi, Strep, S, MBP, Sumo, FLAG, HA, Myc, SBP, E, Calmodulin, Softag 1, Softag 3, TC, V5, VSV, Xpress, Halo, and Fc.

In some embodiments, the protease is selected from the group consisting of: thrombin, TEV, PreScission, MMP-12, MMP-13, MMP-17, MMP-20, Granzyme-B, Enterokinase, and SUMO protease. In some embodiments, the cognate protease is thrombin.

In some embodiments, the first BoNT fragment is from BoNT serotype A, B, C, D, E, F, G, or X. In some embodiments, the first BoNT fragment is from BoNT/X. In some embodiments, the second BoNT fragment is from BoNT serotype A, B, C, D, E, F, G, or X. In some embodiments, the second BoNT fragment is from BoNT/A. In some embodiments, the second BoNT fragment is from BoNT/B. In some embodiments, the second BoNT fragment is from BoNT/C. In some embodiments, the second BoNT fragment is from BoNT/X.

In some embodiments, the transpeptidase is a sortase. In some embodiments, the sortase is from *Staphylococcus aureus* (SrtA).

These and other aspects of the disclosure, as well as various advantages and utilities will be apparent with reference to the Detailed Description of the Invention. Each aspect of the disclosure can encompass various embodiments as will be understood.

All documents identified in this application are incorporated in their entirety herein by reference.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIGS. 1A-1E show the identification of BoNT/X as a new BoNT. FIG. 1A shows a phylogenic tree of the protein sequence alignment for BoNT/A-G, BoNT/F5, TeNT, and BoNT/X, analyzed by ClustalW method. The percentages of sequence identity between each toxin and BoNT/X are denoted after each toxin. The percentages of sequence identity between BoNT/E and BoNT/F, and between BoNT/B and BoNT/G were also noted. FIG. 1B, upper panel, shows a schematic drawing of the three domains of BoNT/X, with conserved protease motif in the LC and the ganglioside binding motif in the $H_C$ noted. FIG. 1B, lower panel, shows a sliding sequence comparison window demonstrating that BoNT/X has a low similarity evenly distributed along its sequence to all other seven BoNTs and TeNT. FIG. 1C is a schematic drawing of the orf gene cluster that hosts BoNT/X gene (upper panel), which has two unique features compared to two known variants of orfX cluster (middle and lower panels): (1) there is an additional orfX2 protein (designated as orfX2b) located next to the BoNT/X gene; (2) the reading frame of orfX genes has the same direction with BoNT/X gene. FIG. 1D is a schematic illustrating the unique gene directionality and additional OrfX2 gene found in BoNT/X. FIG. 1E shows a preliminary structure of the BoNT/X light chain. The dark dot represents the active site zinc. The structure is shown at a 1.9 Å resolution.

FIGS. 2A-2J show the LC of BoNT/X (X-LC) cleaves VAMPs at a unique site. FIG. 2A shows X-LC, with or without pre-treated with EDTA, incubated with rat brain detergent extracts (BDE). Immunoblot analysis was carried out to detect syntaxin 1, SNAP-25, and VAMP2. Synaptophysin (Syp) was also detected as a loading control. The LC of BoNT/A (A-LC) and BoNT/B (B-LC) were analyzed in parallel. Cleavage of VAMP2 by B-LC results in loss of VAMP2 immunoblot signals, while cleavage of SNAP-25 by A-LC generates a smaller fragment of SNAP-25 that can still be detected on immunoblot (marked by an asterisk). Incubation with X-LC resulted in loss of VAMP2 immunoblot signals, suggesting that X-LC cleaved VAMP2. EDTA blocked the activity of X-, A-, and B-LCs. FIG. 2B shows VAMP2 (residues 1-96) purified as a His6-tagged recombinant protein and incubated with X-LC. Samples were analyzed by SDS-PAGE and Coomassie Blue staining. X-LC converted VAMP2 (1-96) into two smaller fragments, indicating that X-LC cleaved VAMP2. FIGS. 2C-2E show VAMP2 (1-96) incubated with X-LC. Whole protein samples were then analyzed by mass spectrometry (LC-MS/MS) to determine the precise molecular weight of cleaved fragments. Eluted peptide peaks from the HPLC column were plotted in FIG. 2C over running time (RT, X-axis). The mass spectrometry data for the two cleavage products are shown in FIGS. 2D and 2E, respectively, with mass-to-charge ratio (m/z) noted for each signal. The molecular weight is deducted by multiplying m with z, followed by subtracting z. The protein sequences for the two cleavage products correspond to SEQ ID NO: 61 and 62 from top to bottom and are shown in FIG. 2C. FIG. 2F shows a sequence alignment between VAMP 1, 2, 3, 4, 5, 7, 8, Sec22b and Ykt6, with cleavage sites for BoNT/B, D, F, G, and X underlined, and two SNARE motifs boxed. The sequences correspond to SEQ ID NOs: 63-71 from top to bottom. FIG. 2G shows HA-tagged VAMP1, 3, 7, and 8, and myc-tagged Sec22b and Ykt6 expressed in HEK293 cells via transient transfection. Cell lysates were incubated with X-LC and subjected to immunoblot analysis detecting the HA or Myc tag. Actin served as a loading control. X-LC cleaved VAMP1, 3 and Ykt6, but not VAMP7, 8 and Sec22. FIG. 2H shows GST-tagged Ykt6 incubated with X-LC (100 nM) for the indicated times. Samples were analyzed by SDS-PAGE and Coomassie Blue staining. X-LC cleaved Ykt6. FIG. 2I shows GST-tagged cytoplasmic domains of VAMP2 (33-86), VAMP4 (1-115), and VAMP5 (1-70) incubated with X-LC for the indicated times. Samples were analyzed by SDS-PAGE and Coomassie Blue staining. X-LC cleaved both VAMP4 and VAMP5. A longer incubation time (360 min) is required to cleave majority of VAMP5. Note that VAMP5 protein contains an additional band that is either degradation product or bacterial protein contaminant, which runs close (but not identical) to the cleavage product on SDS-PAGE. FIG. 2J shows experiments carried out as described in FIG. 2A, except that VAMP4 and Sec22b were detected. Synaptotagmin I (Syt I) was detected as a loading control. X-LC cleaved native VAMP4 in BDE.

FIGS. 3A-3E show activation of BoNT/X by proteolytic cleavage of the linker region between LC and $H_N$. FIG. 3A shows a sequence alignment of the linker regions between LC and $H_N$ of the seven BoNTs and BoNT/X. The sequences correspond to SEQ ID NOs: 72-79 from top to bottom. BoNT/X has the longest linker region among all BoNTs, which contains an extra cysteine in addition to the two conserved cysteines in the LC and in the $H_N$. The Lys-C cutting site under limited proteolysis was identified by mass spectrometry approach. FIG. 3B shows cultured rat cortical neurons exposed to indicated concentrations of X-LC-$H_N$ in media for 12 hours. Cell lysates were harvested and immunoblot analysis was carried out to examine syntaxin 1, SNAP-25, and VAMP2 in neurons. Actin served as a loading control. Trypsin-activated LC-$H_N$ of BoNT/A (A-LC-$H_N$) and BoNT/B (B-LC-$H_N$) were analyzed in parallel as controls. X-LC-$H_N$ entered neurons and cleaved VAMP2, as evidenced by loss of VAMP2 immunoblot signals. X-LC-$H_N$ activated by Lys-C showed a drastically increased potency than non-activated X-LC-$H_N$. X-LC-$H_N$ is more potent than trypsin-activated B-LC-$H_N$ and A-LC-$H_N$, which did not show any detectable cleavage of their SNARE substrates in neurons under the same assay concentrations. FIG. 3C shows X-LC-$H_N$ mutants with indicated cysteine mutated, as well as WT X-LC-$H_N$, activated by limited proteolysis and analyzed by SDS-PAGE and Coomassie Blue staining, with or without DTT. C423S mutation resulted in two 50 kDa fragments, with or without DTT. Mutants harboring C461S or C467S showed a single band at 100 kDa in the absence of DTT, and it separated into two ~50 kDa bands in the presence of DTT, demonstrating that both C461 and C467 on the $H_N$ can form the inter-chain disulfide bond with C423 on the LC. A portion of WT X-LC-$H_N$ formed aggregates at the top of the SDS-PAGE gel. These aggregates are due to formation of inter-molecular disulfide bond, as they disappeared in the presence of DTT. Mutating any one of three cysteines abolished aggregates, indicating that formation of inter-molecular disulfide bond is due to existence of an extra cysteine in the linker region. The majority of activated WT X-LC-$H_N$ also separated to two ~50 kDa bands on SDS-PAGE gel without DTT. This is due to disulfide bond shuffling described in FIG. 3D. FIG. 3D shows WT X-LC-$H_N$ activated by limited proteolysis, followed by pre-incubation with indicated concentrations of NEM to block disulfide bond shuffling. The samples were then analyzed by SDS-PAGE and Coomassie Blue staining, with or without the presence of DTT. Majority of WT X-LC-$H_N$ exist as a single band at 100 kDa without DTT after NEM treatment, indicating that WT X-LC-$H_N$ mainly contains inter-chain disulfide bond. FIG. 3E shows experiments carried out as described in FIG. 3B, except that neurons were exposed to either WT or indicated X-LC-$H_N$ mutants. Mutating the cysteine on the LC (C423) abolished the activity of X-LC-$H_N$, while mutating one of the two cysteines on the $H_N$ (C461 or C467) did not affect the activity of X-LC-$H_N$ on neurons. These results confirmed that formation of the inter-chain disulfide bond is essential for the activity of X-LC-H$_N$.

FIGS. 4A-4F show full-length BoNT/X is active on cultured neurons and in vivo in mice. The sequences are as follows: LVPR-GS (SEQ ID NO: 80), LPETGG-His6 (SEQ ID NO: 81), GG-His6 (SEQ ID NO: 82) and LPETGS (SEQ ID NO: 59). FIG. 4A shows a schematic drawing illustrates synthesis of full-length BoNT/X using sortase ligation method. FIG. 4B shows that sortase ligation reaction mixture and indicated control components were analyzed by SDS-PAGE and Coomassie Blue staining. The asterisk marks aggregates of proteins due to inter-molecular disulfide bond, as these aggregates disappeared in the presence of DTT. The molecular weight marker is in lane 1 (starting from the left side). Full-length BoNT/X (X-FL) only appeared in the sortase ligation mixture (lane 7 and lane 14). FIG. 4C shows that neurons exposed to the same amount (5 μl) of sortase ligation mixture or indicated control components for 12 hours in media. Cell lysates were analyzed by immunoblot. X-LC-HN alone cleaved some VAMP2 due to its high concentration in the reaction mixture. The control mixture containing both X-LC-HN and X-HC but not sortase, slightly enhanced cleavage of VAMP2 as compared to X-LC-HN alone, likely because X-HC associates with X-LC-HN via non-covalent interactions. Ligating X-LC-HN and X-HC by sortase enhanced cleavage of VAMP2 over the mixture of X-LC-HN and X-HC without sortase, demonstrating that ligated X-FL is functional in neurons. FIG. 4D shows that sortase reaction mixture as prepared as described in panel b (lane 7) is active in vivo analyzed using DAS assay in mice. The injected limb developed flaccid paralysis and the toes failed to spread within 12 hours. The left limb was not injected with toxins, serving as a control. FIG. 4E shows that BoNT/A-G, a mosaic toxin BoNT/DC, and BoNT/X were subjected to dot blot analysis (0.2 μg per toxin, spotted on nitrocellulose membranes), using four horse antisera (trivalent anti-BoNT/A, B, and E, anti-BoNT/C, anti-BoNT/DC, and anti-BoNT/F), as well as two goat antisera (anti-BoNT/G and anti-BoNT/D). BoNT/X is composed of purified X-LC-HN and X-HC at 1:1 ratio. These antisera recognized their corresponding target toxins, yet none of them recognized BoNT/X. FIG. 4F shows that full-length inactive form of BoNT/X (BoNT/XRY) was purified as a His6-tagged recombinant protein in *E. coli* and analyzed by SDS-PAGE and Coomassie Blue staining, with or without DTT.

FIG. 5 is a phylogenetic tree showing the distribution and relationship of Clostridial neurotoxins. The tree represents the relationships of different BoNTs and TeNT sequences from the Jackhmmer search. BoNT/X is circled.

FIG. 7A shows a GST-tagged VAMP2 (33-86) incubated with or without X-LC. Samples were analyzed by SDS-PAGE and Coomassie Blue staining. FIGS. 7B-7C show intact GST-tagged VAMP2 (33-86) analyzed by LC-MS/MS mass spectrometry. The HPLC profile was shown in FIG. 7B. The mass spectrometry data was shown in FIG. 7C, with protein sequence (SEQ ID NO: 84) noted in FIG. 7C. VAMP2 (33-66) and VAMP2 (67-86) are marked. FIGS. 7D-7E show GST-tagged VAMP2 (33-86) incubated with X-LC. Samples were then analyzed by LC-MS/MS mass spectrometry. The HPLC profile is shown in FIG. 7D. The mass spectrometry data for the C-terminal fragment (SEQ ID NO: 85) generated by X-LC is shown in FIG. 7E. The mass spectrometry data for the N-terminal fragment (SEQ ID NO: 86) was shown in FIG. 7F. The protein sequences of the C- and N-terminal fragments were indicated in FIGS. 7E-7F, and correspond to SEQ ID NOs: 85 and 86 respectively.

FIG. 8A shows a XA chimeric toxin generated by ligating X-LC-H$_N$ with A-H$_C$ by sortase, similar to generating X-FL as described in FIG. 4A. The sortase ligation mixture and indicated control components were analyzed by SDS-PAGE and Coomassie Blue staining. The ligation is efficient as majority of X-LC-H$_N$ was ligated into XA chimeric toxin. FIG. 8B shows rat cortical neurons exposed to the indicated control components or sortase ligated XA mixture (5 μl) for 12 hours in media. Cell lysates were analyzed by immunoblot. X-LC-H$_N$ alone cleaved some VAMP2 due to its high concentration in the reaction mixture. Ligated XA cleaved VAMP2 in neurons.

FIG. 9 shows that mutating the extra cysteine in the H$_N$ and the cysteine in the H$_C$ does not affect activity of BoNT/X. X-H$_C$ (C1240S) was ligated with WT X-LC-H$_N$, X-LC-H$_N$ (C461S), or X-LC-H$_N$ (C467S) by sortase ligation. Neurons were exposed to sortase ligation mixture or control components (5 μl) for 12 hours in media. Cell lysates were analyzed by immunoblot. Mutating C1240 and one of the cysteine on H$_N$ (C461 or C467) did not affect the activity of BoNT/X, as ligated mutant toxins are capable of entering neurons and cleaved VAMP2.

FIG. 11A shows cultured rat cortical neurons exposed to BoNT/X$_{RY}$ at indicated concentrations. Cell lysates were analyzed by immunoblot. VAMP2 was not cleaved, indicating that BoNT/X$_{RY}$ is not active on neurons. FIG. 11B shows the SDS-PAGE analysis of cell lysate and supernatant (S/N) expression of BoNT/X$_{RY}$ (4-12% BisTris, MOPS buffer). A band at 150 kDa corresponding to BoNT/X is clearly visible in both lysate and soluble fraction. FIG. 11C shows the SDS-PAGE analysis of a final sample of highly purified BoNT/X$_{RY}$ (4-12% BisTris, MOPS buffer). A single band at 150 kDa corresponding to BoNT/X is clearly visible and shows ~90% purity.

FIGS. 12A-12F show that BoNT/X binds to all four brain gangliosides. FIGS. 12A-12D show BoNT/X (squares), and A-Hc (circles) binding to GD1a (FIG. 12A), GT1b (FIG. 12B), GD1b (FIG. 12C), and GM1 (FIG. 12D), respectively. Curves correspond to an average of triplicate ELISA assays and were fitted with Prism? (GraphPad software). FIG. 12E shows a summary of BoNT/X binding to all four gangliosides compared with the overall binding of BoNT/A in FIG. 12F.

FIGS. 13A-13D show 10 μg GST-tagged Ykt6 (1-192), with or without pre-incubation with X-LC, were separated on SDS-PAGE (FIG. 13A). The protein bands were excised as indicated and digested by chymotrypsin. Digested peptides were desalted and analyzed by reversed phase HPLC via C18 column coupled with ESI-MS. The HPLC profiles of GST-Ykt6 without pre-treatment with X-LC was shown in FIG. 13B, and the sample pretreated with X-LC was shown in FIG. 13C. One peptide was identified to be ~100-fold higher intensity in the samples pre-treated with X-LC than in the samples that was not exposed to X-LC (denoted with an asterisk). This peptide was eluted at 37 min RT, with m/z=611 (FIG. 13D), which can only fit the peptide sequence ESLLERGEKLDDLVSK (SEQ ID NO: 87) in Ykt6, indicating that this is the peptide located at the N-terminal side of the cleavage site for X-LC. Therefore the cleavage site is K173-S174 in Ykt6.

FIGS. 14A-14E show the identification of the cleavage sites of X-LC on VAMP4 and VAMP5 by mass spectrometry analysis. FIGS. 14A-14E show experiments carried out as described in FIG. 13, except that VAMP4 (FIGS. 14B, 14C) and VAMP5 (FIGS. 14D, 14E) were analyzed. FIG. 14B is the peptide that marks the N-terminal site of the cleavage site in VAMP4. The sequence of the peptide DELQDK corresponds to SEQ ID NO: 88. FIG. 14C is the peptide that marks the C-terminal site of the cleavage site in VAMP4. The sequence of the peptide SESLSDNATAF corresponds to SEQ ID NO: 89. FIG. 14D is the peptide that marks the N-terminal site of the cleavage site in VAMP5. The sequence of the peptide AELQQR corresponds to SEQ ID NO: 90. FIG. 14E is the peptide that marks the C-terminal site of the cleavage site in VAMP5. The sequence of the peptide SDQLLDMSSTF corresponds to SEQ ID NO: 91. Thus, the cleavage sites were determined to be K87-S88 in VAMP4 and R40-S41 in VAMP5.

DETAILED DESCRIPTION OF SOME EMBODIMENTS

Figure 1D:
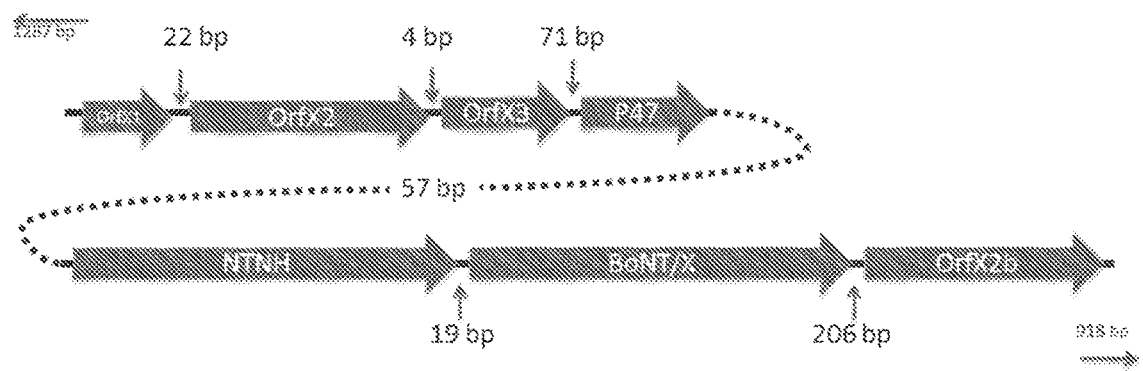
Figure 1E:
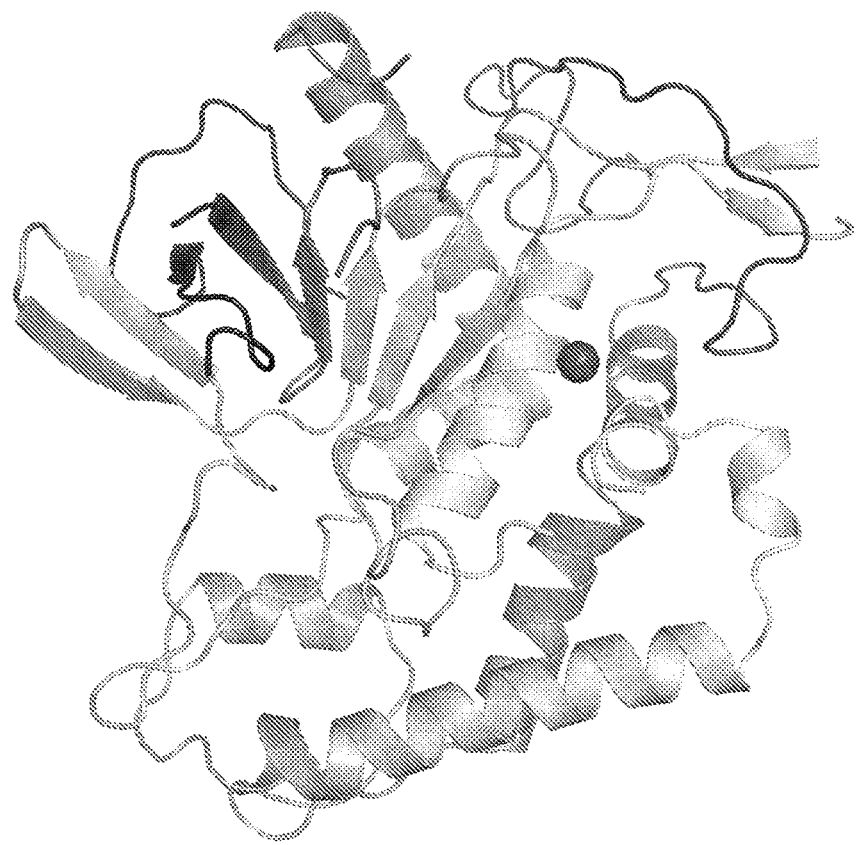

*Clostridium Botulinum* neurotoxins (BoNTs) are a family of bacterial toxins produced by clostridium bacteria, with seven well-established serotypes (BoNT/A-G)[1-3]. They are one of the most dangerous potential bio-terrorism agents, classified as a "Category A" select agent by Center for Disease Control (CDC) of United States[4]. These toxins are produced as a single polypeptide and can be separated by bacterial or host proteases into a light chain (LC, ~50 kDa) and a heavy chain ($H_C$, ~100 kDa). The two chains remain connected via an inter-chain disulfide bond. The $H_C$ contains two sub-domains: the N-terminal $H_N$ domain that mediates translocation of the LC across endosomal membranes, and the C-terminal $H_C$ domain that mediates binding to receptors on neurons. The inter-chain disulfide bond is reduced once the LC translocates into the cytosol[5,6]. Released LC acts as a protease to specifically cleave a set of neuronal proteins: BoNT/A, C, and E cleave at distinct sites on a protein known as SNAP-25; BoNT/B, D, F, and G cleave at different sites on a vesicle protein VAMP; and BoNT/C also cleaves a transmembrane protein syntaxin 1[1-3]. These three proteins form a complex, known as SNARE complex, which is essential for release of neurotransmitters[7,8]. Cleavage of any one of these three SNARE proteins blocks neurotransmitters release from neurons, thus paralyzing muscles.

BoNTs are the most potent toxins known and cause the human and animal disease known as botulism[3]. The major form of botulism is caused by ingesting food contaminated with BoNTs (food botulism). Other forms also exist such as infant botulism, which is due to colonization of the intestine by toxin-producing bacteria in infants. BoNTs are always produced together with another 150 kDa protein known as NTNHA (non-toxic non-hemagglutinin protein), which forms a pH-dependent complex with BoNTs and protects BoNTs from proteases in the gastrointestinal tract[9]. Genes encoding BoNT and NTNHA are found in two types of gene clusters: (1) HA cluster, containing genes for three conserved proteins HA17, HA33 and HA70, which form a complex with BoNT/NTNHA and facilitate absorption of toxins across the intestinal epithelial barrier[10-12]. (2) OrfX cluster, which encodes conserved OrfX1, OrfX2, OrfX3 and P47 proteins with unknown functions[13].

Because local injections of minute amounts of toxins can attenuate neuronal activity in targeted regions, BoNTs have been used to treat a growing list of medical conditions 14-16 including muscle spasms, chronic pain, overactive bladder problems, as well as for cosmetic applications. The market for BoNTs has already surpassed $1.5 billion in 2011 and is projected to reach 2.9 billion by 2018.

BoNTs were traditionally typed by neutralization assays in mice, by injecting culture supernatant of clostridium bacteria into mice, with or without antisera against known BoNTs. The first distinguished serotypes, BoNT/A and BoNT/B, were established in 1919 by Georgina Burke[18]. The last of the seven type, BoNT/G, was recognized in 1969 from soil samples in Argentina[19]. No new serotype of BoNTs has been recognized since 1970. This classification held true after protein sequences for each BoNT was determined in 1990's. The sequence identity between any two pairs among the seven BoNTs ranges from 32% to 65.3%. All seven BoNTs have been identified and characterized before the era of their medical use. Therefore, there is no patent on any of these toxins. Any company is free to produce and market any one of these seven BoNTs. Among the seven types, BoNT/A and BoNT/B are the two toxins that are currently FDA-approved for use in humans[14-16]. BoNT/A is the dominant type used for both medical and cosmetic applications, marketed as Botox from Allergan Inc., Dysport from IPSEN Inc., and Xeomin from Merz Inc. BoNT/B is marketed as Myobloc by USWorld Med. There are considerable interests in developing other BoNT types as therapeutic toxins, for two major reasons:

(1) A major limitation in treatment is generation of neutralizing antibody against BoNT/A or BoNT/B in patients, which renders future treatment with the same toxin ineffective[20]. In this case, patients will need to be treated with a different type of BoNTs. This is why BoNT/B is often utilized to treat patients who have generated neutralizing antibodies against BoNT/A during treatment, but there is a need for alternative toxins for patients who have generated antibodies against both BoNT/A and BoNT/B.

(2) Although all BoNTs share the same structure and function, there are also considerable differences between them. For instance, BoNT/A cleaves SNAP-25 and uses a protein SV2 as its receptor, whereas BoNT/B cleaves VAMP and uses a protein synaptotagmin (Syt) as its receptor[21-27]. These functional variations may translate to potential differences in therapeutic efficacy targeting distinct types of neurons. In addition, the stability and therapeutic duration can be also different among seven types of toxins. Therefore, a different toxin type may have its advantage over BoNT/A and BoNT/B.

Rapid progress on genomic sequencing in recent years has revealed a remarkable diversity of BoNTs[28,29]. First, there are multiple subtypes, which can be recognized by the same antiserum, but contain significant levels of variations on protein sequences (2.6%~31.6% differences)[28,30]. For instance, BoNT/A contains 8 known subtypes, designated as BoNT/A1-A8[13]. Furthermore, multiple mosaic toxins exist, likely derived from recombination of toxin genes. For instance, a "type H" was reported in 2013, but it was later recognized as a chimeric toxin because its LC shares ~80% identity with the LC of a BoNT/F subtype, BoNT/F5, and its $H_C$ shares ~84% identity to the $H_C$ of BoNT/A1[31-34]. Consistently, this toxin can be recognized and neutralized by available antisera against BoNT/A[33].

The gene cluster encoding BoNTs can be on plasmids, bacterial phage, or chromosomes, indicating that the toxin genes are mobile and subject to horizontal gene transfer[13]. There are also cases that a clostridium bacteria strain contains two or even three different toxin genes[32,35,36]. In these cases, one toxin is usually expressed at higher levels (designed with a capital letter) than the other toxin (designated with a lower case letter). For instance, strains that express high levels of BoNT/B and low levels of BoNT/F are known as BoNT/Bf strains. There are also cases that one toxin is expressed, but the other toxin is not expressed, which is known as silent toxin (usually marked with 0). For instance, a survey for infant botulism cases in California showed that 8% strains were BoNT/A(B), which means these strains contain genes for both BoNT/A and BoNT/B, but only express detectable levels of BoNT/A[37-39].

As illustrated in the drawings and examples of the present disclosure, published clostridium bacteria genomic sequence databases were searched, and a novel BoNT gene (hereafter designated "BoNT/X") encoded on the chromosome of *Clostridium botulinum* strain 111 was identified. Strain 111 was first isolated from an infant botulism patient in Japan in 1996[40]. It has been shown that toxicity from strain 111 in mice can be neutralized by BoNT/B antisera[40]. It was later confirmed that this strain expresses a subtype of BoNT/B, BoNT/B2, encoded on a plasmid[41,42]. The sequence of BoNT/X was deposited into PubMed database in February of 2015, as part of genomic sequence of Strain 111. BoNT/X has not been characterized before. It remains unknown whether it is expressed in the strain 111 and whether it is a functional toxin.

Also provided herein are the characterization of BoNT/X at functional levels. Its LC was found to cleave VAMP at a site distinct from known target sites of all other BoNTs. The full-length toxin, produced by covalently linking non-toxic fragments via sortase, was found to enter cultured neurons and cleave VAMP in neurons, inducing flaccid paralysis in mice. Finally, it was found that the toxin is not recognized by antisera raised against all seven known BoNTs, establishing BoNT/X as a novel BoNT serotype. Its identification poses an urgent challenge for developing effective countermeasures. It also has the potential to be developed into a new therapeutic toxin and can be used to generate chimeric toxins with potentially distinct pharmacological properties.

As used herein, the term "Clostridial *Botulinum* neurotoxin (BoNT) polypeptide" encompasses any polypeptide or fragment from a *Botulinum* neurotoxin described herein. In some embodiments, the term BoNT refers to a full-length BoNT. In some embodiments, the term BoNT refers to a fragment of the BoNT that can execute the overall cellular mechanism whereby a BoNT enters a neuron and inhibits neurotransmitter release. In some embodiments, the term BoNT simply refers to a fragment of the BoNT, without requiring the fragment to have any specific function or activity. For example, a BoNT polypeptide may refer to the light chain (LC) of a BoNT, e.g., BoNT/X. Other terms that may be used throughout the present disclosure for "Clostridial *Botulinum* neurotoxins" may be BoNTs, *Botulinum* toxins, or *C. Botulinum* toxins. It is to be understood that these terms are used interchangeably. "BoNT/X" refers to the novel BoNT serotype described and characterized in the present disclosure. The BoNT/X protein sequence (GenBank No. BAQ12790.1; four cysteines are underlined and bolded) is also provided:

(SEQ ID NO: 1)
MKLEINKFNYNDPIDGINVITMRPPRHSDKINKGKGPFKAFQVIKNIWIV

PERYNFTNNTNDLNIPSEPIMEADAIYNPNYLNTPSEKDEFLQGVIKVLE

RIKSKPEGEKLLELISSSIPLPLVSNGALTLSDNETIAYQENNNIVSNLQ

ANLVIYGPGPDIANNATYGLYSTPISNGEGTLSEVSFSPFYLKPFDESYG

NYRSLVNIVNKFVKREFAPDPASTLMHELVHVTHNLYGISNRNFYYNFDT

GKIETSRQQNSLIFEELLTFGGIDSKAISSLIIKKIIETAKNNYTTLISE

RLNTVTVENDLLKYIKNKIPVQGRLGNFKLDTAEFEKKLNTILFVLNESN

LAQRFSILVRKHYLKERPIDPIYVNILDDNSYSTLEGFNISSQGSNDFQG

QLLESSYFEKIESNALRAFIKICPRNGLLYNAIYRNSKNYLNNIDLEDKK

TTSKTNVSYPCSLLNGCIEVENKDLFLISNKDSLNDINLSEEKIKPETTV

FFKDKLPPQDITLSNYDFTEANSIPSISQQNILERNEELYEPIRNSLFEI

KTIYVDKLTTFHFLEAQNIDESIDSSKIRVELTDSVDEALSNPNKVYSPF

KNMSNTINSIETGITSTYIFYQWLRSIVKDFSDETGKIDVIDKSSDTLAI

VPYIGPLLNIGNDIRHGDFVGAIELAGITALLEYVPEFTIPILVGLEVIG

GELAREQVLAIVNNALDKRDQKWAEVYNITKAQWWGTIHLQINTRLAHTY

KALSRQANAIKMNMEFQLANYKGNIDDKAKIKNAISETEILLNKSVEQAM

KNTEKFMIKLSNSYLTKEMIPKVQDNLKNFDLETKKTLDKFIKEKEDILG

TNLSSSLRRKVSIRLNKNIAFDINDIPFSEFDDLINQYKNEIEDYEVLNL

GAEDGKIKDLSGTTSDINIGSDIELADGRENKAIKIKGSENSTIKIAMNK

YLRFSATDNFSISFWIKHPKPTNLLNNGIEYTLVENFNQRGWKISIQDSK

LIWYLRDHNNSIKIVTPDYIAFNGWNLITITNNRSKGSIVYVNGSKIEEK

DISSIWNTEVDDPIIFRLKNNRDTQAFTLLDQFSIYRKELNQNEVVKLYN

YYFNSNYIRDIWGNPLQYNKKYYLQTQDKPGKGLIREYWSSFGYDYVILS

DSKTITFPNNIRYGALYNGSKVLIKNSKKLDGLVRNKDFIQLEIDGYNMG

ISADRFNEDTNYIGTTYGTTHDLTTDFEIIQRQEKYRNYCQLKTPYNIFH

KSGLMSTETSKPTFHDYRDWVYSSAWYFQNYENLNLRKHTKTNWYFIPKD

EGWDED

A "modified Clostridial *Botulinum* neurotoxin (BoNT)" encompasses a BoNT comprising any modifications in the amino acid sequence, e.g., truncation, addition, amino acid substitution, and any combination thereof. For example, a BoNT/X comprising amino acid substitution mutations in C461 or C467 is a modified BoNT. In another example, a fragment or a domain of the full-length BoNT (e.g., the protease domain, or LC) is considered a modified BoNT. In some embodiments, a domain of the BoNT may also comprise amino acid substitution mutations, e.g., a protease domain comprising substitution mutations at positions C461 or C467 of BoNT/X.

The term "enters a cell" when used to describe the action of a BoNT of the present disclosure, encompasses the binding of a BoNT to a low or high affinity receptor complex, binding of a BoNT to ganglioside, the internalization of the toxin, the translocation of the toxin light chain into the cytoplasm and the enzymatic modification of a BoNT substrate.

As used herein, the term "Clostridial *Botulinum* neurotoxin (BoNT) protease domain" is synonymous to "light-chain (LC)." The BoNT protease domain is located in the light chain of the BoNT, and thus is also referred to as the LC. The term means a BoNT domain that can execute the enzymatic target modification step of the intoxication process. If the LC from a specific BoNT serotype is referred to, the term "serotype-LC" is used. For example, "X-LC" means the LC polypeptide from BoNT/X. A BoNT protease domain specifically targets a *C. Botulinum* toxin substrate and encompasses the proteolytic cleavage of a *C. Botulinum* toxin substrate, such as, e.g., SNARE proteins such as a SNAP-25 substrate, a VAMP substrate and a Syntaxin substrate. In BoNT (e.g., BoNT/X, BoNT/A, BoNT/B, BoNT/C, etc.). The protease domain or the LC is considered to correspond to about amino acid 1-439 of BoNT/X. The domain boundary may vary by about 25 amino acids. For example, the protease domain may correspond to amino acids 1-414 or 1-464 of BoNT/X. In some embodiments, the protease domain may correspond to amino acids 1-438, 1-437, 1-436, 1-435, 1-434, 1-433, 1-432, 1-431, 1-430, 1-429, 1-439, 1-440, 1-441, 1-442, 1-443, 1-444, 1-445, 1-446, 1-447, 1-448, or 1-449 of BoNT/X.

As used herein, the term "Clostridial *Botulinum* neurotoxin (BoNT) translocation domain" is synonymous with "$H_N$ domain" and means a BoNT domain that can execute the translocation step of the intoxication process that mediates BoNT light chain translocation. Thus, an $H_N$ facilitates the movement of a BoNT light chain across a membrane into the cytoplasm of a cell. Non-limiting examples of a $H_N$ include a BoNT/A $H_N$, a BoNT/B $H_N$, a BoNT/C1 $H_N$, a BoNT/D $H_N$, a BoNT/E $H_N$, a BoNT/F $H_N$, a BoNT/G $H_N$, and a BoNT/X $H_N$. The translocation domain is located in the N-terminus of the heavy chain (HO, and thus is also referred as $H_N$. It is to be understood that these terms are used interchangeably herein.

As used herein, the term "linker region" refers to the amino acid sequence between the BoNT protease domain and the translocation domain. The linker comprises two cysteines at position 461 and 467, one of which forms an inter-molecular disulfide bond with a cysteine in the protease domain, C423 (C461-C423 disulfide bond, or C467-C423 disulfide bond). The formation of this disulfide bond is essential for the activity of BoNT/X.

As used herein, the term "LC-$H_N$" refers to a BoNT polypeptide encompassing the protease domain, the linker region, and the translocation domain. If the LC-$H_N$ from a specific BoNT serotype is referred to, the term "serotype-LC-$H_N$" is used. For example, "X-LC-$H_N$" means the LC-$H_N$ polypeptide from BoNT/X. The LC-$H_N$ polypeptide is considered to correspond to about amino acid 1-892 of BoNT/X. The domain boundary may vary by about 25 amino acids. For example, LC-$H_N$ polypeptide may correspond to about amino acid 1-917 or 1-867 of BoNT/X. In some embodiments, the LC-$H_N$ polypeptide may correspond to amino acids 1-893, 1-894, 1-895, 1-896, 1-897, 1-898, 1-899, 1-900, 1-901, 1-902, 1-892, 1-891, 1-890, 1-889, 1-888, 1-887, 1-886, 1-885, 1-884, or 1-883 of BoNT/X.

As used herein, the term "Clostridial *Botulinum* neurotoxin (BoNT) receptor-binding domain" is synonymous with "$H_e$ domain" and means any naturally occurring BoNT receptor binding domain that can execute the cell binding step of the intoxication process, including, e.g., the binding of the BoNT to a BoNT-specific receptor system located on the plasma membrane surface of a target cell. Some aspects of present disclosure relate to modified BoNT receptor binding domains from serotype X (BoNT/X). In some embodiments, a "modified BoNT/X receptor binding domain" comprises amino acid substitutions in a position corresponding to C1240 in BoNT/X (SEQ ID NO: 1). The receptor binding domain, or the $H_C$, is considered to correspond to about amino acid 893-1306 of BoNT/X. The domain boundary may vary by about 25 amino acids. For example, the receptor binding domain or $H_C$ may correspond to amino acids 868-1306 or 918-1306. In some embodiments, the receptor binding domain or $H_C$ may correspond to amino acids 893-1306, 894-1306, 895-1306, 896-1306, 897-1306, 898-1306, 899-1306, 900-1306, 901-1306, 902-1306, 892-1306, 891-1306, 890-1306, 889-1306, 888-1306, 887-1306, 886-1306, 885-1306, 884-1306, or 883-1306 of BoNT/X.

By "isolated" is meant a material that is free to varying degrees from components which normally accompany it as found in its native state. "Isolate" denotes a degree of separation from original source or surroundings, e.g., from a cell or from flanking DNA or from the natural source of the DNA. The term "purified" is used to refer to a substance such as a polypeptide that is "substantially pure", with respect to other components of a preparation (e.g., other polypeptides). It can refer to a polypeptide that is at least about 50%, 60%>, 70%>, or 75%, preferably at least about 85%, more preferably at least about 90%, and most preferably at least about 95% pure, with respect to other components. The terms "substantially pure" or "essentially purified", with regard to a polypeptide, refers to a preparation that contains fewer than about 20%, more preferably fewer than about 15%, 10%, 8%, 7%, most preferably fewer than about 5%, 4%, 3%, 2%, 1%, or less than 1%, of one or more other components (e.g., other polypeptides or cellular components).

The term "substitution mutation" without the reference to a specific amino acid, may include any amino acid other than the wild type residue normally found at that position. Such substitutions may be replacement with non-polar (hydrophobic) amino acids, such as glycine, alanine, valine, leucine, isoleucine, methionine, phenylalanine, tryptophan, and proline. Substitutions may be replacement with polar (hydrophilic) amino acids such as serine, threonine, cysteine, tyrosine, asparagine, and glutamine. Substitutions may be replacement with electrically charged amino acids, e.g., negatively electrically charged amino acids such as aspartic acid and glutamic acid and positively electrically charged amino acids such as lysine, arginine, and histidine.

The substitution mutations described herein will typically be replacement with a different naturally occurring amino acid residue, but in some cases non-naturally occurring amino acid residues may also be substituted. Non-natural amino acids, as the term is used herein, are non-proteinogenic (i.e., non-protein coding) amino acids that either occur naturally or are chemically synthesized. Examples include but are not limited to β-amino acids (β and β2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. In some embodiments, the amino acid can be substituted or unsubstituted. The substituted amino acid or substituent can be a halogenated aromatic or aliphatic amino acid, a halogenated aliphatic or aromatic modification on the hydrophobic side chain, or an aliphatic or aromatic modification.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Accordingly, some aspects of the present disclosure provide isolated BoNT polypeptides. In some embodiments, the isolated BoNT polypeptide is a full-length BoNT/X polypeptide. In some embodiments, the isolated BoNT polypeptide comprise the a amino acid sequence of SEQ ID NO: 1. In some embodiments, the isolated BoNT/X polypeptide comprises an amino acid sequence that has at least 85% identity to SEQ ID NO: 1. For example, the isolated BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 1. In some embodiments, the isolated BoNT polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to SEQ ID NO: 1. In some embodiments, the isolated BoNT polypeptide consists of the amino acid sequence of SEQ ID NO: 1.

In some embodiments, the isolated BoNT polypeptide is an X-LC-$H_N$ polypeptide. In some embodiments, the isolated BoNT polypeptide comprise the a amino acid sequence of SEQ ID NO: 2. In some embodiments, the isolated BoNT polypeptide comprises an amino acid sequence that has at least 85% identity to SEQ ID NO: 2. For example, the isolated BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 2. In some embodiments, the isolated BoNT polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to SEQ ID NO: 2. In some embodiments, the isolated BoNT polypeptide consists of the amino acid sequence of SEQ ID NO: 2.

In some embodiments, the isolated BoNT polypeptide is an X-LC polypeptide. In some embodiments, the isolated BoNT polypeptide comprise the a amino acid sequence of SEQ ID NO: 3. In some embodiments, the isolated BoNT polypeptide comprises an amino acid sequence that has at least 85% identity to SEQ ID NO: 3. For example, the isolated BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 3. In some embodiments, the isolated BoNT polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to SEQ ID NO: 3. In some embodiments, the isolated BoNT polypeptide consists of the amino acid sequence of SEQ ID NO: 3.

The X-LC polypeptide may be introduced alone into cells where the cleavage of a BoNT substrate (e.g., a SNARE protein) is desired for research or therapeutic purpose, by any known techniques of expression an exogenous protein in the art, e.g., transfection of LC coding sequence directly into cells, via lentiviral vectors, via AAV vectors, or fusing X-LC with cell penetrating peptides).

In some embodiments, the BoNT polypeptides of the present disclosure is a full-length BoNT/X comprising a protease domain (LC), a linker region, a translocation domain ($H_N$), and a receptor binding domain (HO, wherein the linker region is located between the protease domain and the translocation domain. Like other BoNTs, BoNT/X is initially produced as a single polypeptide and is activated via the cleavage of the linker region between LC and $H_N$ either bacterial or host proteases. This process is known as "activation" and is essential for the activity of BoNT/XAfter the cleavage, the LC and $H_N$ remain connected via an inter-chain disulfide bond prior to translocation of LC into the cytosol of cells, where the disulfide bond is reduced in order to release the LC into the cytosol. BoNT/X contains two cysteines that are conserved compared to other BoNTs, C423 and C467. Interestingly, BoNT/X also contains an additional cysteine (C461), which is unique to BoNT/X. The formation of the inter-chain disulfide bond (C423-C461, or C423-C467) is required for BoNT/X activity.

Figures 4A, 4B, 4C, 4D, 4E, 4F:
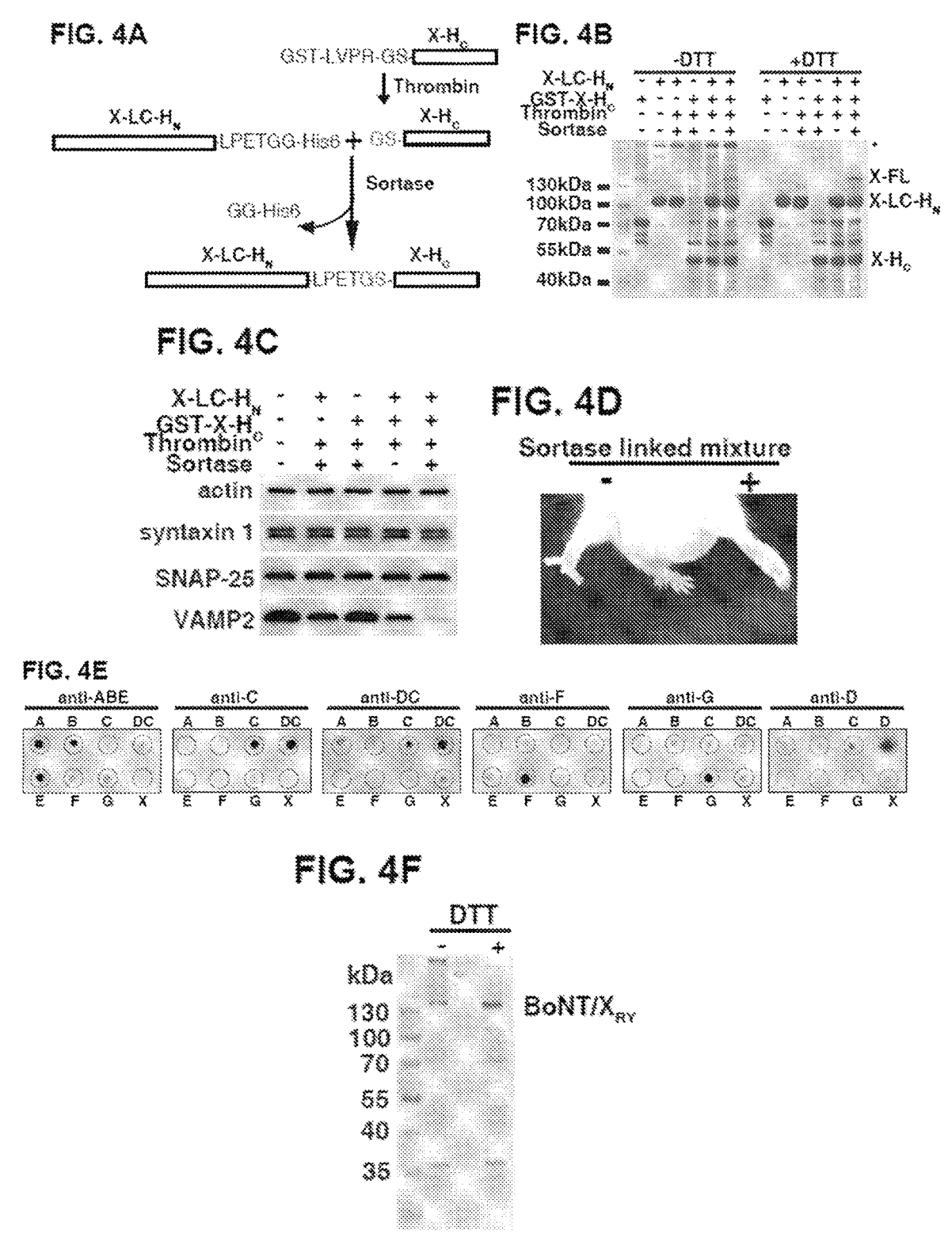

In addition to the cysteines in the linker region, the receptor binding domain of BoNT contains another cysteine, C1240, which can also form inter-molecular disulfide bonds with other cysteines in BoNT/X. These intermolecular disulfide bonds causes BoNT/X to aggregate and destabilizes the protein (FIG. 4B). Replacing the cysteines that are not required for BoNT/X activity may produces BoNT/X polypeptides with increased stability.

Accordingly, some aspects of the present disclosure provide modified BoNT/X polypeptide comprising one or more substitution mutation(s) in C461, C467, or C1240, which are more stable than the wild-type BoNT/X and have comparable activities. The cysteines may be substituted with any amino acids that abolish the formation of disulfide bonds. In some embodiments, the cysteines are substituted with serine (S) or alanine (A). Possible combinations of substitution mutations that may be present in the modified BoNTs of the present disclosure are, without limitation: C461S, C461A, C467S, C467A, C1240S, C1240A, C461S/C1240S, C461A/C1240S, C461S/C1240A, C467A/C1240A, C467S/C1240S, C467A/C1240S, C467S/C1240A, and C467A/C1240A. "/" indicates double mutations. In some embodiments, the modified BoNT/X polypeptide of the present disclosure comprises an amino acid sequence of any one of SEQ ID NOs: 4-17. In some embodiments, the modified BoNT/X polypeptide comprises an amino acid sequence that has at least 85% identity to any one of SEQ ID NO: 4-17, and does not have the amino acid sequence of SEQ ID NO: 1. For example, the modified BoNT/X polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 4-17, and does not have the amino acid sequence of SEQ ID NO: 1. In some embodiments, the modified BoNT/X polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any one of SEQ ID NOs: 4-17, and does not have the amino acid sequence of SEQ ID NO: 1. In some embodiments, the modified BoNT/X polypeptide consists of the amino acid sequence of any one of SEQ ID NOs: 4-17.

In some embodiments, the modified BoNT polypeptide of the present disclosure is a modified BoNT/X-LC-$H_N$ polypeptide comprising the substitution mutations described herein. In some embodiments, the modified BoNT/X-LC-$H_N$ comprises one single substitution mutation in a position corresponding to C461 or C467 in SEQ ID NO: 2. In some embodiments, the modified BoNT/X-LC-$H_N$ comprises one single substitution mutation corresponding to C461A, C461S, C467A, or C467S in SEQ ID NO: 2. In some embodiments, the modified BoNT/X polypeptide of the present disclosure comprises an amino acid sequence of any one of SEQ ID NOs: 18-21. In some embodiments, the modified BoNT/X-LC-$H_N$ polypeptide comprises an amino acid sequence that has at least 85% identity to any one of SEQ ID NO: 18-21, and does not have the amino acid sequence of SEQ ID NO: 2. For example, the modified BoNT/X-LC-$H_N$ polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 18-21, and does not have the amino acid sequence of SEQ ID NO: 2. In some embodiments, the modified BoNT/X-LC-$H_N$ polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any one of SEQ ID NOs: 18-21, and does not have the amino acid sequence of SEQ ID NO: 2. In some embodiments, the modified BoNT/X-LC-$H_N$ polypeptide consists of the amino acid sequence of any one of SEQ ID NOs: 18-21.

The modified BoNT polypeptide comprising one or more substitution mutation(s) (e.g., in C461, C467, or C1240) described herein does not form inter-molecular disulfide bonds that cause aggregation of the protein, and are therefore more stable than their corresponding wild type proteins. The activity of the BoNT polypeptides are not affected by the substitution mutations in the cysteines. Thus, the modified BoNT/X may be more suitable for therapeutic use than the wild type BoNT/X due to its increased stability.

Other aspects of the present disclosure provide chimeric BoNTs comprising BoNT/X-LC-$H_N$ described herein and the receptor binding domain ($H_C$) from a different BoNT. For example, the receptor binding domain may be from any one of BoNT/A, BoNT/B, BoNT/C, BoNT/D, BoNT/E, BoNT/E, BoNT/F, and BoNT/G. Thus, the chimeric BoNTs contemplated herein include BoNT/X-LC-$H_N$-A-$H_C$, BoNT/X-LC-$H_N$-B-$H_C$, BoNT/X-LC-$H_N$-C-$H_C$, BoNT/X-LC-$H_N$-D-$H_C$, BoNT/X-LC-$H_N$-E-$H_C$, BoNT/X-LC-$H_N$-F-$H_C$, and BoNT/X-LC-$H_N$-G-Hc. It is to be understood that the $H_C$ domain of any subtypes of the seven known serotypes (e.g., A, B, C, D, E, F, or G) are suitable for the chimeric toxin. When BoNT/A, BoNT/B, BoNT/C, BoNT/D, BoNT/E, BoNT/F, or BoNT/G is referred to, it encompasses all the subtypes. For example, BoNT/A has 8 subtypes, BoNT/A1, BoNT/A2, BoNT/A3, BoNT/A4, BoNT/A5, BoNT/A6, BoNT/A7, or BoNT/A8, and the $H_C$ of any one of these BoNT/A subtypes are suitable for use in the chimeric BoNT of the present disclosure. Similarly, the $H_C$ of any one of the 8 subtypes of BoNT/B, i.e., BoNT/B1, BoNT/B2, BoNT/B3, BoNT/B4, BoNT/B5, BoNT/B6, BoNT/B7, or BoNT/B8, are suitable for use in the chimeric BoNT of the present disclosure.

In some embodiments, BoNT/X-LC-$H_N$-A1-$H_C$ (SEQ ID NO: 22), BoNT/X-LC-$H_N$-B1-$H_C$ (SEQ ID NO: 23), and BoNT/X-LC-$H_N$-C1-$H_C$ (SEQ ID NO: 24) are provided. In some embodiments, the chimeric BoNT polypeptide comprises an amino acid sequence that has at least 85% identity to any one of SEQ ID NO: 22-24. For example, the chimeric BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 22-24. In some embodiments, the chimeric BoNT polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any one of SEQ ID NOs: 22-24. In some embodiments, the chimeric BoNT polypeptide consists of the amino acid sequence of any one of SEQ ID NOs: 22-24.

In some embodiments, the chimeric BoNT of the present disclosure comprises a modified BoNT/X-LC-$H_N$ comprising a substitution mutation in the linker region, e.g., in a position corresponding to C461 or C467 of SEQ ID NO: 2. For example, the BoNT/X-LC-$H_N$ in the chimeric BoNT may comprise a substitution mutation corresponding to C461A, C467A, C461S, or C467S of SEQ ID NO: 2. For example, the chimeric BoNT polypeptide of the present disclosure may comprise an amino acid sequence of any one of SEQ ID NOs: 25-30. In some embodiments, the chimeric BoNT polypeptide comprises an amino acid sequence that has at least 85% identity to any one of SEQ ID NO: 25-30. For example, the chimeric BoNT polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 25-30. In some embodiments, the chimeric BoNT polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any one of SEQ ID NOs: 25-30. In some embodiments, the chimeric BoNT polypeptide consists of the amino acid sequence of any one of SEQ ID NOs: 25-30.

To generate the chimeric toxins, e.g., the BoNT/X-LC-$H_N$-A1-$H_C$ toxin, the X-LC-$H_N$ fragment comprising amino acid of about 1-892 (SEQ ID NO: 2) is fused to the receptor binding domain of any one of BoNT/A, BoNT/B, BoNT/C, BoNT/D, BoNT/E, BoNT/E, BoNT/F, and BoNT/G. The receptor binding domains of different BoNTs correspond to amino acids of about 860-1291 of BoNT/B1. It is to be understood that the border of the X-LC-$H_N$ fragment and/or the receptor binding domains may vary by 1-25 amino acids. For example, the X-LC-$H_N$ fragment that may be used for the chimeric toxin may comprise amino acids 1-917 or 1-867 of BoNT/X. In some embodiments, the X-LC-$H_N$ fragment that may be used for the chimeric toxin may comprise amino acids 1-893, 1-894, 1-895, 1-896, 1-897, 1-898, 1-899, 1-900, 1-901, 1-902, 1-892, 1-891, 1-890, 1-889, 1-888, 1-887, 1-886, 1-885, 1-884, or 1-883 of BoNT/X. Similarly, the receptor binding that may be used for the chimeric toxin may comprise amino acid corresponding to 885-1291 or 835-1291 of BoNT/X. In some embodiments, the receptor binding that may be used for the chimeric toxin may comprise amino acid corresponding to 860-1291, 861-1291, 862-1291, 863-1291, 864-1291, 865-1291, 866-1291, 867-1291, 868-1291, 869-1291, 870-1291, 860-1291, 859-1291, 858-1291, 857-1291, 856-1291, 855-1291, 854-1291, 853-1291, 852-1291, or 851-1291 of BoNT/B. The skilled artisan is able to identified the domains that may be used for the chimeric toxin of the present disclosure, based on his/her knowledge in protein homology, with or without the assistance of a sequence alignment software. The methods of fusing the fragments are standard recombinant techniques that are well known to one skilled in the art.

Further contemplated herein are modified BoNT/X polypeptides comprising a modified linker region, wherein the linker region comprises a specific protease cleavage site. A "specific protease cleavage site," as used herein, refers to a recognition and cleavage site for a specification protease, as opposed to a sequence that is recognized and cleavage by more than one non-specific proteases. Such specific proteases include, without limitation: thrombin, TEV, PreScission, Factor Xa, MMP-12, MMP-13, MMP-17, MMP-20, Granzyme-B, and Enterokinase. The cleavage site of the specific proteases may be added to the linker region of the BoNT/X polypeptide via insertion or replacement of the existing amino acids in the linker region (e.g., replace amino acids 424-460 of the BoNT/X polypeptide). The sequences of the specific protease cleavage sites sequences are also provided: LVPR|GS (thrombin, SEQ ID NO: 50), ENLYFQ|G (TEV, SEQ ID NO: 51), LEVLFQ|GP (PreScission, SEQ ID NO: 52), IEGR| or IDGR| (Factor Xa, SEQ ID NO: 53 or 54), DDDDK| (Enterokinase, SEQ ID NO: 55) and AHREQIGG| (SUMO protease, SEQ ID NO: 56). "|" indicates where cleavage occurs.

Other aspects of the present disclosure provide the functional characterization of the BoNT/X polypeptides. The BoNT/X polypeptides, modified BoNT/X polypeptides, and chimeric BoNT polypeptides of the present disclosure can bind and enter target cells, e.g., neurons, and cleave its substrate proteins, e.g. SNARE proteins. The term "SNARE proteins," as used herein, refers to SNAP (Soluble NSF Attachment Protein) Receptors, which is a large protein superfamily consisting of more than 60 members in yeast and mammalian cells. The primary role of SNARE proteins is to mediate vesicle fusion, i.e., the fusion of vesicles with their target membrane bound compartments (such as a lysosome). The best studied SNARE proteins are those that mediate docking of synaptic vesicles with the presynaptic membrane in neurons, e.g., SNAP-25, VAMP1, VAMP2, VAMP3, VAMP4, VAMP5, VAMP7, VAMP5, syntaxin1, and Ykt6. Several of these SNARE proteins are substrates of BoNTs. For example, VAMP1, VAMP2, VAMP3, SNAP-25, and syntaxin 1 have been shown to be cleaved by known BoNTs, e.g., BoNT/A and BoNT/B.

Provided herein are data showing that BoNT/X cleaves the SNARE proteins that are known substrates of BoNTs. One surprising finding of the present disclosure is that BoNT/X is able to cleave several SNARE proteins that other BoNTs are not able to cleave, e.g., VAMP4, VAMP5, and Ykt6. VAMP4 is widely expressed and is known to mediate vesicle fusion between trans-Golgi network (TGN) and endosomes, as well as homotypic fusion of endosomes. BoNTs are traditionally known to be limited to target SNAREs that mediate vesicle exocytosis onto plasma membranes. BoNT/X is the first BoNT that is capable of cleaving SNAREs mediating other type fusion events inside cells that is not with plasma membrane as the destine. VAMP4 may also contribute to asynchronous synaptic vesicle exocytosis, enlargeosome exocytosis, and activity-dependent bulk endocytosis (ADBE) in neurons. In addition, VAMP4 has been implicated in granule release in immune cells. Thus, BoNT/X might have a unique potential among all BoNTs to modulate inflammatory secretion in immune cells, which can be exploited therapeutically. VAMP5 is mainly expressed in muscles and its function remains to be established. BoNT/X will be a unique tool for investigating the function of VAMP4 and VAMP5. Ykt6 functions in endoplasmic reticulum to Golgi transport. It also functions in early/recycling endosome to TGN transport. The identification of Ykt6 as a substrate of the BoNT polypeptides described herein is significant because it opens up new therapeutic application for blocking secretion in a wide range of cells by BoNTs.

Another surprising finding of the present disclosure is that BoNT/X cleaves the SNARE proteins at a novel site what was not previously described. As illustrated in the Examples and Figures of the present disclosure, BoNT/X cleaves between amino acids R66-S67 in VAMP1, VAMP2, and VAMP3. R66-A67 is a novel cleavage site distinct from established target sites for all other BoNTs (FIG. 2F). It is also the only BoNT cleavage site located within a region previously known as the SNARE motif (FIG. 2F).

Accordingly, the BoNT polypeptides of the present disclosure have expanded profile of target cells and substrates. In some embodiments, the BoNT polypeptide cleaves a SNARE protein in the cell. In some embodiments, the BoNT polypeptide cleaves a SNARE protein selected from the group consisting of: SNAP-25, VAMP1, VAMP2, VAMP3, VAMP4, VAMP5, Ykt6, and syntaxin 1. In some embodiments, the BoNT polypeptide cleaves VAMP1 (SEQ ID NO: 39). In some embodiments, the BoNT polypeptide cleaves VAMP1 between amino acid residues corresponding to R66 and A67 of SEQ ID NO: 39. In some embodiments, the BoNT polypeptide cleaves VAMP2 (SEQ ID NO: 40). In some embodiments, the BoNT polypeptide cleaves VAMP2 between amino acid residues corresponding to R66 and A67 of SEQ ID NO: 40. In some embodiments, the BoNT polypeptide cleaves VAMP3 (SEQ ID NO: 31). In some embodiments, the BoNT polypeptide cleaves VAMP3 between amino acid residues corresponding to R66 and A67 of SEQ ID NO: 41. In some embodiments, the BoNT polypeptide cleaves VAMP4 (SEQ ID NO: 42). In some embodiments, the BoNT polypeptide cleaves VAMP4 between amino acid residues corresponding to K87 and S88 of SEQ ID NO: 42. In some embodiments, the BoNT polypeptide cleaves VAMP5 (SEQ ID NO: 43). In some embodiments, the BoNT polypeptide cleaves VAMP5 between amino acid residues corresponding to R40 and S41 of SEQ ID NO: 43. In some embodiments, the BoNT polypeptide cleaves Ykt6 (SEQ ID NO: 44). In some embodiments, the BoNT polypeptide cleaves Ykt6 between amino acid residues corresponding to K173 and S174 of SEQ ID NO: 44.

In some embodiments, the BoNT polypeptide of the present disclosure cleaves a SNARE protein in a target cell. As used herein, a "target cell" means a cell that is a naturally occurring cell that BoNT is capable of entering or intoxicating. In some embodiments, a target cell is a secretory cell, e.g., a neuron or a secretory immune cell. Examples of neurons that may be BoNT target cells include, without limitation, motor neurons; sensory neurons; autonomic neurons; such as, e.g., sympathetic neurons and parasympathetic neurons; non-peptidergic neurons, such as, e.g., cholinergic neurons, adrenergic neurons, noradrenergic neurons, serotonergic neurons, GABAergic neurons; and peptidergic neurons, such as, e.g., Substance P neurons, Calcitonin Gene Related Peptide neurons, vasoactive intestinal peptide neurons, Neuropeptide Y neurons, cholecystokinin neurons.

The BoNT polypeptide of the present disclosure, e.g., the BoNT/X or the modified BoNT/X polypeptide, is able to target other types of secretory cells other than neurons, due to its ability to cleave VAMP4 or Ykt6. In some embodiments, the secretory cell targeted by the BoNT polypeptide is a secretory immune cell. A "secretory immune cell," as used herein, refers to immune cells that secrets cytokines, chemokines, or antibodies. Such secretory immune cells may be innate immune cells including, without limitation, natural killer cells, mast cells, eosinophils, basophils, macrophages, neutrophils, and dendritic cells. Secretory immune cells that secret antibodies (e.g., white blood cells) may also be targeted by the BoNT polypeptides of the present disclosure. Non-limiting examples of antibody secreting cells include, without limitation, plasma B cells, plasmocytes, plasmacytes, and effector B cells. In some embodiments, the target cell is a cultured cell, e.g., a cultured neuron or a cultured secretory immune cell. In some embodiments, the target cell is in vivo. In some embodiments, target cell is from a mammal. In some embodiments, the mammal is a human. In embodiments, the mammal is a rodent, e.g., a mouse or a rat.

In some embodiments, the BoNT polypeptide suppresses neuronal activity. In some embodiments, the BoNT polypeptide modulates immune response. In some embodiments, the BoNT polypeptide induces flaccid paralysis. "Flaccid paralysis" refers to a clinical manifestation characterized by weakness or paralysis and reduced muscle tone without other obvious cause (e.g., trauma).

Other aspects of the present disclosure provide modified BoNT/X polypeptides comprising an inactive protease domain. Such BoNT/X polypeptides (also referred to herein as "inactive BoNT/X") can enter the target cells but cannot cleave the substrate proteins (e.g., a SNARE protein) due to the inactivation of the protease domain. In some embodiments, the inactive BoNT/X is an X-LC-$H_N$ fragment comprising: a) an inactive protease domain; b) a linker region; and c) a translocation domain. In some embodiments, the inactive BoNT/X is a full length BoNT/X polypeptide comprising: a) an inactive protease domain; b) a linker region; c) a translocation domain; and d) a receptor binding domain. In some embodiments, the inactive protease domain comprises one or more substitution mutation(s) in a position corresponding to R360, Y363, H227, E228, or H231 of SEQ ID NO: 1. In some embodiments, the one or more substitution mutation(s) corresponds to R360A/Y363F, H227Y, E228Q, or H231Y in SEQ ID NO: 1. It is to be understood that the inactive BoNT/X polypeptide may comprise any mutation(s) that inactivates the protease domain.

In some embodiments, the inactive BoNT/X polypeptide comprises an amino acid sequence of any one of SEQ ID NOs: 31-38. In some embodiments, the inactive BoNT/X polypeptide comprises an amino acid sequence that has at least 85% identity to any one of SEQ ID NOs: 31-38. For example, the inactive BoNT/X polypeptide may comprise an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 31-38. In some embodiments, the inactive BoNT/X polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to any one of SEQ ID NOs: 31-38. In some embodiments, the inactive BoNT/X polypeptide consists of the amino acid sequence of any one of SEQ ID NOs: 31-38.

In some embodiments, the inactive BoNT/X (e.g., inactive X-LC-$H_N$ or inactive full length BoNT/X) further comprises mutations in the linker region. In some embodiments, the modification in the linker region comprises one single substitution mutation in a position corresponding to C461 or C467 of SEQ ID NO: 1. In some embodiments, the single substitution mutation corresponds to C461A, C461S, C467A, or C467S in SEQ ID NO: 1. In some embodiments, the inactive BoNT/X (e.g., the inactive full length BoNT/X) further comprises a modification in the receptor binding domain. In some embodiments, the modification in the receptor binding domain comprises a substitution mutation in a position corresponding to C1240 of SEQ ID NO: 1.

It is also envisioned that the modified BoNT/X polypeptide comprising an inactive protease domain described herein can be utilized as a delivery tool to target cells (e.g., neurons) in humans. For example, the modified BoNT/X can be linked to other therapeutic agents, covalently or non-covalently, and acts as the targeting vehicle to deliver the therapeutic agents to target cells in humans.

As such, another aspect of the disclosure relates to a chimeric polypeptide molecule comprising a first portion that is an inactive BoNT/X, comprising one or more substitution mutations that inactivates the protease domain, linked to a second portion. The second portion of the molecule can be a bioactive molecule such as a therapeutic agent (e.g., a polypeptide or non-polypeptide drug). Linkage of the first and second portions of the molecule can be covalent (e.g., in the form of a fusion protein) or non-covalent. Methods of such linkage are known in the art and can readily be applied by the skilled practitioner. When the second portion of the chimeric molecule is a polypeptide and the chimeric molecule is in the form of a protein, nucleic acids and nucleic acid vectors encoding such chimeric molecules are provided.

Also provided are cells comprising the nucleic acids or nucleic acid vectors, and cells expressing such chimeric molecules. The chimeric molecules in a fusion protein form may be expressed and isolated using the methods disclosed herein.

The modified BoNT/X polypeptides, the chimeric BoNT polypeptides, or the chimeric molecules comprising a second portion that is a polypeptide of the present disclosure (e.g., without limitation, polypeptides comprising amino acid sequence of any one of SEQ ID NOs: 1-38), will generally be produced by expression form recombinant nucleic acids in appropriate cells (e.g., E. coli, or insect cells) and isolated. The nucleic acids encoding the polypeptides described herein may be obtained, and the nucleotide sequence of the nucleic acids determined, by any method known in the art.

Further provided herein are isolated and/or recombinant nucleic acids encoding any of the BoNT polypeptides disclosed herein. The nucleic acids encoding the isolated polypeptide fragments of the present disclosure, may be DNA or RNA, double-stranded or single stranded. In certain aspects, the subject nucleic acids encoding the isolated polypeptide fragments are further understood to include nucleic acids encoding polypeptides that are variants of any one of the modified BoNT polypeptides described herein.

Variant nucleotide sequences include sequences that differ by one or more nucleotide substitutions, additions or deletions, such as allelic variants. In some embodiments, the isolated nucleic acid molecule of the present disclosure comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity of any one of SEQ ID NOs: 1-38. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of any one of SEQ ID NOs: 1-38.

In some embodiments, the nucleic acid is comprised within a vector, such as an expression vector. In some embodiments, the vector comprises a promoter operably linked to the nucleic acid.

A variety of promoters can be used for expression of the polypeptides described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter. Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)].

Other systems include FK506 dimer, VP16 or p65 using astradiol, RU486, diphenol murislerone, or rapamycin. Inducible systems are available from Invitrogen, Clontech and Ariad. Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (HCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89:5547-5551 (1992); Shockett et al., Proc. Natl. Acad. Sci. USA, 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the polypeptides described herein. In some embodiments, the expression of the polypeptides described herein is regulated by a constitutive, an inducible or a tissue-specific promoter.

The host cells used to express the isolated polypeptides described herein may be either bacterial cells such as *Escherichia coli*, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors," Gene 45:101-106; Cockett et al. (1990) "High Level Expression Of Tissue Inhibitor Of Metalloproteinases In Chinese Hamster Ovary Cells Using Glutamine Synthetase Gene Amplification," Biotechnology 8:662-667). A variety of host-expression vector systems may be utilized to express the isolated polypeptides described herein. Such host-expression systems represent vehicles by which the coding sequences of the isolate d polypeptides described herein may be produced and subsequently purified, but also represent cells which may, when transformed or transfected with the appropriate nucleotide coding sequences, express the isolated polypeptides described herein in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the isolated polypeptides described herein; yeast (e.g., *Saccharomyces pichia*) transformed with recombinant yeast expression vectors containing sequences encoding the isolated polypeptides described herein; insect cell systems infected with recombinant virus expression vectors (e.g., baclovirus) containing the sequences encoding the isolated polypeptides described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the isolated polypeptides described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the polypeptides being expressed. For example, when a large quantity of such a protein is to be produced, for the generation of pharmaceutical compositions of polypeptides described herein, vectors which direct the expression of high levels of fusion protein products that are readily purified may be desirable. Such vectors include, but are not limited, to the *E. coli* expression vector pUR278 (Rüther et al. (1983)

"Easy Identification Of cDNA Clones," EMBO J. 2:1791-1794), in which the coding sequence may be ligated individually into the vector in frame with the lac Z coding region so that a fusion protein is produced; pIN vectors (Inouye et al. (1985) "Up-Promoter Mutations In The lpp Gene Of *Escherichia Coli*," Nucleic Acids Res. 13:3101-3110; Van Heeke et al. (1989) "Expression Of Human Asparagine Synthetase In *Escherichia Coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione.

The pGEX vectors are designed to include thrombin or factor Xa protease cleavage sites so that the cloned target gene product can be released from the GST moiety. In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic.

The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544). In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. For example, in certain embodiments, the polypeptides described herein may be expressed as a single gene product (e.g., as a single polypeptide chain, i.e., as a polyprotein precursor), requiring proteolytic cleavage by native or recombinant cellular mechanisms to form separate polypeptides described herein.

The disclosure thus encompasses engineering a nucleic acid sequence to encode a polyprotein precursor molecule comprising the polypeptides described herein, which includes coding sequences capable of directing post translational cleavage of said polyprotein precursor. Post-translational cleavage of the polyprotein precursor results in the polypeptides described herein. The post translational cleavage of the precursor molecule comprising the polypeptides described herein may occur in vivo (i.e., within the host cell by native or recombinant cell systems/mechanisms, e.g. furin cleavage at an appropriate site) or may occur in vitro (e.g. incubation of said polypeptide chain in a composition comprising proteases or peptidases of known activity and/or in a composition comprising conditions or reagents known to foster the desired proteolytic action).

Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli*," Proc. Nat. Acad. Sci. USA 82:7252-7255, and reviewed in Jenny et al. (2003) "A Critical Review Of The Methods For Cleavage Of Fusion Proteins With Thrombin And Factor Xa," Protein Expr. Purif. 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," BiotecH$_N$ology 13:982-987 hereby incorporated by reference herein in its entirety)), furin, and AcTEV (Parks et al. (1994) "Release Of Proteins And Peptides From Fusion Proteins Using A Recombinant Plant Virus Proteinase," Anal. Biochem. 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express polypeptides described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the polypeptides described herein. Such engineered cell lines may be particularly useful in screening and evaluation of polypeptides that interact directly or indirectly with the polypeptides described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection TecH$_N$ique In DNA-Mediated Transformation Of Mammalian Cells First Steps Toward Developing Hybridoma TecH$_N$iques And Gene Therapy," Bioessays 14: 495-500), and adenine phosphoribosyltransferase (Lowy et al. (1980) "Isolation Of Transforming DNA: Cloning The Hamster aprt Gene," Cell 22: 817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human Gene Therapy," Ann. Rev. Biochem. 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156). Methods commonly known in the art of recombinant DNA tecH$_N$ology which can be used are described in Ausubel et al. (eds.), 1993, Current Protocols in Molecular Biology, JOH$_N$ Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, JOH$_N$ Wiley & Sons, NY; Colberre-Garapin et al. (1981) "A New Dominant Hybrid Selective Marker For Higher Eukaryotic Cells," J. Mol. Biol. 150:1-14.

The expression levels of polypeptides described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a polypeptide described herein is amplifiable, increase in the level of inhibitor present in culture of host cell will increase the number of copies of the marker gene. Since the amplified region is associated with the nucleotide sequence of a polypeptide described herein or a polypeptide described herein, production of the polypeptide will also increase (Crouse et al. (1983) "Expression And Amplification Of Engineered Mouse Dihydrofolate Reductase Minigenes," Mol. Cell. Biol. 3:257-266).

Once a polypeptide described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the polypeptide comprises an Fc domain (or portion thereof)), and sizing column chromatography), centrifugation, differential solubility, or by any other standard tech$_n$ique for the purification of polypeptides or antibodies. Other aspects of the present disclosure relate to a cell comprising a nucleic acid described herein or a vector described herein.

The cell may be a prokaryotic or eukaryotic cell. In some embodiments, the cell in a mammalian cell. Exemplary cell types are described herein. Other aspects of the present disclosure related to a cell expressing the modified BoNT polypeptides described herein. The cell may be a prokaryotic or eukaryotic cell. In some embodiments, the cell in a mammalian cell. Exemplary cell types are described herein. The cell can be for propagation of the nucleic acid or for expression of the nucleic acid, or both. Such cells include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECH$_N$IQUES OF CELL CULTURE (Cambridge University Press, 1997); CELL AND TISSUE CULTURE: LABORATORY PROCEDURES (Alan Doyle et al eds., JOH$_N$ Wiley and Sons, 1998); R. Ian FresH$_N$ey, CULTURE OF ANIMAL CELLS: A MANUAL OF BASIC TECH$_N$IQUE (Wiley-Liss, 4.sup.th ed. 2000); ANIMAL CELL CULTURE: A PRACTICAL APPROACH (JOH$_N$ R. W. Masters ed., Oxford University Press, 3.sup.rd ed. 2000); MOLECULAR CLONING A LABORATORY MANUAL, supra, (2001); BASIC CELL CULTURE: A PRACTICAL APPROACH (JOH$_N$ M. Davis, Oxford Press, 2.sup.nd ed. 2002); and CURRENT PROTOCOLS IN MOLECULAR BIOLOGY, supra, (2004).

These protocols are routine procedures within the scope of one skilled in the art and from the teaching herein. Yet other aspects of the present disclosure relate to a method of producing a polypeptide described herein, the method comprising obtaining a cell described herein and expressing nucleic acid described herein in said cell. In some embodiments, the method further comprises isolating and purifying a polypeptide described herein.

In some embodiments, botulinum neurotoxin can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive.

The bacterial strains that make botulinum toxin serotypes A and G possess endogenous proteases and serotypes A and G can therefore be recovered from bacterial cultures in predominantly their active form. In contrast, botulinum toxin serotypes C, D and E are synthesized by non-proteolytic strains and are therefore typically inactive when recovered from culture. Serotypes B and F are produced by both proteolytic and non-proteolytic strains and therefore can be recovered in either the active or inactive form. The proteolytic strains that produce, for example, the botulinum toxin type B serotype may only cleave a portion of the toxin produced. The production of BoNT/X polypeptides using these strains are contemplated herein.

The exact proportion of nicked to un-nicked molecules depends on the length of incubation and the temperature of the culture. Therefore, a certain percentage of a preparation of, for example, the botulinum toxin type B toxin may be inactive. In one embodiment, the neurotoxin of the present disclosure is in an active state. In one embodiment, the neurotoxin is in an inactive state. In one embodiment, a combination of active and inactive neurotoxin is envisioned.

One aspect of the present disclosure provides novel methods of producing BoNTs via an in vitro transpeptidase reaction that ligates two non-toxic fragments of BoNTs. Such methods comprise the steps of: (i) obtaining a first BoNT fragment comprising a light chain (LC) and a N-terminal domain of a heavy chain ($H_N$), wherein the first BoNT fragment comprises a C-terminal LPXTGG (SEQ ID NO: 60) motif; (ii) obtaining a second BoNT fragment comprising a C-terminal domain of the heavy chain (HC); wherein the second BoNT fragment comprise a specific protease cleavage site at its N-terminus; (iii) cleaving the second BoNT fragment with a specific protease, wherein the cleavage results in a free glycine residue at the N-terminus; and (iv) contacting the first BoNT fragment and the second BoNT fragment in the presence of a transpeptidase, thereby ligating the first BoNT fragment and the second BoNT fragment to form a ligated BoNT.

In some embodiments, the first BoNT fragment comprises the X-LC-$H_N$ polypeptide described herein fused to a C-terminal LPXTGG (SEQ ID NO: 60) motif (e.g., SEQ ID NO: 45), or any variants thereof. In some embodiments, the second BoNT fragment comprises the $H_C$ polypeptide described herein, or any variants thereof (e.g., SEQ ID NO: 46). It is to be understood that any BoNT fragments or domains may be ligated using the methods described herein.

The methods described herein may also be used to generate chimeric BoNTs. For example, the first BoNT fragment may be from BoNT serotype A, B, C, D, E, F, G, or X. Similarly, the second BoNT fragment may be from BoNT serotype A, B, C, D, E, F, G, or X. One skilled in the art will be able to discern the combinations that may be made. In some embodiments, the chimeric BoNT polypeptides described herein (e.g., BoNT/X-LC-$H_N$-A1-$H_C$, BoNT/X-LC-$H_N$-B1-$H_C$, or BoNT/X-LC-$H_N$-C1-$H_C$) are made using this method.

In some embodiments, the transpeptidase is a sortase. In some embodiments, the sortase is from *Staphylococcus aureus* (SrtA).

Other peptide ligation systems available in the art may also be used to ligate two non-toxic BoNT fragments. For example, an intein-mediated protein ligation reaction allows the ligation of a synthetic peptide or a protein with an N-terminal cysteine residue to the C-terminus of a bacterially expressed protein through a native peptide bond (Evans et al., (1998) Protein Sci. 7, 2256-2264, Dawson et al., (1994) Science 266, 776-779; Tam et al., (1995) Proc. Natl. Acad. Sci. USA 92, 12485-12489, Muir et al., (1998) Proc. Natl. Acad. Sci. USA 95, 6705-6710; Severinov and Muir (1998) J. Biol. Chem. 273, 16205-16209, the entire contents of which are incorporated herein by references). Kits are commercially available (e.g., from New England Biolabs) for intern-mediated protein ligation reactions.

In some embodiments, the first BoNT fragment further comprises an affinity tag. In some embodiments, the affinity tag is fused to first BoNT fragment at the N-terminus. In some embodiments, the affinity tag is fused to the first BoNT fragment at the C-terminus. In the event that the affinity tag is fused to the C-terminus of the first BoNT fragment, the transpeptidase cleaves between the T and G in the LPXTGG (SEQ ID NO: 60) motif and removes the affinity tag before ligating the first BoNT fragment and the second BoNT fragment.

In some embodiments, the second BoNT fragment further comprises an affinity tag. In some embodiments, the affinity tag is fused to the first BoNT fragment at the N-terminus. In some embodiments, the affinity tag is fused to the second BoNT fragment at the C-terminus. In the event that the affinity tag is fused to the N-terminus of the first BoNT fragment, the specific protease cleaves in the specific protease cleavage site and removes the affinity tag before ligating the first BoNT fragment and the second BoNT fragment by the transpeptidase.

An "affinity tag," as used herein, refers to a polypeptide sequence that can bind specifically to a substance or a moiety, e.g., a tag comprising six Histidines bind specifically to $Ni^{2+}$. Affinity tags may be appended to proteins to facilitate their isolation. The affinity tags are typically fused to proteins via recombinant DNA tech$_n$iques known by those skilled in the art. The use of affinity tags to facilitate protein isolate is also well known in the art. Suitable affinity tags that may be used in accordance with the present disclosure include, without limitation, His6, GST, Avi, Strep, S, MBP, Sumo, FLAG, HA, Myc, SBP, E, Calmodulin, Softag 1, Softag 3, TC, V5, VSV, Xpress, Halo, and Fc.

The second BoNT fragment has a specific protease cleavage at the N-terminus. Cleavage of the site by the specific protease results to a free glycine residue at the N-terminus of the second BoNT fragment. Suitable specific protease that may be used in accordance with the present disclosure include, without limitation: thrombin, TEV, PreScission, Enterokinase, and SUMO protease. In some embodiments, the specific protease is thrombin, and the cleavage site is: LVPRIGS (SEQ ID NO: 50).

The BoNT/X polypeptides described herein affords potential for therapeutic use. For example, BoNT/X might be more potent compared to other BoNT serotypes. BoNT/X is more versatile and may be more effective in a wide range of cells due to its ability to cleave more substrates than other BoNT serotypes.

Thus, the present disclosure also contemplates pharmaceutically compositions comprising the BoNT/X polypeptides or the chimeric molecules of the present disclosure. As it may also become clear later in the present disclosure, the pharmaceutical composition of the present disclosure, may further comprise other therapeutic agents suitable for the specific disease such composition is designed to treat. In some embodiments, the pharmaceutically composition of the present disclosure further comprises pharmaceutically-acceptable carriers.

The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the polypeptide from one site (e.g., the delivery site) of the body, to another site (e.g., organ, tissue or portion of the body).

A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethylcellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, a BoNT polypeptide of the present disclosure in a composition is administered by injection, by means of a catheter, by means of a suppository, or by means of an implant, the implant being of a porous, non-porous, or gelatinous material, including a membrane, such as a sialastic membrane, or a fiber.

Typically, when administering the composition, materials to which the polypeptide of the disclosure does not absorb are used. In other embodiments, the BoNT polypeptides of the present disclosure are delivered in a controlled release system. Such compositions and methods for administration are provides in U.S. Patent publication No. 2007/0020295, the contents of which are herein incorporated by reference. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

The BoNT polypeptides of the present disclosure can be administered as pharmaceutical compositions comprising a therapeutically effective amount of a binding agent and one or more pharmaceutically compatible ingredients. In typical embodiments, the pharmaceutical composition is formulated in accordance with routine procedures as a pharmaceutical composition adapted for intravenous or subcutaneous administration to a subject, e.g., a human being.

Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration. A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated. The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein.

The polypeptides of the present disclosure can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N, N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757. The pharmaceutical compositions of the present disclosure may be administered or packaged as a unit dose, for example.

The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle. In some embodiments, the BoNT/X polypeptides described herein may be conjugated to a therapeutic moiety, e.g., an antibiotic. TecH$_N$iques for conjugating such therapeutic moieties to polypeptides, including e.g., Fc domains, are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al. (1982) "The Preparation And Cytotoxic Properties Of Antibody-Toxin Conjugates," Immunol. Rev., 62:119-158. Further, the pharmaceutical composition can be provided as a pharmaceutical kit comprising (a) a container containing a polypeptide of the disclosure in lyophilized form and (b) a second container containing a pharmaceutically acceptable diluent (e.g., sterile water) for injection. The pharmaceutically acceptable diluent can be used for reconstitution or dilution of the lyophilized polypeptide of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration. In another aspect, an article of manufacture containing materials useful for the treatment of the diseases described above is included. In some embodiments, the article of manufacture comprises a container and a label.

Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is an isolated polypeptide of the disclosure. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

The BoNT polypeptides (e.g., BoNT/X polypeptides), the chimeric molecules, and the pharmaceutical compositions of the present disclosure may be used for the treatment of conditions associated with unwanted neuronal activities. Thus, further provided herein are methods of treating a condition associated with unwanted neuronal activity, the method comprising administering a therapeutically effective amount of the BoNT polypeptide, the chimeric molecule, or the pharmaceutical composition described herein to thereby treat the condition. In some embodiments, the BoNT polypeptides, the chimeric molecules, and the pharmaceutic compositions of the present disclosure contact one or more neuron(s) exhibiting unwanted neuronal activity, Conditions typically treated with a neurotoxin (e.g., skeletal muscle conditions, smooth muscle conditions, glandular conditions, a neuromuscular disorder, an autonomic disorder, pain, or an aesthetic/cosmetic condition) are associated with unwanted neuronal activity, as determined by the skilled practitioner. Administration is by a route that contacts an effective amount of the composition to neurons exhibiting the unwanted activity. In some embodiments, the condition may be associated with overactive neurons or glands. Specific conditions envisioned for treatment by the methods discussed herein include, without limitation, spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions as well as other secretory disorders, pain from muscle spasms, headache pain. In addition, the present disclosure can be used to treat dermato logical or aesthetic/cosmetic conditions, for example, reduction of brow furrows, reduction of skin wrinkles.

One unique property of the BoNT/X polypeptides of the present disclosure is its ability to cleave VAMP4, VAMP5, and Ykt6. Thus, further contemplated herein are therapeutic use of the BoNT/X polypeptides in conditions associated with unwanted secretion activities in a wide range of cells. In some embodiments, the unwanted secretion is immune secretion. Conditions associated with unwanted immune secretion include, without limitation: inflammation, psoriasis, allergy, haemophagocytic lymphohistiocytosis, and alcoholic pancreatic disease.

The present disclosure can also be used in the treatment of sports injuries. Borodic U.S. Pat. No. 5,053,005 discloses methods for treating juvenile spinal curvature, i.e. scoliosis, using botulinum type A. The disclosure of Borodic is incorporated in its entirety herein by reference. In one embodiment, using substantially similar methods as disclosed by Borodic, a BoNT polypeptide can be administered to a mammal, preferably a human, to treat spinal curvature. In a suitable embodiment, a BoNT polypeptide comprising botulinum type E fused with a leucine-based motif is administered. Even more preferably, a BoNT polypeptide comprising botulinum type A-E with a leucine-based motif fused to the carboxyl terminal of its light chain is administered to the mammal, preferably a human, to treat spinal curvature.

In addition, the BoNT polypeptides can be administered to treat neuromuscular disorders using well known techniques that are commonly performed with botulinum type A. For example, the present disclosure can be used to treat pain, for example, headache pain, pain from muscle spasms and various forms of inflammatory pain. For example, Aoki U.S. Pat. No. 5,721,215 and Aoki U.S. Pat. No. 6,113,915 disclose methods of using botulinum toxin type A for treating pain. The disclosure of these two patents is incorporated in its entirety herein by reference.

Autonomic nervous system disorders can also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. disclose methods for treating the autonomic nervous system; for example, treating autonomic nervous system disorders such as excessive sweating, excessive salivation, asthma, etc., using naturally existing botulinum toxins. The disclosure of Sander et al. is incorporated in its entirety by reference herein.

In one embodiment, substantially similar methods to that of Sanders et al. can be employed, but using a BoNT polypeptide, to treat autonomic nervous system disorders such as the ones discussed above. For example, a BoNT polypeptide can be locally applied to the nasal cavity of the mammal in an amount sufficient to degenerate cholinergic neurons of the autonomic nervous system that control the mucous secretion in the nasal cavity. Pain that can be treated by a modified neurotoxin includes pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy can be treated with a naturally occurring botulinum toxin, for example *Botulinum* type A. The disclosures of Binder are incorporated in its entirety herein by reference.

In one embodiment, substantially similar methods to that of Binder can be employed, but using a BoNT polypeptide described herein, to treat headache, especially the ones caused by vascular disturbances, muscular tension, neuralgia and neuropathy. Pain caused by muscle spasm can also be treated by an administration of a BoNT polypeptide described herein. For example, a botulinum type E fused with a leucine-based motif, preferably at the carboxyl terminal of the botulinum type E light chain, can be administered intramuscularly at the pain/spasm location to alleviate pain. Furthermore, a modified neurotoxin can be administered to a mammal to treat pain that is not associated with a muscular disorder, such as spasm.

In one broad embodiment, methods of the present disclosure to treat non-spasm related pain include central administration or peripheral administration of the BoNT polypeptide. For example, Foster et al. in U.S. Pat. No. 5,989,545 discloses that a botulinum toxin conjugated with a targeting moiety can be administered centrally (intrathecally) to alleviate pain. The disclosures of Foster et al. are incorporated in its entirety by reference herein.

In one embodiment, substantially similar methods to that of Foster et al. can be employed, but using the compositions described herein to treat pain. The pain to be treated can be an acute pain or chronic pain. An acute or chronic pain that is not associated with a muscle spasm can also be alleviated with a local, peripheral administration of the modified neurotoxin to an actual or a perceived pain location on the mammal.

In one embodiment, the BoNT polypeptide is administered subcutaneously at or near the location of pain, for example, at or near a cut. In some embodiments, the modified neurotoxin is administered intramuscularly at or near the location of pain, for example, at or near a bruise location on the mammal. In some embodiments, the BoNT polypeptide is injected directly into a joint of a mammal, for treating or alleviating pain caused by arthritic conditions. Also, frequent repeated injection or infusion of the modified neurotoxin to a peripheral pain location is within the scope of the present disclosure. Routes of administration for such methods are known in the art and easily adapted to the methods described herein by the skilled practitioner (e.g., see for example, Harrison's Principles of Internal Medicine (1998), edited by Anthony Fauci et al., 14.sup.th edition, published by McGraw Hill).

By way of non-limiting example, the treatment of a neuromuscular disorder can comprise a step of locally administering an effective amount of the molecule to a muscle or a group of muscles, the treatment of an autonomic disorder can comprise a step of locally administering an effective of the molecule to a gland or glands, and the treatment of pain can comprise a step of administering an effective amount of the molecule the site of the pain. In addition, the treatment of pain can comprise a step of administering an effective amount of a modified neurotoxin to the spinal cord.

"A therapeutically effective amount" as used herein refers to the amount of each therapeutic agent of the present disclosure required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons. Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system.

Frequency of administration may be determined and adjusted over the course of therapy, and is generally, but not necessarily, based on treatment and/or suppression and/or amelioration and/or delay of a disease. Alternatively, sustained continuous release formulations of a polypeptide may be appropriate. Various formulations and devices for achieving sustained release are known in the art. In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional tech$_n$iques and assays.

The dosing regimen (including the polypeptide used) can vary over time. In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the polypeptide (such as the half-life of the polypeptide, and other considerations well known in the art).

For the purpose of the present disclosure, the appropriate dosage of a therapeutic agent as described herein will depend on the specific agent (or compositions thereof) employed, the formulation and route of administration, the type and severity of the disease, whether the polypeptide is administered for preventive or therapeutic purposes, previous therapy, the subject's clinical history and response to the antagonist, and the discretion of the attending physician. Typically the clinician will administer a polypeptide until a dosage is reached that achieves the desired result.

Administration of one or more polypeptides can be continuous or intermittent, depending, for example, upon the recipient's physiological condition, whether the purpose of the administration is therapeutic or prophylactic, and other factors known to skilled practitioners. The administration of a polypeptide may be essentially continuous over a preselected period of time or may be in a series of spaced dose, e.g., either before, during, or after developing a disease. As used herein, the term "treating" refers to the application or administration of a polypeptide or composition including the polypeptide to a subject in need thereof.

"A subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease. In some embodiments, the subject has CDI. In some embodiments, the subject has cancer. In some embodiments, the subject is a mammal. In some embodiments, the subject is a non-human primate. In some embodiments, the subject is human. Alleviating a disease includes delaying the development or progression of the disease, or reducing disease severity. Alleviating the disease does not necessarily require curative results.

As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical tech„iques as well known in the art. However, development also refers to progression that may be undetectable. For purpose of this disclosure, development or progression refers to the biological course of the symptoms. "Development" includes occurrence, recurrence, and onset.

As used herein "onset" or "occurrence" of a disease includes initial onset and/or recurrence. Conventional methods, known to those of ordinary skill in the art of medicine, can be used to administer the isolated polypeptide or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir.

The term "parenteral" as used herein includes subcutaneous, intracutaneous, intravenous, intramuscular, intraarticular, intraarterial, intrasynovial, intrasternal, intrathecal, intralesional, and intracranial injection or infusion tech„iques. In addition, it can be administered to the subject via injectable depot routes of administration such as using 1-, 3-, or 6-month depot injectable or biodegradable materials and methods.

As used herein, a "subject" refers to a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human.

The terms, "patient" and "subject" are used interchangeably herein. A subject can be male or female. A subject can be a fully developed subject (e.g., an adult) or a subject undergoing the developmental process (e.g., a child, infant or fetus). Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with unwanted neuronal activity. In addition, the methods and compositions described herein can be used to treat domesticated animals and/or pets.

The following examples are intended to be illustrative of certain embodiments and are non-limiting. The entire contents of all of the references (including literature references, issued patents, published patent applications, and co pending patent applications) cited throughout this application are hereby expressly incorporated by reference.

EXAMPLES

TABLE 1

BoNT Polypeptide Sequences

| SEQ ID NO. | Description | Sequence |
|---|---|---|
| 1 | WT BoNT/X | MKLEINKFNYNDPIDGINVITMRPPRHSDKINKGKGPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQGSNDFQGQLLESSYFEKIESNALRAFIKICPRNGLLYNA IYRNSKNYLNNIDLEDKKTTSKTNVSYPCSLLNGCIEVENKDLFLISNKDSLNDINLSEEKIKPETTVFFKD KLPPQDITLSNYDFTEANSIPSISQQNILERNEELYEPIRNSLFEIKTIYVDKLTTFHFLEAQNIDESIDSS KIRVELTDSVDEALSNPNKVYSPFKNMSNTINSIETGITSTYIFYQWLRSIVKDFSDETGKIDVIDKSSDTL AIVPYIGPLLNIGNDIRHGDFVGAIELAGITALLEYVPEFTIPILVGLEVIGGELAREQVEAIVNNALDKRD QKWAEVYNITKAQWWGTIHLQINTRLAHTYKALSRQANAIKMNMEFQLANYKGNIDDKAKIKNAISETEILL NKSVEQAMKNTEKFMIKLSNSYLTKEMIPKVQDNLKNFDLETKKTLDKFIKEKEDILGTNLSSSLRRKVSIR LNKNIAFDINDIPFSEFDDLINQYKNEIEDYEVLNLGAEDGKIKDLSGTTSDINIGSDIELADGRENKAIKI |

TABLE 1-continued

BoNT Polypeptide Sequences

| SEQ ID NO. | Description | Sequence |
|---|---|---|
| | | KGSENSTIKIAMNKYLRFSATDNFSISFWIKHPKPTNLLNNGIEYTLVENFNQRGWKISIQDSKLIWYLRDH<br>NNSIKIVTPDYIAFNGWNLITITNNRSKGSIVYVNGSKIEEKDISSIWNTEVDDPIIFRLKNNRDTQAFTLL<br>DQFSIYRKELNQNEVVKLYNYYFNSNYIRDIWGNPLQYNKKYYLQTDKPGKGLIREYWSSFGYDYVILSDS<br>KTITFPNNIRYGALYNGSKVLIKNSKKLDGLVRNKDFIQLEIDGYNMGISADRFNEDTNYIGTTYGTTHDLT<br>TDFEIIQRQEKYRNYCQLKTPYNIFHKSGLMSTETSKPTFHDYRDWVYSSAWYFQNYENLNLRKHTKTNWYF<br>IPKDEGWDED |
| 2 | WT BoNT/X<br>LC-H$_N$ | MKLEINKFNYNDPIDGINVITMRPPRHSDKINKGKGPPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENNN<br>IVSNLQANLVIYGPGPDIANNATYGLYSTPISNGEGTLSEVSFSPFYLKPFDESYGNYRSLVNIVNKFVKRE<br>FAPDPASTLMHELVHVTHNLYGISNRNFYYNFDTGKIETSRQQNSLIFEELLTFGGIDSKAISSLIIKKIIE<br>TAKNNYTTLISERLNTVTVENDLLKYIKNKIPVQGRLGNFKLDTAEFEKKLNTILFVLNESNLAQRFSILVR<br>KHYLKERPIDPIYVNILDDNSYSTLEGFNISSQGSNDFQGQLLESSYFEKIESNALRAFIKICPRNGLLYNA<br>IYRNSKNYLNNIDLEDKKTTSKTNVSYPCSLLNGCIEVENKDLFLISNKDSLNDINLSEEKIKPETTVFFKD<br>KLPPQDITLSNYDFTEANSIPSISQQNILERNEELYEPIRNSLFEIKTIYVDKLTTFHFLEAQNIDESIDSS<br>KIRVELTDSVDEALSNPNKVYSPFKNMSNTINSIETGITSTYIFYQWLRSIVKDFSDETGKIDVIDKSSDTL<br>AIVPYIGPLLNIGNDIRHGDFVGAIELAGITALLEYVPEFTIPILVGLEVIGGELAREQVEAIVNNALDKRD<br>QKWAEVYNITKAQWWGTIHLQINTRLAHTYKALSRQANAIKMNMEFQLANYKGNIDDKAKIKNAISETEILL<br>NKSVEQAMKNTEKFMIKLSNSYLTKEMIPKVQDNLKNFDLETKKTLDKFIKEKEDILGTNLSSSLRRKVSIR<br>LNKNIAFDINDIPFSEFDDLINQYKNEI |
| 3 | WT BoNT/X<br>LC | MKLEINKFNYNDPIDGINVITMRPPRHSDKINKGKGPPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENNN<br>IVSNLQANLVIYGPGPDIANNATYGLYSTPISNGEGTLSEVSFSPFYLKPFDESYGNYRSLVNIVNKFVKRE<br>FAPDPASTLMHELVHVTHNLYGISNRNFYYNFDTGKIETSRQQNSLIFEELLTFGGIDSKAISSLIIKKIIE<br>TAKNNYTTLISERLNTVTVENDLLKYIKNKIPVQGRLGNFKLDTAEFEKKLNTILFVLNESNLAQRFSILVR<br>KHYLKERPIDPIYVNILDDNSYSTLEGFNISSQGSNDFQGQLLESSYFEKIESNALRAFIKICPRNGLLYNA<br>IYRNSKN |
| 4 | WT BoNT/X<br>C461SQ | MKLEINKFNYNDPIDGINVITMRPPRHSDKINKGKGPPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENNN<br>IVSNLQANLVIYGPGPDIANNATYGLYSTPISNGEGTLSEVSFSPFYLKPFDESYGNYRSLVNIVNKFVKRE<br>FAPDPASTLMHELVHVTHNLYGISNRNFYYNFDTGKIETSRQQNSLIFEELLTFGGIDSKAISSLIIKKIIE<br>TAKNNYTTLISERLNTVTVENDLLKYIKNKIPVQGRLGNFKLDTAEFEKKLNTILFVLNESNLAQRFSILVR<br>KHYLKERPIDPIYVNILDDNSYSTLEGFNISSQGSNDFQGQLLESSYFEKIESNALRAFIKICPRNGLLYNA<br>IYRNSKNYLNNIDLEDKKTTSKTNVSYPSSLLNGCIEVENKDLFLISNKDSLNDINLSEEKIKPETTVFFKD<br>KLPPQDITLSNYDFTEANSIPSISQQNILERNEELYEPIRNSLFEIKTIYVDKLTTFHFLEAQNIDESIDSS<br>KIRVELTDSVDEALSNPNKVYSPFKNMSNTINSIETGITSTYIFYQWLRSIVKDFSDETGKIDVIDKSSDTL<br>AIVPYIGPLLNIGNDIRHGDFVGAIELAGITALLEYVPEFTIPILVGLEVIGGELAREQVEAIVNNALDKRD<br>QKWAEVYNITKAQWWGTIHLQINTRLAHTYKALSRQANAIKMNMEFQLANYKGNIDDKAKIKNAISETEILL<br>NKSVEQAMKNTEKFMIKLSNSYLTKEMIPKVQDNLKNFDLETKKTLDKFIKEKEDILGTNLSSSLRRKVSIR<br>LNKNIAFDINDIPFSEFDDLINQYKNEIEDYEVLNLGAEDGKIKDLSGTTSDINIGSDIELADGRENKAIKI<br>KGSENSTIKIAMNKYLRFSATDNFSISFWIKHPKPTNLLNNGIEYTLVENFNQRGWKISIQDSKLIWYLRDH<br>NNSIKIVTPDYIAFNGWNLITITNNRSKGSIVYVNGSKIEEKDISSIWNTEVDDPIIFRLKNNRDTQAFTLL<br>DQFSIYRKELNQNEVVKLYNYYFNSNYIRDIWGNPLQYNKKYYLQTDKPGKGLIREYWSSFGYDYVILSDS<br>KTITFPNNIRYGALYNGSKVLIKNSKKLDGLVRNKDFIQLEIDGYNMGISADRFNEDTNYIGTTYGTTHDLT<br>TDFEIIQRQEKYRNYCQLKTPYNIFHKSGLMSTETSKPTFHDYRDWVYSSAWYFQNYENLNLRKHTKTNWYF<br>IPKDEGWDED |
| 5 | WT BoNT/X<br>C461A | MKLEINKFNYNDPIDGINVITMRPPRHSDKINKGKGPPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENNN<br>IVSNLQANLVIYGPGPDIANNATYGLYSTPISNGEGTLSEVSFSPFYLKPFDESYGNYRSLVNIVNKFVKRE<br>FAPDPASTLMHELVHVTHNLYGISNRNFYYNFDTGKIETSRQQNSLIFEELLTFGGIDSKAISSLIIKKIIE<br>TAKNNYTTLISERLNTVTVENDLLKYIKNKIPVQGRLGNFKLDTAEFEKKLNTILFVLNESNLAQRFSILVR<br>KHYLKERPIDPIYVNILDDNSYSTLEGFNISSQGSNDFQGQLLESSYFEKIESNALRAFIKICPRNGLLYNA<br>IYRNSKNYLNNIDLEDKKTTSKTNVSYP<u>A</u>SLLNGCIEVENKDLFLISNKDSLNDINLSEEKIKPETTVFFKD<br>KLPPQDITLSNYDFTEANSIPSISQQNILERNEELYEPIRNSLFEIKTIYVDKLTTFHFLEAQNIDESIDSS<br>KIRVELTDSVDEALSNPNKVYSPFKNMSNTINSIETGITSTYIFYQWLRSIVKDFSDETGKIDVIDKSSDTL<br>AIVPYIGPLLNIGNDIRHGDFVGAIELAGITALLEYVPEFTIPILVGLEVIGGELAREQVEAIVNNALDKRD<br>QKWAEVYNITKAQWWGTIHLQINTRLAHTYKALSRQANAIKMNMEFQLANYKGNIDDKAKIKNAISETEILL<br>NKSVEQAMKNTEKFMIKLSNSYLTKEMIPKVQDNLKNFDLETKKTLDKFIKEKEDILGTNLSSSLRRKVSIR<br>LNKNIAFDINDIPFSEFDDLINQYKNEIEDYEVLNLGAEDGKIKDLSGTTSDINIGSDIELADGRENKAIKI<br>KGSENSTIKIAMNKYLRFSATDNFSISFWIKHPKPTNLLNNGIEYTLVENFNQRGWKISIQDSKLIWYLRDH<br>NNSIKIVTPDYIAFNGWNLITITNNRSKGSIVYVNGSKIEEKDISSIWNTEVDDPIIFRLKNNRDTQAFTLL<br>DQFSIYRKELNQNEVVKLYNYYFNSNYIRDIWGNPLQYNKKYYLQTDKPGKGLIREYWSSFGYDYVILSDS<br>KTITFPNNIRYGALYNGSKVLIKNSKKLDGLVRNKDFIQLEIDGYNMGISADRFNEDTNYIGTTYGTTHDLT<br>TDFEIIQRQEKYRNYCQLKTPYNIFHKSGLMSTETSKPTFHDYRDWVYSSAWYFQNYENLNLRKHTKTNWYF<br>IPKDEGWDED |
| 6 | WT BoNT/X<br>C467S | MKLEINKFNYNDPIDGINVITMRPPRHSDKINKGKGPPFKAFQVIKNIWIVPERYNFTNNTNDLNIPSEPIME<br>ADAIYNPNQYLNTPSEKDEFLQGVIKVLERIKSKPEGEKLLELISSSIPLPLVSNGALTLSDNETIAYQENNN<br>NIVSNLQANLVIYGPGPDIANNATYGLYSTPISNGEGTLSEVSFSPFYLKPFDESYGNYRSLVNIVNKFVKR<br>EFAPDPASTLMHELVHVTHNLYGISNRNFYYNFDTGKIETSRQQNSLIFEELLTFGGIDSKAISSLIIKKII<br>ETAKNNYTTLISERLNTVTVENDLLKYIKNKIPVQGRLGNFKLDTAEFEKKLNTILFVLNESNLAQRFSILV<br>RKHYLKERPIDPIYVNILDDNSYSTLEGFNISSQGSNDFQGQLLESSYFEKIESNALRAFIKICPRNGLLYN<br>AIYRNSKNYLNNIDLEDKKTTSKTNVSYPCSLLNG<u>S</u>IEVENKDLFLISNKDSLNDINLSEEKIKPETTVFFK |

TABLE 1-continued

BoNT Polypeptide Sequences

| SEQ ID NO. | Description | Sequence |
|---|---|---|
| | | DKLPPQDITLSNYDFTEANSIPSISQQNILERNEELYEPIRNSLFEIKTIYVDKLTTFHFLEAQNIDESIDS<br>SKIRVELTDSVDEALSNPNKVYSPFKNMSNTINSIETGITSTYIFYQWLRSIVKDFSDETGKIDVIDKSSDT<br>LAIVPYIGPLLNIGNDIRHGDFVGAIELAGITALLEYVPEFTIPILVGLEVIGGELAREQVEAIVNNALDKR<br>DQKWAEVYNITKAQWWGTIHLQINTRLAHTYKALSRQANAIKMNMEFQLANYKGNIDDKAKIKNAISETEIL<br>LNKSVEQAMKNTEKFMIKLSNSYLTKEMIPKVQDNLKNFDLETKKTLDKFIKEKEDILGTNLSSSLRRKVSI<br>RLNKNIAFDINDIPFSEFDDLINQYKNEIEDYEVLNLGAEDGKIKDLSGTTSDINIGSDIELADGRENKAIK<br>IKGSENSTIKIAMNKYLRFSATDNFSISFWIKHPKPTNLLNNGIEYTLVENFNQRGWKISIQDSKLIWYLRD<br>HNNSIKIVTPDYIAFNGWNLITITNNRSKGSIVYVNGSKIEEKDISSIWNTEVDDPIIFRLKNNRDTQAFTL<br>LDQFSIYRKELNQNEVVKLYNYYFNSNYIRDIWGNPLQYNKKYYLQTQDKPGKGLIREYWSSFGYDYVILSD<br>SKTITFPNNIRYGALYNGSKVLIKNSKKLDGLVRNKDFIQLEIDGYNMGISADRFNEDTNYIGTTYGTTHDL<br>TTDFEIIQRQEKYRNYCQLKTPYNIFHKSGLMSTETSKPTFHDYRDWVYSSAWYFQNYENLNLRKHTKTNWY<br>FIPKDEGWDED |
| 7 | WT BoNT/X C467A | MKLEINKFNYNDPIDGINVITMRPPRHSDKINKGKGPPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENNN<br>IVSNLQANLVIYGPGPDIANNATYGLYSTPISNGEGTLSEVSFSPFYLKPFDESYGNYRSLVNIVNKFVKRE<br>FAPDPASTLMHELVHVTHNLYGISNRNFYYNFDTGKIETSRQQNSLIFEELLTFGGIDSKAISSLIIKKIIE<br>TAKNNYTTLISERLNTVTVENDLLKYIKNKIPVQGRLGNFKLDTAEFEKKLNTILFVLNESNLAQRFSILVR<br>KHYLKERPIDPIYVNILDDNSYSTLEGFNISSQGSNDFQGQLLESSYFEKIESNALRAFIKICPRNGLLYNA<br>IYRNSKNYLNNIDLEDKKTTSKTNVSYPCSLLNGAIEVENKDLFLISNKDSLNDINLSEEKIKPETTVFFKD<br>KLPPQDITLSNYDFTEANSIPSISQQNILERNEELYEPIRNSLFEIKTIYVDKLTTFHFLEAQNIDESIDSS<br>KIRVELTDSVDEALSNPNKVYSPFKNMSNTINSIETGITSTYIFYQWLRSIVKDFSDETGKIDVIDKSSDTL<br>AIVPYIGPLLNIGNDIRHGDFVGAIELAGITALLEYVPEFTIPILVGLEVIGGELAREQVEAIVNNALDKRD<br>QKWAEVYNITKAQWWGTIHLQINTRLAHTYKALSRQANAIKMNMEFQLANYKGNIDDKAKIKNAISETEILL<br>NKSVEQAMKNTEKFMIKLSNSYLTKEMIPKVQDNLKNFDLETKKTLDKFIKEKEDILGTNLSSSLRRKVSIR<br>LNKNIAFDINDIPFSEFDDLINQYKNEIEDYEVLNLGAEDGKIKDLSGTTSDINIGSDIELADGRENKAIKI<br>KGSENSTIKIAMNKYLRFSATDNFSISFWIKHPKPTNLLNNGIEYTLVENFNQRGWKISIQDSKLIWYLRDH<br>NNSIKIVTPDYIAFNGWNLITITNNRSKGSIVYVNGSKIEEKDISSIWNTEVDDPIIFRLKNNRDTQAFTLL<br>DQFSIYRKELNQNEVVKLYNYYFNSNYIRDIWGNPLQYNKKYYLQTQDKPGKGLIREYWSSFGYDYVILSDS<br>KTITFPNNIRYGALYNGSKVLIKNSKKLDGLVRNKDFIQLEIDGYNMGISADRFNEDTNYIGTTYGTTHDLT<br>TDFEIIQRQEKYRNYCQLKTPYNIFHKSGLMSTETSKPTFHDYRDWVYSSAWYFQNYENLNLRKHTKTNWYF<br>IPKDEGWDED |
| 8 | WT BoNT/X C1240S | MKLEINKFNYNDPIDGINVITMRPPRHSDKINKGKGPPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENNN<br>IVSNLQANLVIYGPGPDIANNATYGLYSTPISNGEGTLSEVSFSPFYLKPFDESYGNYRSLVNIVNKFVKRE<br>FAPDPASTLMHELVHVTHNLYGISNRNFYYNFDTGKIETSRQQNSLIFEELLTFGGIDSKAISSLIIKKIIE<br>TAKNNYTTLISERLNTVTVENDLLKYIKNKIPVQGRLGNFKLDTAEFEKKLNTILFVLNESNLAQRFSILVR<br>KHYLKERPIDPIYVNILDDNSYSTLEGFNISSQGSNDFQGQLLESSYFEKIESNALRAFIKICPRNGLLYNA<br>IYRNSKNYLNNIDLEDKKTTSKTNVSYPCSLLNGCIEVENKDLFLISNKDSLNDINLSEEKIKPETTVFFKD<br>KLPPQDITLSNYDFTEANSIPSISQQNILERNEELYEPIRNSLFEIKTIYVDKLTTFHFLEAQNIDESIDSS<br>KIRVELTDSVDEALSNPNKVYSPFKNMSNTINSIETGITSTYIFYQWLRSIVKDFSDETGKIDVIDKSSDTL<br>AIVPYIGPLLNIGNDIRHGDFVGAIELAGITALLEYVPEFTIPILVGLEVIGGELAREQVEAIVNNALDKRD<br>QKWAEVYNITKAQWWGTIHLQINTRLAHTYKALSRQANAIKMNMEFQLANYKGNIDDKAKIKNAISETEILL<br>NKSVEQAMKNTEKFMIKLSNSYLTKEMIPKVQDNLKNFDLETKKTLDKFIKEKEDILGTNLSSSLRRKVSIR<br>LNKNIAFDINDIPFSEFDDLINQYKNEIEDYEVLNLGAEDGKIKDLSGTTSDINIGSDIELADGRENKAIKI<br>KGSENSTIKIAMNKYLRFSATDNFSISFWIKHPKPTNLLNNGIEYTLVENFNQRGWKISIQDSKLIWYLRDH<br>NNSIKIVTPDYIAFNGWNLITITNNRSKGSIVYVNGSKIEEKDISSIWNTEVDDPIIFRLKNNRDTQAFTLL<br>DQFSIYRKELNQNEVVKLYNYYFNSNYIRDIWGNPLQYNKKYYLQTQDKPGKGLIREYWSSFGYDYVILSDS<br>KTITFPNNIRYGALYNGSKVLIKNSKKLDGLVRNKDFIQLEIDGYNMGISADRFNEDTNYIGTTYGTTHDLT<br>TDFEIIQRQEKYRNYSQLKTPYNIFHKSGLMSTETSKPTFHDYRDWVYSSAWYFQNYENLNLRKHTKTNWYF<br>IPKDEGWDED |
| 9 | WT BoNT/X C1240S | MKLEINKFNYNDPIDGINVITMRPPRHSDKINKGKGPPFKAFQVIKNIWIVPERQYNFTNNTNDLNIPSEPIM<br>EADAIYNPNYLNTPSEKDEFLQGVIKVLERIKSKPEGEKLLELISSSIPLPLVSNGALTLSDNETIAYQENN<br>NIVSNLQANLVIYGPGPDIANNATYGLYSTPISNGEGTLSEVSFSPFYLKPFDESYGNYRSLVNIVNKFVKR<br>EFAPDPASTLMHELVHVTHNLYGISNRNFYYNFDTGKIETSRQQNSLIFEELLTFGGIDSKAISSLIIKKII<br>ETAKNNYTTLISERLNTVTVENDLLKYIKNKIPVQGRLGNFKLDTAEFEKKLNTILFVLNESNLAQRFSILV<br>RKHYLKERPIDPIYVNILDDNSYSTLEGFNISSQGSNDFQGQLLESSYFEKIESNALRAFIKICPRNGLLYN<br>AIYRNSKNYLNNIDLEDKKTTSKTNVSYPCSLLNGCIEVENKDLFLISNKDSLNDINLSEEKIKPETTVFFK<br>DKLPPQDITLSNYDFTEANSIPSISQQNILERNEELYEPIRNSLFEIKTIYVDKLTTFHFLEAQNIDESIDS<br>SKIRVELTDSVDEALSNPNKVYSPFKNMSNTINSIETGITSTYIFYQWLRSIVKDFSDETGKIDVIDKSQSD<br>TLAIVPYIGPLLNIGNDIRHGDFVGAIELAGITALLEYVPEFTIPILVGLEVIGGELAREQVEAIVNNALDK<br>RDQKWAEVYNITKAQWWGTIHLQINTRLAHTYKALSRQANAIKMNMEFQLANYKGNIDDKAKIKNAISETEI<br>LLNKSVEQAMKNTEKFMIKLSNSYLTKEMIPKVQDNLKNFDLETKKTLDKFIKEKEDILGTNLSSSLRRKVS<br>IRLNKNIAFDINDIPFSEFDDLINQYKNEIEDYEVLNLGAEDGKIKDLSGTTSDINIGSDIELADGRENKAI<br>KIKGSENSTIKIAMNKYLRFSATDNFSISFWIKHPKPTNLLNNGIEYTLVENFNQRGWKISIQDSKLIWYLR<br>DHNNSIKIVTPDYIAFNGWNLITITNNRSKGSIVYVNGSKIEEKDISSIWNTEVDDPIIFRLKNNRDTQAFT<br>LLDQFSIYRKELNQNEVVKLYNYYFNSNYIRDIWGNPLQYNKKYYLQTQDKPGKGLIREYWSSFGYDYVILS<br>DSKTITFPNNIRYGALYNGSKVLIKNSKKLDGLVRNKDFIQLEIDGYNMGISADRFNEDTNYIGTTYGTTHD<br>LTTDFEIIQRQEKYRNYAQLKTPYNIFHKSGLMSTETSKPTFHDYRDWVYSSAWYFQNYENLNLRKHTKTNW<br>YFIPKDEGWDED |
| 10 | WT BoNT/X C461S/C1240A | MKLEINKFNYNDPIDGINVITMRPPRHSDKINKGKGPPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENNN<br>IVSNLQANLVIYGPGPDIANNATYGLYSTPISNGEGTLSEVSFSPFYLKPFDESYGNYRSLVNIVNKFVKRE |

TABLE 1-continued

BoNT Polypeptide Sequences

| SEQ ID NO. | Description | Sequence |
|---|---|---|
| | | FAPDPASTLMHELVHVTHNLYGISNRNFYYNFDTGKIETSRQQNSLIFEELLTFGGIDSKAISSLIIKKIIE<br>TAKNNYTTLISERLNTVTVENDLLKYIKNKIPVQGRLGNFKLDTAEFEKKLNTILFVLNESNLAQRFSILVR<br>KHYLKERPIDPIYVNILDDNSYSTLEGFNISSQQGSNDFQGQLLESSYFEKIESNALRAFIKICPRNGLLYN<br>AIYRNSKNYLNNIDLEDKKTTSKTNVSYPSSLLNGCIEVENKDLFLISNKDSLNDINLSEEKIKPETTVFFK<br>DKLPPQDITLSNYDFTEANSIPSISQQNILERNEELYEPIRNSLFEIKTIYVDKLTTFHFLEAQNIDESIDS<br>SKIRVELTDSVDEALSNPNKVYSPFKNMSNTINSIETGITSTYIFYQWLRSIVKDFSDETGKIDVIDKSQSD<br>TLAIVPYIGPLLNIGNDIRHGDFVGAIELAGITALLEYVPEFTIPILVGLEVIGGELAREQVEAIVNNALDK<br>RDQKWAEVYNITKAQWWGTIHLQINTRLAHTYKALSRQANAIKMNMEFQLANYKGNIDDKAKIKNAISETEI<br>LLNKSVEQAMKNTEKFMIKLSNSYLTKEMIPKVQDNLKNFDLETKKTLDKFIKEKEDILGTNLSSSLRRKVS<br>IRLNKNIAFDINDIPFSEFDDLINQYKNEIEDYEVLNLGAEDGKIKDLSGTTSDINIGSDIELADGRENKAI<br>KIKGSENSTIKIAMNKYLRFSATDNFSISFWIKHPKPTNLLNNGIEYTLVENFNQRGWKISIQDSKLIWYLR<br>DHNNSIKIVTPDYIAFNGWNLITITNNRSKGSIVYVNGSKIEEKDISSIWNTEVDDPIIFRLKNNRDTQAFT<br>LLDQFSIYRKELNQNEVVKLYNYYFNSNYIRDIWGNPLQYNKKYYLQTQDKPGKGLIREYWSSFGYDYVILS<br>DSKTITFPNNIRYGALYNGSKVLIKNSKKLDGLVRNKDFIQLEIDGYNMGISADRFNEDTNYIGTTYGTTHD<br>LTTDFEIIQRQEKYRNYAQLKTPYNIFHKSGLMSTETSKPTFHDYRDWVYSSAWYFQNYENLNLRKHTKTNW<br>YFIPKDEGWDED |
| 11 | WT BoNT/X<br>C461S/C1240S | MKLEINKFNYNDPIDGINVITMRPPRHSDKINKGKGPFKAFQVIKNIWIVPERYNFTNNTNDLNIPSEPIME<br>ADAIYNPNYLNTPSEKDEFLQGVIKVLERIKSKPSQEGEKLLELISSSIPLPLVSNGALTLSDNETIAYQEN<br>NNIVSNLQANLVIYGPGPDIANNATYGLYSTPISNGEGTLSEVSFSPFYLKPFDESYGNYRSLVNIVNKFVK<br>REFAPDPASTLMHELVHVTHNLYGISNRNFYYNFDTGKIETSRQQNSLIFEELLTFGGIDSKAISSLIIKKI<br>IETAKNNYTTLISERLNTVTVENDLLKYIKNKIPVQGRLGNFKLDTAEFEKKLNTILFVLNESNLAQRFSIL<br>VRKHYLKERPIDPIYVNILDDNSYSTLEGFNISSQQGSNDFQGQLLESSYFEKIESNALRAFIKICPRNGLL<br>YNAIYRNSKNYLNNIDLEDKKTTSKTNVSYPSSLLNGCIEVENKDLFLISNKDSLNDINLSEEKIKPETTVF<br>FKDKLPPQDITLSNYDFTEANSIPSISQQNILERNEELYEPIRNSLFEIKTIYVDKLTTFHFLEAQNIDESI<br>DSSKIRVELTDSVDEALSNPNKVYSPFKNMSNTINSIETGITSTYIFYQWLRSIVKDFSDETGKIDVIDKSQ<br>SDTLAIVPYIGPLLNIGNDIRHGDFVGAIELAGITALLEYVPEFTIPILVGLEVIGGELAREQVEAIVNNAL<br>DKRDQKWAEVYNITKAQWWGTIHLQINTRLAHTYKALSRQANAIKMNMEFQLANYKGNIDDKAKIKNAISET<br>EILLNKSVEQAMKNTEKFMIKLSNSYLTKEMIPKVQDNLKNFDLETKKTLDKFIKEKEDILGTNLSSSLRRK<br>VSIRLNKNIAFDINDIPFSEFDDLINQYKNEIEDYEVLNLGAEDGKIKDLSGTTSDINIGSDIELADGRENK<br>AIKIKGSENSTIKIAMNKYLRFSATDNFSISFWIKHPKPTNLLNNGIEYTLVENFNQRGWKISIQDSKLIWY<br>LRDHNNSIKIVTPDYIAFNGWNLITITNNRSKGSIVYVNGSKIEEKDISSIWNTEVDDPIIFRLKNNRDTQA<br>FTLLDQFSIYRKELNQNEVVKLYNYYFNSNYIRDIWGNPLQYNKKYYLQTQDKPGKGLIREYWSSFGYDYVI<br>LSDSKTITFPNNIRYGALYNGSKVLIKNSKKLDGLVRNKDFIQLEIDGYNMGISADRFNEDTNYIGTTYGTT<br>HDLTTDFEIIQRQEKYRNYSQLKTPYNIFHKSGLMSTETSKPTFHDYRDWVYSSAWYFQNYENLNLRKHTKT<br>NWYFIPKDEGWDED |
| 12 | WT BoNT/X<br>C461A/C1240S | MKLEINKFNYNDPIDGINVITMRPPRHSDKINKGKGPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENN<br>NIVSNLQANLVIYGPGPDIANNATYGLYSTPISNGEGTLSEVSFSPFYLKPFDESYGNYRSLVNIVNKFVKR<br>EFAPDPASTLMHELVHVTHNLYGISNRNFYYNFDTGKIETSRQQNSLIFEELLTFGGIDSKAISSLIIKKII<br>ETAKNNYTTLISERLNTVTVENDLLKYIKNKIPVQGRLGNFKLDTAEFEKKLNTILFVLNESNLAQRFSILV<br>RKHYLKERPIDPIYVNILDDNSYSTLEGFNISSQQGSNDFQGQLLESSYFEKIESNALRAFIKICPRNGLLY<br>NAIYRNSKNYLNNIDLEDKKTTSKTNVSYPASLLNGCIEVENKDLFLISNKDSLNDINLSEEKIKPETTVFF<br>KDKLPPQDITLSNYDFTEANSIPSISQQNILERNEELYEPIRNSLFEIKTIYVDKLTTFHFLEAQNIDESID<br>SSKIRVELTDSVDEALSNPNKVYSPFKNMSNTINSIETGITSTYIFYQWLRSIVKDFSDETGKIDVIDKSQS<br>DTLAIVPYIGPLLNIGNDIRHGDFVGAIELAGITALLEYVPEFTIPILVGLEVIGGELAREQVEAIVNNALD<br>KRDQKWAEVYNITKAQWWGTIHLQINTRLAHTYKALSRQANAIKMNMEFQLANYKGNIDDKAKIKNAISETE<br>ILLNKSVEQAMKNTEKFMIKLSNSYLTKEMIPKVQDNLKNFDLETKKTLDKFIKEKEDILGTNLSSSLRRKV<br>SIRLNKNIAFDINDIPFSEFDDLINQYKNEIEDYEVLNLGAEDGKIKDLSGTTSDINIGSDIELADGRENKA<br>IKIKGSENSTIKIAMNKYLRFSATDNFSISFWIKHPKPTNLLNNGIEYTLVENFNQRGWKISIQDSQKLIWY<br>LRDHNNSIKIVTPDYIAFNGWNLITITNNRSKGSIVYVNGSKIEEKDISSIWNTEVDDPIIFRLKNNRDTQA<br>FTLLDQFSIYRKELNQNEVVKLYNYYFNSQNYIRDIWGNPLQYNKKYYLQTQDKPGKGLIREYWSSFGYDYV<br>ILSDSKTITFPNNIRYGALYNGSKVLIKNSKKLDGLVRNKDFIQLEIDGYNMGISQADRFNEDTNYIGTTYG<br>TTHDLTTDFEIIQRQEKYRNYSQLKTPYNIFHKSGLMSTETSKPTFHDYRDWVYSSAWYFQNYENLNLRKHT<br>KTNWYFIPKDEGWDED |
| 13 | WT BoNT/X<br>C461A/C1240A | MKLEINKFNYNDPIDGINVITMRPPRHSDKINKGKGPFKAFQVIKNIWIVPERYNFTNNTNDLNIPSEPIME<br>ADAIYNPNYLNTPSEKDEFLQGVIKVLERIKSKPEGEKLLELISSSIPLPLVSNGALTLSDNETIAYQENNN<br>IVSNLQANLVIYGPGPDIANNATYGLYSTPISNGEGTLSEVSFSPFYLKPFDESYGNYRSLVNIVNKFVKRE<br>FAPDPASTLMHELVHVTHNLYGISNRNFYYNFDTGKIETSRQQNSLIFEELLTFGGIDSKAISSLIIKKIIE<br>TAKNNYTTLISERLNTVTVENDLLKYIKNKIPVQGRLGNFKLDTAEFEKKLNTILFVLNESNLAQRFSILVR<br>KHYLKERPIDPIYVNILDDNSYSTLEGFNISSQQGSNDFQGQLLESSYFEKIESNALRAFIKICPRNGLLYN<br>AIYRNSKNYLNNIDLEDKKTTSKTNVSYPASLLNGCIEVENKDLFLISNKDSLNDINLSEEKIKPETTVFFK<br>DKLPPQDITLSNYDFTEANSIPSISQQNILERNEELYEPIRNSLFEIKTIYVDKLTTFHFLEAQNIDESIDS<br>SKIRVELTDSVDEALSNPNKVYSPFKNMSNTINSIETGITSTYIFYQWLRSIVKDFSDETGKIDVIDKSQSD<br>TLAIVPYIGPLLNIGNDIRHGDFVGAIELAGITALLEYVPEFTIPILVGLEVIGGELAREQVEAIVNNALDK<br>RDQKWAEVYNITKAQWWGTIHLQINTRLAHTYKALSRQANAIKMNMEFQLANYKGNIDDKAKIKNAISETEI<br>LLNKSVEQAMKNTEKFMIKLSNSYLTKEMIPKVQDNLKNFDLETKKTLDKFIKEKEDILGTNLSSSLRRKVS<br>IRLNKNIAFDINDIPFSEFDDLINQYKNEIEDYEVLNLGAEDGKIKDLSGTTSDINIGSDIELADGRENKAI<br>KIKGSENSTIKIAMNKYLRFSATDNFSISFWIKHPKPTNLLNNGIEYTLVENFNQRGWKISIQDSQKLIWYL<br>RDHNNSIKIVTPDYIAFNGWNLITITNNRSKGSIVYVNGSKIEEKDISSIWNTEVDDPIIFRLKNNRDTQAF<br>TLLDQFSIYRKELNQNEVVKLYNYYFNSQNYIRDIWGNPLQYNKKYYLQTQDKPGKGLIREYWSSFGYDYVI<br>LSDSKTITFPNNIRYGALYNGSKVLIKNSKKLDGLVRNKDFIQLEIDGYNMGISQADRFNEDTNYIGTTYGT<br>THDLTTDFEIIQRQEKYRNYAQLKTPYNIFHKSGLMSTETSKPTFHDYRDWVYSSAWYFQNYENLNLRKHTK<br>TNWYFIPKDEGWDED |

TABLE 1-continued

BoNT Polypeptide Sequences

| SEQ ID NO. | Description | Sequence |
| --- | --- | --- |
| 14 | WT BoNT/X C467S/C1240A | MKLEINKFNYNDPIDGINVITMRPPRHSDKINKGKGPFKAFQVIKNIWIVPERYNFTNNTDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQQGSNDFQGQLLESSYFEKIESNALRAFIKICPRNGLLYN AIYRNSKNYLNNIDLEDKKTTSKTNVSYPCSLLNGSIEVENKDLFLISNKDSLNDINLSEEKIKPETTVFFK DKLPPQDITLSNYDFTEANSIPSISQQNILERNEELYEPIRNSLFEIKTIYVDKLTTFHFLEAQNIDESIDS SKIRVELTDSVDEALSNPNKVYSPFKNMSNTINSIETGITSTYIFYQWLRSIVKDFSDETGKIDVIDKSQSD TLAIVPYIGPLLNIGNDIRHGDFVGAIELAGITALLEYVPEFTIPILVGLEVIGGELAREQVEAIVNNALDK RDQKWAEVYNITKAQWWGTIHLQINTRLAHTYKALSRQANAIKMNMEFQLANYKGNIDDKAKIKNAISETEI LLNKSVEQAMKNTEKFMIKLSNSYLTKEMIPKVQDNLKNFDLETKKTLDKFIKEKEDILGTNLSSSLRRKVS IRLNKNIAFDINDIPFSEFDDLINQYKNEIEDYEVLNLGAEDGKIKDLSGTTSDINIGSDIELADGRENKAI KIKGSENSTIKIAMNKYLRFSATDNFSISFWIKHPKPTNLLNNGIEYTLVENFNQRGWKISIQDSQKLIWYL RDHNNSIKIVTPDYIAFNGWNLITITNNRSKGSIVYVNGSKIEEKDISSIWNTEVDDPIIFRLKNNRDTQAF TLLDQFSIYRKELNQNEVVKLYNYYFNSQNYIRDIWGNPLQYNKKYYLQTQDKPGKGLIREYWSSFGYDYVI LSDSKTITFPNNIRYGALYNGSKVLIKNSKKLDGLVRNKDFIQLEIDGYNMGISQADRFNEDTNYIGTTYGT THDLTTDFEIIQRQEKYRNYAQLKTPYNIFHKSGLMSTETSKPTFHDYRDWVYSSAWYFQNYENLNLRKHTK TNWYFIPKDEGWDED |
| 15 | WT BoNT/X C467S/C1240S | MKLEINKFNYNDPIDGINVITMRPPRHSDKINKGKGPFKAFQVIKNIWIVPERYNFTNNTDLNIPSEPIME ADAIYNPNYLNTPSEKDEFLQGVIKVLERIKSKPSQEGEKLLELISSSIPLPLVSNGALTLSDNETIAYQEN NNIVSNLQANLVIYGPGPDIANNATYGLYSTPISNGEGTLSEVSFSPFYLKPFDESYGNYRSLVNIVNKFVK REFAPDPASTLMHELVHVTHNLYGISNRNFYYNFDTGKIETSRQQNSLIFEELLTFGGIDSKAISSLIIKKI IETAKNNYTTLISERLNTVTVENDLLKYIKNKIPVQGRLGNFKLDTAEFEKKLNTILFVLNESNLAQRFSIL VRKHYLKERPIDPIYVNILDDNSYSTLEGFNISSQQGSNDFQGQLLESSYFEKIESNALRAFIKICPRNGLL YNAIYRNSKNYLNNIDLEDKKTTSKTNVSYPCSLLNGSIEVENKDLFLISNKDSLNDINLSEEKIKPETTVF FKDKLPPQDITLSNYDFTEANSIPSISQQNILERNEELYEPIRNSLFEIKTIYVDKLTTFHFLEAQNIDESI DSSKIRVELTDSVDEALSNPNKVYSPFKNMSNTINSIETGITSTYIFYQWLRSIVKDFSDETGKIDVIDKSQ SDTLAIVPYIGPLLNIGNDIRHGDFVGAIELAGITALLEYVPEFTIPILVGLEVIGGELAREQVEAIVNNAL DKRDQKWAEVYNITKAQWWGTIHLQINTRLAHTYKALSRQANAIKMNMEFQLANYKGNIDDKAKIKNAISET EILLNKSVEQAMKNTEKFMIKLSNSYLTKEMIPKVQDNLKNFDLETKKTLDKFIKEKEDILGTNLSSSLRRK VSIRLNKNIAFDINDIPFSEFDDLINQYKNEIEDYEVLNLGAEDGKIKDLSGTTSDINIGSDIELADGRENK AIKIKGSENSTIKIAMNKYLRFSATDNFSISFWIKHPKPTNLLNNGIEYTLVENFNQRGWKISIQDSQKLIW YLRDHNNSIKIVTPDYIAFNGWNLITITNNRSKGSIVYVNGSKIEEKDISSIWNTEVDDPIIFRLKNNRDTQ AFTLLDQFSIYRKELNQNEVVKLYNYYFNSQNYIRDIWGNPLQYNKKYYLQTQDKPGKGLIREYWSSFGYDY VILSDSKTITFPNNIRYGALYNGSKVLIKNSKKLDGLVRNKDFIQLEIDGYNMGISQADRFNEDTNYIGTTY GTTHDLTTDFEIIQRQEKYRNYSQLKTPYNIFHKSGLMSTETSKPTFHDYRDWVYSSAWYFQNYENLNLRKH TKTNWYFIPKDEGWDED |
| 16 | WT BoNT/X C467A/C1240S | MKLEINKFNYNDPIDGINVITMRPPRHSDKINKGKGPFKAFQVIKNIWIVPERYNFTNNTDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKR EFAPDPASTLMHELVHVTHNLYGISNRNFYYNFDTGKIETSRQQNSLIFEELLTFGGIDSKAISSLIIKKII ETAKNNYTTLISERLNTVTVENDLLKYIKNKIPVQGRLGNFKLDTAEFEKKLNTILFVLNESNLAQRFSILV RKHYLKERPIDPIYVNILDDNSYSTLEGFNISSQQGSNDFQGQLLESSYFEKIESNALRAFIKICPRNGLLY NAIYRNSKNYLNNIDLEDKKTTSKTNVSYPCSLLNGAIEVENKDLFLISNKDSLNDINLSEEKIKPETTVFF KDKLPPQDITLSNYDFTEANSIPSISQQNILERNEELYEPIRNSLFEIKTIYVDKLTTFHFLEAQNIDESID SSKIRVELTDSVDEALSNPNKVYSPFKNMSNTINSIETGITSTYIFYQWLRSIVKDFSDETGKIDVIDKSQS DTLAIVPYIGPLLNIGNDIRHGDFVGAIELAGITALLEYVPEFTIPILVGLEVIGGELAREQVEAIVNNALD KRDQKWAEVYNITKAQWWGTIHLQINTRLAHTYKALSRQANAIKMNMEFQLANYKGNIDDKAKIKNAISETE ILLNKSVEQAMKNTEKFMIKLSNSYLTKEMIPKVQDNLKNFDLETKKTLDKFIKEKEDILGTNLSSSLRRKV SIRLNKNIAFDINDIPFSEFDDLINQYKNEIEDYEVLNLGAEDGKIKDLSGTTSDINIGSDIELADGRENKA IKIKGSENSTIKIAMNKYLRFSATDNFSISFWIKHPKPTNLLNNGIEYTLVENFNQRGWKISIQDSQKLIWY LRDHNNSIKIVTPDYIAFNGWNLITITNNRSKGSIVYVNGSKIEEKDISSIWNTEVDDPIIFRLKNNRDTQA FTLLDQFSIYRKELNQNEVVKLYNYYFNSQNYIRDIWGNPLQYNKKYYLQTQDKPGKGLIREYWSSFGYDYV ILSDSKTITFPNNIRYGALYNGSKVLIKNSKKLDGLVRNKDFIQLEIDGYNMGISQADRFNEDTNYIGTTYG TTHDLTTDFEIIQRQEKYRNYSQLKTPYNIFHKSGLMSTETSKPTFHDYRDWVYSSAWYFQNYENLNLRKHT KTNWYFIPKDEGWDED |
| 17 | WT BoNT/X C467A/C1240A | MKLEINKFNYNDPIDGINVITMRPPRHSDKINKGKGPFKAFQVIKNIWIVPERYNFTNNTDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQQGSNDFQGQLLESSYFEKIESNALRAFIKICPRNGLLYN AIYRNSKNYLNNIDLEDKKTTSKTNVSYPCSLLNGAIEVENKDLFLISNKDSLNDINLSEEKIKPETTVFFK DKLPPQDITLSNYDFTEANSIPSISQQNILERNEELYEPIRNSLFEIKTIYVDKLTTFHFLEAQNIDESIDS SKIRVELTDSVDEALSNPNKVYSPFKNMSNTINSIETGITSTYIFYQWLRSIVKDFSDETGKIDVIDKSQSD TLAIVPYIGPLLNIGNDIRHGDFVGAIELAGITALLEYVPEFTIPILVGLEVIGGELAREQVEAIVNNALDK RDQKWAEVYNITKAQWWGTIHLQINTRLAHTYKALSRQANAIKMNMEFQLANYKGNIDDKAKIKNAISETEI LLNKSVEQAMKNTEKFMIKLSNSYLTKEMIPKVQDNLKNFDLETKKTLDKFIKEKEDILGTNLSSSLRRKVS IRLNKNIAFDINDIPFSEFDDLINQYKNEIEDYEVLNLGAEDGKIKDLSGTTSDINIGSDIELADGRENKAI KIKGSENSTIKIAMNKYLRFSATDNFSISFWIKHPKPTNLLNNGIEYTLVENFNQRGWKISIQDSQKLIWYL RDHNNSIKIVTPDYIAFNGWNLITITNNRSKGSIVYVNGSKIEEKDISSIWNTEVDDPIIFRLKNNRDTQAF |

TABLE 1-continued

BoNT Polypeptide Sequences

| SEQ ID NO. | Description | Sequence |
|---|---|---|
| | | TLLDQFSIYRKELNQNEVVKLYNYYFNSQNYIRDIWGNPLQYNKKYYLQTQDKPGKGLIREYWSSFGYDYVI LSDSKTITFPNNIRYGALYNGSKVLIKNSKKLDGLVRNKDFIQLEIDGNYMGISQADRFNEDTNYIGTTYGT THDLTTDFEIIQRQEKYRNYAQLKTPYNIFHKSGLMSTETSKPTFHDYRDWVYSSAWYFQNYENLNLRKHTK TNWYFIPKDEGWDED |
| 18 | WT BoNT/X LC-H$_N$ C461A | MKLEINKFNYNDPIDGINVITMRPPRHSDKINKGKGPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQQGSNDFQGQLLESSYFEKIESNALRAFIKICPRNGLLYN AIYRNSKNYLNNIDLEDKKTTSKTNVSYPASLLNGCIEVENKDLFLISNKDSLNDINLSEEKIKPETTVFFK DKLPPQDITLSNYDFTEANSIPSISQQNILERNEELYEPIRNSLFEIKTIYVDKLTTFHFLEAQNIDESIDS SKIRVELTDSVDEALSNPNKVYSPFKNMSNTINSIETGITSTYIFYQWLRSIVKDFSDETGKIDVIDKSQSD TLAIVPYIGPLLNIGNDIRHGDFVGAIELAGITALLEYVPEFTIPILVGLEVIGGELAREQVEAIVNNALDK RDQKWAEVYNITKAQWWGTIHLQINTRLAHTYKALSRQANAIKMNMEFQLANYKGNIDDKAKIKNAISETEI LLNKSVEQAMKNTEKFMIKLSNSYLTKEMIPKVQDNLKNFDLETKKTLDKFIKEKEDILGTNLSSSLRRKVS IRLNKNIAFDINDIPFSEFDDLINQYKNEI |
| 19 | WT BoNT/X LC-H$_N$ C461S | MKLEINKFNYNDPIDGINVITMRPPRHSDKINKGKGPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQQGSNDFQGQLLESSYFEKIESNALRAFIKICPRNGLLYNA IYRNSKNYLNNIDLEDKKTTSKTNVSYPSSLLNGCIEVENKDLFLISNKDSLNDINLSEEKIKPETTVFFKD KLPPQDITLSNYDFTEANSIPSISQQNILERNEELYEPIRNSLFEIKTIYVDKLTTFHFLEAQNIDESIDSS KIRVELTDSVDEALSNPNKVYSPFKNMSNTINSIETGITSTYIFYQWLRSIVKDFSDETGKIDVIDKSQSDT LAIVPYIGPLLNIGNDIRHGDFVGAIELAGITALLEYVPEFTIPILVGLEVIGGELAREQVEAIVNNALDKR DQKWAEVYNITKAQWWGTIHLQINTRLAHTYKALSRQANAIKMNMEFQLANYKGNIDDKAKIKNAISETEIL LNKSVEQAMKNTEKFMIKLSNSYLTKEMIPKVQDNLKNFDLETKKTLDKFIKEKEDILGTNLSSSLRRKVSI RLNKNIAFDINDIPFSEFDDLINQYKNEI |
| 20 | WT BoNT/X LC-H$_N$ C467A | MKLEINKFNYNDPIDGINVITMRPPRHSDKINKGKGPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQQGSNDFQGQLLESSYFEKIESNALRAFIKICPRNGLLYNA IYRNSKNYLNNIDLEDKKTTSKTNVSYPCSLLNGAIEVENKDLFLISNKDSLNDINLSEEKIKPETTVFFKD KLPPQDITLSNYDFTEANSIPSISQQNILERNEELYEPIRNSLFEIKTIYVDKLTTFHFLEAQNIDESIDSS KIRVELTDSVDEALSNPNKVYSPFKNMSNTINSIETGITSTYIFYQWLRSIVKDFSDETGKIDVIDKSQSDT LAIVPYIGPLLNIGNDIRHGDFVGAIELAGITALLEYVPEFTIPILVGLEVIGGELAREQVEAIVNNALDKR DQKWAEVYNITKAQWWGTIHLQINTRLAHTYKALSRQANAIKMNMEFQLANYKGNIDDKAKIKNAISETEIL LNKSVEQAMKNTEKFMIKLSNSYLTKEMIPKVQDNLKNFDLETKKTLDKFIKEKEDILGTNLSSSLRRKVSI RLNKNIAFDINDIPFSEFDDLINQYKNEI |
| 21 | WT BoNT/X LC-H$_N$ C467S | MKLEINKFNYNDPIDGINVITMRPPRHSDKINKGKGPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQQGSNDFQGQLLESSYFEKIESNALRAFIKICPRNGLLYNA IYRNSKNYLNNIDLEDKKTTSKTNVSYPCSLLNGSIEVENKDLFLISNKDSLNDINLSEEKIKPETTVFFKD KLPPQDITLSNYDFTEANSIPSISQQNILERNEELYEPIRNSLFEIKTIYVDKLTTFHFLEAQNIDESIDSS KIRVELTDSVDEALSNPNKVYSPFKNMSNTINSIETGITSTYIFYQWLRSIVKDFSDETGKIDVIDKSQSDT LAIVPYIGPLLNIGNDIRHGDFVGAIELAGITALLEYVPEFTIPILVGLEVIGGELAREQVEAIVNNALDKR DQKWAEVYNITKAQWWGTIHLQINTRLAHTYKALSRQANAIKMNMEFQLANYKGNIDDKAKIKNAISETEIL LNKSVEQAMKNTEKFMIKLSNSYLTKEMIPKVQDNLKNFDLETKKTLDKFIKEKEDILGTNLSSSLRRKVSI RLNKNIAFDINDIPFSEFDDLINQYKNEI |
| 22 | BoNT/X-LC-H$_N$-A1-Hc | MKLEINKFNYNDPIDGINVITMRPPRHSDKINKGKGPFKAFQVIKNIWIVPERYNFTNNTNDLNIPSEPIME ADAIYNPNYLNTPSEKDEFLQGVIKVLERIKSKP EGEKLLELISSSIPLPLVSNGALTLSDNETIAYQENN NIVSNLQANLVIYGPGPDIANNATYGLYSTPISNGEGTLSEVSFSPFYLKPFDESYGNYRSLVNIVNKFVKR EFAPDPASTLMHELVHVTHNLYGISNRNFYYNFDTGKIETSRQQNSLIFEELLTFGGIDSKAISSLIIKKII ETAKNNYTTLISERLNTVTVENDLLKYIKNKIPVQGRLGNFKLDTAEFEKKLNTILFVLNESNLAQRFSILV RKHYLKERPIDPIYVNILDDNSYSTLEGFNISSQQGSNDFQGQLLESSYFEKIESNALRAFIKICPRNGLLYN AIYRNSKNYLNNIDLEDKKTTSKTNVSYPCSLLNGCIEVENKDLFLISNKDSLNDINLSEEKIKPETTVFFK DKLPPQDITLSNYDFTEANSIPSISQQNILERNEELYEPIRNSLFEIKTIYVDKLTTFHFLEAQNIDESIDS SKIRVELTDSVDEALSNPNKVYSPFKNMSNTINSIETGITSTYIFYQWLRSIVKDFSDETGKIDVIDKSQSD TLAIVPYIGPLLNIGNDIRHGDFVGAIELAGITALLEYVPEFTIPILVGLEVIGGELAREQVEAIVNNALDK RDQKWAEVYNITKAQWWGTIHLQINTRLAHTYKALSRQANAIKMNMEFQLANYKGNIDDKAKIKNAISETEI LLNKSVEQAMKNTEKFMIKLSNSYLTKEMIPKVQDNLKNFDLETKKTLDKFIKEKEDILGTNLSSSLRRKVS IRLNKNIAFDINDIPFSEFDDLINQYKNEIIINTSILNLRYESNHLIDLSRYASKINIGSKVNFDPIDKNQI QLFNLESSKIEVILKNAIVYNSMYENFSQTSFWIRIPKYFNSISLNNEYTIINCMENNSGWKVSLNYGEIIW TLQDTQEIKQRVVFKYSQMINISDYINRWIFVTITNNRLNNSKIYINGRLIDQKPISNLGNIHASNNIMFKL |

TABLE 1-continued

BoNT Polypeptide Sequences

| SEQ ID NO. | Description | Sequence |
|---|---|---|
| | | DGCRDTHRYIWIKYFNLFDKELNEKEIKDLYDNQSQNSGILKDFWGDYLQYDKPYYMLNLYDPNKYVDVNNV GIRGYMYLKGPRGSQVMTTNIYLNSSLYRGTKFIIKKYASGNKDNIVRNNDRVYINVVVKNKEYRLATNASQ AGVEKILSALEIPDVGNLSQVVVMKSKNDQGITNKCKMNLQDNNGNDIGFIGFHQFNNIAKLVASNWYNRQI ERSSRTLGCSWEFIPVDDGWGERPL |
| 23 | BoNT/X-LC- $H_N$-B1-Hc | MKLEINKFNYNDPIDGINVITMRPPRHSDKINKGKGPPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQGSNDFQGQLLESSYFEKIESNALRAFIKICPRNGLLYNA IYRNSKNYLNNIDLEDKKTTSKTNVSYPCSLLNGCIEVENKDLFLISNKDSLNDINLSEEKIKPETTVFFKD KLPPQDITLSNYDFTEANSIPSISQQNILERNEELYEPIRNSLFEIKTIYVDKLTTFHFLEAQNIDESIDSS KIRVELTDSVDEALSNPNKVYSPFKNMSNTINSIETGITSTYIFYQWLRSIVKDFSDETGKIDVIDKSQSDT LAIVPYIGPLLNIGNDIRHGDFVGAIELAGITALLEYVPEFTIPILVGLEVIGGELAREQVEAIVNNALDKR DQKWAEVYNITKAQWWGTIHLQINTRLAHTYKALSRQANAIKMNMEFQLANYKGNIDDKAKIKNAISETEIL LNKSVEQAMKNTEKFMIKLSNSYLTKEMIPKVQDNLKNFDLETKKTLDKFIKEKEDILGTNLSSSLRRKVSI RLNKNIAFDINDIPFSEFDDLINQYKNEIILNNIILNLRYKDNNLIDLSGYGAKVEVYDGVELNDKNQFKLT SSANSKIRVTQNQNIIFNSVFLDFSVSFWIRIPKYKNDGIQNYIHNEYTIINCMKNNSGWKISIRGNRIIWT LIDINGKTKSVFFEYNIREDISEYINRWFFVTITNNLNNAKIYINGKLESNTDIKDIREVIANGEIIFKLDG DIDRTQFIWMKYFSIFNTELSQSNIEERYKIQSYSEYLKDFWGNPLMYKEYYMFNAGNKNSYIKLKKDSPV GEILTRSKYNQNSKYINYRDLYIGEKFIIRRKSNSQSINDDIVRKEDYIYLDFFNLNQEWRVYTYKYFKKEE EKLFLAPISDSDEFYNTIQIKEYDEQPTYSCQLLFKKDEESTDEIGLIGIHRFYESGIVFEEYKDYFCISKW YLKEVKRKPYNLKLGCNWQFIPKDEGWTE |
| 24 | BoNT/X-LC- $H_N$-C1-Hc | MKLEINKFNYNDPIDGINVITMRPPRHSDKINKGKGPPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQGSNDFQGQLLESSYFEKIESNALRAFIKICPRNGLLYNA IYRNSKNYLNNIDLEDKKTTSKTNVSYPCSLLNGCIEVENKDLFLISNKDSLNDINLSEEKIKPETTVFFKD KLPPQDITLSNYDFTEANSIPSISQQNILERNEELYEPIRNSLFEIKTIYVDKLTTFHFLEAQNIDESIDSS KIRVELTDSVDEALSNPNKVYSPFKNMSNTINSIETGITSTYIFYQWLRSIVKDFSDETGKIDVIDKSQSDT LAIVPYIGPLLNIGNDIRHGDFVGAIELAGITALLEYVPEFTIPILVGLEVIGGELAREQVEAIVNNALDKR DQKWAEVYNITKAQWWGTIHLQINTRLAHTYKALSRQANAIKMNMEFQLANYKGNIDDKAKIKNAISETEIL LNKSVEQAMKNTEKFMIKLSNSYLTKEMIPKVQDNLKNFDLETKKTLDKFIKEKEDILGTNLSSSLRRKVSI RLNKNIAFDINDIPFSEFDDLINQYKNEIINDSKILSLQNRKNTLVDTSGYNAEVSEEGDVQLNPIPPFDPK LGSSGEDRGKVIVTQNENIVYNSMYESFSISFWIRINKWVSNLPGYTIIDSVKNNSGWSIGIISNFLVFTLK QNEDSEQSINFSQYDISNNAPGYNKWFFVTVTNNMMGNMKIYINGKLIDTIKVKELTGINFSKTITFEINKI PDTGLITSDSDNINMWIRDFYIFAKELDGKDINILFNSLQYTNVVKDYWGNDLRYNKEYYMVNIDYLNRYMY ANSRQIVFNTRRNNNDFNEGYKIIIKRIRGNTNDTRVRGGDILYFDMTINNKAYNLFMKNETMYADNHSTED IYAIGLREQTKDINDNIIFQIQPMNNTYYYASQIFKSNFNGENISGICSIGTYRFRLGGDWYRHNYLVPTVK QGNYASQLLESTSTHWGFVPVSE |
| 25 | BoNT/X-LC- $H_N$-A1-Hc C461S | MKLEINKFNYNDPIDGINVITMRPPRHSDKINKGKGPPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQGSNDFQGQLLESSYFEKIESNALRAFIKICPRNGLLYNA IYRNSKNYLNNIDLEDKKTTSKTNVSYPSSLLNGCIEVENKDLFLISNKDSLNDINLSEEKIKPETTVFFKD KLPPQDITLSNYDFTEANSIPSISQQNILERNEELYEPIRNSLFEIKTIYVDKLTTFHFLEAQNIDESIDSS KIRVELTDSVDEALSNPNKVYSPFKNMSNTINSIETGITSTYIFYQWLRSIVKDFSDETGKIDVIDKSQSDT LAIVPYIGPLLNIGNDIRHGDFVGAIELAGITALLEYVPEFTIPILVGLEVIGGELAREQVEAIVNNALDKR DQKWAEVYNITKAQWWGTIHLQINTRLAHTYKALSRQANAIKMNMEFQLANYKGNIDDKAKIKNAISETEIL LNKSVEQAMKNTEKFMIKLSNSYLTKEMIPKVQDNLKNFDLETKKTLDKFIKEKEDILGTNLSSSLRRKVSI RLNKNIAFDINDIPFSEFDDLINQYKNEIIINTSILNLRYESNHLIDLSRYASKINIGSKVNFDPIDKNQIQ LFNLESSKIEVILKNAIVYNSMYENFSQTSFWIRIPKYFNSISLNNEYTIINCMENNSGWKVSLNYGEIIWT LQDTQEIKQRVVFKYSQMINISDYINRWIFVTITNNRLNNSKIYINGRLIDQKPISNLGNIHASNNIMFKLD GCRDTHRYIWIKYFNLFDKELNEKEIKDLYDNQSQNSGILKDFWGDYLQYDKPYYMLNLYDPNKYVDVNNVG IRGYMYLKGPRGSQVMTTNIYLNSSLYRGTKFIIKKYASGNKDNIVRNNDRVYINVVVKNKEYRLATNASQQ AGVEKILSALEIPDVGNLSQVVVMKSKNDQGITNKCKMNLQDNNGNDIGFIGFHQFNNIAKLVASNWYNRQI ERSSRTLGCSWEFIPVDDGWGERPL |
| 26 | BoNT/X-LC- $H_N$-B1-Hc C461S | MKLEINKFNYNDPIDGINVITMRPPRHSDKINKGKGPPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESYGNYRSLVNIVNKFVKRE FAPDPASTLMHELVHVTHNLYGISNRNFYYNFDTGKIETSRQQNSLIFEELLTFGGIDSKAISSLIIKKIIE TAKNNYTTLISERLNTVTVENDLLKYIKNKIPVQGRLGNFKLDTAEFEKKLNTILFVLNESNLAQRFSILVR KHYLKERPIDPIYVNILDDNSYSTLEGFNISSQGSNDFQGQLLESSYFEKIESNALRAFIKICPRNGLLYNA IYRNSKNYLNNIDLEDKKTTSKTNVSYPSSLLNGCIEVENKDLFLISNKDSLNDINLSEEKIKPETTVFFKD KLPPQDITLSNYDFTEANSIPSISQQNILERNEELYEPIRNSLFEIKTIYVDKLTTFHFLEAQNIDESIDSS KIRVELTDSVDEALSNPNKVYSPFKNMSNTINSIETGITSTYIFYQWLRSIVKDFSDETGKIDVIDKSQSDT LAIVPYIGPLLNIGNDIRHGDFVGAIELAGITALLEYVPEFTIPILVGLEVIGGELAREQVEAIVNNALDKR DQKWAEVYNITKAQWWGTIHLQINTRLAHTYKALSRQANAIKMNMEFQLANYKGNIDDKAKIKNAISETEIL |

TABLE 1-continued

BoNT Polypeptide Sequences

| SEQ ID NO. | Description | Sequence |
|---|---|---|
| | | LNKSVEQAMKNTEKFMIKLSNSYLTKEMIPKVQDNLKNFDLETKKTLDKFIKEKEDILGTNLSSSLRRKVSI RLNKNIAFDINDIPFSEFDDLINQYKNEIILNNIILNLRYKDNNLIDLSGYGAKVEVYDGVELNDKNQFKLT SSANSKIRVTQNQNIIFNSVFLDFSVSFWIRIPKYKNDGIQNYIHNEYTIINCMKNNSGWKISIRGNRIIWT LIDINGKTKSVFFEYNIREDISEYINRWFFVTITNNLNNAKIYINGKLESNTDIKDIREVIANGEIIFKLDG DIDRTQFIWMKYFSIFNTELSQSNIEERYKIQSYSEYLKDFWGNPLMYNKEYYMFNAGNKNSYIKLKKDSPV GEILTRSKYNQNSKYINYRDLYIGEKFIIRRKSNSQQSINDDIVRKEDYIYLDFFNLNQEWRVYTYKYFKKE EEKLFLAPISDSDEFYNTIQIKEYDEQPTYSCQLLFKKDEESTDEIGLIGIHRFYESGIVFEEYKDYFCISK WYLKEVKRKPYNLKLGCNWQFIPKDEGWTE |
| 27 | BoNT/X-LC-$H_N$-C1-Hc C461S | MKLEINKFNYNDPIDGINVITMRPPRHSDKINKGKGPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESQYGNYRSLVNIVNKFVKR EFAPDPASTLMHELVHVTHNLYGISNRNFYYNFDTGKIETSRQQNSLIFEELLTFGGIDSKAISSLIIKKII ETAKNNYTTLISERLNTVTVENDLLKYIKNKIPVQGRLGNFKLDTAEFEKKLNTILFVLNESNLAQRFSILV RKHYLKERPIDPIYVNILDDNSYSTLEGFNISSQGSNDFQGQLLESSYFEKIESNALRAFIKICPRNGLLYN AIYRNSKNYLNNIDLEDKKTTSKTNVSYP<u>S</u>SLLNGCIEVENKDLFLISNKDSLNDINLSEEKIKPETTVFFK DKLPPQDITLSNYDFTEANSIPSISQQNILERNEELYEPIRNSLFEIKTIYVDKLTTFHFLEAQNIDESIDS SKIRVELTDSVDEALSQNPNKVYSPFKNMSNTINSIETGITSTYIFYQWLRSIVKDFSDETGKIDVIDKSSQ DTLAIVPYIGPLLNIGNDIRHGDFVGAIELAGITALLEYVPEFTIPILVGLEVIGGELAREQVEAIVNNALD KRDQKWAEVYNITKAQWWGTIHLQINTRLAHTYKALSRQANAIKMNMEFQLANYKGNIDDKAKIKNAISETE ILLNKSVEQAMKNTEKFMIKLSNSQYLTKEMIPKVQDNLKNFDLETKKTLDKFIKEKEDILGTNLSQSSLRR KVSIRLNKNIAFDINDIPFSEFDDLINQYKNEIINDSKILSLQNRKNTLVDTSGYNAEVSEEGDVQLNPIFP FDFKLGSSGEDRGKVIVTQNENIVYNSMYESFSISFWIRINKWVSNLPGYTIIDSVKNNSGWSIGIISNFLV FTLKQNEDSEQSINFSYDISNNAPGYNKWFFVTVTNNMMGNMKIYINGKLIDTIKVKELTGINFSQKTITFE INKIPDTGLITSDSDNINMWIRDFYIPAKELDGKDINILFNSLQYTNVVKDYWGNDLRYNKEYYMVNIDYLN RYMYANSRQIVFNTRRNNNDFNEGYKIIIKRIRGNTNDTRVRGGDILYFDMTINNKAYNLFMKNETMYADNH STEDIYAIGLREQTKDINDNIIFQIQPMNNTYYYASQIFKSNFNGENISGICSIGTYRFRLGGDWYRHNYLV PTVKQGNYASLLESTSTHWGFVPVSE |
| 28 | BoNT/X-LC-$H_N$-A1-Hc C467S | MKLEINKFNYNDPIDGINVITMRPPRHSDKINKGKGPFKAFQVIKNIWIVPERYNFTNNTNDLNIPSEPIME ADAIYNPNYLNTPSEKDEFLQGVIKVLERIKSKPEGEKLLELISSSIPLPLVSNGALTLSDNETIAYQENNN IVSNLQANLVIYGPGPDIANNATYGLYSTPISNGEGTLSEVSFSPFYLKPFDESQYGNYRSLVNIVNKFVKR EFAPDPASTLMHELVHVTHNLYGISNRNFYYNFDTGKIETSRQQNSLIFEELLTFGGIDSKAISSLIIKKII ETAKNNYTTLISERLNTVTVENDLLKYIKNKIPVQGRLGNFKLDTAEFEKKLNTILFVLNESNLAQRFSILV RKHYLKERPIDPIYVNILDDNSYSTLEGFNISSQGSNDFQGQLLESSYFEKIESNALRAFIKICPRNGLLYN AIYRNSKNYLNNIDLEDKKTTSKTNVSYPCSLLNG<u>S</u>IEVENKDLFLISNKDSLNDINLSEEKIKPETTVFFK DKLPPQDITLSNYDFTEANSIPSISQQNILERNEELYEPIRNSLFEIKTIYVDKLTTFHFLEAQNIDESIDS SKIRVELTDSVDEALSQNPNKVYSPFKNMSNTINSIETGITSTYIFYQWLRSIVKDFSDETGKIDVIDKSSQ DTLAIVPYIGPLLNIGNDIRHGDFVGAIELAGITALLEYVPEFTIPILVGLEVIGGELAREQVEAIVNNALD KRDQKWAEVYNITKAQWWGTIHLQINTRLAHTYKALSRQANAIKMNMEFQLANYKGNIDDKAKIKNAISETE ILLNKSVEQAMKNTEKFMIKLSNSQYLTKEMIPKVQDNLKNFDLETKKTLDKFIKEKEDILGTNLSQSSLRR KVSIRLNKNIAFDINDIPFSEFDDLINQYKNEIIINTSILNLRYESNHLIDLSRYASKINIGSKVNFDPIDK NQIQLFNLESSKIEVILKNAIVYNSMYENFSTSQFWIRIPKYFNSISLNNEYTIINCMENNSGWKVSLNYGE IIWTLQDTQEIKQRVVPKYSQMINISDYINRWIFVTITNNRLNNSQKIYINGRLIDQKPISNLGNIHASNNI MFKLDGCRDTHRYIWIKYFNLFDKELNEKEIKDLYDNQSNSQGILKDFWGDYLQYDKPYYMLNLYDPNKYVD VNNVGIRGYMYLKGPRGSQVMTTNIYLNSSLYRGTKFIIKKYASGNKDNIVRNNDRVYINVVVKNKEYRLAT NASQQAGVEKILSALEIPDVGNLSQVVVMKSKNDQGITNKCKMNLQDNNGNDIGFIGFHQFNNIAKLVASNW YNRQIERSSRTLGCSWEFIPVDDGWGERPL |
| 29 | BoNT/X-LC-$H_N$-B1-Hc C467S | MKLEINKFNYNDPIDGINVITMRPPRHSQDKINKGKGPFKAFQVIKNIWIVPERYNFTNNTNDLNIPSEPIM EADAIYNPNYLNTPSEKDEFLQGVIKVLERIKSKPQEGEKLLELISSSIPLPLVSNGALTLSDNETIAYQEN NNIVSNLQANLVIYGPGPDIANNATYGLYSTPISNGEGTLSEVSFSPFYLKPFDESQYGNYRSLVNIVNKFVK REFAPDPASTLMHELVHVTHNLYGISNRNFYYNFDTGKIETSRQQNSQLIFEELLTFGGIDSKAISSLIIKK IIETAKNNYTTLISERLNTVTVENDLLKYIKNKIPVQGRLGNFKLDTAEFEKKLNTILFVLNESNLAQRFS ILVRKHYLKERPIDPIYVNILDDNSYSTLEGFNISSQGSNDFQGQLLESSYFEKIESNALRAFIKICPRNGL LYNAIYRNSKNYLNNIDLEDKKTTSKTNVSYPCSLLNG<u>S</u>IEVENKDLFLISNKDSLNDINLSEEKIKPETTV FFKDKLPPQDITLSNYDFTEANSIPSISQQNILERNEELYEPIRNSLFEIKTIYVDKLTTFHFLEAQNIDES IDSSKIRVELTDSVDEALSQNPNKVYSPFKNMSNTINSIETGITSTYIFYQWLRSIVKDFSDETGKIDVIDK SSQDTLAIVPYIGPLLNIGNDIRHGDFVGAIELAGITALLEYVPEFTIPILVGLEVIGGELAREQVEAIVNN ALDKRDQKWAEVYNITKAQWWGTIHLQINTRLAHTYKALSRQANAIKMNMEFQLANYKGNIDDKAKIKNAIS ETEILLNKSVEQAMKNTEKFMIKLSNSYLTKEMIPKVQDNLKNFDLETKKTLDKFIKEKEDILGTNLSQSSL RRKVSIRLNKNIAFDINDIPFSEFDDLINQYKNEIILNNIILNLRYKDNNLIDLSGYGAKVEVYDGVELNDK NQFKLTSSANSKIRVTQNQNIIFNSVFLDFSVSFWIRIPKYKNDGIQNYIHNEYTIINCMKNNSGWKISIR GNRIIWTLIDINGKTKSVFFEYNIREDISEYINRWFFVTITNNLNNAKIYINGKLESNTDIKDIREVIANGE IIFKLDGDIDRTQFIWMKYFSIFNTELSQSNIEERYKIQSYSEYLKDFWGNPLMYNKEYYMFNAGNKNSYIK LKKDSPVGEILTRSKYNQNSKYINYRDLYIGEKFIIRRKSNSQSINDDIVRKEDYIYLDFFNLNQEWRVYTY KYFKKEEEKLFLAPISDSDEFYNTIQIKEYDEQPTYSCQLLFKKDEESTDEIGLIGIHRFYESGIVFEEYKD YFCISKWYLKEVKRKPYNLKLGCNWQFIPKDEGWTE |
| 30 | BoNT/X-LC-$H_N$-C1-Hc C467S | MKLEINKFNYNDPIDGINVITMRPPRHSQDKINKGKGPFKAFQVIKNIWIVPERYNFTNNTNDLNIPSEPIM EADAIYNPNYLNTPSEKDEFLQGVIKVLERIKSKPEGEKLLELISSSIPLPLVSNGALTLSDNETIAYQEN NIVSNLQANLVIYGPGPDIANNATYGLYSTPISNGEGTLSEVSFSPFYLKPFDESQYGNYRSLVNIVNKFVKR EFAPDPASTLMHELVHVTHNLYGISNRNFYYNFDTGKIETSRQQNSLIFEELLTFGGIDSKAISSLIIKKI IETAKNNYTTLISERLNTVTVENDLLKYIKNKIPVQGRLGNFKLDTAEFEKKLNTILFVLNESQNLAQRFSI LVRKHYLKERPIDPIYVNILDDNSYSTLEGFNISSQGSNDFQGQLLESSYFEKIESNALRAFIKICPRNGLL YNAIYRNSKNYLNNIDLEDKKTTSKTNVSYPCSLLNG<u>S</u>IEVENKDLFLISNKDSLNDINLSEEKIKPETTVF |

TABLE 1-continued

BoNT Polypeptide Sequences

| SEQ ID NO. | Description | Sequence |
|---|---|---|
| | | FKDKLPPQDITLSNYDFTEANSIPSISQQNILERNEELYEPIRNSLFEIKTIYVDKLTTFHFLEAQNIDESI<br>DSSKIRVELTDSVDEALSQNPNKVYSPFKNMSNTINSIETGITSTYIFYQWLRSIVKDFSDETGKIDVIDKS<br>SQDTLAIVPYIGPLLNIGNDIRHGDFVGAIELAGITALLEYVPEFTIPILVGLEVIGGELAREQVEAIVNNA<br>LDKRDQKWAEVYNITKAQWWGTIHLQINTRLAHTYKALSRQANAIKMNMEFQLANYKGNIDDKAKIKNAISE<br>TEILLNKSVEQAMKNTEKFMIKLSNSYLTKEMIPKVQDNLKNFDLETKKTLDKFIKEKEDILGTNLSQSSLR<br>RKVSIRLNKNIAFDINDIPFSEFDDLINQYKNEIINDSKILSLQNRKNTLVDTSGYNAEVSEEGDVQLNPIF<br>PFDFKLGSSGEDRGKVIVTQNENIVYNSMYESFSISFWIRINKWVSNLPGYTIIDSVKNNSGWSIGIISNFL<br>VFTLKQNEDSEQSINFSYDISQNNAPGYNKWFFVTVTNNMMGNMKIYINGKLIDTIKVKELTGINFSQKTIT<br>FEINKIPDTGLITSDSDNINMWIRDFYIFAKELDGKDINILFNSLQYTNVVKDYWGNDLRYNKEYYMVNIDY<br>LNRYMYANSRQIVFNTRRNNNDFNEGYKIIIKRIRGNTNDTRVRGGDILYFDMTINNKAYNLFMKNETMYAD<br>NHSTEDIYAIGLREQTKDINDNIIFQIQPMNNTYYYASQIFKSNFNGENISGICSIGTYRFRLGGDWYRHNY<br>LVPTVKQGNYASLLESTSTHWGFVPVSE |
| 31 | BoNT/X<br>R360A/Y363F | MKLEINKFNYNDPIDGINVITMRPPRHSQDKINKGKGPFKAFQVIKNIWIVPERYNFTNNTNDLNIPSEPIM<br>EADAIYNPNYLNTPSEKDEFLQGVIKVLERIKSKPEGEKLLELISSSIPLPLVSNGALTLSDNETIAYQENN<br>NIVSNLQANLVIYGPGPDIANNATYGLYSTPISNGEGTLSEVSFSPPFYLKPFDESYGNYRSLVNIVNKFVKR<br>EFAPDPASTLMHELVHVTHNLYGISNRNFYYNFDTGKIETSRQQNSLIFEELLTFGGIDSKAISSLIIKKII<br>ETAKNNYTTLISERLNTVTVENDLLKYIKNKIPVQGRLGNFKLDTAEFEKKLNTILFVLNESQNLAQRFSIL<br>VA<u>KHF</u>LKERPIDPIYVNILDDNSYSTLEGFNISSQGSNDFQGQLLESSYFEKIESNALRAFIKICPRNGLLY<br>NAIYRNSKNYLNNIDLEDKKTTSKTNVSYPCSLLNGCIEVENKDLFLISNKDSLNDINLSEEKIKPETTVFF<br>KDKLPPQDITLSNYDFTEANSIPSISQQNILERNEELYEPIRNSLFEIKTIYVDKLTTFHFLEAQNIDESID<br>SSKIRVELTDSVDEALSQNPNKVYSPFKNMSNTINSIETGITSTYIFYQWLRSIVKDFSDETGKIDVIDKSS<br>QDTLAIVPYIGPLLNIGNDIRHGDFVGAIELAGITALLEYVPEFTIPILVGLEVIGGELAREQVEAIVNNAL<br>DKRDQKWAEVYNITKAQWWGTIHLQINTRLAHTYKALSRQANAIKMNMEFQLANYKGNIDDKAKIKNAISET<br>EILLNKSVEQAMKNTEKFMIKLSNSYLTKEMIPKVQDNLKNFDLETKKTLDKFIKEKEDILGTNLSQSSLRR<br>KVSIRLNKNIAFDINDIPFSEFDDLINQYKNEIEDYEVLNLGAEDGKIKDLSGTTSDINIGSDIELADGREN<br>KAIKIKGSENSTIKIAMNKYLRFSATDNFSISQFWIKHPKPTNLLNNGIEYTLVENFNQRGWKISIQDSKLI<br>WYLRDHNNSIKIVTPDYIAFNGWNLITITNNRSKGSIVYVNGSKIEEKDISSIWNTEVDDPIIFRLKNNRDT<br>QAFTLLDQFSIYRKELNQNEVVKLYNYYFNSQNYIRDIWGNPLQYNKKYYLQTQDKPGKGLIREYWSSFGYD<br>YVILSDSKTITFPNNIRYGALYNGSKVLIKNSKKLDGLVRNKDFIQLEIDGYNMGISADRFNEDTNYIGTTY<br>GTTHDLTTDFEIIQRQEKYRNYCQLKTPYNIFHKSGLMSTETSKPTFHDYRDWVYSSAWYFQNYENLNLRKH<br>TKTNWYFIPKDEGWDED |
| 32 | BoNT/X<br>H227Y | MKLEINKFNYNDPIDGINVITMRPPRHSQDKINKGKGPFKAFQVIKNIWIVPERYNFTNNTNDLNIPSEPIM<br>EADAIYNPNYLNTPSEKDEFLQGVIKVLERIKSKPEGEKLLELISSSIPLPLVSNGALTLSDNETIAYQENN<br>NIVSNLQANLVIYGPGPDIANNATYGLYSTPISNGEGTLSEVSFSPPFYLKPFDESYGNYRSLVNIVNKFVKR<br>EFAPDPASTLMYELVHVTHNLYGISNRNFYYNFDTGKIETSRQQNSLIFEELLTFGGIDSKAISSLIIKKI<br>IETAKNNYTTLISERLNTVTVENDLLKYIKNKIPVQGRLGNFKLDTAEFEKKLNTILFVLNESQNLAQRFSI<br>LVRKHYLKERPIDPIYVNILDDNSYSTLEGFNISSQGSNDFQGQLLESSYFEKIESNALRAFIKICPRNGLL<br>YNAIYRNSKNYLNNIDLEDKKTTSKTNVSYPCSLLNGCIEVENKDLFLISNKDSLNDINLSEEKIKPETTVF<br>FKDKLPPQDITLSNYDFTEANSIPSISQQNILERNEELYEPIRNSLFEIKTIYVDKLTTFHFLEAQNIDESI<br>DSSKIRVELTDSVDEALSQNPNKVYSPFKNMSNTINSIETGITSTYIFYQWLRSIVKDFSDETGKIDVIDKS<br>SQDTLAIVPYIGPLLNIGNDIRHGDFVGAIELAGITALLEYVPEFTIPILVGLEVIGGELAREQVEAIVNNA<br>LDKRDQKWAEVYNITKAQWWGTIHLQINTRLAHTYKALSRQANAIKMNMEFQLANYKGNIDDKAKIKNAISE<br>TEILLNKSVEQAMKNTEKFMIKLSNSYLTKEMIPKVQDNLKNFDLETKKTLDKFIKEKEDILGTNLSQSSLR<br>RKVSIRLNKNIAFDINDIPFSEFDDLINQYKNEIEDYEVLNLGAEDGKIKDLSGTTSDINIGSDIELADGRE<br>NKAIKIKGSENSTIKIAMNKYLRFSATDNFSISQFWIKHPKPTNLLNNGIEYTLVENFNQRGWKISIQDSKL<br>IWYLRDHNNSIKIVTPDYIAFNGWNLITITNNRSKGSIVYVNGSKIEEKDISSIWNTEVDDPIIFRLKNNRD<br>TQAFTLLDQFSIYRKELNQNEVVKLYNYYFNSQNYIRDIWGNPLQYNKKYYLQTQDKPGKGLIREYWSSFGY<br>DYVILSDSKTITFPNNIRYGALYNGSKVLIKNSKKLDGLVRNKDFIQLEIDGYNMGISADRFNEDTNYIGTT<br>YGTTHDLTTDFEIIQRQEKYRNYCQLKTPYNIFHKSGLMSTETSKPTFHDYRDWVYSSAWYFQNYENLNLRK<br>HTKTNWYFIPKDEGWDED |
| 33 | BoNT/X<br>E228Q | MKLEINKFNYNDPIDGINVITMRPPRHSQDKINKGKGPFKAFQVIKNIWIVPERYNFTNNTNDLNIPSEPIM<br>EADAIYNPNYLNTPSEKDEFLQGVIKVLERIKSKPEGEKLLELISSSIPLPLVSNGALTLSDNETIAYQENN<br>NIVSNLQANLVIYGPGPDIANNATYGLYSTPISNGEGTLSEVSFSPPFYLKPFDESYGNYRSLVNIVNKFVKR<br>EFAPDPASTLMHQLVHVTHNLYGISQRNFYYNFDTGKIETSRQQNSLIFEELLTFGGIDSKAISSLIIKKI<br>IETAKNNYTTLISERLNTVTVENDLLKYIKNKIPVQGRLGNFKLDTAEFEKKLNTILFVLNESQNLAQRFSQ<br>ILVRKHYLKERPIDPIYVNILDDNSYSTLEGFNISSQGSNDFQGQLLESSYFEKIESNALRAFIKICPRNGL<br>LYNAIYRNSKNYLNNIDLEDKKTTSKTNVSQYPCSLLNGCIEVENKDLFLISNKDSLNDINLSEEKIKPETT<br>VFFKDKLPPQDITLSNYDFTEANSIPSISQQNILERNEELYEPIRNSLFEIKTIYVDKLTTFHFLEAQNIDE<br>SIDSSKIRVELTDSVDEALSQNPNKVYSPFKNMSNTINSIETGITSTYIFYQWLRSIVKDFSDETGKIDVID<br>KSSQDTLAIVPYIGPLLNIGNDIRHGDFVGAIELAGITALLEYVPEFTIPILVGLEVIGGELAREQVEAIVN<br>NALDKRDQKWAEVYNITKAQWWGTIHLQINTRLAHTYKALSRQANAIKMNMEFQLANYKGNIDDKAKIKNAI<br>SETEILLNKSVEQAMKNTEKFMIKLSNSYLTKEMIPKVQDNLKNFDLETKKTLDKFIKEKEDILGTNLSQS<br>SLRRKVSIRLNKNIAFDINDIPFSEFDDLINQYKNEIEDYEVLNLGAEDGKIKDLSGTTSDINIGSDIELAD<br>GRENKAIKIKGSENSTIKIAMNKYLRFSATDNFSISQFWIKHPKPTNLLNNGIEYTLVENFNQRGWKISIQD<br>SKLIWYLRDHNNSIKIVTPDYIAFNGWNLITITNNRSKGSIVYVNGSKIEEKDISSIWNTEVDDPIIFRLKN<br>NRDTQAFTLLDQFSIYRKELNQNEVVKLYNYYFNSQNYIRDIWGNPLQYNKKYYLQTQDKPGKGLIREYWSS<br>FGYDYVILSDSKTITFPNNIRYGALYNGSKVLIKNSKKLDGLVRNKDFIQLEIDGYNMGISADRFNEDTNYI<br>GTTYGTTHDLTTDFEIIQRQEKYRNYCQLKTPYNIFHKSGLMSQTETSKPTFHDYRDWVYSSAWYFQNYENL<br>NLRKHTKTNWYFIPKDEGWDED |
| 34 | BoNT/X<br>H231Y | MKLEINKFNYNDPIDGINVITMRPPRHSQDKINKGKGPFKAFQVIKNIWIVPERYNFTNNTNDLNIPSEPIM<br>EADAIYNPNYLNTPSEKDEFLQGVIKVLERIKSKPEGEKLLELISSSIPLPLVSNGALTLSDNETIAYQENN<br>NIVSNLQANLVIYGPGPDIANNATYGLYSTPISNGEGTLSEVSFSPPFYLKPFDESYGNYRSLVNIVNKFVKR |

TABLE 1-continued

BoNT Polypeptide Sequences

| SEQ ID NO. | Description | Sequence |
|---|---|---|
| | | EFAPDPASTLMHELVYVTHNLYGISNRNFYYNFDTGKIETSRQQNSLIFEELLTFGGIDSKAISSLIIKKII ETAKNNYTTLISERLNTVTVENDLLKYIKNKIPVQGRLGNFKLDTAEFEKKLNTILFVLNESQNLAQRFSQI LVRKHYLKERPIDPIYVNILDDNSYSTLEGFNISSQGSNDFQGQLLESSYFEKIESNALRAFIKICPRNGLL YNAIYRNSKNYLNNIDLEDKKTTSKTNVSQYPCSLLNGCIEVENKDLFLISNKDSLNDINLSEEKIKPETTV FFKDKLPPQDITLSNYDFTEANSIPSISQQNILERNEELYEPIRNSLFEIKTIYVDKLTTFHFLEAQNIDES IDSSKIRVELTDSVDEALSQNPNKVYSPFKNMSNTINSIETGITSTYIFYQWLRSIVKDFSDETGKIDVIDK SSQDTLAIVPYIGPLLNIGNDIRHGDFVGAIELAGITALLEYVPEFTIPILVGLEVIGGELAREQVEAIVNN ALDKRDQKWAEVYNITKAQWWGTIHLQINTRLAHTYKALSRQANAIKMNMEFQLANYKGNIDDKAKIKNAIS ETEILLNKSVEQAMKNTEKFMIKLSNSQYLTKEMIPKVQDNLKNFDLETKKTLDKFIKEKEDILGTNLSQSS LRRKVSIRLNKNIAFDINDIPFSEFDDLINQYKNEIEDYEVLNLGAEDGKIKDLSGTTSDINIGSDIELADG RENKAIKIKGSENSTIKIAMNKYLRFSATDNFSISQFWIKHPKPTNLLNNGIEYTLVENFNQRGWKISIQDS KLIWYLRDHNNSIKIVTPDYIAFNGWNLITITNNRSKGSIVYVNGSKIEEKDISSIWNTEVDDPIIFRLKNN RDTQAFTLLDQFSIYRKELNQNEVVKLYNYYFNSQNYIRDIWGNPLQYNKKYYLQTQDKPGKGLIREYWSSF GYDYVILSDSKTITFPNNIRYGALYNGSKVLIKNSKKLDGLVRNKDFIQLEIDGYNMGISADRFNEDTNYIG TTYGTTHDLTTDPEIIQRQEKYRNYCQLKTPYNIFHKSGLMSQTETSKPTFHDYRDWVYSSAWYFQNYENLN LRKHTKTNWYFIPKDEGWDED |
| 35 | BoNT/X-LC-H$_N$ R360A/Y363F | MKLEINKFNYNDPIDGINVITMRPPRHSQDKINKGKGPFKAFQVIKNIWIVPERYNFTNNTNDLNIPSEPIM EADAIYNPNYLNTPSEKDEFLQGVIKVLERIKSQKPEGEKLLELISSSIPLPLVSNGALTLSDNETIAYQEN NNIVSNLQANLVIYGPGPDIANNATYGLYSTPISNGEGTLSEVSFSPFYLKPFDESYGNYRSLVNIVNKFVK REFAPDPASTLMHELVHVTHNLYGISNRNFYYNFDTGKIETSRQQNSQLIFEELLTFGGIDSKAISSLIIKK IIETAKNNYTTLISERLNTVTVENDLLKYIKNKIPVQGRLGNFKLDTAEFEKKLNTILFVLNESQNLAQRFS QILVAKHFLKERPIDPIYVNILDDNSYSTLEGFNISSQGSNDFQGQLLESSYFEKIESNALRAFIKICPRNG LLYNAIYRNSKNYLNNIDLEDKKTTSKTNVSQYPCSLLNGCIEVENKDLFLISNKDSLNDINLSEEKIKPET TVFFKDKLPPQDITLSNYDFTEANSIPSISQQNILERNEELYEPIRNSLFEIKTIYVDKLTTFHFLEAQNID ESIDSSKIRVELTDSVDEALSQNPNKVYSPFKNMSNTINSIETGITSTYIFYQWLRSIVKDFSDETGKIDVI DKSSQDTLAIVPYIGPLLNIGNDIRHGDFVGAIELAGITALLEYVPEFTIPILVGLEVIGGELAREQVEAIV NNALDKRDQKWAEVYNITKAQWWGTIHLQINTRLAHTYKALSRQANAIKMNMEFQLANYKGNIDDKAKIKNA ISETEILLNKSQVEQAMKNTEKFMIKLSNSYLTKEMIPKVQDNLKNFDLETKKTLDKFIKEKEDILGTNLSQ SSLRRKVSIRLNKNIAFDINDIPFSEFDDLINQYKNEI |
| 36 | BoNT/X-LC-H$_N$ H227Y | MKLEINKFNYNDPIDGINVITMRPPRHSQDKINKGKGPFKAFQVIKNIWIVPERYNFTNNTNDLNIPSEPIM EADAIYNPNYLNTPSEKDEFLQGVIKVLERIKSQKPEGEKLLELISSSIPLPLVSNGALTLSDNETIAYQEN NNIVSNLQANLVIYGPGPDIANNATYGLYSTPISNGEGTLSEVSFSPFYLKPFDESYGNYRSLVNIVNKFVK REFAPDPASTLMYELVHVTHNLYGISNRNFYYNFDTGKIETSRQQNSQLIFEELLTFGGIDSKAISSLIIKK IIETAKNNYTTLISERLNTVTVENDLLKYIKNKIPVQGRLGNFKLDTAEFEKKLNTILFVLNESNLAQRFSQ ILVRKHYLKERPIDPIYVNILDDNSYSTLEGFNISSQGSNDFQGQLLESSYFEKIESNALRAFIKICPRNGL LYNAIYRNSKNYLNNIDLEDKKTTSKTNVSYPCSLLNGCIEVENKDLFLISNKDSLNDINLSEEKIKPETTV FFKDKLPPQDITLSNYDFTEANSIPSISQQNILERNEELYEPIRNSLFEIKTIYVDKLTTFHFLEAQNIDES IDSSKIRVELTDSVDEALSQNPNKVYSPFKNMSNTINSIETGITSTYIFYQWLRSIVKDFSDETGKIDVIDK SSQDTLAIVPYIGPLLNIGNDIRHGDFVGAIELAGITALLEYVPEFTIPILVGLEVIGGELAREQVEAIVNN ALDKRDQKWAEVYNITKAQWWGTIHLQINTRLAHTYKALSRQANAIKMNMEFQLANYKGNIDDKAKIKNAIS ETEILLNKSQVEQAMKNTEKFMIKLSNSYLTKEMIPKVQDNLKNFDLETKKTLDKFIKEKEDILGTNLSQSS LRRKVSIRLNKNIAFDINDIPFSEFDDLINQYKNEI |
| 37 | BoNT/X-LC-H$_N$ E228Q | MKLEINKFNYNDPIDGINVITMRPPRHSQDKINKGKGPFKAFQVIKNIWIVPERYNFTNNTNDLNIPSEPIM EADAIYNPNYLNTPSEKDEFLQGVIKVLERIKSKPEGEKLLELISSSIPLPLVSNGALTLSDNETIAYQENN NIVSNLQANLVIYGPGPDIANNATYGLYSTPISNGEGTLSEVSFSPFYLKPFDESYGNYRSLVNIVNKFVKR EFAPDPASQTLMHQLVHVTHNLYGISNRNFYYNFDTGKIETSRQQNSLIFEELLTFGGIDSKAISSLIIKKI IETAKNNYTTLISERLNTVTVENDLLKYIKNKIPVQGRLGNFKLDTAEFEKKLNTILFVLNESNLAQRFSQI LVRKHYLKERPIDPIYVNILDDNSYSTLEGFNISSQGSNDFQGQLLESSYFEKIESNALRAFIKICPRNGLL YNAIYRNSKNYLNNIDLEDKKTTSKTNVSYPCSLLNGCIEVENKDLFLISNKDSLNDINLSEEKIKPETTVF FKDKLPPQDITLSNYDFTEANSIPSISQQNILERNEELYEPIRNSLFEIKTIYVDKLTTFHFLEAQNIDESI DSSKIRVELTDSVDEALSQNPNKVYSPFKNMSNTINSIETGITSTYIFYQWLRSIVKDFSDETGKIDVIDKS SQDTLAIVPYIGPLLNIGNDIRHGDFVGAIELAGITALLEYVPEFTIPILVGLEVIGGELAREQVEAIVNNA LDKRDQKWAEVYNITKAQWWGTIHLQINTRLAHTYKALSRQANAIKMNMEFQLANYKGNIDDKAKIKNAISE TEILLNKSQVEQAMKNTEKFMIKLSNSYLTKEMIPKVQDNLKNFDLETKKTLDKFIKEKEDILGTNLSQSSL RRKVSIRLNKNIAFDINDIPFSEFDDLINQYKNEI |
| 38 | BoNT/X-LC-H$_N$ H231Y | MKLEINKFNYNDPIDGINVITMRPPRHSQDKINKGKGPFKAFQVIKNIWIVPERYNFTNNTNDLNIPSEPIM EADAIYNPNYLNTPSEKDEFLQGVIKVLERIKSQKPEGEKLLELISSSIPLPLVSNGALTLSDNETIAYQEN NNIVSNLQANLVIYGPGPDIANNATYGLYSTPISNGEGTLSEVSFSPFYLKPFDESYGNYRSLVNIVNKFVK REFAPDPASTLMHELVYVTHNLYGISNRNFYYNFDTGKIETSRQQNSQLIFEELLTFGGIDSKAISSLIIKK IIETAKNNYTTLISERLNTVTVENDLLKYIKNKIPVQGRLGNFKLDTAEFEKKLNTILFVLNESNLAQRFSQ ILVRKHYLKERPIDPIYVNILDDNSYSTLEGFNISSQGSNDFQGQLLESSYFEKIESNALRAFIKICPRNGL LYNAIYRNSKNYLNNIDLEDKKTTSKTNVSYPCSLLNGCIEVENKDLFLISNKDSLNDINLSEEKIKPETTV FFKDKLPPQDITLSNYDFTEANSIPSISQQNILERNEELYEPIRNSLFEIKTIYVDKLTTFHFLEAQNIDES IDSSKIRVELTDSVDEALSQNPNKVYSPFKNMSNTINSIETGITSTYIFYQWLRSIVKDFSDETGKIDVIDK SSQDTLAIVPYIGPLLNIGNDIRHGDFVGAIELAGITALLEYVPEFTIPILVGLEVIGGELAREQVEAIVNN ALDKRDQKWAEVYNITKAQWWGTIHLQINTRLAHTYKALSRQANAIKMNMEFQLANYKGNIDDKAKIKNAIS ETEILLNKSQVEQAMKNTEKFMIKLSNSYLTKEMIPKVQDNLKNFDLETKKTLDKFIKEKEDILGTNLSQS SLRRKVSIRLNKNIAFDINDIPFSEFDDLINQYKNEI |
| 39 | VAMP1 | MSAPAQPPAEGTEGTAPGGGPPGPPPNMTSQNRRLQQTQAQVEEVVDIIRVNVDKVLERDQKLSELDDRADA LQAGASQFESQSAAKLKRKYWWKNCKMMIMLGAICAIIVVVIVIYFFT |

TABLE 1-continued

BoNT Polypeptide Sequences

| SEQ ID NO. | Description | Sequence |
| --- | --- | --- |
| 40 | VAMP2 | MSATAATAPPAAPAGEGGPPAPPPNLTSQNRRLQQTQAQVDEVVDIMRVNVDKVLERDQKLSQELDDRADAL<br>QAGASQQFETSQAAKLKRKYWWKNLKMMIILGVICAIILIIIIVYFSSQ |
| 41 | VAMP3 | MSTGVPSGSSAATGSNRRLQQTQNQVDEVVDIMRVNVDKVLERDQKLSELDDRADALQAGASQFETSAAKLK<br>RKYWWKNCKMWAIGISQVLVIIVIIIIVWCVSQ |
| 42 | VAMP4 | MPPKFKRHLNDDDVTGSQVKSERRNLLEDDSDEEEDFFLRGPSGPRFGPRNDKIKHVQNQVDEVIDVMQENI<br>TKVIERGERLDELQDKSESLSDNATAFSNRSKQLRRQMWWRGCKIKAIMALVAAILLLVIIILIVMKYRT |
| 43 | VAMP5 | MAGIELERCQQQANEVTEIMRNNFGKVLERGVKLAELQQRSDQLLDMSSTFNKTTQNLAQKKCWENIRYRIC<br>VGLVVVGVLLIILIVLLVVFLPQSSDSSSAPRTQDAGIASGPGN |
| 44 | Ykt6 | MKLYSLSVLYKGEAKVVLLKAAYDVSSFSFFQRSSVQEFMTFTSQLIVERSSQKGTRASVKEQDYLCHVYVR<br>NDSLAGVVIADNEYPSRVAFTLLEKVLDEFSKQVDRIDWPVGSPATIHYPALDGHLSRYQNPREADPMTKVQ<br>AELDTEKIILHNTMESLLERGEKLDDLVSKSEVLGTQSKAFYKTARKQNSCCAII |
| 45 | BoNT/X-LC-<br>$H_N$-LPETGG | MKLEINKFNYNDPIDGINVITMRPPRHSQDKINKGKGPFKAFQVIKNIWIVPERYNFTNNTNDLNIPSEPIM<br>EADAIYNPNYLNTPSEKDEFLQGVIKVLERIKSQKPEGEKLLELISSSIPLPLVSNGALTLSDNETIAYQEN<br>NNIVSNLQANLVIYGPGPDIANNATYGLYSTPISNGEGTLSEVSFSPFYLKPFDESYGNYRSLVNIVNKFVK<br>REFAPDPASTLMHELVHVTHNLYGISNRNFYYNFDTGKIETSRQQNSQLIFEELLTFGGIDSKAISSLIIKK<br>IIETAKNNYTTLISERLNTVTVENDLLKYINKIPVQGRLGNFKLDTAEFEKKLNTILFVLNESNLAQRFSI<br>LVRKHYLKERPIDPIYVNILDDNSYSTLEGFNISSQGSNDFQGQLLESSYFEKIESNALRAFIKICPRNGLL<br>YNAIYRNSKNYLNNIDLEDKKTTSKTNVSQYPCSLLNGCIEVENKDLFLISNKDSLNDINLSEEKIKPETTV<br>FFKDKLPPQDITLSNYDFTEANSIPSISQQNILERNEELYEPIRNSLFEIKTIYVDKLTTFHFLEAQNIDES<br>IDSSKIRVELTDSVDEALSQNPNKVYSPFKNMSNTINSIETGITSTYIFYQWLRSIVKDFSDETGKIDVIDK<br>SSQDTLAIVPYIGPLLNIGNDIRHGDFVGAIELAGITALLEYVPEFTIPILVGLEVIGGELAREQVEAIVNN<br>ALDKRDQKWAEVYNITKAQWWGTIHLQINTRLAHTYKALSRQANAIKMNMEFQLANYKGNIDDKAKIKNAIS<br>ETEILLNKSQVEQAMKNTEKFMIKLSNSQYLTKEMIPKVQDNLKNFDLETKKTLDKFIKEKEDILGTNLSQS<br>SLRRKVSIRLNKNIAFDINDIPPSFEFDDLINQYKNEIL<ins>LPETGG</ins> |
| 46 | G-BoNT/X-Hc | GEDYEVLNLGAEDGKIKDLSGTTSDINIGSDIELADGRENKAIKIKGSENSTIKIAMNKYLRFSATDNFSIS<br>FWIKHPKPTNLLNNGIEYTLVENFNQRGWKISIQDSKLIWYLRDHNNSIKIVTPDYIAFNGWNLITITNNRS<br>KGSIVYVNGSKIEEKDISSIWNTEVDDPIIFRLKNNRDTQAFTLLDQFSIYRKELNQNEVVKLYNYYFNSN<br>YIRDIWGNPLQYNKKYYLQTQDKPGKGLSPFGYDYVILSDSKTITFPNNIRYGALYNGSQKVLIKN<br>SKKLDGLVRNKDFIQLEIDGYNMGISADRFNEDTNYIGTTYGTTHDLTTDFEIIQRQEKYRNYCQLKTPYNI<br>FHKSQGLMSTETSKPTFHDYRDWVYSSAWYFQNYENLNLRKHTKTNWYFIPKDEGWDED |
| 47 | BoNT/A1-Hc | IINTSILNLRYESNHLIDLSRYASKINIGSKVNFDPIDKNQIQLFNLESSKIEVILKNAIVYNSMYENFSTS<br>FWIRIPKYFNSISLNNEYTIINCMENNSGWKVSLNYGEIIWTLQDTQEIKQRVVFKYSQMINISDYINRWIF<br>VTITNNRLNNSKIYINGRLIDQKPISNLGNIHASNNIMFKLDGCRDTHRYIWIKYFNLFDKELNEKEIKDLY<br>DNQSNSGILKDFWGDYLQYDKPYYMLNLYDPNKYVDVNNVGIRGYMYLKGPRGSVMTTNIYLNSSQLYRGTK<br>FIIKKYASGNKDNIVRNNDRVYINVVVKNKEYRLATNASQAGVEKILSALEIPDVGNLSQVVVMKSQKNDQG<br>ITNKCKMNLQDNNGNDIGFIGFHQFNNIAKLVASNWYNRQIERSSRTLGCSWEFIPVDDGWGERPL |
| 48 | BoNT/B1-Hc | ILNNIILNLRYKDNNLIDLSQGYGAKVEVYDGVELNDKNQFKLTSQSANSKIRVTQNQNIIFNSVFLDFSVS<br>FWIRIPKYKNDGIQNYIHNEYTIINCMKNNSQGWKISYQIRGNRIIWTLIDINGKTKSQVFFEYNIREDISEY<br>INRWFFVTITNNLNNAKIYINGKLESNTDIKDIREVIANGEIIFKLDGDIDRTQFIWMKYFSQIFNTELSQS<br>NIEERYKIQSYSEYLKDFWGNPLMYNKEYYMFNAGNKNSYIKLKKDSPVGEILTRSKYNQNSKYINYRDLYI<br>GEKFIIRRKSNSQSQINDDIVRKEDYIYLDFFNLNQEWRVYTYKYFKKEEEKLFLAPISDSDEFYNTIQIKE<br>YDEQPTYSCQLLFKKDEESTDEIGLIGIHRFYESGIVFEEYKDYFCISKWYLKEVKRKPYNLKLGCNWQFIP<br>KDEGWTE |
| 49 | BoNT/C1-Hc | INDSKILSLQNRKNTLVDTSGYNAEVSQEEGDVQLNPIFPFDFKLGSSGEDRGKVIVTQNENIVYNSQMYES<br>FSISFWIRINKWVSNLPGYTIIDSVKNNSGWSIGIISQNFLVFTLKQNEDSEQSINFSYDISNNAPGYNKWF<br>FVTVTNNMMGNMKIYINGKLIDTIKVKELTGINFSKTITFEINKIPDTGLITSDSDNINMWIRDFYIFAKEL<br>DGKDINILFNSLQYTNVVKDYWGNDLRYNKEYYMVNIDYLNRYMYANSQRQIVFNTRRNNDFNEGYKIIIK<br>RIRGNTNDTRVRGGDILYFDMTINNKAYNLFMKNETMYADNHSTEDIYAIGLREQTKDINDNIIFQIQPMNN<br>TYYYASQQIFKSQNFNGENISGICSIGTYRFRLGGDWYRHNYLVPTVKQGNYASQLLESTSTHWGFVPVSE |
| 50 | Thrombin<br>cleavage site | LVPRIGSQ |
| 51 | TEV | ENLYFQIG |
| 52 | PreScission<br>cleavage site | LEVLFQIGP |
| 53 | Factor Xa<br>cleavage site | IEGRI |
| 54 | Factor Xa<br>cleavage site | IDGRI |
| 55 | Enterokinase<br>cleavage site | DDDDKI |

TABLE 1-continued

BoNT Polypeptide Sequences

| SEQ ID NO. | Description | Sequence |
|---|---|---|
| 56 | SUMO protease cleavage site | AHREQIGGI |

*mutations are indicated by underlining

A Novel *Botulinum* Neurotoxin and its Derivatives

*Botulinum* neurotoxins (BoNTs) are among the most dangerous potential bioterrorism agents and are also used clinically to treat a growing list of medical conditions. There are seven serotypes of BoNTs (BoNT/A-G) known to date, and no new types have been recognized for the past 45 years. Genomic database searching of *Clostridium botulinum* strains revealed a novel BoNT type, named BoNT/X. This toxin showed the lowest sequence identity with other BoNTs and it is not recognized by antisera raised against known BoNT types. It cleaves vesicle associated membrane protein (VAMP) in neurons, which is also the target of BoNT/B/D/F/G, but BoNT/X cleaves at a site (between Arg66-Ala67 on VAMP2) unique to this toxin. To validate the activity of BoNT/X, a limited amount of full-length BoNT/X were assembled by covalently linking two non-toxic fragments of BoNT/X using a transpeptidase (sortase). Assembled BoNT/X entered cultured neurons and cleaved VAMP2, and caused flaccid paralysis in mice measured by Digit Abduction Score assay. Together, these data established BoNT/X as a novel BoNT type. Its discovery poses an urgent challenge for developing effective countermeasures and also presents a novel tool for potential therapeutic applications.

Searching Genomic Databases Revealed a Novel BoNT Gene

Figure 5:
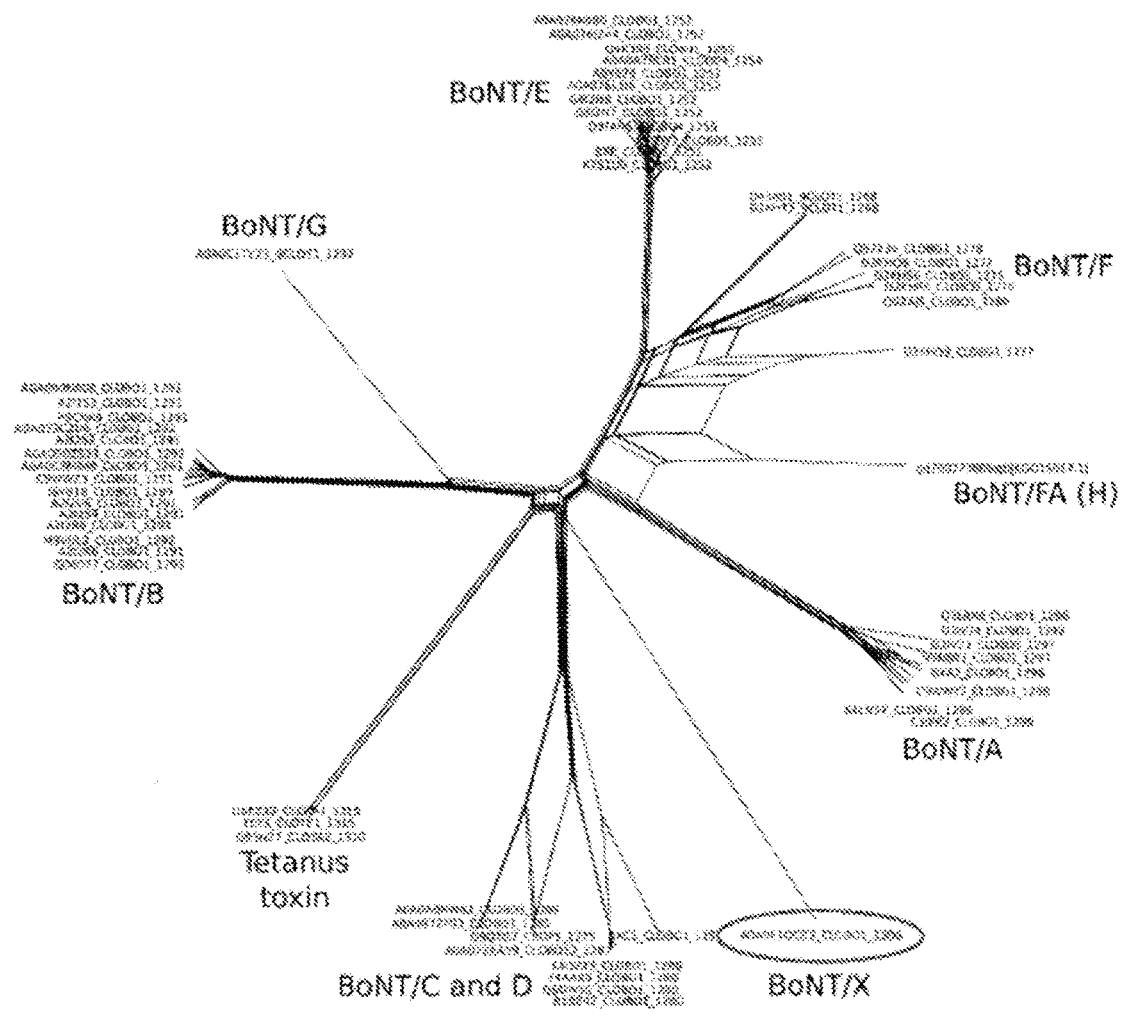

In an attempt to survey the evolutionary landscape of BoNTs, iterative Hidden Markov model searches of the PubMed sequence database were performed, utilizing sequences of the seven BoNTs as probes. The search successfully identified major BoNT serotypes, subtypes, and mosaic toxins, as well as related tetanus neurotoxin (TeNT) (FIG. 5). Unexpectedly, it also revealed a novel BoNT gene (GenBank No. BAQ12790.1), from the recently reported genomic sequence of *Clostridium botulinum* strain 111. This toxin gene is herein designated as BoNT/X.

Phylogenetic analysis revealed that BoNT/X is clear distinct from all other BoNTs and TeNT (FIG. 1A). It has the least protein sequence identity (<31%) from any other BoNTs among pair-wise comparisons within BoNT/TeNT family (FIG. 1A). For instance, BoNT/A and BoNT/B share 39% sequence identity, and BoNT/B and BoNT/G have 58% sequence identity. Furthermore, a sliding sequence comparison window demonstrated that the low similarity is evenly distributed along BoNT/X sequence as compared to the other seven BoNTs and TeNT (FIG. 1B), indicating that it is not a mosaic toxin.

Despite the low sequence identity, the overall domain arrangement and a few key features of BoNTs appear to be conserved in BoNT/X (FIG. 1B), including: (1) a conserved zinc-dependent protease motif HExxH (residues 227-231, HELVH (SEQ ID NO: 92)) is located in the putative LC; (2) there are two conserved cysteines located at the border between the putative LC and HC, which may form the essential inter-chain disulfide bond; (3) a conserved receptor binding motif SxWY exists in the putative $H_C$ (residues 1274-1277, SAWY (SEQ ID NO: 93)), which recognizes lipid co-receptor gangliosides[43,44].

As expected, BoNT/X gene is preceded with a putative NTNHA gene (FIG. 1C). They are located in an OrfX gene cluster. However, the OrfX gene cluster of BoNT/X has two unique features compared to the other two known OrfX clusters (FIG. 1C): (1) there is an additional OrfX2 protein (designated as OrfX2b) located next to the BoNT/X gene, which has not been reported for any other OrfX clusters; (2) the reading frame of OrfX genes has the same direction with the BoNT/X gene, while they are usually opposite to the direction of BoNT gene in other OrfX clusters (FIG. 1C). Together, these features suggest that BoNT/X may constitute a unique evolutionary branch of the BoNT family.

The LC of BoNT/X Cleaves VAMP2 at a Novel Site

Whether BoNT/X is a functional toxin was next examined. First, the LC of BoNT/X (X-LC) was investigated. The border of the LC (residues 1-439) was determined by sequence alignment with other BoNTs. The cDNA encoding the LC was synthesized and the LC was produced as a His6-tagged recombinant protein in *E. coli*. X-LC was incubated with rat brain detergent extracts (BDE) and immunoblot analysis was used to examine whether the three dominant SNARE proteins in the brain, SNAP-25, VAMP2, and syntaxin 1, were cleaved. LCs of BoNT/A (A-LC) and BoNT/B (B-LC) were assayed in parallel as controls. Cleavage of SNAP-25 by BoNT/A generates a smaller fragment that can still be recognized on immunoblot, while cleavage of VAMP2 by BoNT/B abolishes the immunoblot signal of VAMP2 (FIG. 2A). Synaptophysin (Syp), a synaptic vesicle protein, was also detected as an internal loading control. Incubation of X-LC with rat brain DTE did not affect syntaxin 1 or SNAP-25, but abolished VAMP2 signals (FIG. 2A). LCs of BoNTs are zinc-dependent proteases[25]. As expected, EDTA prevented cleavage of SNARE proteins by X-, A-, and B-LCs (FIG. 2A). To further confirm that X-LC cleaves VAMP2, the cytosolic domain of VAMP2 (residues 1-96) as a His6-tagged protein was purified. Incubation of VAMP2 (1-96) with X-LC converted the VAMP2 band into two lower molecular weight bands on SDS-PAGE gel (FIG. 2B), confirming that X-LC cleaves VAMP2.

Figure 6:
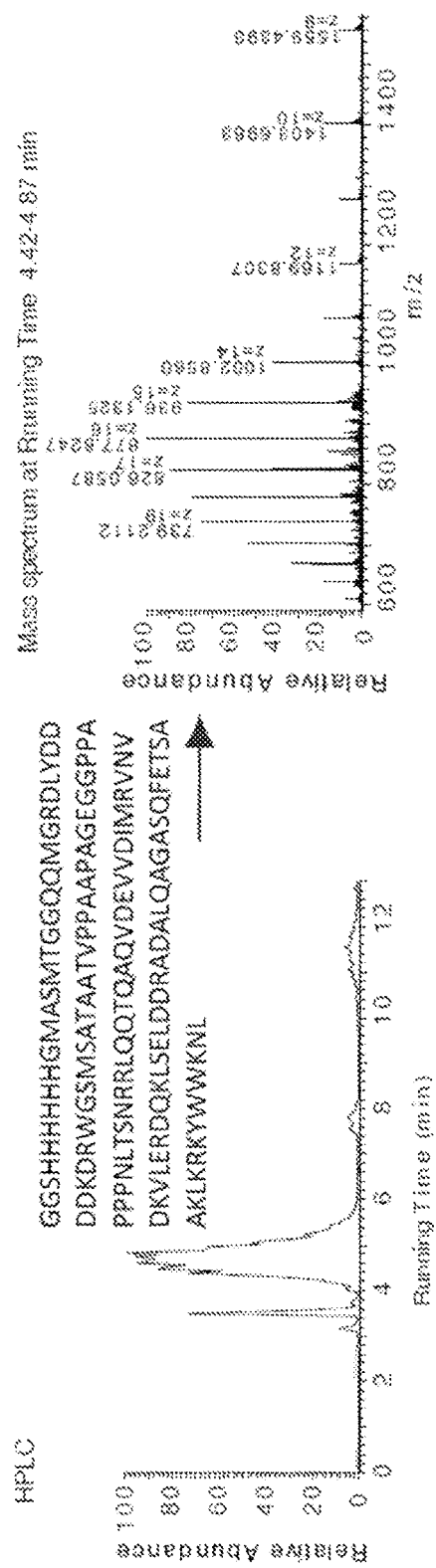
FIG. 6 shows a mass spectrometry analysis of intact VAMP2 (1-96). His6-tagged VAMP2 (1-96) was analyzed by LC-MS/MS mass spectrometry. The HPLC profile is listed in the left panel, together with the protein sequence. The mass spectrometry data for full-length VAMP2 (1-96) was shown in the right panel and corresponds to SEQ ID NO: 83, with m/z value marked for each signal.
Figure 7A:
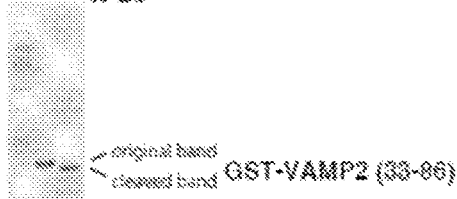
FIGS. 7A-7F shows the identification of the cleavage site on GST-VAMP2 (33-86) by X-LC.
Figure 7B:
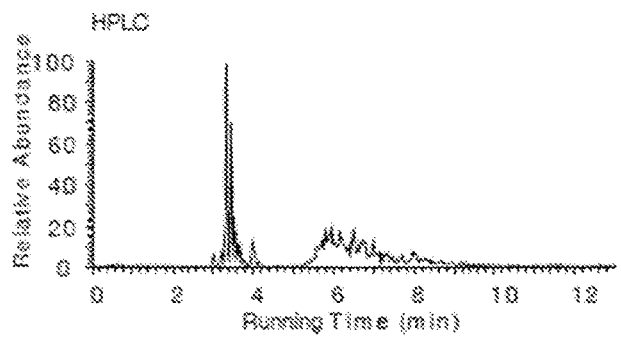
Figure 7C:
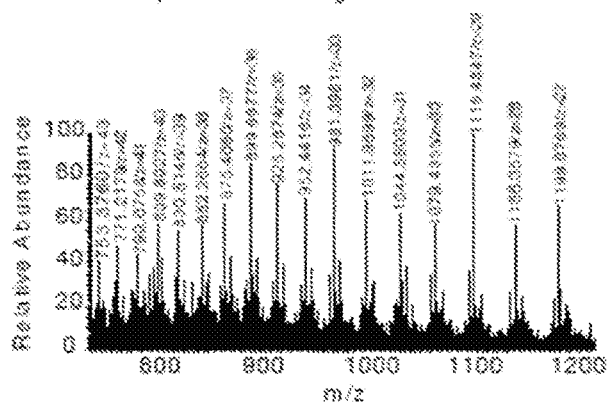
Figure 7D:
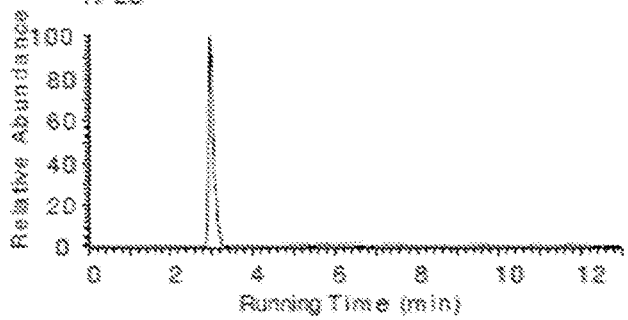
Figure 7E:
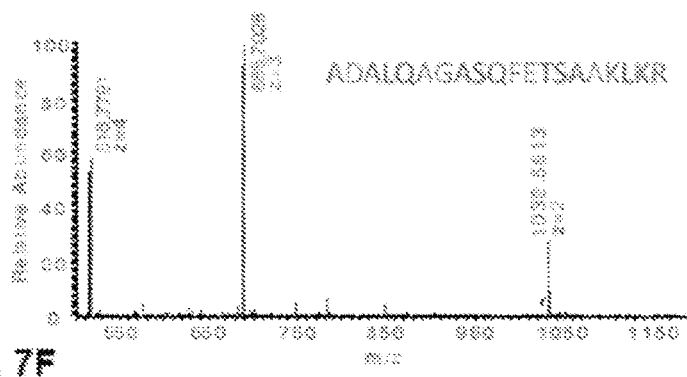
Figure 7F:
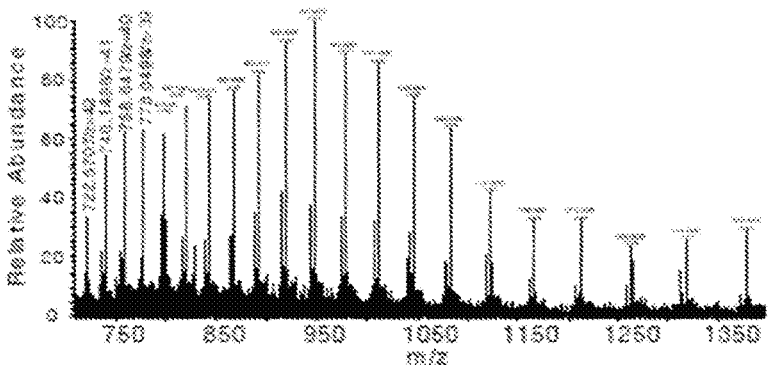

To identify the cleavage site on VAMP2, the VAMP2 (1-96) protein was analyzed with or without pre-incubation with X-LC, by liquid chromatography-tandem mass spectrometry (LC-MS/MS, FIGS. 2C-2E, see below for detail). A single dominant peptide peak appeared after incubation with X-LC (FIGS. 2C, 2E, and 6). Its molecular weight was determined to be 3081.7, which fits only the peptide sequence of residues A67-L96 of VAMP2 (FIGS. 2C, 2E). Consistently, the other fragment from the beginning of the His6-tag to the residue R66 of VAMP2 was also detected (FIG. 2D). To further confirm this result, the assay was repeated with a different VAMP2 fragment: GST-tagged recombinant VAMP2 (33-86) (FIG. 7). Incubation with X-LC generated a single dominant peak, with a molecular weight of 2063.1, which fits only the peptide sequence of residues A67-R86 of VAMP2 (FIGS. 7D-7E). As expected, the other fragment from the beginning of the GST tag to the residue R66 of VAMP2 was also detected (FIG. 7F). Together, these results demonstrated that X-LC has a single cleavage site on VAMP2 between R66 and A67.

R66-A67 is a novel cleavage site distinct from established target sites for all other BoNTs (FIG. 2F). It is also the only BoNT cleavage site located within a region previously known as SNARE motif (FIG. 2F, shaded regions)[45]. VAMP family proteins include VAMP1, 2, 3, 4, 5, 7, 8, as well as related Sec22b and Ykt6. R66-A67 is conserved in VAMP1 and VAMP3, which are highly homologous to VAMP2, but not in other VAMP homologs such as VAMP7 and VAMP8. To validate the specificity of X-LC, HA-tagged full-length VAMP1, 3, 7, 8 and myc-tagged Sec22b and Ykt6 were expressed in HEK293 cells via transient transfection. Cell lysates were incubated with X-LC (FIG. 2G). Both VAMP1 and 3 were cleaved by X-LC, as evidenced by the shift of immunoblot signal to lower molecular weight, while VAMP7, VAMP8, and Sec22B were resistant to X-LC (FIG. 2G).

Figure 13A:
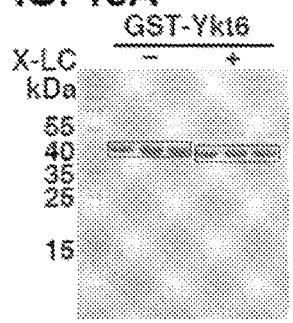
FIGS. 13A-13D show the identification of the cleavage sites of X-LC on Ykt6 by mass spectrometry analysis.
Figure 13B:
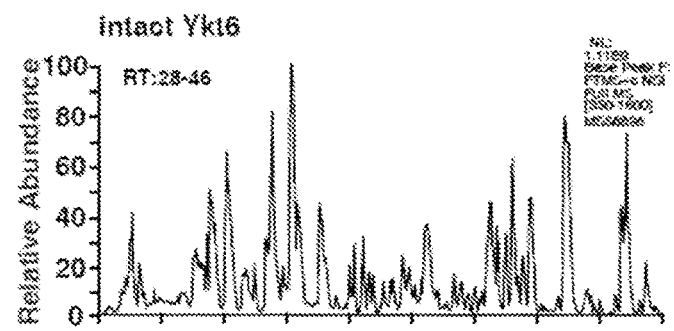
Figure 13C:
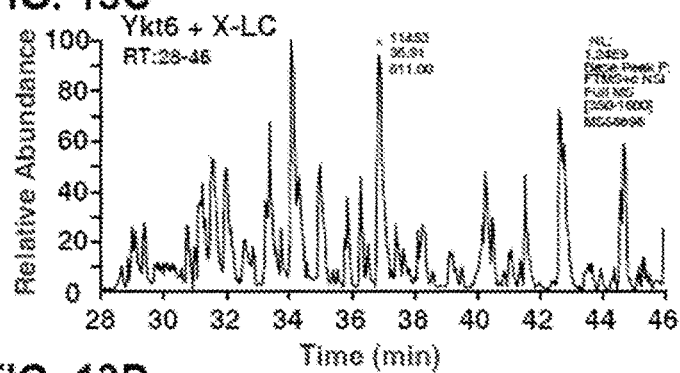
Figure 13D:
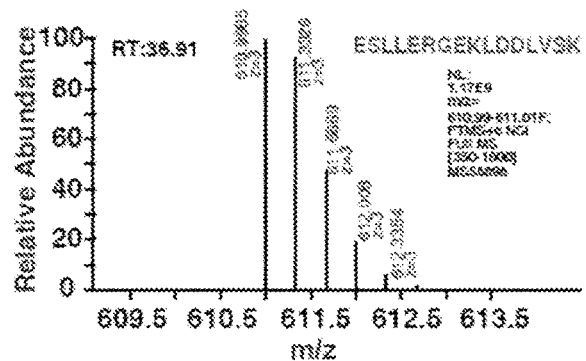
Figure 14A:
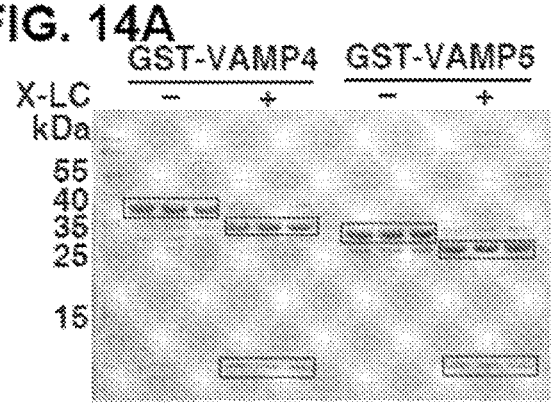
Figure 14B:
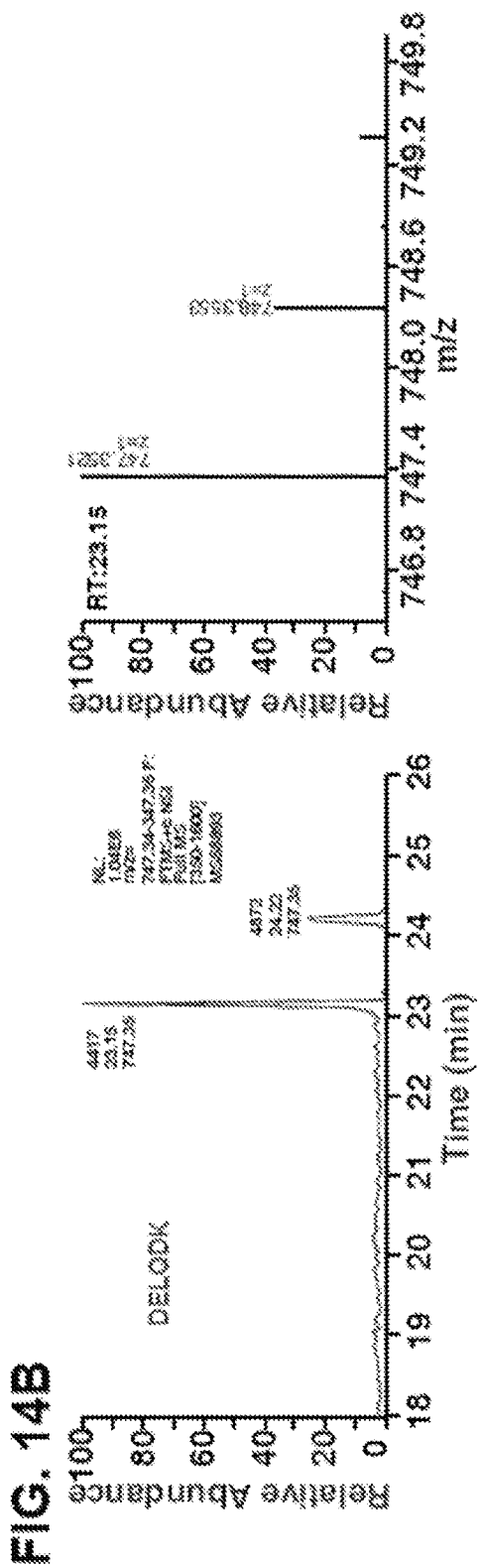
Figure 14C:
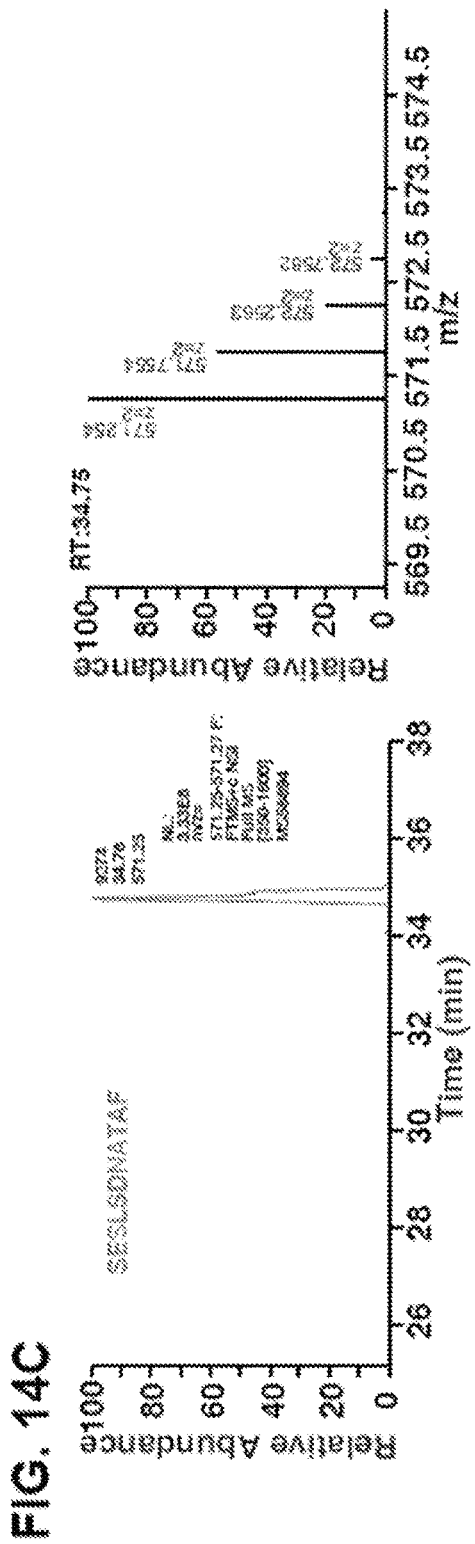
Figure 14D:
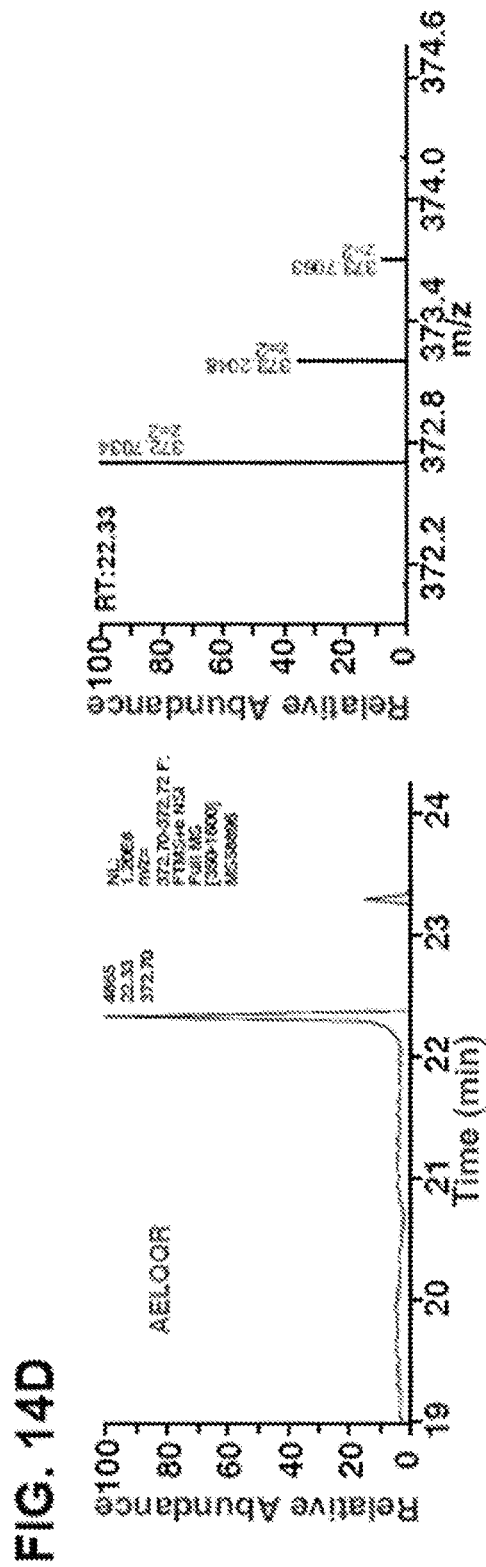

Unexpectedly, Ykt6 was cleaved by X-LC (FIG. 2G). This finding was confirmed using purified GST-tagged Ykt6 fragment, which shifted to a lower molecular weight band after incubation with X-LC (FIG. 2H). The cleavage site was determined to be K173-S174 by mass spectrometry analysis of the intact Ykt6 versus the Ykt6 cleaved by X-LC (FIG. 13A). This is the homologous site to the cleavage site in VAMP2 (FIG. 2F), indicating that the location of the cleavage site is conserved across different VAMPs. Among VAMP members, VAMP4 contains the same pair of residues (K87-S88) at this site as Ykt6. It was found that GST-tagged cytoplasmic domain of VAMP4 was efficiently cleaved by X-LC (FIG. 2I). Consistently, X-LC cleaved native VAMP4 in BDE (FIG. 2J). As a control, Sec22b was not cleaved by X-LC in BDE. In addition, GST-tagged cytoplasmic domain of VAMP5 was also cleaved, although at a slower rate than VAMP2 and VAMP4 (FIG. 2I). The cleavage sites were confirmed to be K87-S88 in VAMP4 and R40-541 in VAMP5 by mass spectrometry analysis (FIG. 14). Both are the homologous sites to the cleavage site in VAMP2 (FIG. 2F). The ability of X-LC to cleave VAMP4, VAMP5, and Ykt6 is highly unusual, as their sequences are substantially different from VAMP1/2/3. BoNT/X is the first BoNT can cleave VAMPs beyond the canonical targets VAMP1/2/3[66]. X-LC also cleaved VAMP4 in BDE, and the cleavage was blocked by EDTA (FIG. 2J).

A remarkable feature of BoNT/X is its unique ability to cleave VAMP4 and Ykt6. VAMP4 is widely expressed and is known to mediate vesicle fusion between trans-Golgi network (TGN) and endosomes, as well as homotypic fusion of endosomes[59,60]. Ykt6 is an atypical SNARE without a transmembrane domain[67-70]. It is anchored to membranes via lipidation, which allows dynamic regulation of its membrane association. Ykt6 is an essential protein in yeast, implicated in multiple membrane fusion events including ER-Golgi, intra-Golgi, endosome-Golgi-vacuolar, and autophagesome formation. Its function in mammalian cells remains to be established. BoNTs are traditionally known to be limited to target SNAREs that mediate vesicle exocytosis onto plasma membranes. BoNT/X is the first BoNT that is capable of cleaving SNAREs mediating various intracellular membrane trafficking events.

Interestingly, both VAMP4 and Ykt6 are enriched in neurons. Recent studies suggested that VAMP4 may also contribute to asynchronous synaptic vesicle exocytosis, enlargeosome exocytosis, and activity-dependent bulk endocytosis (ADBE) in neurons[61-63]. The role of Ykt6 in neurons remains to be established, but it has been shown to suppress the toxicity of α-synuclein in Parkinson's disease models[71-72]. The other substrate of BoNT/X, VAMP5, is mainly expressed in muscle cells and its function remains to be established[64]. BoNT/X will be a powerful tool for investigating VAMP4, Ykt6, and VAMP5 functions and related membrane trafficking events. In addition, VAMP4 has been implicated in granule release in immune cells[65], thus BoNT/X might have a unique potential among all BoNTs to modulate inflammatory secretion in immune cells.

Proteolytic Activation of BoNT/X

BoNTs are initially produced as a single polypeptide. The linker region between LC and $H_N$ needs to be cleaved by either bacterial or host proteases in a process known as "activation", which is essential for the activity of BoNTs. LC and $H_N$ of BoNTs remain connected via an inter-chain disulfide bond prior to translocation of LC into the cytosol of cells, where the disulfide bond is reduced in order to release the LC into the cytosol. Sequence alignment revealed that BoNT/X contains the longest linker region between two conserved cysteines compared to all other BoNTs (C423-C467, FIG. 3A). In addition, the linker region of BoNT/X contains an additional cysteine (C461), which is unique to BoNT/X.

To examine whether the linker region between the LC and $H_N$ of BoNT/X is susceptible to proteolytic cleavage, a recombinant X-LC-$H_N$ fragment (residues 1-891) was produced in E. coli and subjected to limited proteolysis by endoproteinase Lys-C, which cuts at the C-terminal side of lysine residues. To identify the susceptible cleavage site under limited proteolysis conditions, X-LC-$H_N$ was analyzed using Tandem Mass Tag (TMT) labeling and tandem mass spectrometry approach. TMT labels free N-terminus (and lysines). Limited proteolysis by Lys-C produces additional free N-termini, which would not exist in intact X-LC-$H_N$ sample (see below for details). Briefly, intact X-LC-$H_N$ samples were labeled with the light TMT and equal amount of X-LC-$H_N$ samples were exposed to Lys-C and then labeled with the heavy TMT. Both samples were then digested with chymotrypsin, combined together, and subjected to quantitative mass spectrometry analysis. A list of identified peptides was shown in Table 2, below. The light TMT:heavy TMT ratios were usually within 2-fold of each other for each peptide, with the exception for 5 peptides starting with N439, which showed no signal for the light TMT labeling, indicating that this is a new N-terminal generated by Lys-C cutting (FIG. 3A, Table 2). Thus, Lys-C preferentially cuts K438-N439 under limited proteolytic conditions, demonstrating that the linker region is susceptible to proteases (FIG. 3A).

Whether this proteolytic activation is important for the function of BoNT/X was examined next. It has been previously shown that incubation of high concentrations of LC-$H_N$ of BoNTs with cultured neurons resulted in entry of LC-$H_N$ into neurons, likely through non-specific uptake into neurons[46,47]. Using this approach, the potency of intact versus activated X-LC-$H_N$ on cultured rat cortical neurons was compared. Neurons were exposed to X-LC-$H_N$ in media for 12 hours. Cell lysates were harvested and immunoblot analysis was carried out to examine cleavage of SNARE proteins. As shown in FIG. 3B, X-LC-$H_N$ entered neurons and cleaved VAMP2 in a concentration-dependent manner. X-LC-$H_N$ activated by Lys-C showed a drastically increased potency than intact X-LC-$H_N$: 10 nM activated X-LC-$H_N$ cleaved similar levels of VAMP2 as 150 nM intact X-LC-$H_N$ (FIG. 3B). Note that the intact X-LC-H$_N$ is likely susceptible to proteolytic cleavage by cell surface proteases, which is why it is still active on neurons at high concentrations. Interestingly, activated X-LC-H$_N$ appears to be more potent than activated LC-H$_N$ of BoNT/A (A-LC-H$_N$) and BoNT/B (B-LC-H$_N$), which did not show any detectable cleavage of their SNARE substrates in neurons under the same assay conditions (FIG. 3B).

TABLE 2

Peptide fragments of X-LC-HN under limited proteolysis analyzed by TMT labeling and quantitative mass spectrometry.

| ScanF | z | Theo m/z | PPM | X Corr | Δ Corr | Ref | Peptide | Start Pos | End Pos | Max Heavy | Max Light | H/L ratio |
|---|---|---|---|---|---|---|---|---|---|---|---|---|
| 16633 | 2 | 611.384 | 1.46 | 1.751 | 0.651 | xLcHN | K.L]EINK#F.N | 3 | 8 | 4.03E+04 | 2.92E+04 | 1.38 |
| 16638 | 2 | 606.3736 | 0.95 | 1.71 | 0.654 | xLcHN | K.IEINKF.N | 3 | 8 | 4.03E+04 | 2.92E+04 | 1.38 |
| 15946 | 2 | 912.456 | 2.74 | 4.083 | 0.877 | xLcHN | F.N]YNDPIDGINVITM*.R | 9 | 22 | 4.34E+05 | 9.26E+05 | 0.47 |
| 15942 | 2 | 909.9508 | 2.28 | 4.546 | 0.661 | xLcHN | F.NYNDPIDGINVITM*.R | 9 | 22 | 4.34E+05 | 9.26E+05 | 0.47 |
| 17201 | 2 | 785.9092 | 1.26 | 2.455 | 0.273 | xLcHN | F.NYNDPIDGINVLT | 9 | 20 | 1.14E+06 | 1.94E+06 | 0.59 |
| 11082 | 2 | 679.833 | 1.17 | 1.74 | 0.754 | xLcHN | F.NYNDPIDGIN.V | 9 | 18 | 8.01E+05 | 1.20E+06 | 0.67 |
| 11083 | 2 | 682.3382 | 0.96 | 2.6 | 0.742 | xLcHN | F.N]YNDPIDGIN.V | 9 | 18 | 8.01E+05 | 1.20E+06 | 0.67 |
| 19628 | 2 | 535.3264 | 0.97 | 1.391 | 0.701 | xLcHN | D.P]IDGINVLT | 13 | 20 | 6.55E+04 | 1.23E+05 | 0.53 |
| 19626 | 2 | 532.8211 | 0.68 | 1.474 | 0.608 | xLcHN | D.PIDGINVLT | 13 | 20 | 6.55E+04 | 1.23E+05 | 0.53 |
| 20815 | 4 | 802.2073 | 2.19 | 2.962 | 0.582 | xLcHN | Y.N]PNYLNTPSEK#DEFLQGVIK#VL.E | 78 | 99 | 4.57E+04 | 1.21E+05 | 0.38 |
| 20463 | 4 | 802.2073 | 1.96 | 2.726 | 0.385 | xLcHN | Y.N]PNYLNTPSEK#DEFLQGVIK#VL.E | 78 | 99 | 2.96E+04 | 8.18E+04 | 0.36 |
| 20799 | 4 | 798.4495 | 1.91 | 3.647 | 0.659 | xLcHN | Y.NPNYLNTPSEKDEFLQGVIKVL.E | 78 | 99 | 4.57E+04 | 1.21E+05 | 0.38 |
| 20568 | 4 | 798.4495 | 1.63 | 2.639 | 0.419 | xLcHN | Y.NPNYLNTPSEKDEFLQGVIKVL.E | 78 | 99 | 2.96E+04 | 8.18E+04 | 0.36 |
| 22720 | 2 | 753.4631 | 1.96 | 2.339 | 0.222 | xLcHN | L.LELISSSQIPLPL.V | 112 | 123 | 1.40E+04 | 2.80E+04 | 0.50 |
| 21170 | 2 | 696.9211 | 1.9 | 1.781 | 0.326 | xLcHN | LELISSSIPLPL.V | 113 | 123 | 2.75E+04 | 4.15E+04 | 0.66 |
| 21281 | 2 | 696.9211 | 1.86 | 2.099 | 0.282 | xLcHN | LELISSSIPLPL.V | 113 | 123 | 2.75E+04 | 4.15E+04 | 0.66 |
| 21378 | 2 | 696.9211 | 1.83 | 1.593 | 0.149 | xLcHN | LELISSSIPLPL.V | 113 | 123 | 2.75E+04 | 4.15E+04 | 0.66 |
| 19246 | 2 | 578.363 | 1.18 | 1.443 | 0.27 | xLcHN | L.I]SSSIPLPL.V | 115 | 123 | 1.61E+04 | 4.12E+04 | 0.39 |
| 19365 | 2 | 578.363 | 1.08 | 1.624 | 0.135 | xLcHN | L.I]SSSIPLPL.V | 115 | 123 | 1.61E+04 | 4.12E+04 | 0.39 |

TABLE 2-continued

Peptide fragments of X-LC-HN under limited proteolysis analyzed by
TMT labeling and quantitative mass spectrometry.

| ScanF | z | Theo m/z | PPM | X Corr | Δ Corr | Ref | Peptide | Start Pos | End Pos | Max Heavy | Max Light | H/L ratio |
|---|---|---|---|---|---|---|---|---|---|---|---|---|
| 19241 | 2 | 575.8577 | 1 | 1.484 | 0.209 | xLcHN | LISSSIPLPL.V | 115 | 123 | 1.61E+04 | 4.12E+04 | 0.39 |
| 19360 | 2 | 575.8577 | 0.91 | 1.673 | 0.298 | xLcHN | LISSSIPLPL.V | 115 | 123 | 1.61E+04 | 4.12E+04 | 0.39 |
| 13952 | 2 | 948.9912 | 2.47 | 2.562 | 0.54 | xLcHN | L.V]SNGALTLSDNETIAY.Q | 124 | 139 | 2.51E+05 | 3.67E+05 | 0.68 |
| 13949 | 2 | 946.486 | 2.42 | 1.729 | 0.599 | xLcHN | L.VSNGALTLSDNETIAY.Q | 124 | 139 | 2.51E+05 | 3.67E+05 | 0.68 |
| 6712 | 2 | 392.7318 | 0.19 | 1.523 | 0.206 | xLcHN | L.VSNGAL.T | 124 | 129 | 1.18E+05 | 2.03E+05 | 0.58 |
| 10243 | 2 | 678.3482 | 0.73 | 1.499 | 0.616 | xLcHN | L.T]LSDNETIAY.Q | 130 | 139 | 2.14E+05 | 3.67E+05 | 0.58 |
| 10242 | 2 | 675.843 | 0.69 | 1.594 | 0.842 | xLcHN | L.TLSDNETIAY.Q | 130 | 139 | 2.14E+05 | 3.67E+05 | 0.58 |
| 15890 | 2 | 1110.579 | 2.74 | 2.243 | 0.6 | xLcHN | L.Q]ANLVIYGPGPDIANNATY.G | 150 | 168 | 5.20E+04 | 9.82E+04 | 0.53 |
| 15881 | 2 | 1108.073 | 1.86 | 2.121 | 0.673 | xLcHN | L.QANLVIYGPGPDIANNATY.G | 150 | 168 | 5.20E+04 | 9.82E+04 | 0.53 |
| 11142 | 2 | 727.3879 | 1.39 | 1.945 | 0.635 | xLcHN | L.VIYGPGPDIANN.A | 154 | 165 | 1.91E+04 | 3.90E+04 | 0.49 |
| 12879 | 2 | 894.962 | 1.24 | 2.673 | 0.731 | xLcHN | L.VIYGPGPDIANNATY.G | 154 | 168 | 6.62E+05 | 1.25E+06 | 0.53 |
| 10964 | 2 | 707.3541 | 2.8 | 1.39 | 0.466 | xLcHN | Y.GPGPDIANNATY.G | 157 | 168 | 1.42E+04 | 2.24E+04 | 0.63 |
| 11091 | 2 | 456.2473 | 0.78 | 1.352 | 0.765 | xLcHN | N.ATYGLY.S | 166 | 171 | 3.55E+04 | 8.08E+04 | 0.44 |
| 17435 | 2 | 1094.055 | 2.53 | 3.418 | 0.69 | xLcHN | Y.G]LYSTPISNGEGTLSEVSF.S | 169 | 187 | 1.55E+05 | 2.27E+05 | 0.68 |
| 17410 | 2 | 1091.549 | 2.48 | 3.748 | 0.738 | xLcHN | Y.GLYSTPISNGEGTLSEVSF.S | 169 | 187 | 1.55E+05 | 2.27E+05 | 0.68 |
| 19830 | 2 | 1259.631 | 2.15 | 2.885 | 0.676 | xLcHN | Y.G]LYSTPISNGEGTLSEVSFSPF.Y | 169 | 190 | 1.98E+04 | 2.46E+04 | 0.81 |
| 20131 | 3 | 838.4197 | 2.08 | 2.781 | 0.742 | xLcHN | Y.GLYSTPISNGEGTLSEVSFSPF.Y | 169 | 190 | 4.60E+05 | 5.32E+05 | 0.86 |
| 12546 | 2 | 862.9488 | 1.9 | 1.817 | 0.401 | xLcHN | Y.G]LYSTPISNGEGTLS.E | 169 | 183 | 7.95E+04 | 7.83E+04 | 1.02 |
| 12571 | 2 | 860.4436 | 1.84 | 1.528 | 0.588 | xLcHN | Y.GLYSTPISNGEGTLS.E | 169 | 183 | 7.95E+04 | 7.83E+04 | 1.02 |
| 19819 | 3 | 838.4197 | 1.61 | 2.655 | 0.662 | xLcHN | Y.GLYSTPISNGEGTLSEVSFSPF.Y | 169 | 190 | 4.13E+04 | 4.59E+04 | 0.90 |

TABLE 2-continued

Peptide fragments of X-LC-HN under limited proteolysis analyzed by
TMT labeling and quantitative mass spectrometry.

| ScanF | z | Theo m/z | PPM | X Corr | Δ Corr | Ref | Peptide | Start Pos | End Pos | Max Heavy | Max Light | H/L ratio |
|---|---|---|---|---|---|---|---|---|---|---|---|---|
| 9948 | 2 | 851.4307 | 2.54 | 2.044 | 0.765 | xLcHN | Y.STPISNGEGTLSEVS.F | 172 | 186 | 1.92E+04 | 2.39E+04 | 0.81 |
| 18409 | 2 | 1090.541 | 2.45 | 4.434 | 0.844 | xLcHN | Y.STPISNGEGTLSEVSFSPF.Y | 172 | 190 | 8.21E+05 | 9.22E+05 | 0.89 |
| 18417 | 2 | 1090.541 | 2.39 | 3.307 | 0.82 | xLcHN | Y.STPISNGEGTLSEVSFSPF.Y | 172 | 190 | 8.21E+05 | 9.22E+05 | 0.89 |
| 18418 | 2 | 1093.047 | 2.39 | 2.983 | 0.845 | xLcHN | Y.S]TPISNGEGTLSEVSFSPF.Y | 172 | 190 | 8.21E+05 | 9.22E+05 | 0.89 |
| 18876 | 2 | 1093.047 | 1.97 | 1.841 | 0.679 | xLcHN | Y.S]TPISNGEGTLSEVSFSPF.Y | 172 | 190 | 8.21E+05 | 9.22E+05 | 0.89 |
| 14591 | 2 | 927.4701 | 1.96 | 3.362 | 0.646 | xLcHN | Y.S]TPISNGEGTLSEVSF.S | 172 | 187 | 2.09E+05 | 1.42E+05 | 1.48 |
| 14803 | 2 | 924.9649 | 1.88 | 1.934 | 0.462 | xLcHN | Y.STPISNGEGTLSEVSF.S | 172 | 187 | 2.96E+05 | 4.65E+05 | 0.64 |
| 14852 | 2 | 924.9649 | 1.87 | 1.538 | 0.369 | xLcHN | Y.STPISNGEGTLSEVSF.S | 172 | 187 | 2.96E+05 | 4.65E+05 | 0.64 |
| 18554 | 2 | 1093.047 | 1.72 | 3.044 | 0.86 | xLcHN | Y.S]TPISNGEGTLSEVSFSPF.Y | 172 | 190 | 8.21E+05 | 9.22E+05 | 0.89 |
| 18552 | 2 | 1090.541 | 1.68 | 3.643 | 0.813 | xLcHN | Y.STPISNGEGTLSEVSFSPF.Y | 172 | 190 | 8.21E+05 | 9.22E+05 | 0.89 |
| 14978 | 2 | 927.4701 | 1.68 | 1.401 | 0.31 | xLcHN | Y.S]TPISNGEGTLSEVSF.S | 172 | 187 | 4.96E+04 | 7.37E+04 | 0.67 |
| 18680 | 2 | 1093.047 | 1.66 | 1.656 | 0.717 | xLcHN | Y.S]TPISNGEGTLSEVSFSPF.Y | 172 | 190 | 8.21E+05 | 9.22E+05 | 0.89 |
| 20660 | 2 | 1093.047 | 1.63 | 2.182 | 0.831 | xLcHN | Y.S]TPISNGEGTLSEVSFSPF.Y | 172 | 190 | 5.24E+05 | 5.44E+05 | 0.96 |
| 17226 | 2 | 924.9649 | 1.62 | 2.459 | 0.698 | xLcHN | Y.STPISNGEGTLSEVSF.S | 172 | 187 | 3.25E+05 | 5.31E+05 | 0.61 |
| 17306 | 2 | 924.9649 | 1.62 | 2.126 | 0.588 | xLcHN | Y.STPISNGEGTLSEVSF.S | 172 | 187 | 3.25E+05 | 5.31E+05 | 0.61 |
| 10139 | 2 | 696.3644 | 1.61 | 1.942 | 0.628 | xLcHN | Y.S]TPISNGEGTLS.E | 172 | 183 | 6.39E+04 | 8.46E+04 | 0.76 |
| 18674 | 2 | 1090.541 | 1.59 | 2.423 | 0.765 | xLcHN | Y.STPISNGEGTLSEVSFSPF.Y | 172 | 190 | 8.21E+05 | 9.22E+05 | 0.89 |
| 20642 | 2 | 1090.541 | 1.55 | 2.608 | 0.823 | xLcHN | Y.STPISNGEGTLSEVSFSPF.Y | 172 | 190 | 5.24E+05 | 5.44E+05 | 0.96 |

TABLE 2-continued

Peptide fragments of X-LC-HN under limited proteolysis analyzed by
TMT labeling and quantitative mass spectrometry.

| ScanF | z | Theo m/z | PPM | X Corr | Δ Corr | Ref | Peptide | Start Pos | End Pos | Max Heavy | Max Light | H/L ratio |
|---|---|---|---|---|---|---|---|---|---|---|---|---|
| 8077 | 2 | 696.3644 | 1.54 | 1.763 | 0.707 | xLcHN | Y.S]TPISNGEGTLS.E | 172 | 183 | 1.09E+05 | 1.29E+05 | 0.84 |
| 18476 | 2 | 562.2872 | 1.17 | 1.812 | 0.784 | xLcHN | L.SEVSFSQPF.Y | 183 | 190 | 4.49E+04 | 7.11E+04 | 0.63 |
| 18478 | 2 | 564.7924 | 0.95 | 1.57 | 0.965 | xLcHN | L.S]EVSFSQPF.Y | 183 | 190 | 4.49E+04 | 7.11E+04 | 0.63 |
| 13190 | 3 | 652.0048 | 0.97 | 2.099 | 0.697 | xLcHN | F.Y]LK#PFDESYGNY.R | 191 | 202 | 1.98E+06 | 3.09E+06 | 0.64 |
| 12839 | 3 | 540.6289 | 0.38 | 2.441 | 0.423 | xLcHN | F.Y]LK#PFDESY.G | 191 | 199 | 2.43E+05 | 5.45E+05 | 0.44 |
| 7115 | 2 | 538.7403 | 0.69 | 1.476 | 0.615 | xLcHN | F.D]ESYGNY.R | 196 | 202 | 1.44E+05 | 3.14E+05 | 0.46 |
| 16124 | 3 | 661.3911 | 1.14 | 2.123 | 0.575 | xLcHN | Y.G]NYRSQLVNIVNK#F.V | 200 | 212 | 2.81E+04 | 2.27E+04 | 1.24 |
| 11646 | 3 | 474.5894 | 0.49 | 2.077 | 0.602 | xLcHN | H.NLYGISQNRNF.Y | 235 | 244 | 2.80E+05 | 4.38E+05 | 0.64 |
| 10091 | 4 | 603.8103 | 1.23 | 2.98 | 0.756 | xLcHN | F.YYNFDTGKIETSRQQN.S | 245 | 260 | 3.05E+05 | 1.94E+05 | 1.57 |
| 9932 | 4 | 603.8103 | 1.08 | 2.5 | 0.638 | xLcHN | F.YYNFDTGKIETSRQQN.S | 245 | 260 | 3.05E+05 | 1.94E+05 | 1.57 |
| 10782 | 3 | 820.4359 | 0.65 | 2.156 | 0.438 | xLcHN | Y.Y]NFDTGK#IETSRQQNSL.I | 246 | 262 | 7.40E+04 | 1.33E+05 | 0.56 |
| 15039 | 3 | 819.1317 | 1.41 | 2.281 | 0.516 | xLcHN | L.ISERLNTVTVENDLLKY.I | 298 | 314 | 1.45E+05 | 2.76E+05 | 0.53 |
| 13824 | 3 | 619.6838 | 1.27 | 2.021 | 0.44 | xLcHN | L.NTVTVENDLLKY.I | 303 | 314 | 3.10E+04 | 5.07E+04 | 0.61 |
| 10975 | 2 | 760.4251 | 1.45 | 2.089 | 0.663 | xLcHN | F.V]LNESQNLAQRF.S | 345 | 355 | 4.63E+05 | 6.60E+05 | 0.70 |
| 17696 | 3 | 966.86 | 2.14 | 2.704 | 0.532 | xLcHN | H.Y]LK#ERPIDPIYVNILDDNSQY.S | 363 | 382 | 8.61E+04 | 1.42E+05 | 0.61 |
| 20823 | 2 | 827.9299 | 2.21 | 2.495 | 0.806 | xLcHN | D.P]IYVNILDDNSY.SQ | 371 | 382 | 7.80E+04 | 8.16E+04 | 0.96 |
| 20825 | 2 | 825.4247 | 2.17 | 2.958 | 0.881 | xLcHN | D.PIYVNILDDNSY.S | 371 | 382 | 7.80E+04 | 8.16E+04 | 0.96 |
| 12614 | 2 | 685.3561 | 1.34 | 1.843 | 0.609 | xLcHN | N.I]LDDNSYSTL.E | 376 | 385 | 1.01E+05 | 2.57E+05 | 0.39 |
| 11272 | 2 | 441.7421 | 1.48 | 1.795 | 0.903 | xLcHN | Y.S]TLEGF.N | 383 | 388 | 4.45E+04 | 1.36E+05 | 0.33 |
| 11261 | 2 | 439.2369 | 1.08 | 1.536 | 0.514 | xLcHN | Y.STLEGF.N | 383 | 388 | 4.45E+04 | 1.36E+05 | 0.33 |
| 14260 | 2 | 441.7421 | 0.49 | 1.462 | 0.848 | xLcHN | Y.S]TLEGF.N | 383 | 388 | 5.41E+04 | 1.32E+05 | 0.41 |

TABLE 2-continued

Peptide fragments of X-LC-HN under limited proteolysis analyzed by TMT labeling and quantitative mass spectrometry.

| ScanF | z | Theo m/z | PPM | X Corr | Δ Corr | Ref | Peptide | Start Pos | End Pos | Max Heavy | Max Light | H/L ratio |
|---|---|---|---|---|---|---|---|---|---|---|---|---|
| 14246 | 2 | 439.2369 | 0.38 | 1.46 | 0.844 | xLcHN | Y.STLEGF.N | 383 | 388 | 5.41E+04 | 1.32E+05 | 0.41 |
| 13808 | 2 | 916.4629 | 2.48 | 2.036 | 0.498 | xLcHN | F.NISSQGSNDFQGQLL.E | 389 | 403 | 2.86E+04 | 6.39E+04 | 0.45 |
| 17314 | 3 | 815.7238 | 2.05 | 2.149 | 0.621 | xLcHN | F.NISSQGSNDFQGQLLESSYF.E | 389 | 408 | 1.26E+05 | 2.71E+05 | 0.47 |
| 6340 | 2 | 803.3788 | 0.75 | 2.554 | 0.721 | xLcHN | F.NISSQGSNDFQGQ.L | 389 | 401 | 1.03E+04 | 2.21E+04 | 0.47 |
| 11696 | 2 | 493.2814 | 0.67 | 1.62 | 0.518 | xLcHN | L.L]YNAIY.R | 429 | 434 | 1.19E+05 | 1.87E+05 | 0.63 |
| 11692 | 2 | 490.7762 | 0.6 | 1.57 | 0.118 | xLcHN | LLYNAIY.R | 429 | 434 | 1.19E+05 | 1.87E+05 | 0.63 |
| 14021 | 3 | 756.4332 | 2A4 | 2.305 | 0.363 | xLcHN | K.N1YLNNIDLEDK#K#T.T | 439 | 451 | 6.85E+05 | 5.12E+03 | 133.95 |
| 12997 | 3 | 1009.909 | 1.93 | 3.044 | 0.553 | xLcHN | KK.N1YLNNIDLEDK#K#TTSK#TN.Y | 439 | 456 | 4.24E+05 | 0.00E+00 | #DIV/0! |
| 12932 | 3 | 1009.909 | 1.92 | 4.251 | 0.695 | xLcHN | K.N1YLNNIDLEDK#K#TTSK#TN.Y | 439 | 456 | 4.24E+05 | 0.00E+00 | #DIV/0! |
| 14003 | 3 | 790.1157 | 1.59 | 2.894 | 0.542 | xLcHN | K.N1YLNNIDLEDK#K#TT | 439 | 452 | 4.40E+06 | 1.13E+04 | 389.24 |
| 13105 | 4 | 729.173 | 1 | 3 | a599 | xLcHN | K.N1YLNNIDLEDK#K#TTSK#T.N | 439 | 455 | 3.39E+06 | 3.14E+03 | 1078.97 |
| 11567 | 3 | 747.091 | 1.33 | 2.711 | 0.518 | xLcHN | N.YLNNIDLEDKKTT.S | 440 | 452 | 1.22E+04 | 9.52E+04 | 0.13 |
| 11515 | 3 | 747.091 | 1.33 | 2.729 | 0.496 | xLcHN | N.YLNNIDLEDKKTT.S | 440 | 452 | 1.22E+04 | 9.52E+04 | 0.13 |
| 17001 | 2 | 857.9579 | 1.99 | 1.967 | 0.713 | xLcHN | G.CIEVENKDLF.L | 467 | 476 | 3.29E+04 | 1.64E+05 | 0.20 |
| 16337 | 4 | 941.793 | 1.76 | 2.419 | 0.135 | xLcHN | F.L]ISNK#DSLNDINLSEEK#IK#PETTVF.F | 477 | 501 | 1.27E+06 | 1.06E+06 | 1.19 |
| 16394 | 4 | 941.793 | 1.72 | 2.19 | 0.391 | xLcHN | F.L]ISNK#DSLNDINLSEEK#IK#PETTVF.F | 477 | 501 | 1.27E+06 | 1.06E+06 | 1.19 |
| 17983 | 3 | 993.888 | 2.4 | 3.193 | 0.657 | xLcHN | K.D]SLNDINLSEEK#IK#PETTVF.F | 482 | 501 | 3.27E+04 | 2.59E+03 | 12.64 |

TABLE 2-continued

Peptide fragments of X-LC-HN under limited proteolysis analyzed by
TMT labeling and quantitative mass spectrometry.

| ScanF | z | Theo m/z | PPM | X Corr | Δ Corr | Ref | Peptide | Start Pos | End Pos | Max Heavy | Max Light | H/L ratio |
|---|---|---|---|---|---|---|---|---|---|---|---|---|
| 18031 | 3 | 955.5456 | 2.06 | 3.607 | 0.764 | xLcHN | D.S]LNDI NLSEEK#I K#PETTVF .F | 483 | 501 | 4.90E+04 | 4.12E+04 | 1.19 |
| 11720 | 2 | 834.8912 | 2.14 | 1.689 | 0.726 | xLcHN | L.SNYDFT EANSIPS. I | 514 | 526 | 2.91E+04 | 2.50E+04 | 1.17 |
| 13409 | 2 | 1065.513 | 2.12 | 4.742 | 0.769 | xLcHN | L.S]NYDF TEANSIPS QISQQ.N | 514 | 530 | 7.05E+04 | 7.52E+04 | 0.94 |
| 8896 | 2 | 642.7908 | 1.42 | 1.851 | 0.708 | xLcHN | L.SNYDFT EAN.S | 514 | 522 | 2.12E+05 | 2.27E+05 | 0.94 |
| 8883 | 2 | 645.296 | 1.39 | 2.362 | 0.879 | xLcHN | L.S]NYDF TEAN.S | 514 | 522 | 2.12E+05 | 2.27E+05 | 0.94 |
| 17774 | 2 | 1051.044 | 2.7 | 1.967 | 0.9 | xLcHN | Y.DFTEAN SIPSISQQ NIL.E | 517 | 533 | 3.52E+04 | 3.28E+04 | 1.07 |
| 17438 | 2 | 1051.044 | 2.55 | 1.944 | 0.665 | xLcHN | Y.DFTEAN SIPSISQQ NIL.E | 517 | 533 | 9.04E+04 | 8.08E+04 | 1.12 |
| 12784 | 2 | 880.9387 | 1.87 | 2.537 | 0.778 | xLcHN | Y.DFTEAN SIPSISQQ .N | 517 | 530 | 4.72E+05 | 5.06E+05 | 0.93 |
| 12779 | 2 | 883.4439 | 1.73 | 3.423 | 0.797 | xLcHN | Y.D]FTEA NSIPSISQ Q.N | 517 | 530 | 4.72E+05 | 5.06E+05 | 0.93 |
| 16126 | 4 | 911.7114 | 1.6 | 3.934 | 0.579 | xLcHN | Y.DFTEAN SIPSISQQ NILERNEE LYEPIRN. S | 517 | 545 | 5.41E+05 | 2.02E+05 | 2.67 |
| 12449 | 2 | 937.9602 | 1.56 | 3.012 | 0.73 | xLcHN | Y.DFTEAN SIPSISQQ N.I | 517 | 531 | 5.16E+05 | 5.72E+05 | 0.90 |
| 12151 | 2 | 940.4654 | 1.47 | 1.476 | 0.458 | xLcHN | Y.D]FTEA NSIPSISQ QN.I | 517 | 531 | 4.65E+05 | 4.96E+05 | 0.94 |
| 20080 | 3 | 1106.923 | 2.52 | 3.592 | 0.677 | xLcHN | N.S]IPSI SQQQNILE RNEELYEP IRNSLF.E | 523 | 548 | 1.86E+04 | 1.52E+04 | 1.23 |
| 11314 | 3 | 700.7002 | 1.59 | 2.563 | 0.763 | xLcHN | L.TDSVDE ALSNPNKV Y.S | 583 | 597 | 1.74E+05 | 1.84E+05 | 0.95 |
| 11315 | 3 | 704.0405 | 1.56 | 2.444 | 0.262 | xLcHN | L.T]DSVD EALSNPNK #VY.S | 583 | 597 | 1.74E+05 | 1.84E+05 | 0.95 |
| 11916 | 3 | 700.7002 | 1.52 | 2.049 | 0.508 | xLcHN | L.TDSVDE ALSNPNKV Y.S | 583 | 597 | 2.27E+05 | 2.78E+05 | 0.82 |
| 7902 | 2 | 635.3637 | 0.25 | 1.478 | 0.567 | xLcHN | L.SNPNKV Y.S | 591 | 597 | 6.79E+05 | 8.90E+05 | 0.76 |
| 7903 | 2 | 640.3742 | 0.25 | 1.485 | 0.282 | xLcHN | L.S]NPNK #VY.S | 591 | 597 | 6.79E+05 | 8.90E+05 | 0.76 |

TABLE 2-continued

Peptide fragments of X-LC-HN under limited proteolysis analyzed by TMT labeling and quantitative mass spectrometry.

| ScanF | z | Theo m/z | PPM | X Corr | Δ Corr | Ref | Peptide | Start Pos | End Pos | Max Heavy | Max Light | H/L ratio |
|---|---|---|---|---|---|---|---|---|---|---|---|---|
| 14536 | 3 | 927.1457 | 1.59 | 2.027 | 0.553 | xLcHN | Y.S]PFK#NM*SNTINSIETGITSTY.I | 598 | 618 | 1.47E+05 | 8.07E+04 | 1.83 |
| 14487 | 3 | 923.8054 | 1.54 | 2.35 | 0.708 | xLcHN | Y.SPFKNM*SNTINSIETGITSQTY.I | 598 | 618 | 1.47E+05 | 8.07E+04 | 1.83 |
| 13108 | 3 | 813.421 | 2.03 | 2.046 | 0.548 | xLcHN | F.KNM*SQNTINSIETGITSTY.I | 601 | 618 | 2.41E+06 | 2.42E+06 | 1.00 |
| 12962 | 3 | 813.421 | 1.98 | 2.378 | 0.482 | xLcHN | F.KNM*SQNTINSIETGITSTY.I | 601 | 618 | 2.41E+06 | 2.42E+06 | 1.00 |
| 13079 | 3 | 813.421 | 1.98 | 2.245 | 0.617 | xLcHN | F.KNM*SQNTINSIETGITSTY.I | 601 | 618 | 2.41E+06 | 2.42E+06 | 1.00 |
| 13194 | 2 | 915.4701 | 2.12 | 1.504 | 0.654 | xLcHN | M.S]NTINSIETGITSQTY.I | 604 | 618 | 1.74E+05 | 3.22E+05 | 0.54 |
| 13170 | 2 | 912.9649 | 1.99 | 1.791 | 0.699 | xLcHN | M.SNTINSQIETGITSTY.I | 604 | 618 | 1.74E+05 | 3.22E+05 | 0.54 |
| 12405 | 2 | 812.4274 | 2.38 | 1.349 | 0.781 | xLcHN | N.TINSIETGITSTY.I | 606 | 618 | 2.94E+04 | 3.41E+04 | 0.86 |
| 14318 | 3 | 837.465 | 1.53 | 2.439 | 0.647 | xLcHN | F.S]DETGK#IDVIDK#SSDTLA | 632 | 648 | 2.23E+04 | 1.55E+04 | 1.44 |
| 19535 | 2 | 586.368 | 0.52 | 1.753 | 0.731 | xLcHN | L.A]IVPYIGPL.L | 649 | 657 | 7.93E+05 | 1.16E+06 | 0.69 |
| 19564 | 2 | 442.268 | 0.43 | 1.498 | 0.892 | xLcHN | V.PYIGPL.L | 652 | 657 | 1.30E+04 | 2.64E+04 | 0.49 |
| 9998 | 2 | 715.396 | 1.76 | 2.148 | 0.33 | xLcHN | V.I]GGELAREQVE.A | 699 | 709 | 8.53E+04 | 1.32E+04 | 6.44 |
| 5372 | 3 | 494.9536 | 0.34 | 2.943 | 0.626 | xLcHN | L.SRQANAIKM*.N | 754 | 762 | 2.50E+05 | 1.57E+04 | 15.97 |
| 5363 | 3 | 494.9536 | 0.32 | 3.357 | 0.734 | xLcHN | L.SRQANAIKM*.N | 754 | 762 | 2.50E+05 | 1.57E+04 | 15.97 |
| 17794 | 2 | 734.3537 | 1.89 | 2.212 | 0.79 | xLcHN | F.SEFDDLINQY.K | 879 | 888 | 3.00E+05 | 4.05E+05 | 0.74 |
| 14171 | 4 | 757.641 | 0.97 | 2.289 | 0.421 | xLcHN | F.DDLINQYKNEGSILPETGGLEHH.H | 882 | 904 | 1.02E+04 | 3.96E+04 | 0.26 |
| 7676 | 4 | 679.3532 | 1.49 | 2.624 | 0.624 | xLcHN | Y.KNEGSILPETGGLEHHHHHH.- | 889 | 908 | 3.63E+04 | 3.74E+04 | 0.97 |
| 13193 | 3 | 588.3365 | 1.18 | 2.307 | 0.629 | xLcHN | Y.KNEGSILPETGGL.E | 889 | 901 | 2.81E+05 | 3.08E+05 | 0.91 |
| 10362 | 3 | 677.037 | 1.15 | 2.582 | 0.615 | xLcHN | Y.KNEGSILPETGGLEH.H | 889 | 903 | 8.01E+05 | 1.17E+06 | 0.68 |

TABLE 2-continued

Peptide fragments of X-LC-HN under limited proteolysis analyzed by
TMT labeling and quantitative mass spectrometry.

| ScanF | z | Theo m/z | PPM | X Corr | Δ Corr | Ref | Peptide | Start Pos | End Pos | Max Heavy | Max Light | H/L ratio |
|---|---|---|---|---|---|---|---|---|---|---|---|---|
| 9325 | 4 | 542.2943 | 1.06 | 2.617 | 0.58 | xLcHN | Y.KNEGSI LPETGGLE HH.H | 889 | 904 | 2.17E+05 | 2.96E+05 | 0.73 |

His6-tagged recombinant X-LC-$H_N$ was labeled with the light TMT. Equal amount of X-LC-$H_N$ samples were exposed to Lys-C and then labeled with the heavy TMT. Both samples were then digested with chymotrypsin, combined together, and subjected to quantitative mass spectrometry analysis. A list of identified peptides was shown. The light TMT:heavy TMT ratios are within 2-fold of each other for all peptide, except five peptides (underlined) starting with N439. These five peptides showed no signal for the light TMT labeling, indicating that N439 is a new N-terminal generated by Lys-C cutting. The peptide sequences in Table 2 correspond, from top to bottom, to SEQ ID NOs: 94-226.

Unique Feature of the Disulfide Bond in BoNT/X

The linker region of BoNT/X contains an additional cysteine (C461), which is unique to BoNT/X. To determine which cysteine forms the disulfide bond connecting the LC and HC, three X-LC-$H_N$ mutants were generated, with each of the three cysteine residues mutated (C423S, C461S, and C467S). These three cysteine mutants, as well as wild type (WT) X-LC-$H_N$ were subjected to limited proteolysis and then analyzed via SDS-PAGE and Coomassie Blue staining, with or without reducing agent DTT (FIG. 3C). It was found that mutating the cysteine on the LC (C423S) resulted in a protein that separated into two ~50 kDa bands, with or without DTT, indicating that C423S abolished the inter-chain disulfide bond. In contrast, mutants containing either C461S or C467S showed a single band at 100 kDa in the absence of DTT, which separated into two ~50 kDa bands in the presence of DTT, suggesting that both C461 and C467 on the $H_N$ can form inter-chain disulfide bond with C423 on the LC. Also the X-LC-$H_N$ (C423S) mutant appears to be more susceptible to Lys-C than both C461S and C467S mutants, resulting in further degradation of the protein (FIG. 3C). This result suggests that losing the inter-chain disulfide bond may increase the freedom of the LC and $H_N$, thus exposing more surface areas. Furthermore, a portion of WT X-LC-$H_N$ formed aggregates at the top of the SDS-PAGE gel (FIG. 3C). These aggregates are due to formation of inter-molecular disulfide bond, as they disappeared in the presence of DTT (FIG. 3C, +DTT). C423, C461 and C467 are the only three cysteines in X-LC-$H_N$. Mutating any one of three cysteines abolished the X-LC-$H_N$ aggregates (FIG. 3C, −DTT), indicating that formation of inter-molecular disulfide bond is due to existence of an extra cysteine in the linker region.

The majority of activated WT X-LC-$H_N$ also separated to two ~50 kDa bands on SDS-PAGE gel without DTT (FIG. 3C). On the other hand, WT X-LC-$H_N$ is similarly resistant to Lys-C as C461S and C467S mutants, and it showed no further degradation as C423S mutant did (FIG. 3C, +DTT), suggesting that WT X-LC-$H_N$ is different from C423S mutant. One possible explanation is disulfide bond shuffling due to the existence of two cysteines close to each on the $H_N$ (C461 and C467), which can rearrange the disulfide bond from inter-chain C423-C467 or C423-C467 to intra-chain C461-C467 under denatured conditions[48,49]. To test this hypothesis, an alkylating reagent, N-Ethylmaleimide (NEM), which reacts with sulfhydryls of free cysteine and permanently block any free cysteines, was used. As shown in FIG. 3D, WT X-LC-$H_N$ pretreated with NEM showed largely as a single band at 100 kDa in the absence of DTT, and separated into two ~50 kDa bands in the presence of DTT. These results confirmed that native WT X-LC-$H_N$ contains mainly inter-chain disulfide bond, which is susceptible to disulfide bond shuffling due to the existence of the third cysteine in the linker region.

Finally, the activity of the three X-LC-$H_N$ cysteine mutants on cultured neurons was examined. As shown in FIG. 3E, mutating the cysteine on the LC (C423S) abolished the activity of X-LC-$H_N$, as evidenced by lack of VAMP2 cleavage in neurons. Mutating one of the two cysteines on the $H_N$ (C461 or C467) did not significantly affect the potency of X-LC-$H_N$ compared to wild type (WT) X-LC-$H_N$ (FIG. 3E). These results confirmed that the inter-chain disulfide bond is essential for the activity of BoNT/X and demonstrated that functional inter-chain disulfide bond can be formed via either C423-C461 or C423-C467.

Generating Full-Length BoNT/X Via Sortase-Mediated Ligation

To evaluate whether BoNT/X is a functional toxin, it was necessary to generate and test full-length BoNT/X. However, BoNTs are one of the most dangerous potential bioterrorism agents. Therefore, the necessary precaution was taken, and the full-length active toxin gene was not generated. Instead, an approach to generate limited amounts of full-length BoNTs in test tubes under controlled conditions by the enzymatic ligation of two non-toxic fragments of BoNTs was developed. This method utilizes a transpeptidase known as sortase, which recognizes specific peptide motifs and covalently link two peptides together by forming a native peptide bond (FIG. 4A). This approach has been previously utilized to generate chimeric toxins and other fusion proteins[50,51].

An engineered sortase A, known as SrtA*, from *Staphylococcus aureus* was generated[51]. SrtA* recognizes the peptide motif LPXTG (SEQ ID NO: 57), cleaves between T-G, and concurrently forms a new peptide bond between the protein containing LPXTG (SEQ ID NO: 57) with other proteins/peptides containing one or more N-terminal glycine (FIG. 4A). Two non-toxic fragments of BoNT/X: (1) LC-$H_N$ with LPETGG (SEQ ID NO: 58) motif and a His6-tag fused to the C-terminus; (2) the $H_C$ of BoNT/X (X-$H_C$) with a GST tag and thrombin cleavage site at its N-terminus were produced. Cutting by thrombin releases X-$H_C$ with a free glycine at the N-terminus. Incubation of these two fragments with SrtA* generated limited amount of ~150 kD full-length BoNT/X containing a short linker (LPETGS, SEQ ID NO: 59) between LC-$H_N$ and $H_C$ (FIGS. 4A-4B).

Figure 8A:
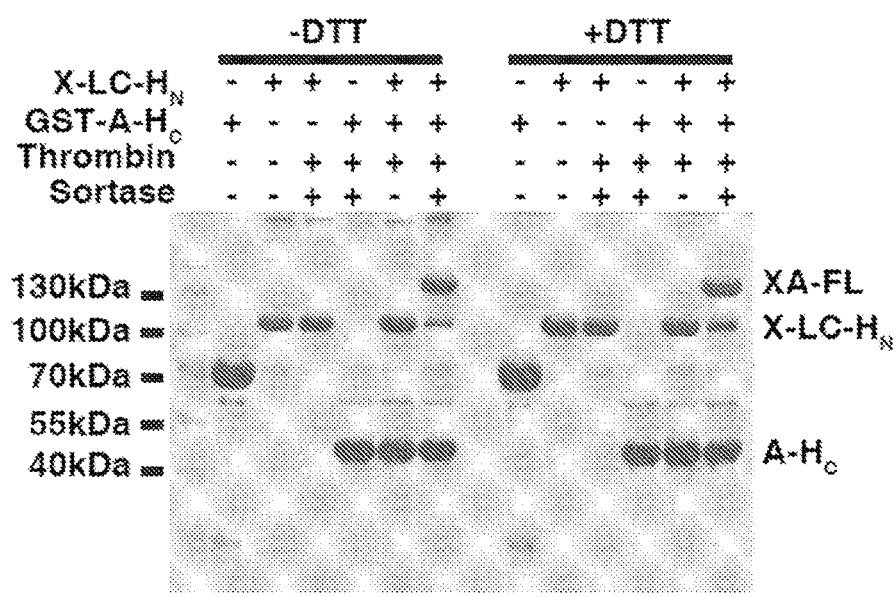
FIGS. 8A-8B show that XA chimeric toxin is active on neurons.

It was observed that X-H$_C$ showed a strong tendency for aggregation in solution for unknown reasons once it is cut from GST tag, which might be the reason why the ligation efficiency is low for BoNT/X (FIG. 4B). In contrast, ligation of X-LC-H$_N$ with the H$_C$ of BoNT/A (A-H$_C$) using the same approach achieved a much higher efficiency, with majority of X-LC-H$_N$ ligated into a full-length XA chimeric toxin (FIG. 8A).

BoNT/X is Active on Cultured Neurons

Figure 8B:
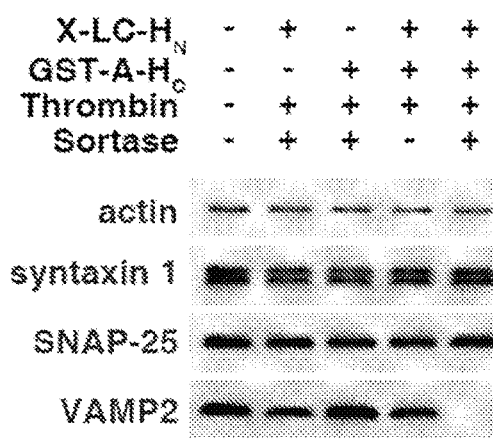

To analyze the activity of full-length BoNT/X, cultured rat cortical neurons as a model system were used. Neurons were exposed to the sortase ligation mixture and various control mixtures in media. Cell lysates were harvested 12 hours later and immunoblot analysis was carried out to examine cleavage of SNARE proteins. As shown in FIG. 4C, X-LC-H$_N$ alone cleaved some VAMP2 due to its high concentration in the reaction mixture. The control mixture containing X-LC-H$_N$ and X-H$_C$ but not sortase slightly enhanced cleavage of VAMP2 compared to X-LC-H$_N$ alone. This result suggests that X-H$_C$ might be associated with X-LC-H$_N$ via non-covalent interactions. This interaction appears to be specific as the control mixture containing X-LC-H$_N$ and A-H$_C$ showed the same level of VAMP2 cleavage as X-LC-H$_N$ alone (FIG. 8B). Ligating X-LC-H$_N$ and X-H$_C$ by sortase enhanced cleavage of VAMP2 over the mixture of X-LC-H$_N$ and X-H$_C$ without sortase (FIG. 4C), demonstrating that ligated full-length BoNT/X can enter neurons and cleave VAMP2. Similarly, ligated full-length XA chimeric toxin also entered neurons and cleaved VAMP2 (FIG. 8B).

Figure 9:
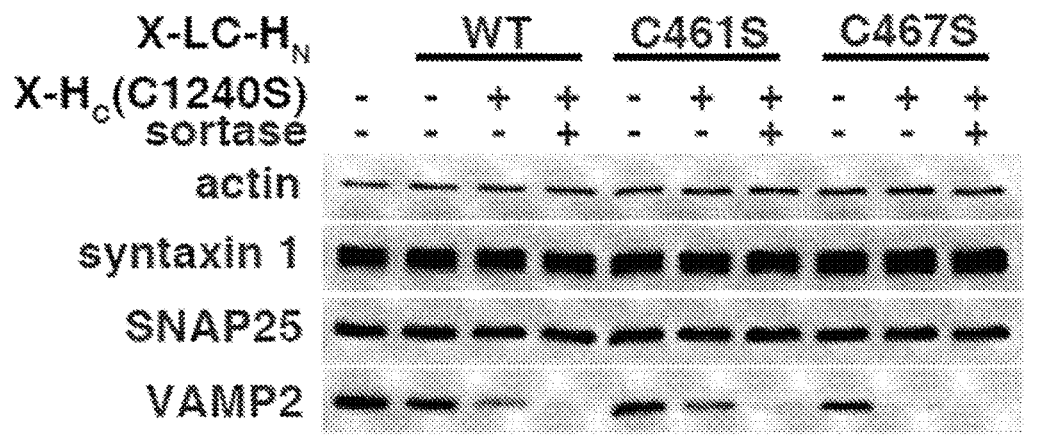

Mixing X-H$_C$ with X-LC-H$_N$ increased the amounts of aggregates at the top of the SDS-PAGE gel compared to X-LC-H$_N$ alone. These aggregates disappeared in the presence of DTT, suggesting that a portion of X-H$_C$ formed inter-molecular disulfide bond with X-LC-H$_N$. The presence of DTT also increased the amount of ligated full-length BoNT/X, suggesting that a portion of BoNT/X aggregated via inter-molecular disulfide bond (FIG. 4B). The formation of these aggregates could significantly reduce the effective toxin monomer concentrations in solution. This could be an intrinsic weakness of BoNT/X sequence. X-H$_C$ contains a single cysteine (C1240) and mutating this cysteine did not affect the activity of ligated BoNT/X (FIG. 9). Furthermore, C1240S mutant can be combined with C461S or C467S mutations in the X-LC-H$_N$ to generate a modified BoNT/X with no free cysteines (FIG. 9). These mutant toxins maintained the same levels of activity as WT BoNT/X, but are more stable in solution as monomers than WT BoNT/X.

BoNT/X Induced Flaccid Paralysis In Vivo in Mice

Whether BoNT/X is active in vivo was examined using a well-established non-lethal assay in mice, known as Digit Abduction Score (DAS). This assay measures local muscle paralysis following injection of BoNTs into mouse hind limb muscles[52,53]. BoNTs cause flaccid paralysis of limb muscles, which can be detected by the failure to spread the toes during the startle response. An activated sortase reaction mixture (FIG. 4B, lane 7) was injected into the gastrocnemius muscles of the right hind limb in mice. Within 12 hours, the right limb developed typical flaccid paralysis and the toes failed to spread (FIG. 4D). These results confirmed that BoNT/X is capable of causing flaccid paralysis in vivo as other BoNTs.

BoNT/X was not Recognized by Antisera Raised Against all Known BoNTs

Figure 10:
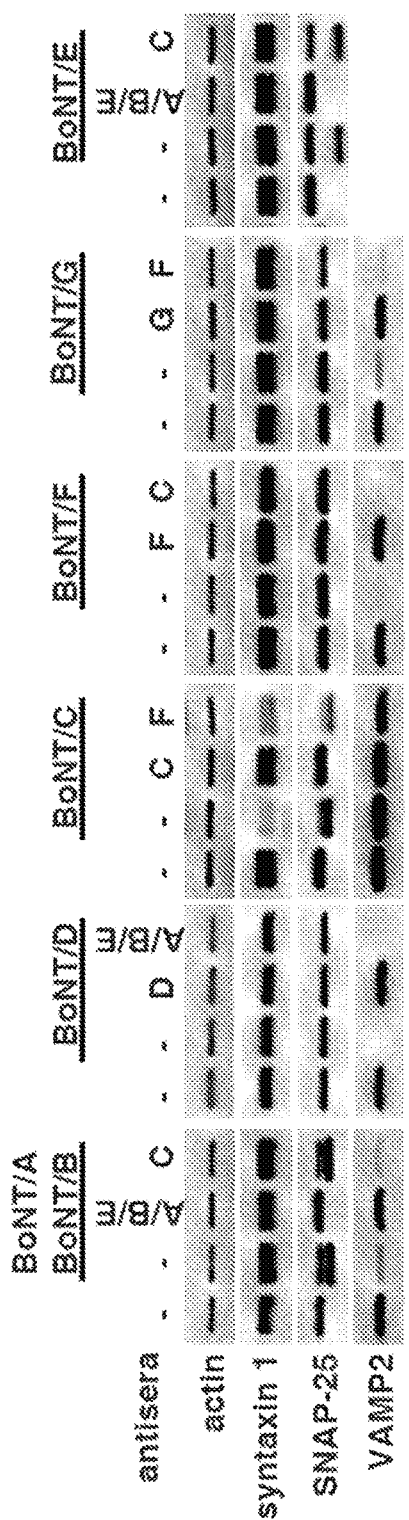
FIG. 10 shows antisera raised against the seven serotypes of BoNTs neutralizing their target BoNTs on neurons. Cultured rat cortical neurons were exposed to indicated BoNTs, with or without pre-incubation with indicated antisera. Cell lysates were harvested 12 hours later and subjected to immunoblot analysis. All antisera specifically neutralized their target BoNTs, without affecting the activity of a different serotype of BoNTs, thus validating the specificity and potency of these antisera. The concentrations for BoNTs were: BoNT/A (50 pM), BoNT/B (2 nM), BoNT/C (1.5 nM), BoNT/D (100 pM), BoNT/E (0.5 nM), BoNT/F (0.5 nM), BoNT/G (5 nM). The antiserum against BoNT/A/B/E was used at 20 μl per well. All the other antisera were used at 10 μl per well. BoNTs were pre-incubated with indicated antisera for 30 mins at 37° C. prior to adding into culture media.

To further confirm that BoNT/X is a serologically unique BoNT, dot blot assays were carried out using antisera raised against known BoNTs, including all seven serotypes as well as one mosaic toxin (BoNT/DC). Four horse antisera were utilized (trivalent anti-BoNT/A, B, and E, anti-BoNT/C, anti-BoNT/DC, and anti-BoNT/F), as well as two goat antisera (anti-BoNT/G and anti-BoNT/D). These antisera were all capable of neutralizing their corresponding target BoNTs and prevented cleavage of SNARE proteins in neurons (FIG. 10), thus validating their specificity and potency. As shown in FIG. 4E, these antisera recognized their corresponding target toxins, yet none of them recognized BoNT/X. Note that the antisera raised against BoNT/DC and BoNT/C cross-react with each other, as they share high degree of similarity in their H$_C$. These result established BoNT/X as a new serological type of BoNTs.

Full-length inactive BoNT/X

Figure 11A:
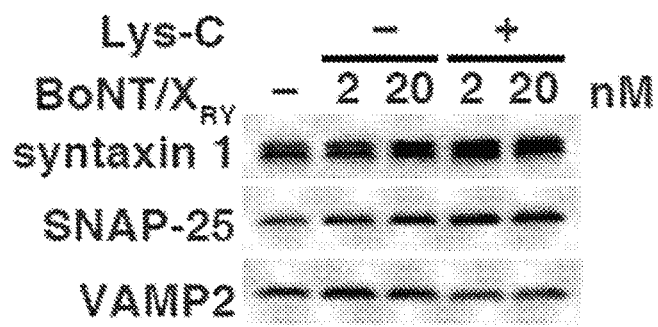
FIGS. 11A-11C show that BoNT/X$_{RY}$ is not active on neurons.

Finally, whether full-length BoNT/X can be produced as a soluble protein was examined. To ensure the biosafety requirement, mutations in the LC of BoNT/X were introduced that inactivate its toxicity. Mutations at two residues R362A/Y365F in BoNT/A have been shown to inactivate the protease activity of the LC in vitro and abolishes the toxicity of full-length BoNT/A in mice in vivo[54-56]. These two residues are conserved in all BoNTs including BoNT/X. Therefore, the corresponding mutations were introduced at these two sites (R360A/Y363F in BoNT/X). As shown in FIG. 4F, this full-length inactivated form of BoNT/X (BoNT/X$_{RY}$) was produced and purified as a His6-tagged protein in E. coli recombinantly. It does not have any activity on neurons as VAMP2 was not cleaved in neurons (FIG. 11).

A substantial portion of BoNT/X$_{RY}$ formed aggregates at the top of the SDS-PAGE gel (FIG. 4F). This is likely due to formation of inter-molecular disulfide bond from the extra cysteine in the linker region and the cysteine in the H$_C$, as adding DTT converted the aggregates to monomeric BoNT/X$_{RY}$ (FIG. 4F). Mutating these cysteines does not affect the activity of BoNT/X (FIG. 9), and has the benefit of preventing formation of inter-molecular disulfide bond and aggregations of BoNT/X.

An inactive form of BoNT/X might be utilized as a vehicle to deliver therapeutics into neurons. Inactivation can be achieved by mutations at any one of the following residues or their combinations: R360, Y363, H227, E228, or H231, with the later three residues forming the conserved protease motif.

Purification of Full-Length Inactive BoNT/X at Industrial-Scale

Figure 11B:
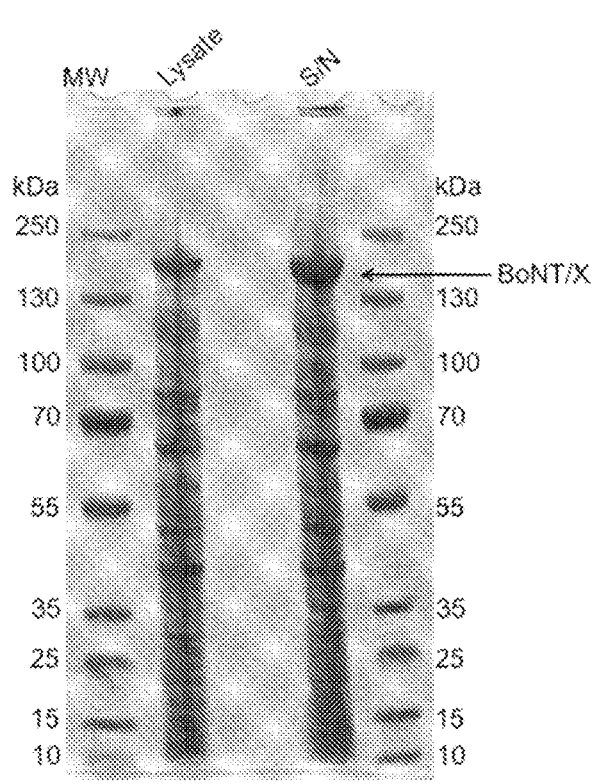

Whether full-length BoNT/X can be purified to a high degree of purity and with a good yield, which will be important for industrial production of BoNT/X (or its derivative) as a therapeutic toxin, was investigated. Several parameters of cell growth and expression were tested, such as temperature, time of induction and IPTG concentrations. The optimal parameters chosen for protein expression were culture of the cells at 37° C. until they reached exponential growth, at which stage the temperature was reduced to 18° C. and expression induced by addition of 1 mM IPTG to the media. Cells were then cultured for 16 to 18 hours before harvesting. Presence of BoNT/X was verified by SDS-PAGE and showed a high level of over-expression in the soluble fraction (FIG. 11B).

Several small-scale purification trials were carried out to optimize the production process. Mechanical cell lysis using an Emulsiflex-C3 (Avestin, Mannheim, Germany) was the preferred method for intracellular protein extraction, and appeared more efficient that sonication. Various buffer conditions also had to be assessed for optimal recovery of BoNT/X. A reducing agent was included throughout the purification process and greatly decreased the propensity to unwanted aggregation. Additionally, glycerol was used as an additive during the early stage of the purification process and improved protein stability.

The BoNT/X construct was expressed with a HIS6-tag that could be used for affinity chromatography as a first purification step. For small-scale trials, a 5 ml HIsTrapFF column (GE Healthcare, Danderyd, Sweden) was used. In order to achieve the highest purity from the initial chromatography, various concentrations of imidazole were tested. BoNT/X eluted from a concentration of 100 mM imidazole; however, a major contaminant readily co-purified with the toxin. This contaminant appeared to non-specifically interact with BoNT/X and was identified by mass spectrometry as an *E. coli* host protein (bifunctional polymyxin resistance protein ArnA). The presence of this contaminant was dramatically reduced with the introduction of a high salt concentration (500 mM NaCl) and by carrying out an additional washing step at 100 mM imidazole during purification. This allowed for elution of a purer BoNT/X fraction at 250 mM imidazole. This later fraction could then be polished by size exclusion chromatography.

Figure 11C:
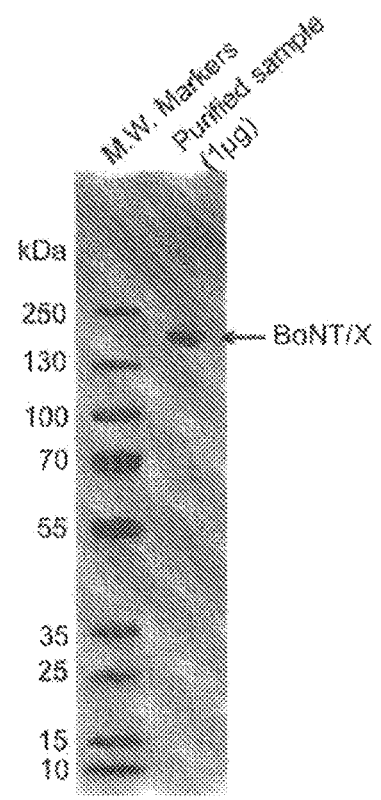

Once in place, this protocol was scaled up by expressing up to 12 L of media with the conditions described above. Additionally, a larger affinity chromatography matrix was prepared consisting of 15 ml of Protino® Ni-NTA agarose (Macherey-Nagel, Duren, Germany) to increase the yield of BoNT/X recovery. The final purification step was performed by size exclusion chromatography using a Superdex200-16/60 column (GE Healthcare, Danderyd, Sweden). Using this method, between 85 and 90% purity was obtained (FIG. 11C). The protein could be concentrated (using a Vivaspin concentrator with a 100 kDa cut-off; GE Healthcare, Danderyd, Sweden) and appeared stable up to 10 mg/ml. Complete details of the protein production process are described below. The yield of BoNT/X obtained was approximately 3 mg per liter of cell culture. Together these results demonstrated that BoNT/X can be purified at industrial scale to high purity.

Note that the purification was done in the presence of reducing agent, which would reduce the disulfide bond between the LC and the HC, so purified toxin would not be active. However, a designed BoNT/X derivative containing mutations at the cysteine sties (one mutation at C461 or C467, combined with mutating C1240) would be able to be purified without reducing agents. Note that an inactive form of BoNT/X (and its cysteine mutation derivative) might be utilized as a vehicle to deliver therapeutics into neurons. Inactivation can be achieved by mutations at any one of the following residues or their combinations: R360, Y363, H227, E228, or H231 (the later three residues form the conserved protease motif).

Identification of Gangliosides as Receptors for BoNT/X

Gangliosides are well-established lipid co-receptors for all BoNTs and a ganglioside-binding motif is well-conserved in BoNT/X (FIG. 1C). Highly purified full-length inactive BoNT/X was used to examine whether BoNT/X binds to neuronal cells via gangliosides/An in vitro ELISA assay was developed to test for interaction with four major brain gangliosides: GD1a, GD1b, GT1b, and GM1. A-LC was use as a negative control to assess unspecific binding. Direct comparison with the receptor binding domain of BoNT/A (A-HC) was also performed. Binding of proteins were detected using an anti-His6-tag antibody. It was found that BoNT/X showed a dose-dependent binding to all four gangliosides over the non-specific binding level of A-LC (FIG. 12), suggesting that BoNT/X is capable of utilizing all four brain gangliosides as co-receptors. In accordance with previous reports, BoNT/A presented an equal preference for GD1a and GT1b (FIG. 12F) and their terminal NAcGal-Gal-NAcNeu moiety (with apparent EC50 values of 0.7 and 1.0 µM, respectively, when fitted with a sigmoidal dose-response model). In contrast, BoNT/X showed higher affinity for GD1b and GM1 over GD1a and GT1b (FIG. 12E). This would suggest BoNT/X has a preferred sialic acid recognition pattern, also seen in BoNT/B and TeNT. BoNT/X possesses the conserved SxWY motif at a homologous location to the one of the other toxins. The fact that it could recognize all four gangliosises, albeit with low affinity, may be an indication of multiple carbohydrate binding sites.

Discussion

The eighth serotype of BoNTs over 45 years after the identification of the last major BoNT serotype has been identified. BoNT/X has the lowest protein sequence identity to any other BoNTs and TeNT among this family of toxins, and this low level of identity is evenly distributed along the toxin sequence. As expected, BoNT/X was not recognized by any antisera raised against known BoNTs. It clearly represents a unique and distinct evolutionary branch of the toxin family.

BoNT/X was revealed by searching genomic sequences of *Clostridium botulinum* strains and it represents the first major toxin type identified by genomic sequencing and bioinformatics approach. The strain 111 that contains BoNT/X gene was initially identified from an infant botulism patient in 1990s. Previous characterizations using classic neutralization assay have established BoNT/B2 as the major toxin of this strain. It is likely that BoNT/X is a silent toxin gene, or it was not expressed at detectable toxicity levels under the culture conditions in the lab. Therefore, it can only be identified by sequencing strain 111. This illustrates the importance of genomic sequencing and bioinformatics approaches for understanding microbial virulent factors.

Silent BoNT genes have been frequently found previously in various *Clostridium botulinum* strains. It is not clear why these bacteria keep a silent toxin gene. It could be an evolutionarily degenerated gene. This is clearly the case when silent toxin genes contain premature stop code mutations. However, there are also cases that the silent gene encodes a full-length BoNT. Whether these silent full-length BoNTs might be expressed and exhibit toxicity under certain environmental conditions remains an intriguing question.

The general three-domain structures and functions of BoNTs are well conserved in BoNT/X, but it also has a few unique characteristics: (1) it shares VAMP as its target in neurons with BoNT/B, D, F, and G, but it cuts VAMP at a novel site (R66-A67 in VAMP2) that is unique to this toxin. This further expands the repertoire of toxins that can be used to ablate VAMP at different sites. (2) The inter-chain disulfide bond connecting LC and $H_N$ is conserved in BoNT/X, but it also contains a unique additional cysteine in the linker region, which may lead to disulfide bond shuffling. The extra cysteine on $H_N$ is not essential for the activity of LC-$H_N$ (FIG. 3D), and mutating it has the benefit of preventing formation of inter-molecular disulfide bond (FIG. 3D, 4B).

His6-tagged X-LC-$H_N$ fragment are stable in buffers as recombinant proteins. It showed a higher level of activity on neurons than both A-LC-$H_N$ and B-LC-$H_N$ (FIG. 3B), suggesting that its membrane translocation and/or protease activity might be more efficient than the corresponding fragments in BoNT/A and BoNT/B. X-LC-$H_N$ could be a useful reagent for targeting VAMP1/2/3 in a broad range of cell types and tissues as its entry might not be restricted to neurons. For instance, it potentially can be utilized to reduce pain in a local region by targeting both sensory neurons and other cells that secrete inflammatory signals. It could also be used to generate chimeric toxins, such as XA (FIG. 8).

X-$H_C$ is functional as its presence enhanced cleavage of VAMP2 in neurons than LC-$H_N$ alone (FIG. 4C). However, X-$H_C$ may have some unfavorable characterizes that remain to be further evaluated. For instance, sufficient levels of soluble X-$H_C$ were only produced when it was fused with GST, which is known to facilitate protein folding/solubility, but not with His6 tag. Once released from GST tag, X-$H_C$ is prone to aggregation. In addition, the cysteine in X-$H_C$ may also form inter-molecular disulfide bond (FIG. 4B). Full-length inactive BoNT/X can be purified and exist as a soluble protein, suggesting that the solubility issue with X-$H_C$ might at least partially due to separation of this domain from X-LC-$H_N$. For instance, X-LC-$H_N$ might interact with X-$H_C$ and covers its potential hydrophobic segments in the full-length context, which is not unusual for a multi-domain protein.

Gangliosides have long been established as neuronal receptors for all BoNT subtypes. It is demonstrated that BoNT/X can bind to all four of the most abundant gangliosides: GD1a, GD1b, GT1b, and GM1. Additionally it does so with remarkable difference in affinity and specificity when compared to BoNT/A. This is an intriguing property, as other BoNTs appear to have various degrees of preferences toward a subgroup of gangliosides. For instance, BoNT/A, E, F, and G prefer GD1a and GT1b. BoNT/X might potentially recognize a broader range of neuron types compared to other BoNTs.

It is possible that BoNT/X has a low toxicity in vivo, which might explain why BoNT/X activity was not detected in the original study on strain 111. If this is the case, the reduced toxicity is likely due to its $H_C$ domain, as X-LC-$H_N$ appears to be more active than both A-LC-$H_N$ and B-LC-$H_N$. The formation of inter-molecular disulfide bond might also reduce the effective toxin concentration. It will be necessary to produce full-length native BoNT/X in order to determine its potency in vivo, but it will be important to generate neutralizing antisera using non-toxic fragments of BoNT/X prior to producing full-length toxin.

Introducing full-length active toxin gene into any expression systems/organisms is always a significant biosafety concern and it has become a formidable hurdle for structure-function studies of biological toxins. This is particularly an important consideration for BoNTs as they are one of the six category A potential bioterrorism agents[4]. Here a method to assemble limited amount of full-length toxin biochemically from two complementary and non-toxic fragments was developed. Each fragment is expressed and purified individually, and then ligated together by sortase in test tubes. Other protein ligation methods such as split intein systems, which fuse two protein fragments through protein trans-splicing, can also be utilized[57]. By controlling the amount of precursor fragments in the reaction, the amount of ligated full-length toxin can be strictly controlled. This "semi-synthesis" approach can be used to produce multi-domain biological toxins and other toxic proteins under controlled conditions. It also provides a versatile platform for generating fusion and chimeric toxins, such as swapping the $H_C$ of two BoNTs, replacing $H_C$ of BoNTs with other targeting proteins, or attaching additional cargo to toxins. As there is no full-length toxin cDNA ever generated and no expression of toxins in bacteria or any other living organisms, this approach significantly mitigates the biosafety concerns associated with producing wild type and mutant toxins and will greatly facilitate structure-function studies of biological toxins and toxic proteins.

Materials and Methods

Materials:

Mouse monoclonal antibodies for syntaxin 1 (HPC-1), SNAP-25 (C171.2), and VAMP2 (C169.1) were generously provided by E. Chapman (Madison, Wis.) and are available from Synaptic Systems (Goettingen, Germany). Mouse monoclonal antibody for actin was purchased from Sigma (AC-15). Equine polyclonal antisera against BoNT/A/B/E, BoNT/C, BoNT/DC, BoNT/F, and goat polyclonal antisera against BoNT/G were obtained from the FDA. Goat polyclonal antibody against BoNT/D was purchased from Fisher Scientific (NB10062469). BoNT/A, BoNT/B, BoNT/C, BoNT/DC, BoNT/E, BoNT/F, and BoNT/G were purchased from Metabiologics (Madison, Wis.). BoNT/D was generously provided by E. Johnson (Madison, Wis.).

cDNA and Constructs:

The cDNAs encoding X-LC (residues 1-439) and X-$H_C$ (residues 893-1306) was synthesized. The cDNA encoding X-$H_N$ was generated in-house using Gibson assembly method. The cDNAs encoding A-LC (residues 1-425, M30196) and B-LC (residues 1-439, AB232927) were synthesized by GenScript (New Brunswick, N.J.). These LCs were cloned into pET28 vectors for expression as His6-tagged proteins. X-$H_C$ was cloned into pGEX4T to express as a GST-tagged protein. X-LC-$H_N$, A-LC-$H_N$, and B-LC-$H_N$ were subcloned into pET28 vector, with a peptide sequence LPETGG (SEQ ID NO: 58) fused to their C-termini, and were purified as His6-tagged proteins. Full-length inactive form of BoNT/X was assembled in-house from mutated X-LC (R360A/Y363F), X-$H_N$, and X-$H_C$. It was cloned into pET28 vector with a His6-tagg fused to the C-terminus of BoNT/X. The cDNA encoding rat VAMP2 was generously provided by E. Chapman (Madison, Wis.). VAMP2 (1-96) was cloned into pET28 vector and expressed as a His6-tagged protein. VAMP2 (33-86) was cloned into a pGEX4T vector and expressed as a GST-tagged protein. The cDNA encoding mouse VAMP1, VAMP5, rat VAMP7, and VAMP8 was generously provided by C. Hu (Louisville, Ky.). They were cloned into a modified pcDNA3.1 vectors, with a HA tag fused to their C-termini. The construct encoding His6-tagged sortase (SrtA*) was generously provided by B. Pentelute (Boston, Mass.) and has been described previously[51].

Bioinformatics:

The Uniprot database was searched with jackhmmer at the HMMER web server using a BoNT type A sequence (Uniprot accession number A5HZZ9) until convergence. Returned sequences were aligned with Clustal Omega and a NeighborNet phylogenetic network estimated with SplitsTree4.

Protein Purification:

E. coli BL21 (DE3) was utilized for protein expression. Induction of expression was carried out with 0.1 mM IPTG at 22° C. overnight. Bacterial pellets were disrupted in lysis buffer (50 mM Tris pH 7.5, 150 mM NaCl) by sonication and supernatants were collected after centrifugation at 20000 g for 30 min at 4° C. Protein purification was carried out using AKTA Prime FPLC system (GE) and purified proteins were further desalted with PD-10 column (GE, 17-0851-01). Specifically, full-length inactive BoNT/X (BoNT/$X_{RY}$) was cloned into a pET22b vector. The corresponding plasmid was transformed into E. coli BL21 (DE3) competent cells. Resulting colonies were used to inoculate 100 ml overnight cultures of TB medium containing 100

μg/ml Carbenicillin in 250 ml shake-flask and grown at 37° C. Cultures for expression were first grown using a LEX Bioreactor (Epiphyte3, Ontario, Canada) at 37° C. in 1.5 L of TB media until $OD_{600}$ reached 0.8. The temperature was then reduced to 18° C. for induction of expression with 1 mM IPTG, and grown for 16-17 hours. Cells were harvested and re-suspended on ice in 50 mM HEPES pH 7.2, 500 mM NaCl, 25 mM imidazole, 5% glycerol, 2 mM TCEP to allow for cell lysis with an Emulsiflex-C3 (Avestin, Mannheim, German) at 20,000 psi. Lysate was ultra-centrifuged at 200,000 g for 45 minutes at 4° C. Supernatnt was loaded onto a 15 ml Protino® Ni-NTA agarose (Macherey-Nagen, Duren, Germany) column that was then washed with 50 mM HEPES pH 7.2, 500 mM NaCl, 100 mM imidazole, 5% glycerol, 1 mM TCEP. Elution was carried out with 50 mM HEPES pH 7.2, 500 mM NaCl, 250 mM imidazole, 5% glycerol, 1 mM TCEP. The eluate was dialyzed overnight in 50 mM HEPES pH 7.2, 500 mM NaCl, 5% glycerol, 0.5 mM TCEP at 4° C. Dialysate was concentrated using a Vivaspin concentrator (100 kDa cut-off, GE Healthcare, Danderyd, Sweden) before being loaded on a Superdex200-16/60 column (GE Healthcare, Danderyd, Sweden) pre-equilibrated in the same buffer as was used for dialysis. The elution peak corresponding to BoNT/X was collected and concentrated so that the final sample was at a concentration of 10 mg/ml. The sample was aliquoted and flash-frozen in liquid nitrogen for storage at −80° C.

Ganglioside Binding Assay:

Purified gangliosides GD1a, GD1b, GT1b, and GM1 (Carbosynth, Compton, UK) were dissolved in DMSO and diluted in methanol to reach a final concentration of 2.5 μg/ml; 100 μL was applied to each well of a 96-well PVC assay plate (catalog no. 2595, Corning; Corning, N.Y.). After solvent evaporation at 21° C., the wells were washed with 200 μL PBS/0.1% (w/v) BSA. Nonspecific binding sites were blocked by incubation for 2.5 h at 4° C. in 200 μL of PBS/2% (w/v) BSA. Binding assays were performed in 100 μL PBS/0.1% (w/v) BSA per well for 1 h at 4° C. containing samples (triplicate) at concentrations ranging from 6 μM to 0.05 μM (in serial 2-fold dilution). Following incubation, wells were washed three times with PBS/0.1% (w/v) BSA and incubated with an HRP-conjugated anti-6×His monoclonal antibody (1:2000, ThermoFisher) for 1 h at 4° C. After three washing steps with PBS/0.1% (w/v) BSA, bound samples were detected using Ultra-TMB (100 μL/well, ThermoFisher) as the substrate. The reaction was stopped after 15 minutes by addition of 100 μL 0.2M $H_2SO_4$, and the absorbance at 450 nm was measured using an Infinite M200PRO plate reader (Tecan, Männedorf, Switzerland). Data were analyzed with Prism? (GraphPad Software).

Cleavage of SNARE Proteins in Rat Brain Detergent Extracts (BDE):

Rat BDE were prepared from fresh dissected adult rat brains as previously described[58]. Briefly, a rat brain was homogenized in 15 ml 320 mM sucrose buffer, followed by a centrifugation at 5000 rpm for 2 min at 4° C. Supernatants were collected and centrifuged at 11,000 rpm for 12 min. The pellet was collected and solubilized for 30 min in 15 ml Tris-buffered saline (TBS: 20 mM Tris, 150 mM NaCl) plus 2% of Triton X-100 and a cocktail of protease inhibitors (Roche, Calif.). Samples were subsequently centrifuged at 17,000 rpm for 20 min to remove the insoluble materials. The final BDE concentration is −2 mg/ml proteins. BDE (60 μl) were incubated with X-LC (0.5 μM), A-LC (1 μM), or B-LC (1 μM), respectively, for 1 hour at 37° C., and were then analyzed by immunoblot using the enhanced chemiluminescence (ECL) method (Pierce). As controls, LCs were pre-incubated with 20 mM EDTA for 20 minutes at room temperature (RT) to de-active their activity prior to adding into BDE.

Cleavage of Recombinant VAMP by X-LC:

VAMP2 (1-96) was expressed and purified as a His6-tagged protein and VAMP2 (33-86) was expressed and purified as a GST-tagged protein. These proteins (0.6 mg/ml) were incubated with 0.1 μM X-LC in TBS buffer for 1 hour at 37° C. Samples were either analyzed by SDS-PAGE gels and Coomassie Blue staining, or subjected to mass spectrometry analysis.

Cleavage of VAMPs in Cell Lysates:

Full-length HA-tagged VAMP1, 3, 7, and 8 were transfected into HEK293 cells using PolyJet transfection reagents (SignaGen, MD) following the manufacturer's instruction. Cell lysates were harvested 48 hours later in RIPA buffer (50 mM Tris, 1% NP40, 150 mM NaCl, 0.5% sodium deoxycholate, 0.1% SDS, 400 μl per 10-cm dish) plus a protease inhibitor cocktail (Sigma-Aldrich). Cell lysates (250 μl) were incubated with X-LC (0.5 μM) for 1 hour at 37° C. Samples were then analyzed by immunoblot.

Whole Protein Analysis by LC-MS/MS:

Samples were analyzed at Taplin Biological Mass Spectrometry Core Facility at Harvard Medical School. Briefly, whole protein samples were loaded onto a 100 μm internal diameter C18 reverse phase HPLC column packed with 3 cm of beads off-line using a pressure cell. The column was re-attached to an Accela 600 Pump (Thermo Fisher Scientific, Waltham, Mass.). A rapid gradient of increasing acetonitrile was used to elute the protein/peptide from the HPLC column. As peptides eluted, they were subjected to electrospray ionization and then entered into an LTQ Orbitrap Velos Pro ion-trap mass spectrometer (Thermo Fisher Scientific, Waltham, Mass.) to acquire a high resolution FTMS scan at 60000 resolution, a second scan at low resolution in the ion trap, and a final scan to perform data dependent MS/MS. The charge state envelopes were de-convoluted manually to obtain mono-isotopic masses when possible or average masses for the proteins. Peptide and protein identity were determined by matching protein databases with the acquired fragmentation pattern by the software program, Sequest (Thermo Fisher Scientific). All databases include a reversed version of all the sequences and the data was filtered to between a one and two percent peptide false discovery rate.

Identification of the Protease Cleavage Site Between LC and $H_N$:

His6-tagged recombinant X-LC-$H_N$ fragment (residues 1-891) was purified in *E. coli* and subjected to limited proteolysis by endoproteinase Lys-C(Sigma P2289, 100:1 (toxin:Lys-C) molar ratio, 25 minutes at room temperature). The cleavage site was determined by Tandem Mass Tag (TMT) labeling and tandem mass spectrometry approach. Briefly, intact X-LC-$H_N$ samples were labeled with the light TMT and equal amount of X-LC-$H_N$ samples were exposed to Lys-C and then labeled with the heavy TMT. Both samples were then digested with chymotrypsin, combined together, and subjected to quantitative mass spectrometry analysis.

Cysteine Alkylation by NEM:

Lys-C activated X-LC-$H_N$ fragment was diluted into sodium phosphate buffer (10 mM, pH 6.5) at the final concentration of 0.3 mg/ml, with or without NEM at indicated concentrations (20, 10, and 5 mM) and incubated for 10 minutes at RT. NEM was freshly prepared in sodium phosphate buffer. Samples were mixed with 3× neutral loading dyes (200 mM Tris pH 6.8, 30% glycerol, 6%

Lithium Dodecyl sulfate, 10 mM NEM and 0.06% BPB). For samples without NEM, the same 3×SDS loading dye without NEM was used. Samples were further incubated with the loading dye at RT for 10 minutes, heated for 10 min at 55° C., and then analyzed by SDS-PAGE and Coomassie Blue staining.

Neuron Culture and Immunoblot Analysis:

Primary rat cortical neurons were prepared from E18-19 embryos using a papain dissociation kit (Worthington Biochemical, NJ), as we described previously[58]. Experiments were carried out on DIV 14-16. Neurons were exposed to BoNT/X fragments or sortase ligation mixture in media for 12 hrs. Cells were then washed and lysed with RIPA buffer (50 mM Tris, 1% NP40, 150 mM NaCl, 0.5% sodium deoxycholate, 0.1% SDS) plus a protease inhibitor cocktail (Sigma-Aldrich). Lysates were centrifuged for 10 min at maximum speed using a microcentrifuge at 4° C. Supernatants were subjected to SDS-PAG and immunoblot analysis.

Dot Blot:

BoNTs (0.2 μg in 1 μl) were spotted onto nitrocellulose membranes and dried (10 minutes at room temperature). The membranes were blocked with 5% milk in TBST (TBS plus 0.05% Tween20) for 30 min and then incubated with indicated antisera (1:500 dilution) for 30 min. The membranes were then washed three times with TBST and incubated with HRP (horseradish peroxidase) conjugated secondary antibodies for 30 min, washed three more times with TBST, and analyzed with the ECL method (Pierce). We note that the BoNT/X sample was composed of purified X-LC-$H_N$ and X-$H_C$ at 1:1 ratio.

Sortase-Mediated Ligation:

GST-X-$H_C$ was cleaved overnight at 4° C. by thrombin before adding into the mixture of proteins. Ligation reaction was set up in 50 μl TBS buffer with addition of X-LC-$H_N$ (8 μM), thrombin-cleaved GST-X-$H_C$ (25 μM), $Ca^{2+}$ (10 mM), and sortase (10 μM), for 40 min at RT. In FIG. 4C, neurons were exposed to 5 μl of the mixture in media for 12 hrs. In DAS assay described in FIG. 4D, 25 μl of the mixture was injected into the hind leg of mice.

DAS assay: Sortase ligation mixture was first activated with limited proteolysis using trypsin (60:1 molar ratio (the total amount of the proteins:trypsin), 30 min at RT). We chose trypsin instead of Lys-C here as we can stop the proteolysis by adding trypsin inhibitor (Soybean trypsin inhibitor, 1:10 ratio (trypsin:trypsin inhibitor). Mice (CD-1 strain, 21-25 g, n=6) were anesthetized with isoflurane (3-4%) and were injected with sortase ligation mixture using a 30-gauge needle attached to the sterile Hamilton Syringes, into the gastrocnemius muscles of the right hind limb. BoNTs result in paralysis of the hind paw in the startle response. Muscle paralysis was observed within 12 hours after the injection as previously described[52,53].

REFERENCES

1. Schiavo, G., Matteoli, M. & Montecucco, C. Neurotoxins affecting neuroexocytosis. *Physiol Rev* 80, 717-766 (2000).
2. Montal, M. *Botulinum* neurotoxin: a marvel of protein design. *Annu Rev Biochem* 79, 591-617 (2010).
3. Rossetto, O., Pirazzini, M. & Montecucco, C. *Botulinum* neurotoxins: genetic, structural and mechanistic insights. *Nat Rev Microbiol* 12, 535-549 (2014).
4. Arnon, S. S., et al. *Botulinum* toxin as a biological weapon: medical and public health management. *Jama* 285, 1059-1070 (2001).
5. Pirazzini, M., et al. Thioredoxin and its reductase are present on synaptic vesicles, and their inhibition prevents the paralysis induced by *botulinum* neurotoxins. *Cell Rep* 8, 1870-1878 (2014).
6. Pirazzini, M., et al. The thioredoxin reductase—Thioredoxin redox system cleaves the interchain disulphide bond of *botulinum* neurotoxins on the cytosolic surface of synaptic vesicles. *Toxicon* 107, 32-36 (2015).
7. Ja$H_N$, R. & Scheller, R. H. SNAREs—engines for membrane fusion. *Nat Rev Mol Cell Biol* 7, 631-643 (2006).
8. Sudhof, T. C. & Rothman, J. E. Membrane fusion: grappling with SNARE and SM proteins. *Science* 323, 474-477 (2009).
9. Gu, S., et al. *Botulinum* neurotoxin is shielded by NTNHA in an interlocked complex. *Science* 335, 977-981 (2012).
10. Lee, K., et al. Molecular basis for disruption of E-cadherin adhesion by *botulinum* neurotoxin A complex. *Science* 344, 1405-1410 (2014).
11. Lee, K., et al. Structure of a bimodular *botulinum* neurotoxin complex provides insights into its oral toxicity. *PLoS Pathog* 9, e1003690 (2013).
12. Sugawara, Y., et al. *Botulinum* hemagglutinin disrupts the intercellular epithelial barrier by directly binding E-cadherin. *J Cell Biol* 189, 691-700 (2010).
13. Hill, K. K., Xie, G., Foley, B. T. & Smith, T. J. Genetic diversity within the *botulinum* neurotoxin-producing bacteria and their neurotoxins. Toxicon 107, 2-8 (2015).
14. Johnson, E. A. Clostridial toxins as therapeutic agents: benefits of nature's most toxic proteins. *Annu Rev Microbiol* 53, 551-575 (1999).
15. Aoki, K. R. *Botulinum* toxin: a successful therapeutic protein. *Curr Med Chem* 11, 3085-3092 (2004).
16. Montecucco, C. & Molgo, J. Botulinal neurotoxins: revival of an old killer. *Curr Opin Pharmacol* 5, 274-279 (2005).
17. Dolly, J. O., Lawrence, G. W., Meng, J. & Wang, J. Neuro-exocytosis: *botulinum* toxins as inhibitory probes and versatile therapeutics. *Curr Opin Pharmacol* 9, 326-335 (2009).
18. Burke, G. S. Notes on *Bacillus* botulinus. *J Bacteriol* 4, 555-570 551 (1919).
19. Gimenez, D. F. & Ciccarelli, A. S. Another type of *Clostridium botulinum*. Zentralbl Bakteriol Orig 215, 221-224 (1970).
20. Lange, O., et al. Neutralizing antibodies and secondary therapy failure after treatment with *botulinum* toxin type A: much ado about nothing? *Clin Neuropharmacol* 32, 213-218 (2009).
21. Dong, M., et al. SV2 is the protein receptor for *botulinum* neurotoxin A. *Science* 312, 592-596 (2006).
22. Dong, M., et al. Synaptotagmins I and II mediate entry of *botulinum* neurotoxin B into cells. *J Cell Biol* 162, 1293-1303 (2003).
23. Mahrhold, S., Rummel, A., Bigalke, H., Davletov, B. & Binz, T. The synaptic vesicle protein 2C mediates the uptake of *botulinum* neurotoxin A into phrenic nerves. *FEBS Lett* 580, 2011-2014 (2006).
24. Nishiki, T., et al. Identification of protein receptor for *Clostridium botulinum* type B neurotoxin in rat brain synaptosomes. *J Biol Chem* 269, 10498-10503 (1994).
25. Schiavo, G., et al. Tetanus and *botulinum*-B neurotoxins block neurotransmitter release by proteolytic cleavage of synaptobrevin. *Nature* 359, 832-835 (1992).
26. Schiavo, G., et al. *Botulinum* neurotoxins serotypes A and E cleave SNAP-25 at distinct COOH-terminal peptide bonds. *FEBS Lett* 335, 99-103 (1993).

27. Blasi, J., et al. *Botulinum* neurotoxin A selectively cleaves the synaptic protein SNAP-25. *Nature* 365, 160-163 (1993).
28. Smith, T. J., et al. Sequence variation within *botulinum* neurotoxin serotypes impacts antibody binding and neutralization. *Infect Immun* 73, 5450-5457 (2005).
29. Hill, K. K., et al. Genetic diversity among *Botulinum* Neurotoxin-producing clostridial strains. *J Bacteriol* 189, 818-832 (2007).
30. Montecucco, C. & Rasotto, M. B. On *botulinum* neurotoxin variability. *MBio* 6(2015).
31. Dover, N., Barash, J. R., Hill, K. K., Xie, G. & Arnon, S. S. Molecular characterization of a novel *botulinum* neurotoxin type H gene. *J Infect Dis* 209, 192-202 (2014).
32. Barash, J. R. & Arnon, S. S. A novel strain of *Clostridium botulinum* that produces type B and type H *botulinum* toxins. *J Infect Dis* 209, 183-191 (2014).
33. Maslanka, S. E., et al. A Novel *Botulinum* Neurotoxin, Previously Reported as Serotype H, Has a Hybrid-Like Structure With Regions of Similarity to the Structures of Serotypes A and F and Is Neutralized With Serotype A Antitoxin. *J Infect Dis* (2015).
34. Kalb, S. R., et al. Functional characterization of *botulinum* neurotoxin serotype H as a hybrid of known serotypes F and A (BoNT F/A). *Anal Chem* 87, 3911-3917 (2015).
35. Luquez, C., Raphael, B. H. & Maslanka, S. E. Neurotoxin gene clusters in *Clostridium botulinum* type Ab strains. *Appl Environ Microbiol* 75, 6094-6101 (2009).
36. Dover, N., et al. *Clostridium botulinum* strain Af84 contains three neurotoxin gene clusters: bont/A2, bont/F4 and bont/F5. *PLoS One* 8, e61205 (2013).
37. Dabritz, H. A., et al. *Molecular epidemiology of infant botulism in California and elsewhere, 1976-2010. J Infect Dis* 210, 1711-1722 (2014).
38. Franciosa, G., Ferreira, J. L. & Hatheway, C. L. Detection of type A, B, and E botulism neurotoxin genes in *Clostridium botulinum* and other *Clostridium* species by PCR: evidence of unexpressed type B toxin genes in type A toxigenic organisms. *J Clin Microbiol* 32, 1911-1917 (1994).
39. Hutson, R. A., et al. Genetic characterization of *Clostridium botulinum* type A containing silent type B neurotoxin gene sequences. *J Biol Chem* 271, 10786-10792 (1996).
40. Kakinuma, H., Maruyama, H., Takahashi, H., Yamakawa, K. & Nakamura, S. The first case of type B infant botulism in Japan. *Acta Paediatr Jpn* 38, 541-543 (1996).
41. Kozaki, S., et al. Characterization of *Clostridium botulinum* type B neurotoxin associated with infant botulism in japan. *Infect Immun* 66, 4811-4816 (1998).
42. Ihara, H., et al. Sequence of the gene for *Clostridium botulinum* type B neurotoxin associated with infant botulism, expression of the C-terminal half of heavy chain and its binding activity. *Biochim Biophys Acta* 1625, 19-26 (2003).
43. Rummel, A., Bade, S., Alves, J., Bigalke, H. & Binz, T. Two carbohydrate binding sites in the H(CC)-domain of tetanus neurotoxin are required for toxicity. *J Mol Biol* 326, 835-847 (2003).
44. Rummel, A., Mahrhold, S., Bigalke, H. & Binz, T. The HCC-domain of *botulinum* neurotoxins A and B exhibits a singular ganglioside binding site displaying serotype specific carbohydrate interaction. *Mol Microbiol* 51, 631-643 (2004).
45. Rossetto, O., et al. SNARE motif and neurotoxins. *Nature* 372, 415-416 (1994).
46. Masuyer, G., Beard, M., Cadd, V. A., Chaddock, J. A. & Acharya, K. R. Structure and activity of a functional derivative of *Clostridium botulinum* neurotoxin B. *J Struct Biol* 174, 52-57 (2011).
47. Chaddock, J. A., et al. Expression and purification of catalytically active, non-toxic endopeptidase derivatives of *Clostridium botulinum* toxin type A. *Protein Expr Purif* 25, 219-228 (2002).
48. Ewbank, J. J. & Creighton, T. E. The molten globule protein conformation probed by disulphide bonds. *Nature* 350, 518-520 (1991).
49. Nagy, P. Kinetics and mechanisms of thiol-disulfide exchange covering direct substitution and thiol oxidation-mediated pathways. *Antioxid Redox Signal* 18, 1623-1641 (2013).
50. Popp, M. W., Antos, J. M., Grotenbreg, G. M., Spooner, E. & Ploegh, H. L. Sortagging: a versatile method for protein labeling. *Nat Chem Biol* 3, 707-708 (2007).
51. McCluskey, A. J. & Collier, R. J. Receptor-directed chimeric toxins created by sortase-mediated protein fusion. *Mol Cancer Ther* 12, 2273-2281 (2013).
52. Broide, R. S., et al. The rat Digit Abduction Score (DAS) assay: a physiological model for assessing *botulinum* neurotoxin-induced skeletal muscle paralysis. *Toxicon* 71, 18-24 (2013).
53. Aoki, K. R. A comparison of the safety margins of *botulinum* neurotoxin serotypes A, B, and F in mice. *Toxicon* 39, 1815-1820 (2001).
54. Binz, T., Bade, S., Rummel, A., Kollewe, A. & Alves, J. Arg(362) and Tyr(365) of the *botulinum* neurotoxin type a light chain are involved in transition state stabilization. *Biochemistry* 41, 1717-1723 (2002).
55. Fu, Z., et al. Light chain of *botulinum* neurotoxin serotype A: structural resolution of a catalytic intermediate. *Biochemistry* 45, 8903-8911 (2006).
56. Pier, C. L., et al. Recombinant holotoxoid vaccine against botulism. *Infect Immun* 76, 437-442 (2008).
57. Mootz, H. D. Split inteins as versatile tools for protein semisynthesis. *Chembiochem* 10, 2579-2589 (2009).
58. Peng, L., Tepp, W. H., JoH$_N$son, E. A. & Dong, M. *Botulinum* neurotoxin D uses synaptic vesicle protein SV2 and gangliosides as receptors. *PLoS Pathog* 7, e1002008 (2011).
59. Steegmaier, M., Klumperman, J., Foletti, D. L., Yoo, J. S. & Scheller, R. H. Vesicle-associated membrane protein 4 is implicated in trans-Golgi network vesicle trafficking. *Mol Biol Cell* 10, 1957-1972 (1999).
60. Brandhorst, D., et al. Homotypic fusion of early endosomes: SNAREs do not determine fusion specificity. *Proc Natl Acad Sci USA* 103, 2701-2706 (2006).
61. Raingo, J., et al. VAMP4 directs synaptic vesicles to a pool that selectively maintains asynchronous neurotransmission. *Nat Neurosci* 15, 738-745 (2012).
62. Cocucci, E., Racchetti, G., Rupnik, M. & Meldolesi, J. The regulated exocytosis of enlargeosomes is mediated by a SNARE machinery that includes VAMP4. *J Cell Sci* 121, 2983-2991 (2008).
63. Nicholson-Fish, J. C., Kokotos, A. C., Gillingwater, T. H., Smillie, K. J. & Cousin, M. A. VAMP4 Is an Essential Cargo Molecule for Activity-Dependent Bulk Endocytosis. *Neuron* 88, 973-984 (2015).
64. Zeng, Q., et al. A novel synaptobrevin/VAMP homologous protein (VAMP5) is increased during in vitro myogenesis and present in the plasma membrane. *Mol Biol Cell* 9, 2423-2437 (1998).

65. Krzewski, K., Gil-Krzewska, A., Watts, J., Stern, J. N. & Strominger, J. L. VAMP4- and VAMP7-expressing vesicles are both required for cytotoxic granule exocytosis in NK cells. *Eur J Immunol* 41, 3323-3329 (2011).
66. Yamamoto, H., et al. Specificity of *botulinum* protease for human VAMP family proteins. *Microbiol Immunol* 56, 245-253 (2012).
67. McNew, J. A., et al. Ykt6p, a prenylated SNARE essential for endoplasmic reticulum-Golgi transport. *J Biol Chem* 272, 17776-17783 (1997).
68. Kweon, Y., Rothe, A., Conibear, E. & Stevens, T. H. Ykt6p is a multifunctional yeast R-SNARE that is required for multiple membrane transport pathways to the vacuole. *Mol Biol Cell* 14, 1868-1881 (2003).
69. Hasegawa, H., et al. Mammalian ykt6 is a neuronal SNARE targeted to a specialized compartment by its profilin-like amino terminal domain. *Mol Biol Cell* 14, 698-720 (2003).
70. Daste, F., Galli, T. & Tareste, D. Structure and function of longin SNAREs. *J Cell Sci* 128, 4263-4272 (2015).
71. Cooper, A. A., et al. Alpha-synuclein blocks ER-Golgi traffic and Rab1 rescues neuron loss in Parkinson's models. *Science* 313, 324-328 (2006).
72. Thayanidhi, N., et al. Alpha-synuclein delays endoplasmic reticulum (ER)-to-Golgi transport in mammalian cells by antagonizing ER/Golgi SNAREs. *Mol Biol Cell* 21, 1850-1863 (2010).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An isolated BoNT polypeptide, comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to any one of SEQ ID NOs: 1-3, wherein the isolated BoNT polypeptide does not comprise the amino acid sequence of any one of SEQ ID NOs: 1-3.

2. A modified Clostridial *Botulinum* neurotoxin (BoNT) polypeptide, comprising one or more substitution mutation(s) in a position corresponding to C461, C467, or C1240 of SEQ ID NO: 1.

3. A modified Clostridial *Botulinum* neurotoxin (BoNT) polypeptide, comprising a single substitution mutation in a position corresponding to C461 or C467 of SEQ ID NO: 2.

4. A modified Clostridial *Botulinum* neurotoxin (BoNT) polypeptide comprising:
   (a) a protease domain;
   (b) a modified linker region; and
   (c) a translocation domain;
   wherein (a), (b), and (c) are from BoNT serotype X, and wherein the modified linker region comprises one single substitution mutation in a position corresponding to C461 or C467 of SEQ ID NO: 1.

5. The modified BoNT polypeptide of claim 4, further comprising: (d) a receptor binding domain.

6. The modified BoNT polypeptide of claim 5, wherein the receptor binding domain is from BoNT/X.

7. The modified BoNT polypeptide of claim 6, wherein the receptor binding domain comprises a substitution mutation corresponding to C1240S or C1240A in SEQ ID NO: 1.

8. The modified BoNT polypeptide of claim 5, wherein the receptor binding domain is from serotype selected from the group consisting of A, B, C, D, E, F, and G.

9. The modified BoNT polypeptide of claim 4, wherein the modified linker region comprises an artificial linker.

10. The modified BoNT polypeptide of claim 9, wherein the artificial linker comprises a cleavage site of a protease.

11. A modified Clostridial *Botulinum* neurotoxin (BoNT) polypeptide, comprising one or more substitution mutation(s) in a position corresponding to R360, Y363, H227, E228, or H231 in SEQ ID NO: 1.

12. A modified Clostridial *Botulinum* neurotoxin, serotype X (BoNT/X) polypeptide comprising:
   (a) an inactive protease domain;
   (b) a linker region; and
   (c) a translocation domain.

13. The modified BoNT/X polypeptide of claim 12, wherein the modified BoNT/X further comprises a receptor binding domain.

14. The modified BoNT/X polypeptide of claim 12, wherein the inactive protease domain comprises one or more substitution mutation(s) in a position corresponding to R360, Y363, H227, E228, or H231 of SEQ ID NO: 1.

15. An isolated BoNT/X comprising a light chain and a heavy chain,
   wherein the LC comprises the amino acid sequence of SEQ ID NO: 3;
   wherein the heavy chain comprises an amino acid sequence set forth as amino acids 468-1306 of SEQ ID NO: 1;
   and wherein the light chain and heavy chain is connected via an inter-chain disulfide bond.

* * * * *

SEQUENCE LISTING

```
<160> NUMBER OF SEQ ID NOS: 226

<210> SEQ ID NO 1
<211> LENGTH: 1306
<212> TYPE: PRT
<213> ORGANISM: Clostridium botulinum

<400> SEQUENCE: 1

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285
```

```
Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
        435                 440                 445

Lys Lys Thr Thr Ser Lys Thr Asn Val Ser Tyr Pro Cys Ser Leu Leu
    450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Lys Ile Lys Pro
                485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
    610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
    690                 695                 700
```

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
            725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
            755                 760                 765

Ala Asn Tyr Lys Gly Asn Ile Asp Asp Lys Ala Lys Ile Lys Asn Ala
            770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
                835                 840                 845

Leu Gly Thr Asn Leu Ser Ser Ser Leu Arg Arg Lys Val Ser Ile Arg
            850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                    885                 890                 895

Val Leu Asn Leu Gly Ala Glu Asp Gly Lys Ile Lys Asp Leu Ser Gly
                900                 905                 910

Thr Thr Ser Asp Ile Asn Ile Gly Ser Asp Ile Glu Leu Ala Asp Gly
                915                 920                 925

Arg Glu Asn Lys Ala Ile Lys Ile Lys Gly Ser Glu Asn Ser Thr Ile
            930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
                980                 985                 990

Lys Ile Ser Ile Gln Asp Ser Lys Leu Ile Trp Tyr Leu Arg Asp His
            995                1000                1005

Asn Asn Ser Ile Lys Ile Val Thr Pro Asp Tyr Ile Ala Phe Asn
       1010                1015                1020

Gly Trp Asn Leu Ile Thr Ile Thr Asn Asn Arg Ser Lys Gly Ser
       1025                1030                1035

Ile Val Tyr Val Asn Gly Ser Lys Ile Glu Glu Lys Asp Ile Ser
       1040                1045                1050

Ser Ile Trp Asn Thr Glu Val Asp Asp Pro Ile Ile Phe Arg Leu
       1055                1060                1065

Lys Asn Asn Arg Asp Thr Gln Ala Phe Thr Leu Leu Asp Gln Phe
       1070                1075                1080

Ser Ile Tyr Arg Lys Glu Leu Asn Gln Asn Glu Val Val Lys Leu
       1085                1090                1095

Tyr Asn Tyr Tyr Phe Asn Ser Asn Tyr Ile Arg Asp Ile Trp Gly
       1100                1105                1110

Asn Pro Leu Gln Tyr Asn Lys Lys Tyr Tyr Leu Gln Thr Gln Asp

```
                   1115                1120                1125

Lys Pro Gly Lys Gly Leu Ile Arg Glu Tyr Trp Ser Ser Phe Gly
        1130                1135                1140

Tyr Asp Tyr Val Ile Leu Ser Asp Ser Lys Thr Ile Thr Phe Pro
        1145                1150                1155

Asn Asn Ile Arg Tyr Gly Ala Leu Tyr Asn Gly Ser Lys Val Leu
        1160                1165                1170

Ile Lys Asn Ser Lys Lys Leu Asp Gly Leu Val Arg Asn Lys Asp
        1175                1180                1185

Phe Ile Gln Leu Glu Ile Asp Gly Tyr Asn Met Gly Ile Ser Ala
        1190                1195                1200

Asp Arg Phe Asn Glu Asp Thr Asn Tyr Ile Gly Thr Thr Tyr Gly
        1205                1210                1215

Thr Thr His Asp Leu Thr Thr Asp Phe Glu Ile Ile Gln Arg Gln
        1220                1225                1230

Glu Lys Tyr Arg Asn Tyr Cys Gln Leu Lys Thr Pro Tyr Asn Ile
        1235                1240                1245

Phe His Lys Ser Gly Leu Met Ser Thr Glu Thr Ser Lys Pro Thr
        1250                1255                1260

Phe His Asp Tyr Arg Asp Trp Val Tyr Ser Ser Ala Trp Tyr Phe
        1265                1270                1275

Gln Asn Tyr Glu Asn Leu Asn Leu Arg Lys His Thr Lys Thr Asn
        1280                1285                1290

Trp Tyr Phe Ile Pro Lys Glu Gly Trp Asp Glu Asp
        1295                1300                1305

<210> SEQ ID NO 2
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 2

Met Lys Leu Glu Ile Asn Lys Phe Asn Tyr Asn Asp Pro Ile Asp Gly
1               5                   10                  15

Ile Asn Val Ile Thr Met Arg Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
```

```
                165                 170                 175
Asn Gly Glu Gly Thr Leu Ser Glu Val Ser Phe Ser Pro Phe Tyr Leu
                    180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
        210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                    245                 250                 255

Arg Gln Gln Asn Ser Leu Ile Phe Glu Glu Leu Leu Thr Phe Gly Gly
                260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
        290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                    325                 330                 335

Lys Lys Leu Asn Thr Ile Leu Phe Val Leu Asn Glu Ser Asn Leu Ala
                340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
        370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                    405                 410                 415

Arg Ala Phe Ile Lys Ile Cys Pro Arg Asn Gly Leu Leu Tyr Asn Ala
                420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
        450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                    485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
        530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                    565                 570                 575

Lys Ile Arg Val Glu Leu Thr Asp Ser Val Asp Glu Ala Leu Ser Asn
                580                 585                 590
```

```
Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
    610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
    690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
    770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
    850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile
                885                 890

<210> SEQ ID NO 3
<211> LENGTH: 439
<212> TYPE: PRT
<213> ORGANISM: Artificial Sequence
<220> FEATURE:
<223> OTHER INFORMATION: Synthetic Polypeptide

<400> SEQUENCE: 3

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60
```

Ile Pro Ser Glu Pro Ile Met Glu Ala Asp Ala Ile Tyr Asn Pro Asn
 65                  70                  75                  80

Tyr Leu Asn Thr Pro Ser Glu Lys Asp Glu Phe Leu Gln Gly Val Ile
                 85                  90                  95

Lys Val Leu Glu Arg Ile Lys Ser Lys Pro Glu Gly Lys Leu Leu
                100                 105                 110

Glu Leu Ile Ser Ser Ser Ile Pro Leu Pro Leu Val Ser Asn Gly Ala
                115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
                180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Leu Leu Thr Phe Gly Gly
                260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
                340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
            370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Arg Asn Ser Lys Asn
        435

<210> SEQ ID NO 4
<211> LENGTH: 1306
<212> TYPE: PRT
<213> ORGANISM: Artificial Sequence
<220> FEATURE:

<223> OTHER INFORMATION: Synthetic Polypeptide

<400> SEQUENCE: 4

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
                100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400
```

```
Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Ser Ser Leu Leu
450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
            530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
            610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
            690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
            755                 760                 765

Ala Asn Tyr Lys Gly Asn Ile Asp Asp Lys Ala Lys Ile Lys Asn Ala
            770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
```

```
                820                 825                 830
Glu Thr Lys Lys Thr Leu Asp Lys Phe Ile Lys Glu Lys Glu Asp Ile
                835                 840                 845
Leu Gly Thr Asn Leu Ser Ser Ser Leu Arg Arg Lys Val Ser Ile Arg
850                 855                 860
Leu Asn Lys Asn Ile Ala Phe Asp Ile Asn Asp Ile Pro Phe Ser Glu
865                 870                 875                 880
Phe Asp Asp Leu Ile Asn Gln Tyr Lys Asn Glu Ile Glu Asp Tyr Glu
                885                 890                 895
Val Leu Asn Leu Gly Ala Glu Asp Gly Lys Ile Lys Asp Leu Ser Gly
                900                 905                 910
Thr Thr Ser Asp Ile Asn Ile Gly Ser Asp Ile Glu Leu Ala Asp Gly
                915                 920                 925
Arg Glu Asn Lys Ala Ile Lys Ile Lys Gly Ser Glu Asn Ser Thr Ile
                930                 935                 940
Lys Ile Ala Met Asn Lys Tyr Leu Arg Phe Ser Ala Thr Asp Asn Phe
945                 950                 955                 960
Ser Ile Ser Phe Trp Ile Lys His Pro Lys Pro Thr Asn Leu Leu Asn
                965                 970                 975
Asn Gly Ile Glu Tyr Thr Leu Val Glu Asn Phe Asn Gln Arg Gly Trp
                980                 985                 990
Lys Ile Ser Ile Gln Asp Ser Lys  Leu Ile Trp Tyr Leu  Arg Asp His
                995                 1000                1005
Asn Asn  Ser Ile Lys Ile Val  Thr Pro Asp Tyr Ile  Ala Phe Asn
1010                1015                1020
Gly Trp  Asn Leu Ile Thr Ile  Thr Asn Asn Arg Ser  Lys Gly Ser
1025                1030                1035
Ile Val  Tyr Val Asn Gly Ser  Lys Ile Glu Glu Lys  Asp Ile Ser
1040                1045                1050
Ser Ile  Trp Asn Thr Glu Val  Asp Asp Pro Ile Ile  Phe Arg Leu
1055                1060                1065
Lys Asn  Asn Arg Asp Thr Gln  Ala Phe Thr Leu Leu  Asp Gln Phe
1070                1075                1080
Ser Ile  Tyr Arg Lys Glu Leu  Asn Gln Asn Glu Val  Val Lys Leu
1085                1090                1095
Tyr Asn  Tyr Tyr Phe Asn Ser  Asn Tyr Ile Arg Asp  Ile Trp Gly
1100                1105                1110
Asn Pro  Leu Gln Tyr Asn Lys  Lys Tyr Tyr Leu Gln  Thr Gln Asp
1115                1120                1125
Lys Pro  Gly Lys Gly Leu Ile  Arg Glu Tyr Trp Ser  Ser Phe Gly
1130                1135                1140
Tyr Asp  Tyr Val Ile Leu Ser  Asp Ser Lys Thr Ile  Thr Phe Pro
1145                1150                1155
Asn Asn  Ile Arg Tyr Gly Ala  Leu Tyr Asn Gly Ser  Lys Val Leu
1160                1165                1170
Ile Lys  Asn Ser Lys Lys Leu  Asp Gly Leu Val Arg  Asn Lys Asp
1175                1180                1185
Phe Ile  Gln Leu Glu Ile Asp  Gly Tyr Asn Met Gly  Ile Ser Ala
1190                1195                1200
Asp Arg  Phe Asn Glu Asp Thr  Asn Tyr Ile Gly Thr  Thr Tyr Gly
1205                1210                1215
Thr Thr  His Asp Leu Thr Thr  Asp Phe Glu Ile Ile  Gln Arg Gln
1220                1225                1230
```

```
Glu Lys Tyr Arg Asn Tyr Cys Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 5
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 5

Met Lys Leu Glu Ile Asn Lys Phe Asn Tyr Asn Asp Pro Ile Asp Gly
1               5                   10                  15

Ile Asn Val Ile Thr Met Arg Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285
```

```
Thr Ala Lys Asn Asn Tyr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
                340                 345                 350

Gln Arg Phe Ser Ile Leu Val Arg Lys His Tyr Leu Lys Glu Arg Pro
                355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Arg Asn Ser Lys Asn Tyr Leu Asn Asn Ile Asp Leu Glu Asp
                435                 440                 445

Lys Lys Thr Thr Ser Lys Thr Asn Val Ser Tyr Pro Ala Ser Leu Leu
    450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
                515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
                595                 600                 605

Ser Ile Glu Thr Gly Ile Thr Ser Thr Tyr Ile Phe Tyr Gln Trp Leu
    610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
                675                 680                 685

Thr Ile Pro Ile Leu Val Gly Leu Glu Val Ile Gly Gly Glu Leu Ala
    690                 695                 700
```

-continued

```
Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
            725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
            755                 760                 765

Ala Asn Tyr Lys Gly Asn Ile Asp Asp Lys Ala Lys Ile Lys Asn Ala
            770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
                835                 840                 845

Leu Gly Thr Asn Leu Ser Ser Ser Leu Arg Arg Lys Val Ser Ile Arg
            850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                    885                 890                 895

Val Leu Asn Leu Gly Ala Glu Asp Gly Lys Ile Lys Asp Leu Ser Gly
                900                 905                 910

Thr Thr Ser Asp Ile Asn Ile Gly Ser Asp Ile Glu Leu Ala Asp Gly
                915                 920                 925

Arg Glu Asn Lys Ala Ile Lys Ile Lys Gly Ser Glu Asn Ser Thr Ile
            930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
                980                 985                 990

Lys Ile Ser Ile Gln Asp Ser Lys  Leu Ile Trp Tyr Leu Arg Asp His
                995                 1000                1005

Asn Asn Ser Ile Lys Ile Val  Thr Pro Asp Tyr Ile  Ala Phe Asn
    1010                1015                1020

Gly Trp Asn Leu Ile Thr Ile  Thr Asn Asn Arg Ser  Lys Gly Ser
    1025                1030                1035

Ile Val Tyr Val Asn Gly Ser  Lys Ile Glu Glu Lys  Asp Ile Ser
    1040                1045                1050

Ser Ile Trp Asn Thr Glu Val  Asp Asp Pro Ile Ile  Phe Arg Leu
    1055                1060                1065

Lys Asn Asn Arg Asp Thr Gln  Ala Phe Thr Leu Leu  Asp Gln Phe
    1070                1075                1080

Ser Ile Tyr Arg Lys Glu Leu  Asn Gln Asn Glu Val  Val Lys Leu
    1085                1090                1095

Tyr Asn Tyr Tyr Phe Asn Ser  Asn Tyr Ile Arg Asp  Ile Trp Gly
    1100                1105                1110

Asn Pro Leu Gln Tyr Asn Lys  Lys Tyr Tyr Leu Gln  Thr Gln Asp
```

```
              1115                1120                1125
Lys Pro Gly Lys Gly Leu Ile Arg Glu Tyr Trp Ser Ser Phe Gly
        1130                1135                1140

Tyr Asp Tyr Val Ile Leu Ser Asp Ser Lys Thr Ile Thr Phe Pro
        1145                1150                1155

Asn Asn Ile Arg Tyr Gly Ala Leu Tyr Asn Gly Ser Lys Val Leu
        1160                1165                1170

Ile Lys Asn Ser Lys Lys Leu Asp Gly Leu Val Arg Asn Lys Asp
        1175                1180                1185

Phe Ile Gln Leu Glu Ile Asp Gly Tyr Asn Met Gly Ile Ser Ala
        1190                1195                1200

Asp Arg Phe Asn Glu Asp Thr Asn Tyr Ile Gly Thr Thr Tyr Gly
        1205                1210                1215

Thr Thr His Asp Leu Thr Thr Asp Phe Glu Ile Ile Gln Arg Gln
        1220                1225                1230

Glu Lys Tyr Arg Asn Tyr Cys Gln Leu Lys Thr Pro Tyr Asn Ile
        1235                1240                1245

Phe His Lys Ser Gly Leu Met Ser Thr Glu Thr Ser Lys Pro Thr
        1250                1255                1260

Phe His Asp Tyr Arg Asp Trp Val Tyr Ser Ser Ala Trp Tyr Phe
        1265                1270                1275

Gln Asn Tyr Glu Asn Leu Asn Leu Arg Lys His Thr Lys Thr Asn
        1280                1285                1290

Trp Tyr Phe Ile Pro Lys Glu Gly Trp Asp Glu Asp
        1295                1300                1305

<210> SEQ ID NO 6
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 6

Met Lys Leu Glu Ile Asn Lys Phe Asn Tyr Asn Asp Pro Ile Asp Gly
1               5                   10                  15

Ile Asn Val Ile Thr Met Arg Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
```

```
              165                 170                 175
Asn Gly Glu Gly Thr Leu Ser Glu Val Ser Phe Ser Pro Phe Tyr Leu
              180                 185                 190
Lys Pro Phe Asp Glu Ser Tyr Gly Asn Tyr Arg Ser Leu Val Asn Ile
              195                 200                 205
Val Asn Lys Phe Val Lys Arg Glu Phe Ala Pro Asp Pro Ala Ser Thr
              210                 215                 220
Leu Met His Glu Leu Val His Val Thr His Asn Leu Tyr Gly Ile Ser
225               230                 235                 240
Asn Arg Asn Phe Tyr Tyr Asn Phe Asp Thr Gly Lys Ile Glu Thr Ser
                  245                 250                 255
Arg Gln Gln Asn Ser Leu Ile Phe Glu Glu Leu Leu Thr Phe Gly Gly
              260                 265                 270
Ile Asp Ser Lys Ala Ile Ser Ser Leu Ile Ile Lys Lys Ile Ile Glu
              275                 280                 285
Thr Ala Lys Asn Asn Tyr Thr Thr Leu Ile Ser Glu Arg Leu Asn Thr
              290                 295                 300
Val Thr Val Glu Asn Asp Leu Leu Lys Tyr Ile Lys Asn Lys Ile Pro
305               310                 315                 320
Val Gln Gly Arg Leu Gly Asn Phe Lys Leu Asp Thr Ala Glu Phe Glu
                  325                 330                 335
Lys Lys Leu Asn Thr Ile Leu Phe Val Leu Asn Glu Ser Asn Leu Ala
              340                 345                 350
Gln Arg Phe Ser Ile Leu Val Arg Lys His Tyr Leu Lys Glu Arg Pro
              355                 360                 365
Ile Asp Pro Ile Tyr Val Asn Ile Leu Asp Asp Asn Ser Tyr Ser Thr
              370                 375                 380
Leu Glu Gly Phe Asn Ile Ser Ser Gln Gly Ser Asn Asp Phe Gln Gly
385               390                 395                 400
Gln Leu Leu Glu Ser Ser Tyr Phe Glu Lys Ile Glu Ser Asn Ala Leu
                  405                 410                 415
Arg Ala Phe Ile Lys Ile Cys Pro Arg Asn Gly Leu Leu Tyr Asn Ala
                  420                 425                 430
Ile Tyr Arg Asn Ser Lys Asn Tyr Leu Asn Asn Ile Asp Leu Glu Asp
                  435                 440                 445
Lys Lys Thr Thr Ser Lys Thr Asn Val Ser Tyr Pro Cys Ser Leu Leu
450               455                 460
Asn Gly Ser Ile Glu Val Glu Asn Lys Asp Leu Phe Leu Ile Ser Asn
465               470                 475                 480
Lys Asp Ser Leu Asn Asp Ile Asn Leu Ser Glu Lys Ile Lys Pro
                  485                 490                 495
Glu Thr Thr Val Phe Phe Lys Asp Lys Leu Pro Pro Gln Asp Ile Thr
                  500                 505                 510
Leu Ser Asn Tyr Asp Phe Thr Glu Ala Asn Ser Ile Pro Ser Ile Ser
                  515                 520                 525
Gln Gln Asn Ile Leu Glu Arg Asn Glu Glu Leu Tyr Glu Pro Ile Arg
              530                 535                 540
Asn Ser Leu Phe Glu Ile Lys Thr Ile Tyr Val Asp Lys Leu Thr Thr
545               550                 555                 560
Phe His Phe Leu Glu Ala Gln Asn Ile Asp Glu Ser Ile Asp Ser Ser
                  565                 570                 575
Lys Ile Arg Val Glu Leu Thr Asp Ser Val Asp Glu Ala Leu Ser Asn
              580                 585                 590
```

```
Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
        610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
            690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
            755                 760                 765

Ala Asn Tyr Lys Gly Asn Ile Asp Asp Lys Ala Lys Ile Lys Asn Ala
            770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
            835                 840                 845

Leu Gly Thr Asn Leu Ser Ser Leu Arg Arg Lys Val Ser Ile Arg
            850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
                900                 905                 910

Thr Thr Ser Asp Ile Asn Ile Gly Ser Asp Ile Glu Leu Ala Asp Gly
            915                 920                 925

Arg Glu Asn Lys Ala Ile Lys Ile Lys Gly Ser Glu Asn Ser Thr Ile
930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
            980                 985                 990

Lys Ile Ser Ile Gln Asp Ser Lys  Leu Ile Trp Tyr Leu  Arg Asp His
            995                 1000                 1005
```

```
Asn Asn Ser Ile Lys Ile Val Thr Pro Asp Tyr Ile Ala Phe Asn
    1010                1015                1020

Gly Trp Asn Leu Ile Thr Ile Thr Asn Asn Arg Ser Lys Gly Ser
    1025                1030                1035

Ile Val Tyr Val Asn Gly Ser Lys Ile Glu Glu Lys Asp Ile Ser
    1040                1045                1050

Ser Ile Trp Asn Thr Glu Val Asp Asp Pro Ile Ile Phe Arg Leu
    1055                1060                1065

Lys Asn Asn Arg Asp Thr Gln Ala Phe Thr Leu Leu Asp Gln Phe
    1070                1075                1080

Ser Ile Tyr Arg Lys Glu Leu Asn Gln Asn Glu Val Val Lys Leu
    1085                1090                1095

Tyr Asn Tyr Tyr Phe Asn Ser Asn Tyr Ile Arg Asp Ile Trp Gly
    1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Cys Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 7
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 7

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45
```

```
Ile Val Pro Glu Arg Tyr Asn Phe Thr Asn Asn Thr Asn Asp Leu Asn
 50                  55                  60

Ile Pro Ser Glu Pro Ile Met Glu Ala Asp Ala Ile Tyr Asn Pro Asn
 65                  70                  75                  80

Tyr Leu Asn Thr Pro Ser Glu Lys Asp Glu Phe Leu Gln Gly Val Ile
                 85                  90                  95

Lys Val Leu Glu Arg Ile Lys Ser Lys Pro Glu Gly Glu Lys Leu Leu
                100                 105                 110

Glu Leu Ile Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
            290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
            370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
450                 455                 460

Asn Gly Ala Ile Glu Val Glu Asn Lys Asp Leu Phe Leu Ile Ser Asn
```

-continued

```
            465                 470                 475                 480
        Lys Asp Ser Leu Asn Asp Ile Asn Leu Ser Glu Glu Lys Ile Lys Pro
                        485                 490                 495
        Glu Thr Thr Val Phe Lys Asp Lys Leu Pro Pro Gln Asp Ile Thr
                    500                 505                 510
        Leu Ser Asn Tyr Asp Phe Thr Glu Ala Asn Ser Ile Pro Ser Ile Ser
                    515                 520                 525
        Gln Gln Asn Ile Leu Glu Arg Asn Glu Glu Leu Tyr Glu Pro Ile Arg
                530                 535                 540
        Asn Ser Leu Phe Glu Ile Lys Thr Ile Tyr Val Asp Lys Leu Thr Thr
        545                 550                 555                 560
        Phe His Phe Leu Glu Ala Gln Asn Ile Asp Glu Ser Ile Asp Ser Ser
                            565                 570                 575
        Lys Ile Arg Val Glu Leu Thr Asp Ser Val Asp Glu Ala Leu Ser Asn
                        580                 585                 590
        Pro Asn Lys Val Tyr Ser Pro Phe Lys Asn Met Ser Asn Thr Ile Asn
                    595                 600                 605
        Ser Ile Glu Thr Gly Ile Thr Ser Thr Tyr Ile Phe Tyr Gln Trp Leu
                610                 615                 620
        Arg Ser Ile Val Lys Asp Phe Ser Asp Glu Thr Gly Lys Ile Asp Val
        625                 630                 635                 640
        Ile Asp Lys Ser Ser Asp Thr Leu Ala Ile Val Pro Tyr Ile Gly Pro
                        645                 650                 655
        Leu Leu Asn Ile Gly Asn Asp Ile Arg His Gly Asp Phe Val Gly Ala
                    660                 665                 670
        Ile Glu Leu Ala Gly Ile Thr Ala Leu Leu Glu Tyr Val Pro Glu Phe
                    675                 680                 685
        Thr Ile Pro Ile Leu Val Gly Leu Glu Val Ile Gly Gly Glu Leu Ala
                690                 695                 700
        Arg Glu Gln Val Glu Ala Ile Val Asn Ala Leu Asp Lys Arg Asp
        705                 710                 715                 720
        Gln Lys Trp Ala Glu Val Tyr Asn Ile Thr Lys Ala Gln Trp Trp Gly
                        725                 730                 735
        Thr Ile His Leu Gln Ile Asn Thr Arg Leu Ala His Thr Tyr Lys Ala
                    740                 745                 750
        Leu Ser Arg Gln Ala Asn Ala Ile Lys Met Asn Met Glu Phe Gln Leu
                755                 760                 765
        Ala Asn Tyr Lys Gly Asn Ile Asp Asp Lys Ala Lys Ile Lys Asn Ala
                770                 775                 780
        Ile Ser Glu Thr Glu Ile Leu Leu Asn Lys Ser Val Glu Gln Ala Met
        785                 790                 795                 800
        Lys Asn Thr Glu Lys Phe Met Ile Lys Leu Ser Asn Ser Tyr Leu Thr
                        805                 810                 815
        Lys Glu Met Ile Pro Lys Val Gln Asp Asn Leu Lys Asn Phe Asp Leu
                    820                 825                 830
        Glu Thr Lys Lys Thr Leu Asp Lys Phe Ile Lys Glu Lys Glu Asp Ile
                835                 840                 845
        Leu Gly Thr Asn Leu Ser Ser Ser Leu Arg Arg Lys Val Ser Ile Arg
                850                 855                 860
        Leu Asn Lys Asn Ile Ala Phe Asp Ile Asn Asp Ile Pro Phe Ser Glu
        865                 870                 875                 880
        Phe Asp Asp Leu Ile Asn Gln Tyr Lys Asn Glu Ile Glu Asp Tyr Glu
                        885                 890                 895
```

-continued

```
Val Leu Asn Leu Gly Ala Glu Asp Gly Lys Ile Lys Asp Leu Ser Gly
            900                 905                 910

Thr Thr Ser Asp Ile Asn Ile Gly Ser Asp Ile Glu Leu Ala Asp Gly
        915                 920                 925

Arg Glu Asn Lys Ala Ile Lys Ile Lys Gly Ser Glu Asn Ser Thr Ile
    930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
            980                 985                 990

Lys Ile Ser Ile Gln Asp Ser Lys Leu Ile Trp Tyr Leu Arg Asp His
        995                 1000                1005

Asn Asn Ser Ile Lys Ile Val Thr Pro Asp Tyr Ile Ala Phe Asn
    1010                1015                1020

Gly Trp Asn Leu Ile Thr Ile Thr Asn Asn Arg Ser Lys Gly Ser
    1025                1030                1035

Ile Val Tyr Val Asn Gly Ser Lys Ile Glu Glu Lys Asp Ile Ser
    1040                1045                1050

Ser Ile Trp Asn Thr Glu Val Asp Asp Pro Ile Ile Phe Arg Leu
    1055                1060                1065

Lys Asn Asn Arg Asp Thr Gln Ala Phe Thr Leu Leu Asp Gln Phe
    1070                1075                1080

Ser Ile Tyr Arg Lys Glu Leu Asn Gln Asn Glu Val Val Lys Leu
    1085                1090                1095

Tyr Asn Tyr Tyr Phe Asn Ser Asn Tyr Ile Arg Asp Ile Trp Gly
    1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Cys Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290
```

```
Trp Tyr Phe Ile Pro Lys Asp Glu Gly Trp Asp Glu Asp
    1295                1300                1305
```

<210> SEQ ID NO 8
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 8

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350
```

```
Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
            755                 760                 765

Ala Asn Tyr Lys Gly Asn Ile Asp Asp Lys Ala Lys Ile Lys Asn Ala
```

```
            770             775             780
Ile Ser Glu Thr Glu Ile Leu Leu Asn Lys Ser Val Glu Gln Ala Met
785             790             795             800

Lys Asn Thr Glu Lys Phe Met Ile Lys Leu Ser Asn Ser Tyr Leu Thr
            805             810             815

Lys Glu Met Ile Pro Lys Val Gln Asp Asn Leu Lys Asn Phe Asp Leu
        820             825             830

Glu Thr Lys Lys Thr Leu Asp Lys Phe Ile Lys Glu Lys Glu Asp Ile
        835             840             845

Leu Gly Thr Asn Leu Ser Ser Ser Leu Arg Arg Lys Val Ser Ile Arg
    850             855             860

Leu Asn Lys Asn Ile Ala Phe Asp Ile Asn Asp Ile Pro Phe Ser Glu
865             870             875             880

Phe Asp Asp Leu Ile Asn Gln Tyr Lys Asn Glu Ile Glu Asp Tyr Glu
                885             890             895

Val Leu Asn Leu Gly Ala Glu Asp Gly Lys Ile Lys Asp Leu Ser Gly
            900             905             910

Thr Thr Ser Asp Ile Asn Ile Gly Ser Asp Ile Glu Leu Ala Asp Gly
            915             920             925

Arg Glu Asn Lys Ala Ile Lys Ile Lys Gly Ser Glu Asn Ser Thr Ile
        930             935             940

Lys Ile Ala Met Asn Lys Tyr Leu Arg Phe Ser Ala Thr Asp Asn Phe
945             950             955             960

Ser Ile Ser Phe Trp Ile Lys His Pro Lys Pro Thr Asn Leu Leu Asn
                965             970             975

Asn Gly Ile Glu Tyr Thr Leu Val Glu Asn Phe Asn Gln Arg Gly Trp
            980             985             990

Lys Ile Ser Ile Gln Asp Ser Lys Leu Ile Trp Tyr Leu Arg Asp His
            995             1000            1005

Asn Asn Ser Ile Lys Ile Val Thr Pro Asp Tyr Ile Ala Phe Asn
    1010            1015            1020

Gly Trp Asn Leu Ile Thr Ile Thr Asn Asn Arg Ser Lys Gly Ser
    1025            1030            1035

Ile Val Tyr Val Asn Gly Ser Lys Ile Glu Glu Lys Asp Ile Ser
    1040            1045            1050

Ser Ile Trp Asn Thr Glu Val Asp Asp Pro Ile Ile Phe Arg Leu
    1055            1060            1065

Lys Asn Asn Arg Asp Thr Gln Ala Phe Thr Leu Leu Asp Gln Phe
    1070            1075            1080

Ser Ile Tyr Arg Lys Glu Leu Asn Gln Asn Glu Val Val Lys Leu
    1085            1090            1095

Tyr Asn Tyr Tyr Phe Asn Ser Asn Tyr Ile Arg Asp Ile Trp Gly
    1100            1105            1110

Asn Pro Leu Gln Tyr Asn Lys Lys Tyr Tyr Leu Gln Thr Gln Asp
    1115            1120            1125

Lys Pro Gly Lys Gly Leu Ile Arg Glu Tyr Trp Ser Ser Phe Gly
    1130            1135            1140

Tyr Asp Tyr Val Ile Leu Ser Asp Ser Lys Thr Ile Thr Phe Pro
    1145            1150            1155

Asn Asn Ile Arg Tyr Gly Ala Leu Tyr Asn Gly Ser Lys Val Leu
    1160            1165            1170

Ile Lys Asn Ser Lys Lys Leu Asp Gly Leu Val Arg Asn Lys Asp
    1175            1180            1185
```

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Ser Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 9
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 9

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

-continued

```
Asn Arg Asn Phe Tyr Tyr Asn Phe Asp Thr Gly Lys Ile Glu Thr Ser
                245                 250                 255

Arg Gln Gln Asn Ser Leu Ile Phe Glu Leu Leu Thr Phe Gly Gly
        260                 265                 270

Ile Asp Ser Lys Ala Ile Ser Ser Leu Ile Lys Lys Ile Ile Glu
    275                 280                 285

Thr Ala Lys Asn Asn Tyr Thr Thr Leu Ile Ser Glu Arg Leu Asn Thr
290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
        435                 440                 445

Lys Lys Thr Thr Ser Lys Thr Asn Val Ser Tyr Pro Cys Ser Leu Leu
    450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
    610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655
```

```
Leu Leu Asn Ile Gly Asn Asp Ile Arg His Gly Asp Phe Val Gly Ala
        660                 665                 670

Ile Glu Leu Ala Gly Ile Thr Ala Leu Leu Glu Tyr Val Pro Glu Phe
    675                 680                 685

Thr Ile Pro Ile Leu Val Gly Leu Glu Val Ile Gly Gly Glu Leu Ala
    690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
    770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
    850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
            900                 905                 910

Thr Thr Ser Asp Ile Asn Ile Gly Ser Asp Ile Glu Leu Ala Asp Gly
        915                 920                 925

Arg Glu Asn Lys Ala Ile Lys Ile Lys Gly Ser Glu Asn Ser Thr Ile
    930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
            980                 985                 990

Lys Ile Ser Ile Gln Asp Ser Lys Leu Ile Trp Tyr Leu Arg Asp His
        995                 1000                1005

Asn Asn Ser Ile Lys Ile Val Thr Pro Asp Tyr Ile Ala Phe Asn
        1010                1015                1020

Gly Trp Asn Leu Ile Thr Ile Thr Asn Asn Arg Ser Lys Gly Ser
        1025                1030                1035

Ile Val Tyr Val Asn Gly Ser Lys Ile Glu Glu Lys Asp Ile Ser
        1040                1045                1050

Ser Ile Trp Asn Thr Glu Val Asp Asp Pro Ile Ile Phe Arg Leu
        1055                1060                1065

Lys Asn Asn Arg Asp Thr Gln Ala Phe Thr Leu Leu Asp Gln Phe
```

```
                1070                1075                1080

Ser Ile Tyr Arg Lys Glu Leu Asn Gln Asn Val Val Lys Leu
    1085                1090                1095

Tyr Asn Tyr Tyr Phe Asn Ser Asn Tyr Ile Arg Asp Ile Trp Gly
    1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Ala Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 10
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 10

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
```

```
            115                 120                 125
Leu Thr Leu Ser Asp Asn Glu Thr Ile Ala Tyr Gln Glu Asn Asn
        130                 135                 140
Ile Val Ser Asn Leu Gln Ala Asn Leu Val Ile Tyr Gly Pro Gly Pro
145                 150                 155                 160
Asp Ile Ala Asn Asn Ala Thr Tyr Gly Leu Tyr Ser Thr Pro Ile Ser
                165                 170                 175
Asn Gly Glu Gly Thr Leu Ser Glu Val Ser Phe Ser Pro Phe Tyr Leu
                180                 185                 190
Lys Pro Phe Asp Glu Ser Tyr Gly Asn Tyr Arg Ser Leu Val Asn Ile
                195                 200                 205
Val Asn Lys Phe Val Lys Arg Glu Phe Ala Pro Asp Pro Ala Ser Thr
210                 215                 220
Leu Met His Glu Leu Val His Val Thr His Asn Leu Tyr Gly Ile Ser
225                 230                 235                 240
Asn Arg Asn Phe Tyr Tyr Asn Phe Asp Thr Gly Lys Ile Glu Thr Ser
                245                 250                 255
Arg Gln Gln Asn Ser Leu Ile Phe Glu Glu Leu Leu Thr Phe Gly Gly
                260                 265                 270
Ile Asp Ser Lys Ala Ile Ser Ser Leu Ile Ile Lys Lys Ile Ile Glu
                275                 280                 285
Thr Ala Lys Asn Asn Tyr Thr Thr Leu Ile Ser Glu Arg Leu Asn Thr
                290                 295                 300
Val Thr Val Glu Asn Asp Leu Leu Lys Tyr Ile Lys Asn Lys Ile Pro
305                 310                 315                 320
Val Gln Gly Arg Leu Gly Asn Phe Lys Leu Asp Thr Ala Glu Phe Glu
                325                 330                 335
Lys Lys Leu Asn Thr Ile Leu Phe Val Leu Asn Glu Ser Asn Leu Ala
                340                 345                 350
Gln Arg Phe Ser Ile Leu Val Arg Lys His Tyr Leu Lys Glu Arg Pro
                355                 360                 365
Ile Asp Pro Ile Tyr Val Asn Ile Leu Asp Asp Asn Ser Tyr Ser Thr
370                 375                 380
Leu Glu Gly Phe Asn Ile Ser Ser Gln Gly Ser Asn Asp Phe Gln Gly
385                 390                 395                 400
Gln Leu Leu Glu Ser Ser Tyr Phe Glu Lys Ile Glu Ser Asn Ala Leu
                405                 410                 415
Arg Ala Phe Ile Lys Ile Cys Pro Arg Asn Gly Leu Leu Tyr Asn Ala
                420                 425                 430
Ile Tyr Arg Asn Ser Lys Asn Tyr Leu Asn Asn Ile Asp Leu Glu Asp
                435                 440                 445
Lys Lys Thr Thr Ser Lys Thr Asn Val Ser Tyr Pro Ser Ser Leu Leu
                450                 455                 460
Asn Gly Cys Ile Glu Val Glu Asn Lys Asp Leu Phe Leu Ile Ser Asn
465                 470                 475                 480
Lys Asp Ser Leu Asn Asp Ile Asn Leu Ser Glu Lys Ile Lys Pro
                485                 490                 495
Glu Thr Thr Val Phe Lys Asp Lys Leu Pro Pro Gln Asp Ile Thr
                500                 505                 510
Leu Ser Asn Tyr Asp Phe Thr Glu Ala Asn Ser Ile Pro Ser Ile Ser
                515                 520                 525
Gln Gln Asn Ile Leu Glu Arg Asn Glu Glu Leu Tyr Glu Pro Ile Arg
                530                 535                 540
```

```
Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
            900                 905                 910

Thr Thr Ser Asp Ile Asn Ile Gly Ser Asp Ile Glu Leu Ala Asp Gly
        915                 920                 925

Arg Glu Asn Lys Ala Ile Lys Ile Lys Gly Ser Glu Asn Ser Thr Ile
930                 935                 940

Lys Ile Ala Met Asn Lys Tyr Leu Arg Phe Ser Ala Thr Asp Asn Phe
945                 950                 955                 960
```

Ser Ile Ser Phe Trp Ile Lys His Pro Lys Pro Thr Asn Leu Leu Asn
       965                 970                 975

Asn Gly Ile Glu Tyr Thr Leu Val Glu Asn Phe Asn Gln Arg Gly Trp
       980                 985                 990

Lys Ile Ser Ile Gln Asp Ser Lys Leu Ile Trp Tyr Leu Arg Asp His
       995                1000                1005

Asn Asn Ser Ile Lys Ile Val Thr Pro Asp Tyr Ile Ala Phe Asn
    1010                1015                1020

Gly Trp Asn Leu Ile Thr Ile Thr Asn Arg Ser Lys Gly Ser
    1025                1030                1035

Ile Val Tyr Val Asn Gly Ser Lys Ile Glu Glu Lys Asp Ile Ser
    1040                1045                1050

Ser Ile Trp Asn Thr Glu Val Asp Asp Pro Ile Ile Phe Arg Leu
    1055                1060                1065

Lys Asn Asn Arg Asp Thr Gln Ala Phe Thr Leu Leu Asp Gln Phe
    1070                1075                1080

Ser Ile Tyr Arg Lys Glu Leu Asn Gln Asn Glu Val Val Lys Leu
    1085                1090                1095

Tyr Asn Tyr Tyr Phe Asn Ser Asn Tyr Ile Arg Asp Ile Trp Gly
    1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Ala Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 11
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 11

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Thr Asn Asp Leu Asn
50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
            85                  90                  95

Lys Val Leu Glu Arg Ile Lys Ser Lys Pro Glu Gly Glu Lys Leu Leu
            100                 105                 110

Glu Leu Ile Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
            130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
            165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
            245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
            290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
            325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
            370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
            405                 410                 415

Arg Ala Phe Ile Lys Ile Cys Pro Arg Asn Gly Leu Leu Tyr Asn Ala
```

```
              420             425             430
Ile Tyr Arg Asn Ser Lys Asn Tyr Leu Asn Asn Ile Asp Leu Glu Asp
            435                 440                 445
Lys Lys Thr Thr Ser Lys Thr Asn Val Ser Tyr Pro Ser Ser Leu Leu
    450                 455                 460
Asn Gly Cys Ile Glu Val Glu Asn Lys Asp Leu Phe Leu Ile Ser Asn
465                 470                 475                 480
Lys Asp Ser Leu Asn Asp Ile Asn Leu Ser Glu Glu Lys Ile Lys Pro
                485                 490                 495
Glu Thr Thr Val Phe Phe Lys Asp Lys Leu Pro Pro Gln Asp Ile Thr
                    500                 505                 510
Leu Ser Asn Tyr Asp Phe Thr Glu Ala Asn Ser Ile Pro Ser Ile Ser
            515                 520                 525
Gln Gln Asn Ile Leu Glu Arg Asn Glu Glu Leu Tyr Glu Pro Ile Arg
        530                 535                 540
Asn Ser Leu Phe Glu Ile Lys Thr Ile Tyr Val Asp Lys Leu Thr Thr
545                 550                 555                 560
Phe His Phe Leu Glu Ala Gln Asn Ile Asp Glu Ser Ile Asp Ser Ser
                565                 570                 575
Lys Ile Arg Val Glu Leu Thr Asp Ser Val Asp Glu Ala Leu Ser Asn
                    580                 585                 590
Pro Asn Lys Val Tyr Ser Pro Phe Lys Asn Met Ser Asn Thr Ile Asn
            595                 600                 605
Ser Ile Glu Thr Gly Ile Thr Ser Thr Tyr Ile Phe Tyr Gln Trp Leu
        610                 615                 620
Arg Ser Ile Val Lys Asp Phe Ser Asp Glu Thr Gly Lys Ile Asp Val
625                 630                 635                 640
Ile Asp Lys Ser Ser Asp Thr Leu Ala Ile Val Pro Tyr Ile Gly Pro
                645                 650                 655
Leu Leu Asn Ile Gly Asn Asp Ile Arg His Gly Asp Phe Val Gly Ala
                    660                 665                 670
Ile Glu Leu Ala Gly Ile Thr Ala Leu Leu Glu Tyr Val Pro Glu Phe
            675                 680                 685
Thr Ile Pro Ile Leu Val Gly Leu Glu Val Ile Gly Gly Glu Leu Ala
        690                 695                 700
Arg Glu Gln Val Glu Ala Ile Val Asn Asn Ala Leu Asp Lys Arg Asp
705                 710                 715                 720
Gln Lys Trp Ala Glu Val Tyr Asn Ile Thr Lys Ala Gln Trp Trp Gly
                725                 730                 735
Thr Ile His Leu Gln Ile Asn Thr Arg Leu Ala His Thr Tyr Lys Ala
                    740                 745                 750
Leu Ser Arg Gln Ala Asn Ala Ile Lys Met Asn Met Glu Phe Gln Leu
            755                 760                 765
Ala Asn Tyr Lys Gly Asn Ile Asp Asp Lys Ala Lys Ile Lys Asn Ala
        770                 775                 780
Ile Ser Glu Thr Glu Ile Leu Leu Asn Lys Ser Val Glu Gln Ala Met
785                 790                 795                 800
Lys Asn Thr Glu Lys Phe Met Ile Lys Leu Ser Asn Ser Tyr Leu Thr
                805                 810                 815
Lys Glu Met Ile Pro Lys Val Gln Asp Asn Leu Lys Asn Phe Asp Leu
                    820                 825                 830
Glu Thr Lys Lys Thr Leu Asp Lys Phe Ile Lys Glu Lys Glu Asp Ile
            835                 840                 845
```

```
Leu Gly Thr Asn Leu Ser Ser Ser Leu Arg Arg Lys Val Ser Ile Arg
    850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
            900                 905                 910

Thr Thr Ser Asp Ile Asn Ile Gly Ser Asp Ile Glu Leu Ala Asp Gly
        915                 920                 925

Arg Glu Asn Lys Ala Ile Lys Ile Lys Gly Ser Glu Asn Ser Thr Ile
    930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
            980                 985                 990

Lys Ile Ser Ile Gln Asp Ser Lys  Leu Ile Trp Tyr Leu  Arg Asp His
        995                 1000                 1005

Asn Asn  Ser Ile Lys Ile Val  Thr Pro Asp Tyr Ile  Ala Phe Asn
    1010                 1015                 1020

Gly Trp  Asn Leu Ile Thr Ile  Thr Asn Asn Arg Ser  Lys Gly Ser
    1025                 1030                 1035

Ile Val  Tyr Val Asn Gly Ser  Lys Ile Glu Glu Lys  Asp Ile Ser
    1040                 1045                 1050

Ser Ile  Trp Asn Thr Glu Val  Asp Asp Pro Ile Ile  Phe Arg Leu
    1055                 1060                 1065

Lys Asn  Asn Arg Asp Thr Gln  Ala Phe Thr Leu Leu  Asp Gln Phe
    1070                 1075                 1080

Ser Ile  Tyr Arg Lys Glu Leu  Asn Gln Asn Glu Val  Val Lys Leu
    1085                 1090                 1095

Tyr Asn  Tyr Tyr Phe Asn Ser  Asn Tyr Ile Arg Asp  Ile Trp Gly
    1100                 1105                 1110

Asn Pro  Leu Gln Tyr Asn Lys  Lys Tyr Tyr Leu Gln  Thr Gln Asp
    1115                 1120                 1125

Lys Pro  Gly Lys Gly Leu Ile  Arg Glu Tyr Trp Ser  Ser Phe Gly
    1130                 1135                 1140

Tyr Asp  Tyr Val Ile Leu Ser  Asp Ser Lys Thr Ile  Thr Phe Pro
    1145                 1150                 1155

Asn Asn  Ile Arg Tyr Gly Ala  Leu Tyr Asn Gly Ser  Lys Val Leu
    1160                 1165                 1170

Ile Lys  Asn Ser Lys Lys Leu  Asp Gly Leu Val Arg  Asn Lys Asp
    1175                 1180                 1185

Phe Ile  Gln Leu Glu Ile Asp  Gly Tyr Asn Met Gly  Ile Ser Ala
    1190                 1195                 1200

Asp Arg  Phe Asn Glu Asp Thr  Asn Tyr Ile Gly Thr  Thr Tyr Gly
    1205                 1210                 1215

Thr Thr  His Asp Leu Thr Thr  Asp Phe Glu Ile Ile  Gln Arg Gln
    1220                 1225                 1230

Glu Lys  Tyr Arg Asn Tyr Ser  Gln Leu Lys Thr Pro  Tyr Asn Ile
    1235                 1240                 1245
```

```
Phe His Lys Ser Gly Leu Met Ser Thr Glu Thr Ser Lys Pro Thr
    1250                1255                1260

Phe His Asp Tyr Arg Asp Trp Val Tyr Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 12
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 12

Met Lys Leu Glu Ile Asn Lys Phe Asn Tyr Asn Asp Pro Ile Asp Gly
 1               5                  10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300
```

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
            325                 330                 335

Lys Lys Leu Asn Thr Ile Leu Phe Val Leu Asn Glu Ser Asn Leu Ala
                340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
            405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Ala Ser Leu Leu
450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
            485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
            565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
            645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
            690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly

```
                    725                 730                 735
Thr Ile His Leu Gln Ile Asn Thr Arg Leu Ala His Thr Tyr Lys Ala
                740                 745                 750
Leu Ser Arg Gln Ala Asn Ala Ile Lys Met Asn Met Glu Phe Gln Leu
            755                 760                 765
Ala Asn Tyr Lys Gly Asn Ile Asp Asp Lys Ala Lys Ile Lys Asn Ala
        770                 775                 780
Ile Ser Glu Thr Glu Ile Leu Leu Asn Lys Ser Val Glu Gln Ala Met
785                 790                 795                 800
Lys Asn Thr Glu Lys Phe Met Ile Lys Leu Ser Asn Ser Tyr Leu Thr
                805                 810                 815
Lys Glu Met Ile Pro Lys Val Gln Asp Asn Leu Lys Asn Phe Asp Leu
                820                 825                 830
Glu Thr Lys Lys Thr Leu Asp Lys Phe Ile Lys Glu Lys Glu Asp Ile
                835                 840                 845
Leu Gly Thr Asn Leu Ser Ser Ser Leu Arg Arg Lys Val Ser Ile Arg
        850                 855                 860
Leu Asn Lys Asn Ile Ala Phe Asp Ile Asn Asp Ile Pro Phe Ser Glu
865                 870                 875                 880
Phe Asp Asp Leu Ile Asn Gln Tyr Lys Asn Glu Ile Glu Asp Tyr Glu
                    885                 890                 895
Val Leu Asn Leu Gly Ala Glu Asp Gly Lys Ile Lys Asp Leu Ser Gly
                900                 905                 910
Thr Thr Ser Asp Ile Asn Ile Gly Ser Asp Ile Glu Leu Ala Asp Gly
                915                 920                 925
Arg Glu Asn Lys Ala Ile Lys Ile Lys Gly Ser Glu Asn Ser Thr Ile
        930                 935                 940
Lys Ile Ala Met Asn Lys Tyr Leu Arg Phe Ser Ala Thr Asp Asn Phe
945                 950                 955                 960
Ser Ile Ser Phe Trp Ile Lys His Pro Lys Pro Thr Asn Leu Leu Asn
                965                 970                 975
Asn Gly Ile Glu Tyr Thr Leu Val Glu Asn Phe Asn Gln Arg Gly Trp
                980                 985                 990
Lys Ile Ser Ile Gln Asp Ser Lys  Leu Ile Trp Tyr Leu  Arg Asp His
        995                 1000                1005
Asn Asn Ser Ile Lys Ile Val  Thr Pro Asp Tyr Ile  Ala Phe Asn
        1010                1015                1020
Gly Trp Asn Leu Ile Thr Ile  Thr Asn Asn Arg Ser  Lys Gly Ser
        1025                1030                1035
Ile Val  Tyr Val Asn Gly Ser  Lys Ile Glu Glu Lys  Asp Ile Ser
    1040                1045                1050
Ser Ile Trp Asn Thr Glu Val  Asp Asp Pro Ile Ile  Phe Arg Leu
    1055                1060                1065
Lys Asn Asn Arg Asp Thr Gln  Ala Phe Thr Leu Leu  Asp Gln Phe
    1070                1075                1080
Ser Ile Tyr Arg Lys Glu Leu  Asn Gln Asn Glu Val  Val Lys Leu
    1085                1090                1095
Tyr Asn Tyr Tyr Phe Asn Ser  Asn Tyr Ile Arg Asp  Ile Trp Gly
    1100                1105                1110
Asn Pro Leu Gln Tyr Asn Lys  Lys Tyr Tyr Leu Gln  Thr Gln Asp
    1115                1120                1125
Lys Pro Gly Lys Gly Leu Ile  Arg Glu Tyr Trp Ser  Ser Phe Gly
    1130                1135                1140
```

Tyr Asp Tyr Val Ile Leu Ser Asp Ser Lys Thr Ile Thr Phe Pro
1145                1150                1155

Asn Asn Ile Arg Tyr Gly Ala Leu Tyr Asn Gly Ser Lys Val Leu
1160                1165                1170

Ile Lys Asn Ser Lys Lys Leu Asp Gly Leu Val Arg Asn Lys Asp
1175                1180                1185

Phe Ile Gln Leu Glu Ile Asp Gly Tyr Asn Met Gly Ile Ser Ala
1190                1195                1200

Asp Arg Phe Asn Glu Asp Thr Asn Tyr Ile Gly Thr Thr Tyr Gly
1205                1210                1215

Thr Thr His Asp Leu Thr Thr Asp Phe Glu Ile Ile Gln Arg Gln
1220                1225                1230

Glu Lys Tyr Arg Asn Tyr Ser Gln Leu Lys Thr Pro Tyr Asn Ile
1235                1240                1245

Phe His Lys Ser Gly Leu Met Ser Thr Glu Thr Ser Lys Pro Thr
1250                1255                1260

Phe His Asp Tyr Arg Asp Trp Val Tyr Ser Ser Ala Trp Tyr Phe
1265                1270                1275

Gln Asn Tyr Glu Asn Leu Asn Leu Arg Lys His Thr Lys Thr Asn
1280                1285                1290

Trp Tyr Phe Ile Pro Lys Asp Glu Gly Trp Asp Glu Asp
1295                1300                1305

<210> SEQ ID NO 13
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 13

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

```
Lys Pro Phe Asp Glu Ser Tyr Gly Asn Tyr Arg Ser Leu Val Asn Ile
        195                 200                 205
Val Asn Lys Phe Val Lys Arg Glu Phe Ala Pro Asp Pro Ala Ser Thr
    210                 215                 220
Leu Met His Glu Leu Val His Val Thr His Asn Leu Tyr Gly Ile Ser
225                 230                 235                 240
Asn Arg Asn Phe Tyr Tyr Asn Phe Asp Thr Gly Lys Ile Glu Thr Ser
                245                 250                 255
Arg Gln Gln Asn Ser Leu Ile Phe Glu Glu Leu Leu Thr Phe Gly Gly
            260                 265                 270
Ile Asp Ser Lys Ala Ile Ser Ser Leu Ile Ile Lys Lys Ile Ile Glu
        275                 280                 285
Thr Ala Lys Asn Asn Tyr Thr Thr Leu Ile Ser Glu Arg Leu Asn Thr
290                 295                 300
Val Thr Val Glu Asn Asp Leu Leu Lys Tyr Ile Lys Asn Lys Ile Pro
305                 310                 315                 320
Val Gln Gly Arg Leu Gly Asn Phe Lys Leu Asp Thr Ala Glu Phe Glu
                325                 330                 335
Lys Lys Leu Asn Thr Ile Leu Phe Val Leu Asn Glu Ser Asn Leu Ala
            340                 345                 350
Gln Arg Phe Ser Ile Leu Val Arg Lys His Tyr Leu Lys Glu Arg Pro
        355                 360                 365
Ile Asp Pro Ile Tyr Val Asn Ile Leu Asp Asp Asn Ser Tyr Ser Thr
370                 375                 380
Leu Glu Gly Phe Asn Ile Ser Ser Gln Gly Ser Asn Asp Phe Gln Gly
385                 390                 395                 400
Gln Leu Leu Glu Ser Ser Tyr Phe Glu Lys Ile Glu Ser Asn Ala Leu
                405                 410                 415
Arg Ala Phe Ile Lys Ile Cys Pro Arg Asn Gly Leu Leu Tyr Asn Ala
            420                 425                 430
Ile Tyr Arg Asn Ser Lys Asn Tyr Leu Asn Asn Ile Asp Leu Glu Asp
        435                 440                 445
Lys Lys Thr Thr Ser Lys Thr Asn Val Ser Tyr Pro Ala Ser Leu Leu
450                 455                 460
Asn Gly Cys Ile Glu Val Glu Asn Lys Asp Leu Phe Leu Ile Ser Asn
465                 470                 475                 480
Lys Asp Ser Leu Asn Asp Ile Asn Leu Ser Glu Glu Lys Ile Lys Pro
                485                 490                 495
Glu Thr Thr Val Phe Phe Lys Asp Lys Leu Pro Pro Gln Asp Ile Thr
            500                 505                 510
Leu Ser Asn Tyr Asp Phe Thr Glu Ala Asn Ser Ile Pro Ser Ile Ser
        515                 520                 525
Gln Gln Asn Ile Leu Glu Arg Asn Glu Glu Leu Tyr Glu Pro Ile Arg
530                 535                 540
Asn Ser Leu Phe Glu Ile Lys Thr Ile Tyr Val Asp Lys Leu Thr Thr
545                 550                 555                 560
Phe His Phe Leu Glu Ala Gln Asn Ile Asp Glu Ser Ile Asp Ser Ser
                565                 570                 575
Lys Ile Arg Val Glu Leu Thr Asp Ser Val Asp Glu Ala Leu Ser Asn
            580                 585                 590
Pro Asn Lys Val Tyr Ser Pro Phe Lys Asn Met Ser Asn Thr Ile Asn
        595                 600                 605
```

```
Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
                675                 680                 685

Thr Ile Pro Ile Leu Val Gly Leu Glu Val Ile Gly Gly Glu Leu Ala
690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
                755                 760                 765

Ala Asn Tyr Lys Gly Asn Ile Asp Asp Lys Ala Lys Ile Lys Asn Ala
770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
                835                 840                 845

Leu Gly Thr Asn Leu Ser Ser Leu Arg Arg Lys Val Ser Ile Arg
850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
                900                 905                 910

Thr Thr Ser Asp Ile Asn Ile Gly Ser Asp Ile Glu Leu Ala Asp Gly
                915                 920                 925

Arg Glu Asn Lys Ala Ile Lys Ile Lys Gly Ser Glu Asn Ser Thr Ile
930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
                980                 985                 990

Lys Ile Ser Ile Gln Asp Ser Lys Leu Ile Trp Tyr Leu Arg Asp His
                995                 1000                1005

Asn Asn Ser Ile Lys Ile Val Thr Pro Asp Tyr Ile Ala Phe Asn
    1010                1015                1020

Gly Trp Asn Leu Ile Thr Ile Thr Asn Asn Arg Ser Lys Gly Ser
```

```
                        1025                1030                1035

Ile  Val  Tyr  Val  Asn  Gly  Ser  Lys  Ile  Glu  Glu  Lys  Asp  Ile  Ser
               1040                1045                1050

Ser  Ile  Trp  Asn  Thr  Glu  Val  Asp  Asp  Pro  Ile  Ile  Phe  Arg  Leu
          1055                1060                1065

Lys  Asn  Asn  Arg  Asp  Thr  Gln  Ala  Phe  Thr  Leu  Leu  Asp  Gln  Phe
     1070                1075                1080

Ser  Ile  Tyr  Arg  Lys  Glu  Leu  Asn  Gln  Asn  Glu  Val  Val  Lys  Leu
1085                1090                1095

Tyr  Asn  Tyr  Tyr  Phe  Asn  Ser  Asn  Tyr  Ile  Arg  Asp  Ile  Trp  Gly
     1100                1105                1110

Asn  Pro  Leu  Gln  Tyr  Asn  Lys  Lys  Tyr  Tyr  Leu  Gln  Thr  Gln  Asp
     1115                1120                1125

Lys  Pro  Gly  Lys  Gly  Leu  Ile  Arg  Glu  Tyr  Trp  Ser  Ser  Phe  Gly
     1130                1135                1140

Tyr  Asp  Tyr  Val  Ile  Leu  Ser  Asp  Ser  Lys  Thr  Ile  Thr  Phe  Pro
     1145                1150                1155

Asn  Asn  Ile  Arg  Tyr  Gly  Ala  Leu  Tyr  Asn  Gly  Ser  Lys  Val  Leu
     1160                1165                1170

Ile  Lys  Asn  Ser  Lys  Lys  Leu  Asp  Gly  Leu  Val  Arg  Asn  Lys  Asp
     1175                1180                1185

Phe  Ile  Gln  Leu  Glu  Ile  Asp  Gly  Tyr  Asn  Met  Gly  Ile  Ser  Ala
     1190                1195                1200

Asp  Arg  Phe  Asn  Glu  Asp  Thr  Asn  Tyr  Ile  Gly  Thr  Thr  Tyr  Gly
     1205                1210                1215

Thr  Thr  His  Asp  Leu  Thr  Thr  Asp  Phe  Glu  Ile  Ile  Gln  Arg  Gln
     1220                1225                1230

Glu  Lys  Tyr  Arg  Asn  Tyr  Ala  Gln  Leu  Lys  Thr  Pro  Tyr  Asn  Ile
     1235                1240                1245

Phe  His  Lys  Ser  Gly  Leu  Met  Ser  Thr  Glu  Thr  Ser  Lys  Pro  Thr
     1250                1255                1260

Phe  His  Asp  Tyr  Arg  Asp  Trp  Val  Tyr  Ser  Ser  Ala  Trp  Tyr  Phe
     1265                1270                1275

Gln  Asn  Tyr  Glu  Asn  Leu  Asn  Leu  Arg  Lys  His  Thr  Lys  Thr  Asn
     1280                1285                1290

Trp  Tyr  Phe  Ile  Pro  Lys  Asp  Glu  Gly  Trp  Asp  Glu  Asp
     1295                1300                1305

<210> SEQ ID NO 14
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 14

Met  Lys  Leu  Glu  Ile  Asn  Lys  Phe  Asn  Tyr  Asn  Asp  Pro  Ile  Asp  Gly
1                   5                  10                  15

Ile  Asn  Val  Ile  Thr  Met  Arg  Pro  Pro  Arg  His  Ser  Asp  Lys  Ile  Asn
                20                  25                  30

Lys  Gly  Lys  Gly  Pro  Phe  Lys  Ala  Phe  Gln  Val  Ile  Lys  Asn  Ile  Trp
            35                  40                  45

Ile  Val  Pro  Glu  Arg  Tyr  Asn  Phe  Thr  Asn  Asn  Thr  Asn  Asp  Leu  Asn
        50                  55                  60

Ile  Pro  Ser  Glu  Pro  Ile  Met  Glu  Ala  Asp  Ala  Ile  Tyr  Asn  Pro  Asn
```

-continued

```
               65                  70                  75                  80
Tyr Leu Asn Thr Pro Ser Glu Lys Asp Glu Phe Leu Gln Gly Val Ile
                        85                  90                  95

Lys Val Leu Glu Arg Ile Lys Ser Lys Pro Glu Gly Glu Lys Leu Leu
                       100                 105                 110

Glu Leu Ile Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                       165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                       245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
            290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                       325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
            370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                       405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
450                 455                 460

Asn Gly Ser Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
            485                 490                 495
```

```
Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
        530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
        610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
        690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
        770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
        850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
            900                 905                 910
```

```
Thr Thr Ser Asp Ile Asn Ile Gly Ser Asp Ile Glu Leu Ala Asp Gly
            915                 920                 925

Arg Glu Asn Lys Ala Ile Lys Ile Lys Gly Ser Glu Asn Ser Thr Ile
        930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
            980                 985                 990

Lys Ile Ser Ile Gln Asp Ser Lys Leu Ile Trp Tyr Leu Arg Asp His
        995                 1000                1005

Asn Asn Ser Ile Lys Ile Val Thr Pro Asp Tyr Ile Ala Phe Asn
    1010                1015                1020

Gly Trp Asn Leu Ile Thr Ile Thr Asn Asn Arg Ser Lys Gly Ser
    1025                1030                1035

Ile Val Tyr Val Asn Gly Ser Lys Ile Glu Glu Lys Asp Ile Ser
    1040                1045                1050

Ser Ile Trp Asn Thr Glu Val Asp Asp Pro Ile Ile Phe Arg Leu
    1055                1060                1065

Lys Asn Asn Arg Asp Thr Gln Ala Phe Thr Leu Leu Asp Gln Phe
    1070                1075                1080

Ser Ile Tyr Arg Lys Glu Leu Asn Gln Asn Glu Val Val Lys Leu
    1085                1090                1095

Tyr Asn Tyr Tyr Phe Asn Ser Asn Tyr Ile Arg Asp Ile Trp Gly
    1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Ala Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305
```

```
<210> SEQ ID NO 15
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 15

Met Lys Leu Glu Ile Asn Lys Phe Asn Tyr Asn Asp Pro Ile Asp Gly
1               5                   10                  15

Ile Asn Val Ile Thr Met Arg Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
```

```
                370                 375                 380
Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Arg Asn Ser Lys Asn Tyr Leu Asn Asn Ile Asp Leu Glu Asp
                435                 440                 445

Lys Lys Thr Thr Ser Lys Thr Asn Val Ser Tyr Pro Cys Ser Leu Leu
                450                 455                 460

Asn Gly Ser Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
                515                 520                 525

Gln Gln Asn Ile Leu Glu Arg Asn Glu Glu Leu Tyr Glu Pro Ile Arg
                530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
                595                 600                 605

Ser Ile Glu Thr Gly Ile Thr Ser Thr Tyr Ile Phe Tyr Gln Trp Leu
                610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
                675                 680                 685

Thr Ile Pro Ile Leu Val Gly Leu Glu Val Ile Gly Gly Glu Leu Ala
                690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
                755                 760                 765

Ala Asn Tyr Lys Gly Asn Ile Asp Asp Lys Ala Lys Ile Lys Asn Ala
                770                 775                 780

Ile Ser Glu Thr Glu Ile Leu Leu Asn Lys Ser Val Glu Gln Ala Met
785                 790                 795                 800
```

```
Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
    850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
            900                 905                 910

Thr Thr Ser Asp Ile Asn Ile Gly Ser Asp Ile Glu Leu Ala Asp Gly
        915                 920                 925

Arg Glu Asn Lys Ala Ile Lys Ile Lys Gly Ser Glu Asn Ser Thr Ile
    930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
            980                 985                 990

Lys Ile Ser Ile Gln Asp Ser Lys Leu Ile Trp Tyr Leu Arg Asp His
        995                 1000                1005

Asn Asn Ser Ile Lys Ile Val Thr Pro Asp Tyr Ile Ala Phe Asn
    1010                1015                1020

Gly Trp Asn Leu Ile Thr Ile Thr Asn Asn Arg Ser Lys Gly Ser
    1025                1030                1035

Ile Val Tyr Val Asn Gly Ser Lys Ile Glu Glu Lys Asp Ile Ser
    1040                1045                1050

Ser Ile Trp Asn Thr Glu Val Asp Asp Pro Ile Ile Phe Arg Leu
    1055                1060                1065

Lys Asn Asn Arg Asp Thr Gln Ala Phe Thr Leu Leu Asp Gln Phe
    1070                1075                1080

Ser Ile Tyr Arg Lys Glu Leu Asn Gln Asn Glu Val Val Lys Leu
    1085                1090                1095

Tyr Asn Tyr Tyr Phe Asn Ser Asn Tyr Ile Arg Asp Ile Trp Gly
    1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200
```

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Ser Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 16
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 16

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

```
Arg Gln Gln Asn Ser Leu Ile Phe Glu Leu Leu Thr Phe Gly Gly
                260                 265                 270
Ile Asp Ser Lys Ala Ile Ser Ser Leu Ile Ile Lys Lys Ile Glu
            275                 280                 285
Thr Ala Lys Asn Asn Tyr Thr Thr Leu Ile Ser Glu Arg Leu Asn Thr
        290                 295                 300
Val Thr Val Glu Asn Asp Leu Leu Lys Tyr Ile Lys Asn Lys Ile Pro
305                 310                 315                 320
Val Gln Gly Arg Leu Gly Asn Phe Lys Leu Asp Thr Ala Glu Phe Glu
                325                 330                 335
Lys Lys Leu Asn Thr Ile Leu Phe Val Leu Asn Glu Ser Asn Leu Ala
            340                 345                 350
Gln Arg Phe Ser Ile Leu Val Arg Lys His Tyr Leu Lys Glu Arg Pro
        355                 360                 365
Ile Asp Pro Ile Tyr Val Asn Ile Leu Asp Asp Asn Ser Tyr Ser Thr
370                 375                 380
Leu Glu Gly Phe Asn Ile Ser Ser Gln Gly Ser Asn Asp Phe Gln Gly
385                 390                 395                 400
Gln Leu Leu Glu Ser Ser Tyr Phe Glu Lys Ile Glu Ser Asn Ala Leu
                405                 410                 415
Arg Ala Phe Ile Lys Ile Cys Pro Arg Asn Gly Leu Leu Tyr Asn Ala
            420                 425                 430
Ile Tyr Arg Asn Ser Lys Asn Tyr Leu Asn Asn Ile Asp Leu Glu Asp
        435                 440                 445
Lys Lys Thr Thr Ser Lys Thr Asn Val Ser Tyr Pro Cys Ser Leu Leu
450                 455                 460
Asn Gly Ala Ile Glu Val Glu Asn Lys Asp Leu Phe Leu Ile Ser Asn
465                 470                 475                 480
Lys Asp Ser Leu Asn Asp Ile Asn Leu Ser Glu Lys Ile Lys Pro
                485                 490                 495
Glu Thr Thr Val Phe Phe Lys Asp Lys Leu Pro Pro Gln Asp Ile Thr
            500                 505                 510
Leu Ser Asn Tyr Asp Phe Thr Glu Ala Asn Ser Ile Pro Ser Ile Ser
        515                 520                 525
Gln Gln Asn Ile Leu Glu Arg Asn Glu Glu Leu Tyr Glu Pro Ile Arg
530                 535                 540
Asn Ser Leu Phe Glu Ile Lys Thr Ile Tyr Val Asp Lys Leu Thr Thr
545                 550                 555                 560
Phe His Phe Leu Glu Ala Gln Asn Ile Asp Glu Ser Ile Asp Ser Ser
                565                 570                 575
Lys Ile Arg Val Glu Leu Thr Asp Ser Val Asp Glu Ala Leu Ser Asn
            580                 585                 590
Pro Asn Lys Val Tyr Ser Pro Phe Lys Asn Met Ser Asn Thr Ile Asn
        595                 600                 605
Ser Ile Glu Thr Gly Ile Thr Ser Thr Tyr Ile Phe Tyr Gln Trp Leu
610                 615                 620
Arg Ser Ile Val Lys Asp Phe Ser Asp Glu Thr Gly Lys Ile Asp Val
625                 630                 635                 640
Ile Asp Lys Ser Ser Asp Thr Leu Ala Ile Val Pro Tyr Ile Gly Pro
                645                 650                 655
Leu Leu Asn Ile Gly Asn Asp Ile Arg His Gly Asp Phe Val Gly Ala
            660                 665                 670
Ile Glu Leu Ala Gly Ile Thr Ala Leu Leu Glu Tyr Val Pro Glu Phe
```

-continued

```
                675                 680                 685
Thr Ile Pro Ile Leu Val Gly Leu Glu Val Ile Gly Gly Glu Leu Ala
    690                 695                 700
Arg Glu Gln Val Glu Ala Ile Val Asn Asn Ala Leu Asp Lys Arg Asp
705                 710                 715                 720
Gln Lys Trp Ala Glu Val Tyr Asn Ile Thr Lys Ala Gln Trp Trp Gly
                725                 730                 735
Thr Ile His Leu Gln Ile Asn Thr Arg Leu Ala His Thr Tyr Lys Ala
            740                 745                 750
Leu Ser Arg Gln Ala Asn Ala Ile Lys Met Asn Met Glu Phe Gln Leu
        755                 760                 765
Ala Asn Tyr Lys Gly Asn Ile Asp Asp Lys Ala Lys Ile Lys Asn Ala
770                 775                 780
Ile Ser Glu Thr Glu Ile Leu Leu Asn Lys Ser Val Glu Gln Ala Met
785                 790                 795                 800
Lys Asn Thr Glu Lys Phe Met Ile Lys Leu Ser Asn Ser Tyr Leu Thr
                805                 810                 815
Lys Glu Met Ile Pro Lys Val Gln Asp Asn Leu Lys Asn Phe Asp Leu
            820                 825                 830
Glu Thr Lys Lys Thr Leu Asp Lys Phe Ile Lys Glu Lys Glu Asp Ile
        835                 840                 845
Leu Gly Thr Asn Leu Ser Ser Ser Leu Arg Arg Lys Val Ser Ile Arg
    850                 855                 860
Leu Asn Lys Asn Ile Ala Phe Asp Ile Asn Asp Ile Pro Phe Ser Glu
865                 870                 875                 880
Phe Asp Asp Leu Ile Asn Gln Tyr Lys Asn Glu Ile Glu Asp Tyr Glu
                885                 890                 895
Val Leu Asn Leu Gly Ala Glu Asp Gly Lys Ile Lys Asp Leu Ser Gly
            900                 905                 910
Thr Thr Ser Asp Ile Asn Ile Gly Ser Asp Ile Glu Leu Ala Asp Gly
        915                 920                 925
Arg Glu Asn Lys Ala Ile Lys Ile Lys Gly Ser Glu Asn Ser Thr Ile
    930                 935                 940
Lys Ile Ala Met Asn Lys Tyr Leu Arg Phe Ser Ala Thr Asp Asn Phe
945                 950                 955                 960
Ser Ile Ser Phe Trp Ile Lys His Pro Lys Pro Thr Asn Leu Leu Asn
                965                 970                 975
Asn Gly Ile Glu Tyr Thr Leu Val Glu Asn Phe Asn Gln Arg Gly Trp
            980                 985                 990
Lys Ile Ser Ile Gln Asp Ser Lys Leu Ile Trp Tyr Leu Arg Asp His
        995                 1000                1005
Asn Asn Ser Ile Lys Ile Val Thr Pro Asp Tyr Ile Ala Phe Asn
    1010                1015                1020
Gly Trp Asn Leu Ile Thr Ile Thr Asn Asn Arg Ser Lys Gly Ser
    1025                1030                1035
Ile Val Tyr Val Asn Gly Ser Lys Ile Glu Glu Lys Asp Ile Ser
    1040                1045                1050
Ser Ile Trp Asn Thr Glu Val Asp Asp Pro Ile Ile Phe Arg Leu
    1055                1060                1065
Lys Asn Asn Arg Asp Thr Gln Ala Phe Thr Leu Leu Asp Gln Phe
    1070                1075                1080
Ser Ile Tyr Arg Lys Glu Leu Asn Gln Asn Glu Val Val Lys Leu
    1085                1090                1095
```

Tyr Asn Tyr Tyr Phe Asn Ser Asn Tyr Ile Arg Asp Ile Trp Gly
        1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Ser Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 17
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 17

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

```
Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Ile Asp Leu Glu Asp
        435                 440                 445

Lys Lys Thr Thr Ser Lys Thr Asn Val Ser Tyr Pro Cys Ser Leu Leu
    450                 455                 460

Asn Gly Ala Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560
```

```
Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
                595                 600                 605

Ser Ile Glu Thr Gly Ile Thr Ser Thr Tyr Ile Phe Tyr Gln Trp Leu
                610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
                675                 680                 685

Thr Ile Pro Ile Leu Val Gly Leu Glu Val Ile Gly Gly Glu Leu Ala
                690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
                755                 760                 765

Ala Asn Tyr Lys Gly Asn Ile Asp Asp Lys Ala Lys Ile Lys Asn Ala
                770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
                835                 840                 845

Leu Gly Thr Asn Leu Ser Ser Ser Leu Arg Arg Lys Val Ser Ile Arg
                850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
                900                 905                 910

Thr Thr Ser Asp Ile Asn Ile Gly Ser Asp Ile Glu Leu Ala Asp Gly
                915                 920                 925

Arg Glu Asn Lys Ala Ile Lys Ile Lys Gly Ser Glu Asn Ser Thr Ile
                930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
```

```
                  980             985             990
Lys Ile Ser Ile Gln Asp Ser Lys Leu Ile Trp Tyr Leu Arg Asp His
                      995             1000            1005

Asn Asn Ser Ile Lys Ile Val Thr Pro Asp Tyr Ile Ala Phe Asn
    1010            1015            1020

Gly Trp Asn Leu Ile Thr Ile Thr Asn Asn Arg Ser Lys Gly Ser
    1025            1030            1035

Ile Val Tyr Val Asn Gly Ser Lys Ile Glu Glu Lys Asp Ile Ser
    1040            1045            1050

Ser Ile Trp Asn Thr Glu Val Asp Asp Pro Ile Ile Phe Arg Leu
    1055            1060            1065

Lys Asn Asn Arg Asp Thr Gln Ala Phe Thr Leu Leu Asp Gln Phe
    1070            1075            1080

Ser Ile Tyr Arg Lys Glu Leu Asn Gln Asn Glu Val Val Lys Leu
    1085            1090            1095

Tyr Asn Tyr Tyr Phe Asn Ser Asn Tyr Ile Arg Asp Ile Trp Gly
    1100            1105            1110

Asn Pro Leu Gln Tyr Asn Lys Lys Tyr Tyr Leu Gln Thr Gln Asp
    1115            1120            1125

Lys Pro Gly Lys Gly Leu Ile Arg Glu Tyr Trp Ser Ser Phe Gly
    1130            1135            1140

Tyr Asp Tyr Val Ile Leu Ser Asp Ser Lys Thr Ile Thr Phe Pro
    1145            1150            1155

Asn Asn Ile Arg Tyr Gly Ala Leu Tyr Asn Gly Ser Lys Val Leu
    1160            1165            1170

Ile Lys Asn Ser Lys Lys Leu Asp Gly Leu Val Arg Asn Lys Asp
    1175            1180            1185

Phe Ile Gln Leu Glu Ile Asp Gly Tyr Asn Met Gly Ile Ser Ala
    1190            1195            1200

Asp Arg Phe Asn Glu Asp Thr Asn Tyr Ile Gly Thr Thr Tyr Gly
    1205            1210            1215

Thr Thr His Asp Leu Thr Thr Asp Phe Glu Ile Ile Gln Arg Gln
    1220            1225            1230

Glu Lys Tyr Arg Asn Tyr Ala Gln Leu Lys Thr Pro Tyr Asn Ile
    1235            1240            1245

Phe His Lys Ser Gly Leu Met Ser Thr Glu Thr Ser Lys Pro Thr
    1250            1255            1260

Phe His Asp Tyr Arg Asp Trp Val Tyr Ser Ser Ala Trp Tyr Phe
    1265            1270            1275

Gln Asn Tyr Glu Asn Leu Asn Leu Arg Lys His Thr Lys Thr Asn
    1280            1285            1290

Trp Tyr Phe Ile Pro Lys Asp Glu Gly Trp Asp Glu Asp
    1295            1300            1305

<210> SEQ ID NO 18
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 18

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
```

```
                20              25              30
Lys Gly Lys Gly Pro Phe Lys Ala Phe Gln Val Ile Lys Asn Ile Trp
            35              40              45

Ile Val Pro Glu Arg Tyr Asn Phe Thr Asn Asn Thr Asn Asp Leu Asn
 50              55              60

Ile Pro Ser Glu Pro Ile Met Glu Ala Asp Ala Ile Tyr Asn Pro Asn
 65              70              75              80

Tyr Leu Asn Thr Pro Ser Glu Lys Asp Glu Phe Leu Gln Gly Val Ile
            85              90              95

Lys Val Leu Glu Arg Ile Lys Ser Lys Pro Glu Gly Glu Lys Leu Leu
            100             105             110

Glu Leu Ile Ser Ser Ile Pro Leu Pro Leu Val Ser Asn Gly Ala
            115             120             125

Leu Thr Leu Ser Asp Asn Glu Thr Ile Ala Tyr Gln Glu Asn Asn
            130             135             140

Ile Val Ser Asn Leu Gln Ala Asn Leu Val Ile Tyr Gly Pro Gly Pro
145             150             155             160

Asp Ile Ala Asn Asn Ala Thr Tyr Gly Leu Tyr Ser Thr Pro Ile Ser
            165             170             175

Asn Gly Glu Gly Thr Leu Ser Glu Val Ser Phe Ser Pro Phe Tyr Leu
            180             185             190

Lys Pro Phe Asp Glu Ser Tyr Gly Asn Tyr Arg Ser Leu Val Asn Ile
            195             200             205

Val Asn Lys Phe Val Lys Arg Glu Phe Ala Pro Asp Pro Ala Ser Thr
            210             215             220

Leu Met His Glu Leu Val His Val Thr His Asn Leu Tyr Gly Ile Ser
225             230             235             240

Asn Arg Asn Phe Tyr Tyr Asn Phe Asp Thr Gly Lys Ile Glu Thr Ser
            245             250             255

Arg Gln Gln Asn Ser Leu Ile Phe Glu Glu Leu Leu Thr Phe Gly Gly
            260             265             270

Ile Asp Ser Lys Ala Ile Ser Ser Leu Ile Ile Lys Lys Ile Ile Glu
            275             280             285

Thr Ala Lys Asn Asn Tyr Thr Thr Leu Ile Ser Glu Arg Leu Asn Thr
            290             295             300

Val Thr Val Glu Asn Asp Leu Leu Lys Tyr Ile Lys Asn Lys Ile Pro
305             310             315             320

Val Gln Gly Arg Leu Gly Asn Phe Lys Leu Asp Thr Ala Glu Phe Glu
            325             330             335

Lys Lys Leu Asn Thr Ile Leu Phe Val Leu Asn Glu Ser Asn Leu Ala
            340             345             350

Gln Arg Phe Ser Ile Leu Val Arg Lys His Tyr Leu Lys Glu Arg Pro
            355             360             365

Ile Asp Pro Ile Tyr Val Asn Ile Leu Asp Asp Asn Ser Tyr Ser Thr
            370             375             380

Leu Glu Gly Phe Asn Ile Ser Ser Gln Gly Ser Asn Asp Phe Gln Gly
385             390             395             400

Gln Leu Leu Glu Ser Ser Tyr Phe Glu Lys Ile Glu Ser Asn Ala Leu
            405             410             415

Arg Ala Phe Ile Lys Ile Cys Pro Arg Asn Gly Leu Leu Tyr Asn Ala
            420             425             430

Ile Tyr Arg Asn Ser Lys Asn Tyr Leu Asn Asn Ile Asp Leu Glu Asp
            435             440             445
```

```
Lys Lys Thr Thr Ser Lys Thr Asn Val Ser Tyr Pro Ala Ser Leu Leu
    450             455                 460

Asn Gly Cys Ile Glu Val Glu Asn Lys Asp Leu Phe Leu Ile Ser Asn
465             470                 475                 480

Lys Asp Ser Leu Asn Asp Ile Asn Leu Ser Glu Glu Lys Ile Lys Pro
            485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
    595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
    690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
    755                 760                 765

Ala Asn Tyr Lys Gly Asn Ile Asp Asp Lys Ala Lys Ile Lys Asn Ala
770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
    835                 840                 845

Leu Gly Thr Asn Leu Ser Ser Ser Leu Arg Arg Lys Val Ser Ile Arg
    850                 855                 860
```

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile
            885                 890

<210> SEQ ID NO 19
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 19

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
                100                 105                 110

Glu Leu Ile Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

```
Lys Lys Leu Asn Thr Ile Leu Phe Val Leu Asn Glu Ser Asn Leu Ala
                340                 345                 350

Gln Arg Phe Ser Ile Leu Val Arg Lys His Tyr Leu Lys Glu Arg Pro
                355                 360                 365

Ile Asp Pro Ile Tyr Val Asn Ile Leu Asp Asp Asn Ser Tyr Ser Thr
                370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Arg Asn Ser Lys Asn Tyr Leu Asn Asn Ile Asp Leu Glu Asp
                435                 440                 445

Lys Lys Thr Thr Ser Lys Thr Asn Val Ser Tyr Pro Ser Ser Leu Leu
                450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
                515                 520                 525

Gln Gln Asn Ile Leu Glu Arg Asn Glu Glu Leu Tyr Glu Pro Ile Arg
                530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
                595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
                675                 680                 685

Thr Ile Pro Ile Leu Val Gly Leu Glu Val Ile Gly Gly Glu Leu Ala
                690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
```

```
                755                 760                 765
Ala Asn Tyr Lys Gly Asn Ile Asp Asp Lys Ala Lys Ile Lys Asn Ala
        770                 775                 780
Ile Ser Glu Thr Glu Ile Leu Leu Asn Lys Ser Val Glu Gln Ala Met
785                 790                 795                 800
Lys Asn Thr Glu Lys Phe Met Ile Lys Leu Ser Asn Ser Tyr Leu Thr
                805                 810                 815
Lys Glu Met Ile Pro Lys Val Gln Asp Asn Leu Lys Asn Phe Asp Leu
            820                 825                 830
Glu Thr Lys Lys Thr Leu Asp Lys Phe Ile Lys Glu Lys Glu Asp Ile
            835                 840                 845
Leu Gly Thr Asn Leu Ser Ser Ser Leu Arg Arg Lys Val Ser Ile Arg
        850                 855                 860
Leu Asn Lys Asn Ile Ala Phe Asp Ile Asn Asp Ile Pro Phe Ser Glu
865                 870                 875                 880
Phe Asp Asp Leu Ile Asn Gln Tyr Lys Asn Glu Ile
                885                 890

<210> SEQ ID NO 20
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 20

Met Lys Leu Glu Ile Asn Lys Phe Asn Tyr Asn Asp Pro Ile Asp Gly
1               5                   10                  15
Ile Asn Val Ile Thr Met Arg Pro Pro Arg His Ser Asp Lys Ile Asn
                20                  25                  30
Lys Gly Lys Gly Pro Phe Lys Ala Phe Gln Val Ile Lys Asn Ile Trp
        35                  40                  45
Ile Val Pro Glu Arg Tyr Asn Phe Thr Asn Asn Thr Asn Asp Leu Asn
    50                  55                  60
Ile Pro Ser Glu Pro Ile Met Glu Ala Asp Ala Ile Tyr Asn Pro Asn
65                  70                  75                  80
Tyr Leu Asn Thr Pro Ser Glu Lys Asp Glu Phe Leu Gln Gly Val Ile
                85                  90                  95
Lys Val Leu Glu Arg Ile Lys Ser Lys Pro Glu Gly Glu Lys Leu Leu
                100                 105                 110
Glu Leu Ile Ser Ser Ser Ile Pro Leu Pro Leu Val Ser Asn Gly Ala
            115                 120                 125
Leu Thr Leu Ser Asp Asn Glu Thr Ile Ala Tyr Gln Glu Asn Asn Asn
        130                 135                 140
Ile Val Ser Asn Leu Gln Ala Asn Leu Val Ile Tyr Gly Pro Gly Pro
145                 150                 155                 160
Asp Ile Ala Asn Asn Ala Thr Tyr Gly Leu Tyr Ser Thr Pro Ile Ser
                165                 170                 175
Asn Gly Glu Gly Thr Leu Ser Glu Val Ser Phe Ser Pro Phe Tyr Leu
            180                 185                 190
Lys Pro Phe Asp Glu Ser Tyr Gly Asn Tyr Arg Ser Leu Val Asn Ile
        195                 200                 205
Val Asn Lys Phe Val Lys Arg Glu Phe Ala Pro Asp Pro Ala Ser Thr
    210                 215                 220
Leu Met His Glu Leu Val His Val Thr His Asn Leu Tyr Gly Ile Ser
```

```
              225                 230                 235                 240
Asn Arg Asn Phe Tyr Tyr Asn Phe Asp Thr Gly Lys Ile Glu Thr Ser
                245                 250                 255
Arg Gln Gln Asn Ser Leu Ile Phe Glu Glu Leu Leu Thr Phe Gly Gly
                260                 265                 270
Ile Asp Ser Lys Ala Ile Ser Ser Leu Ile Ile Lys Lys Ile Ile Glu
                275                 280                 285
Thr Ala Lys Asn Asn Tyr Thr Thr Leu Ile Ser Glu Arg Leu Asn Thr
290                 295                 300
Val Thr Val Glu Asn Asp Leu Leu Lys Tyr Ile Lys Asn Lys Ile Pro
305                 310                 315                 320
Val Gln Gly Arg Leu Gly Asn Phe Lys Leu Asp Thr Ala Glu Phe Glu
                325                 330                 335
Lys Lys Leu Asn Thr Ile Leu Phe Val Leu Asn Glu Ser Asn Leu Ala
                340                 345                 350
Gln Arg Phe Ser Ile Leu Val Arg Lys His Tyr Leu Lys Glu Arg Pro
                355                 360                 365
Ile Asp Pro Ile Tyr Val Asn Ile Leu Asp Asp Asn Ser Tyr Ser Thr
                370                 375                 380
Leu Glu Gly Phe Asn Ile Ser Ser Gln Gly Ser Asn Asp Phe Gln Gly
385                 390                 395                 400
Gln Leu Leu Glu Ser Ser Tyr Phe Glu Lys Ile Glu Ser Asn Ala Leu
                405                 410                 415
Arg Ala Phe Ile Lys Ile Cys Pro Arg Asn Gly Leu Leu Tyr Asn Ala
                420                 425                 430
Ile Tyr Arg Asn Ser Lys Asn Tyr Leu Asn Asn Ile Asp Leu Glu Asp
                435                 440                 445
Lys Lys Thr Thr Ser Lys Thr Asn Val Ser Tyr Pro Cys Ser Leu Leu
                450                 455                 460
Asn Gly Ala Ile Glu Val Glu Asn Lys Asp Leu Phe Leu Ile Ser Asn
465                 470                 475                 480
Lys Asp Ser Leu Asn Asp Ile Asn Leu Ser Glu Glu Lys Ile Lys Pro
                485                 490                 495
Glu Thr Thr Val Phe Phe Lys Asp Lys Leu Pro Pro Gln Asp Ile Thr
                500                 505                 510
Leu Ser Asn Tyr Asp Phe Thr Glu Ala Asn Ser Ile Pro Ser Ile Ser
                515                 520                 525
Gln Gln Asn Ile Leu Glu Arg Asn Glu Glu Leu Tyr Glu Pro Ile Arg
                530                 535                 540
Asn Ser Leu Phe Glu Ile Lys Thr Ile Tyr Val Asp Lys Leu Thr Thr
545                 550                 555                 560
Phe His Phe Leu Glu Ala Gln Asn Ile Asp Glu Ser Ile Asp Ser Ser
                565                 570                 575
Lys Ile Arg Val Glu Leu Thr Asp Ser Val Asp Glu Ala Leu Ser Asn
                580                 585                 590
Pro Asn Lys Val Tyr Ser Pro Phe Lys Asn Met Ser Asn Thr Ile Asn
                595                 600                 605
Ser Ile Glu Thr Gly Ile Thr Ser Thr Tyr Ile Phe Tyr Gln Trp Leu
                610                 615                 620
Arg Ser Ile Val Lys Asp Phe Ser Asp Glu Thr Gly Lys Ile Asp Val
625                 630                 635                 640
Ile Asp Lys Ser Ser Asp Thr Leu Ala Ile Val Pro Tyr Ile Gly Pro
                645                 650                 655
```

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
    770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
    850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile
                885                 890

<210> SEQ ID NO 21
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 21

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

```
Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Gly Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
        435                 440                 445

Lys Lys Thr Thr Ser Lys Thr Asn Val Ser Tyr Pro Cys Ser Leu Leu
450                 455                 460

Asn Gly Ser Ile Glu Val Glu Asn Lys Asp Leu Phe Leu Ile Ser Asn
465                 470                 475                 480

Lys Asp Ser Leu Asn Asp Ile Asn Leu Ser Glu Lys Ile Lys Pro
                485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Glu Leu Tyr Glu Pro Ile Arg
530                 535                 540
```

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile
                885                 890

<210> SEQ ID NO 22
<211> LENGTH: 1316
<212> TYPE: PRT
<213> ORGANISM: Artificial Sequence
<220> FEATURE:
<223> OTHER INFORMATION: Synthetic Polypeptide

<400> SEQUENCE: 22

Met Lys Leu Glu Ile Asn Lys Phe Asn Tyr Asn Asp Pro Ile Asp Gly
1               5                   10                  15

```
Ile Asn Val Ile Thr Met Arg Pro Arg His Ser Asp Lys Ile Asn
            20                  25                  30
Lys Gly Lys Gly Pro Phe Lys Ala Phe Gln Val Ile Lys Asn Ile Trp
        35                  40                  45
Ile Val Pro Glu Arg Tyr Asn Phe Thr Asn Asn Thr Asn Asp Leu Asn
50                  55                  60
Ile Pro Ser Glu Pro Ile Met Glu Ala Asp Ala Ile Tyr Asn Pro Asn
65                  70                  75                  80
Tyr Leu Asn Thr Pro Ser Glu Lys Asp Glu Phe Leu Gln Gly Val Ile
                85                  90                  95
Lys Val Leu Glu Arg Ile Lys Ser Lys Pro Glu Gly Glu Lys Leu Leu
            100                 105                 110
Glu Leu Ile Ser Ser Ser Ile Pro Leu Pro Leu Val Ser Asn Gly Ala
        115                 120                 125
Leu Thr Leu Ser Asp Asn Glu Thr Ile Ala Tyr Gln Glu Asn Asn Asn
130                 135                 140
Ile Val Ser Asn Leu Gln Ala Asn Leu Val Ile Tyr Gly Pro Gly Pro
145                 150                 155                 160
Asp Ile Ala Asn Asn Ala Thr Tyr Gly Leu Tyr Ser Thr Pro Ile Ser
                165                 170                 175
Asn Gly Glu Gly Thr Leu Ser Glu Val Ser Phe Ser Pro Phe Tyr Leu
            180                 185                 190
Lys Pro Phe Asp Glu Ser Tyr Gly Asn Tyr Arg Ser Leu Val Asn Ile
        195                 200                 205
Val Asn Lys Phe Val Lys Arg Glu Phe Ala Pro Asp Pro Ala Ser Thr
210                 215                 220
Leu Met His Glu Leu Val His Val Thr His Asn Leu Tyr Gly Ile Ser
225                 230                 235                 240
Asn Arg Asn Phe Tyr Tyr Asn Phe Asp Thr Gly Lys Ile Glu Thr Ser
                245                 250                 255
Arg Gln Gln Asn Ser Leu Ile Phe Glu Glu Leu Leu Thr Phe Gly Gly
            260                 265                 270
Ile Asp Ser Lys Ala Ile Ser Ser Leu Ile Ile Lys Lys Ile Ile Glu
        275                 280                 285
Thr Ala Lys Asn Asn Tyr Thr Thr Leu Ile Ser Glu Arg Leu Asn Thr
290                 295                 300
Val Thr Val Glu Asn Asp Leu Leu Lys Tyr Ile Lys Asn Lys Ile Pro
305                 310                 315                 320
Val Gln Gly Arg Leu Gly Asn Phe Lys Leu Asp Thr Ala Glu Phe Glu
                325                 330                 335
Lys Lys Leu Asn Thr Ile Leu Phe Val Leu Asn Glu Ser Asn Leu Ala
            340                 345                 350
Gln Arg Phe Ser Ile Leu Val Arg Lys His Tyr Leu Lys Glu Arg Pro
        355                 360                 365
Ile Asp Pro Ile Tyr Val Asn Ile Leu Asp Asp Asn Ser Tyr Ser Thr
370                 375                 380
Leu Glu Gly Phe Asn Ile Ser Ser Gln Gly Ser Asn Asp Phe Gln Gly
385                 390                 395                 400
Gln Leu Leu Glu Ser Ser Tyr Phe Glu Lys Ile Glu Ser Asn Ala Leu
                405                 410                 415
Arg Ala Phe Ile Lys Ile Cys Pro Arg Asn Gly Leu Leu Tyr Asn Ala
            420                 425                 430
Ile Tyr Arg Asn Ser Lys Asn Tyr Leu Asn Asn Ile Asp Leu Glu Asp
```

-continued

```
            435                 440                 445
Lys Lys Thr Thr Ser Lys Thr Asn Val Ser Tyr Pro Cys Ser Leu Leu
            450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
        530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
        690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
        770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
850                 855                 860
```

```
Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Ile Asn Thr
            885                 890                 895

Ser Ile Leu Asn Leu Arg Tyr Glu Ser Asn His Leu Ile Asp Leu Ser
                900                 905                 910

Arg Tyr Ala Ser Lys Ile Asn Ile Gly Ser Lys Val Asn Phe Asp Pro
            915                 920                 925

Ile Asp Lys Asn Gln Ile Gln Leu Phe Asn Leu Glu Ser Ser Lys Ile
            930                 935                 940

Glu Val Ile Leu Lys Asn Ala Ile Val Tyr Asn Ser Met Tyr Glu Asn
945                 950                 955                 960

Phe Ser Thr Ser Phe Trp Ile Arg Ile Pro Lys Tyr Phe Asn Ser Ile
                965                 970                 975

Ser Leu Asn Asn Glu Tyr Thr Ile Ile Asn Cys Met Glu Asn Asn Ser
                980                 985                 990

Gly Trp Lys Val Ser Leu Asn Tyr Gly Glu Ile Ile Trp Thr Leu Gln
                995                 1000                1005

Asp Thr Gln Glu Ile Lys Gln Arg Val Val Phe Lys Tyr Ser Gln
    1010                1015                1020

Met Ile Asn Ile Ser Asp Tyr Ile Asn Arg Trp Ile Phe Val Thr
    1025                1030                1035

Ile Thr Asn Asn Arg Leu Asn Asn Ser Lys Ile Tyr Ile Asn Gly
    1040                1045                1050

Arg Leu Ile Asp Gln Lys Pro Ile Ser Asn Leu Gly Asn Ile His
    1055                1060                1065

Ala Ser Asn Asn Ile Met Phe Lys Leu Asp Gly Cys Arg Asp Thr
    1070                1075                1080

His Arg Tyr Ile Trp Ile Lys Tyr Phe Asn Leu Phe Asp Lys Glu
    1085                1090                1095

Leu Asn Glu Lys Glu Ile Lys Asp Leu Tyr Asp Asn Gln Ser Asn
    1100                1105                1110

Ser Gly Ile Leu Lys Asp Phe Trp Gly Asp Tyr Leu Gln Tyr Asp
    1115                1120                1125

Lys Pro Tyr Tyr Met Leu Asn Leu Tyr Asp Pro Asn Lys Tyr Val
    1130                1135                1140

Asp Val Asn Asn Val Gly Ile Arg Gly Tyr Met Tyr Leu Lys Gly
    1145                1150                1155

Pro Arg Gly Ser Val Met Thr Thr Asn Ile Tyr Leu Asn Ser Ser
    1160                1165                1170

Leu Tyr Arg Gly Thr Lys Phe Ile Ile Lys Lys Tyr Ala Ser Gly
    1175                1180                1185

Asn Lys Asp Asn Ile Val Arg Asn Asn Asp Arg Val Tyr Ile Asn
    1190                1195                1200

Val Val Val Lys Asn Lys Glu Tyr Arg Leu Ala Thr Asn Ala Ser
    1205                1210                1215

Gln Ala Gly Val Glu Lys Ile Leu Ser Ala Leu Glu Ile Pro Asp
    1220                1225                1230

Val Gly Asn Leu Ser Gln Val Val Val Met Lys Ser Lys Asn Asp
    1235                1240                1245

Gln Gly Ile Thr Asn Lys Cys Lys Met Asn Leu Gln Asp Asn Asn
    1250                1255                1260
```

-continued

```
Gly Asn Asp Ile Gly Phe Ile Gly Phe His Gln Phe Asn Asn Ile
            1265                1270                1275

Ala Lys Leu Val Ala Ser Asn Trp Tyr Asn Arg Gln Ile Glu Arg
        1280                1285                1290

Ser Ser Arg Thr Leu Gly Cys Ser Trp Glu Phe Ile Pro Val Asp
    1295                1300                1305

Asp Gly Trp Gly Glu Arg Pro Leu
1310                1315

<210> SEQ ID NO 23
<211> LENGTH: 1324
<212> TYPE: PRT
<213> ORGANISM: Artificial Sequence
<220> FEATURE:
<223> OTHER INFORMATION: Synthetic Polypeptide

<400> SEQUENCE: 23

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300
```

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
            325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
            405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Lys Ile Lys Pro
            485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
            565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
            645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
            690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly

```
            725              730              735
Thr Ile His Leu Gln Ile Asn Thr Arg Leu Ala His Thr Tyr Lys Ala
            740              745              750
Leu Ser Arg Gln Ala Asn Ala Ile Lys Met Asn Met Glu Phe Gln Leu
            755              760              765
Ala Asn Tyr Lys Gly Asn Ile Asp Asp Lys Ala Lys Ile Lys Asn Ala
            770              775              780
Ile Ser Glu Thr Glu Ile Leu Leu Asn Lys Ser Val Glu Gln Ala Met
785              790              795              800
Lys Asn Thr Glu Lys Phe Met Ile Lys Leu Ser Asn Ser Tyr Leu Thr
            805              810              815
Lys Glu Met Ile Pro Lys Val Gln Asp Asn Leu Lys Asn Phe Asp Leu
            820              825              830
Glu Thr Lys Lys Thr Leu Asp Lys Phe Ile Lys Glu Lys Glu Asp Ile
            835              840              845
Leu Gly Thr Asn Leu Ser Ser Ser Leu Arg Arg Lys Val Ser Ile Arg
            850              855              860
Leu Asn Lys Asn Ile Ala Phe Asp Ile Asn Asp Ile Pro Phe Ser Glu
865              870              875              880
Phe Asp Asp Leu Ile Asn Gln Tyr Lys Asn Glu Ile Ile Leu Asn Asn
            885              890              895
Ile Ile Leu Asn Leu Arg Tyr Lys Asp Asn Asn Leu Ile Asp Leu Ser
            900              905              910
Gly Tyr Gly Ala Lys Val Glu Val Tyr Asp Gly Val Glu Leu Asn Asp
            915              920              925
Lys Asn Gln Phe Lys Leu Thr Ser Ser Ala Asn Ser Lys Ile Arg Val
            930              935              940
Thr Gln Asn Gln Asn Ile Ile Phe Asn Ser Val Phe Leu Asp Phe Ser
945              950              955              960
Val Ser Phe Trp Ile Arg Ile Pro Lys Tyr Lys Asn Asp Gly Ile Gln
            965              970              975
Asn Tyr Ile His Asn Glu Tyr Thr Ile Ile Asn Cys Met Lys Asn Asn
            980              985              990
Ser Gly Trp Lys Ile Ser Ile Arg  Gly Asn Arg Ile Ile  Trp Thr Leu
            995             1000             1005
Ile Asp Ile Asn Gly Lys Thr  Lys Ser Val Phe Phe  Glu Tyr Asn
            1010             1015             1020
Ile Arg Glu Asp Ile Ser Glu  Tyr Ile Asn Arg Trp  Phe Phe Val
            1025             1030             1035
Thr Ile  Thr Asn Asn Leu Asn  Asn Ala Lys Ile Tyr  Ile Asn Gly
            1040             1045             1050
Lys Leu  Glu Ser Asn Thr Asp  Ile Lys Asp Ile Arg  Glu Val Ile
            1055             1060             1065
Ala Asn Gly Glu Ile Ile Phe  Lys Leu Asp Gly Asp  Ile Asp Arg
            1070             1075             1080
Thr Gln  Phe Ile Trp Met Lys  Tyr Phe Ser Ile Phe  Asn Thr Glu
            1085             1090             1095
Leu Ser  Gln Ser Asn Ile Glu  Glu Arg Tyr Lys Ile  Gln Ser Tyr
            1100             1105             1110
Ser Glu  Tyr Leu Lys Asp Phe  Trp Gly Asn Pro Leu  Met Tyr Asn
            1115             1120             1125
Lys Glu  Tyr Tyr Met Phe Asn  Ala Gly Asn Lys Asn  Ser Tyr Ile
            1130             1135             1140
```

```
Lys Leu Lys Lys Asp Ser Pro Val Gly Glu Ile Leu Thr Arg Ser
1145                1150                1155

Lys Tyr Asn Gln Asn Ser Lys Tyr Ile Asn Tyr Arg Asp Leu Tyr
1160                1165                1170

Ile Gly Glu Lys Phe Ile Ile Arg Arg Lys Ser Asn Ser Gln Ser
1175                1180                1185

Ile Asn Asp Asp Ile Val Arg Lys Glu Asp Tyr Ile Tyr Leu Asp
1190                1195                1200

Phe Phe Asn Leu Asn Gln Glu Trp Arg Val Tyr Thr Tyr Lys Tyr
1205                1210                1215

Phe Lys Lys Glu Glu Lys Leu Phe Leu Ala Pro Ile Ser Asp
1220                1225                1230

Ser Asp Glu Phe Tyr Asn Thr Ile Gln Ile Lys Glu Tyr Asp Glu
1235                1240                1245

Gln Pro Thr Tyr Ser Cys Gln Leu Leu Phe Lys Lys Asp Glu Glu
1250                1255                1260

Ser Thr Asp Glu Ile Gly Leu Ile Gly Ile His Arg Phe Tyr Glu
1265                1270                1275

Ser Gly Ile Val Phe Glu Glu Tyr Lys Asp Tyr Phe Cys Ile Ser
1280                1285                1290

Lys Trp Tyr Leu Lys Glu Val Lys Arg Lys Pro Tyr Asn Leu Lys
1295                1300                1305

Leu Gly Cys Asn Trp Gln Phe Ile Pro Lys Asp Glu Gly Trp Thr
1310                1315                1320

Glu
```

<210> SEQ ID NO 24
<211> LENGTH: 1316
<212> TYPE: PRT
<213> ORGANISM: Artificial Sequence
<220> FEATURE:
<223> OTHER INFORMATION: Synthetic Polypeptide

<400> SEQUENCE: 24

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160
```

-continued

```
Asp Ile Ala Asn Asn Ala Thr Tyr Gly Leu Tyr Ser Thr Pro Ile Ser
            165                 170                 175

Asn Gly Glu Gly Thr Leu Ser Glu Val Ser Phe Ser Pro Phe Tyr Leu
        180                 185                 190

Lys Pro Phe Asp Glu Ser Tyr Gly Asn Tyr Arg Ser Leu Val Asn Ile
    195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Ile Asp Leu Glu Asp
        435                 440                 445

Lys Lys Thr Thr Ser Lys Thr Asn Val Ser Tyr Pro Cys Ser Leu Leu
    450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
```

-continued

```
              580                 585                 590
Pro Asn Lys Val Tyr Ser Pro Phe Lys Asn Met Ser Asn Thr Ile Asn
            595                 600                 605
Ser Ile Glu Thr Gly Ile Thr Ser Thr Tyr Ile Phe Tyr Gln Trp Leu
            610                 615                 620
Arg Ser Ile Val Lys Asp Phe Ser Asp Glu Thr Gly Lys Ile Asp Val
625                 630                 635                 640
Ile Asp Lys Ser Ser Asp Thr Leu Ala Ile Val Pro Tyr Ile Gly Pro
                645                 650                 655
Leu Leu Asn Ile Gly Asn Asp Ile Arg His Gly Asp Phe Val Gly Ala
            660                 665                 670
Ile Glu Leu Ala Gly Ile Thr Ala Leu Leu Glu Tyr Val Pro Glu Phe
            675                 680                 685
Thr Ile Pro Ile Leu Val Gly Leu Glu Val Ile Gly Gly Glu Leu Ala
            690                 695                 700
Arg Glu Gln Val Glu Ala Ile Val Asn Asn Ala Leu Asp Lys Arg Asp
705                 710                 715                 720
Gln Lys Trp Ala Glu Val Tyr Asn Ile Thr Lys Ala Gln Trp Trp Gly
                725                 730                 735
Thr Ile His Leu Gln Ile Asn Thr Arg Leu Ala His Thr Tyr Lys Ala
            740                 745                 750
Leu Ser Arg Gln Ala Asn Ala Ile Lys Met Asn Met Glu Phe Gln Leu
            755                 760                 765
Ala Asn Tyr Lys Gly Asn Ile Asp Asp Lys Ala Lys Ile Lys Asn Ala
            770                 775                 780
Ile Ser Glu Thr Glu Ile Leu Leu Asn Lys Ser Val Glu Gln Ala Met
785                 790                 795                 800
Lys Asn Thr Glu Lys Phe Met Ile Lys Leu Ser Asn Ser Tyr Leu Thr
                805                 810                 815
Lys Glu Met Ile Pro Lys Val Gln Asp Asn Leu Lys Asn Phe Asp Leu
            820                 825                 830
Glu Thr Lys Lys Thr Leu Asp Lys Phe Ile Lys Glu Lys Glu Asp Ile
            835                 840                 845
Leu Gly Thr Asn Leu Ser Ser Ser Leu Arg Arg Lys Val Ser Ile Arg
            850                 855                 860
Leu Asn Lys Asn Ile Ala Phe Asp Ile Asn Asp Ile Pro Phe Ser Glu
865                 870                 875                 880
Phe Asp Asp Leu Ile Asn Gln Tyr Lys Asn Glu Ile Ile Asn Asp Ser
                885                 890                 895
Lys Ile Leu Ser Leu Gln Asn Arg Lys Asn Thr Leu Val Asp Thr Ser
            900                 905                 910
Gly Tyr Asn Ala Glu Val Ser Glu Glu Gly Asp Val Gln Leu Asn Pro
            915                 920                 925
Ile Phe Pro Phe Asp Phe Lys Leu Gly Ser Ser Gly Glu Asp Arg Gly
            930                 935                 940
Lys Val Ile Val Thr Gln Asn Glu Asn Ile Val Tyr Asn Ser Met Tyr
945                 950                 955                 960
Glu Ser Phe Ser Ile Ser Phe Trp Ile Arg Ile Asn Lys Trp Val Ser
                965                 970                 975
Asn Leu Pro Gly Tyr Thr Ile Ile Asp Ser Val Lys Asn Asn Ser Gly
            980                 985                 990
Trp Ser Ile Gly Ile Ile Ser Asn  Phe Leu Val Phe Thr  Leu Lys Gln
            995                     1000                    1005
```

Asn Glu Asp Ser Glu Gln Ser Ile Asn Phe Ser Tyr Asp Ile Ser
            1010                1015                1020

Asn Asn Ala Pro Gly Tyr Asn Lys Trp Phe Phe Val Thr Val Thr
    1025                1030                1035

Asn Asn Met Met Gly Asn Met Lys Ile Tyr Ile Asn Gly Lys Leu
    1040                1045                1050

Ile Asp Thr Ile Lys Val Lys Glu Leu Thr Gly Ile Asn Phe Ser
    1055                1060                1065

Lys Thr Ile Thr Phe Glu Ile Asn Lys Ile Pro Asp Thr Gly Leu
    1070                1075                1080

Ile Thr Ser Asp Ser Asp Asn Ile Asn Met Trp Ile Arg Asp Phe
    1085                1090                1095

Tyr Ile Phe Ala Lys Glu Leu Asp Gly Lys Asp Ile Asn Ile Leu
    1100                1105                1110

Phe Asn Ser Leu Gln Tyr Thr Asn Val Val Lys Asp Tyr Trp Gly
    1115                1120                1125

Asn Asp Leu Arg Tyr Asn Lys Glu Tyr Tyr Met Val Asn Ile Asp
    1130                1135                1140

Tyr Leu Asn Arg Tyr Met Tyr Ala Asn Ser Arg Gln Ile Val Phe
    1145                1150                1155

Asn Thr Arg Arg Asn Asn Asn Asp Phe Asn Glu Gly Tyr Lys Ile
    1160                1165                1170

Ile Ile Lys Arg Ile Arg Gly Asn Thr Asn Asp Thr Arg Val Arg
    1175                1180                1185

Gly Gly Asp Ile Leu Tyr Phe Asp Met Thr Ile Asn Asn Lys Ala
    1190                1195                1200

Tyr Asn Leu Phe Met Lys Asn Glu Thr Met Tyr Ala Asp Asn His
    1205                1210                1215

Ser Thr Glu Asp Ile Tyr Ala Ile Gly Leu Arg Glu Gln Thr Lys
    1220                1225                1230

Asp Ile Asn Asp Asn Ile Ile Phe Gln Ile Gln Pro Met Asn Asn
    1235                1240                1245

Thr Tyr Tyr Tyr Ala Ser Gln Ile Phe Lys Ser Asn Phe Asn Gly
    1250                1255                1260

Glu Asn Ile Ser Gly Ile Cys Ser Ile Gly Thr Tyr Arg Phe Arg
    1265                1270                1275

Leu Gly Gly Asp Trp Tyr Arg His Asn Tyr Leu Val Pro Thr Val
    1280                1285                1290

Lys Gln Gly Asn Tyr Ala Ser Leu Leu Glu Ser Thr Ser Thr His
    1295                1300                1305

Trp Gly Phe Val Pro Val Ser Glu
    1310                1315

<210> SEQ ID NO 25
<211> LENGTH: 1316
<212> TYPE: PRT
<213> ORGANISM: Artificial Sequence
<220> FEATURE:
<223> OTHER INFORMATION: Synthetic Polypeptide

<400> SEQUENCE: 25

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

-continued

```
Lys Gly Lys Gly Pro Phe Lys Ala Phe Gln Val Ile Lys Asn Ile Trp
        35                  40                  45
Ile Val Pro Glu Arg Tyr Asn Phe Thr Asn Asn Thr Asn Asp Leu Asn
 50                  55                  60
Ile Pro Ser Glu Pro Ile Met Glu Ala Asp Ala Ile Tyr Asn Pro Asn
 65                  70                  75                  80
Tyr Leu Asn Thr Pro Ser Glu Lys Asp Glu Phe Leu Gln Gly Val Ile
                 85                  90                  95
Lys Val Leu Glu Arg Ile Lys Ser Lys Pro Glu Gly Glu Lys Leu Leu
            100                 105                 110
Glu Leu Ile Ser Ser Ile Pro Leu Pro Leu Val Ser Asn Gly Ala
            115                 120                 125
Leu Thr Leu Ser Asp Asn Glu Thr Ile Ala Tyr Gln Glu Asn Asn Asn
        130                 135                 140
Ile Val Ser Asn Leu Gln Ala Asn Leu Val Ile Tyr Gly Pro Gly Pro
145                 150                 155                 160
Asp Ile Ala Asn Asn Ala Thr Tyr Gly Leu Tyr Ser Thr Pro Ile Ser
                165                 170                 175
Asn Gly Glu Gly Thr Leu Ser Glu Val Ser Phe Ser Pro Phe Tyr Leu
            180                 185                 190
Lys Pro Phe Asp Glu Ser Tyr Gly Asn Tyr Arg Ser Leu Val Asn Ile
        195                 200                 205
Val Asn Lys Phe Val Lys Arg Glu Phe Ala Pro Asp Pro Ala Ser Thr
    210                 215                 220
Leu Met His Glu Leu Val His Val Thr His Asn Leu Tyr Gly Ile Ser
225                 230                 235                 240
Asn Arg Asn Phe Tyr Tyr Asn Phe Asp Thr Gly Lys Ile Glu Thr Ser
                245                 250                 255
Arg Gln Gln Asn Ser Leu Ile Phe Glu Glu Leu Leu Thr Phe Gly Gly
            260                 265                 270
Ile Asp Ser Lys Ala Ile Ser Ser Leu Ile Ile Lys Lys Ile Ile Glu
        275                 280                 285
Thr Ala Lys Asn Asn Tyr Thr Thr Leu Ile Ser Glu Arg Leu Asn Thr
    290                 295                 300
Val Thr Val Glu Asn Asp Leu Leu Lys Tyr Ile Lys Asn Lys Ile Pro
305                 310                 315                 320
Val Gln Gly Arg Leu Gly Asn Phe Lys Leu Asp Thr Ala Glu Phe Glu
                325                 330                 335
Lys Lys Leu Asn Thr Ile Leu Phe Val Leu Asn Glu Ser Asn Leu Ala
            340                 345                 350
Gln Arg Phe Ser Ile Leu Val Arg Lys His Tyr Leu Lys Glu Arg Pro
        355                 360                 365
Ile Asp Pro Ile Tyr Val Asn Ile Leu Asp Asp Asn Ser Tyr Ser Thr
    370                 375                 380
Leu Glu Gly Phe Asn Ile Ser Ser Gln Gly Ser Asn Asp Phe Gln Gly
385                 390                 395                 400
Gln Leu Leu Glu Ser Ser Tyr Phe Glu Lys Ile Glu Ser Asn Ala Leu
                405                 410                 415
Arg Ala Phe Ile Lys Ile Cys Pro Arg Asn Gly Leu Leu Tyr Asn Ala
            420                 425                 430
Ile Tyr Arg Asn Ser Lys Asn Tyr Leu Asn Asn Ile Asp Leu Glu Asp
        435                 440                 445
```

-continued

```
Lys Lys Thr Thr Ser Lys Thr Asn Val Ser Tyr Pro Ser Ser Leu Leu
    450             455                 460

Asn Gly Cys Ile Glu Val Glu Asn Lys Asp Leu Phe Leu Ile Ser Asn
465             470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
                515                 520                 525

Gln Gln Asn Ile Leu Glu Arg Asn Glu Glu Leu Tyr Glu Pro Ile Arg
530             535                 540

Asn Ser Leu Phe Glu Ile Lys Thr Ile Tyr Val Asp Lys Leu Thr Thr
545             550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
610             615                 620

Arg Ser Ile Val Lys Asp Phe Ser Asp Glu Thr Gly Lys Ile Asp Val
625             630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
                675                 680                 685

Thr Ile Pro Ile Leu Val Gly Leu Glu Val Ile Gly Gly Glu Leu Ala
                690                 695                 700

Arg Glu Gln Val Glu Ala Ile Val Asn Asn Ala Leu Asp Lys Arg Asp
705             710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
                755                 760                 765

Ala Asn Tyr Lys Gly Asn Ile Asp Asp Lys Ala Lys Ile Lys Asn Ala
                770                 775                 780

Ile Ser Glu Thr Glu Ile Leu Leu Asn Lys Ser Val Glu Gln Ala Met
785             790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
                835                 840                 845

Leu Gly Thr Asn Leu Ser Ser Ser Leu Arg Arg Lys Val Ser Ile Arg
                850                 855                 860

Leu Asn Lys Asn Ile Ala Phe Asp Ile Asn Asp Ile Pro Phe Ser Glu
```

```
              865                 870                 875                 880
        Phe Asp Asp Leu Ile Asn Gln Tyr Lys Asn Glu Ile Ile Asn Thr
                        885                 890                 895
        Ser Ile Leu Asn Leu Arg Tyr Glu Ser Asn His Leu Ile Asp Leu Ser
                        900                 905                 910
        Arg Tyr Ala Ser Lys Ile Asn Ile Gly Ser Lys Val Asn Phe Asp Pro
                        915                 920                 925
        Ile Asp Lys Asn Gln Ile Gln Leu Phe Asn Leu Glu Ser Ser Lys Ile
                        930                 935                 940
        Glu Val Ile Leu Lys Asn Ala Ile Val Tyr Asn Ser Met Tyr Glu Asn
        945                 950                 955                 960
        Phe Ser Thr Ser Phe Trp Ile Arg Ile Pro Lys Tyr Phe Asn Ser Ile
                        965                 970                 975
        Ser Leu Asn Asn Glu Tyr Thr Ile Ile Asn Cys Met Glu Asn Asn Ser
                        980                 985                 990
        Gly Trp Lys Val Ser Leu Asn Tyr  Gly Glu Ile Ile Trp  Thr Leu Gln
                        995                 1000                1005
        Asp Thr  Gln Glu Ile Lys Gln  Arg Val Val Phe Lys  Tyr Ser Gln
            1010                1015                1020
        Met Ile Asn Ile Ser Asp Tyr  Ile Asn Arg Trp Ile  Phe Val Thr
            1025                1030                1035
        Ile Thr  Asn Asn Arg Leu Asn  Asn Ser Lys Ile Tyr  Ile Asn Gly
            1040                1045                1050
        Arg Leu  Ile Asp Gln Lys Pro  Ile Ser Asn Leu Gly  Asn Ile His
            1055                1060                1065
        Ala Ser Asn Asn Ile Met Phe  Lys Leu Asp Gly Cys  Arg Asp Thr
            1070                1075                1080
        His Arg  Tyr Ile Trp Ile Lys  Tyr Phe Asn Leu Phe  Asp Lys Glu
            1085                1090                1095
        Leu Asn  Glu Lys Glu Ile Lys  Asp Leu Tyr Asp Asn  Gln Ser Asn
            1100                1105                1110
        Ser Gly  Ile Leu Lys Asp Phe  Trp Gly Asp Tyr Leu  Gln Tyr Asp
            1115                1120                1125
        Lys Pro  Tyr Tyr Met Leu Asn  Leu Tyr Asp Pro Asn  Lys Tyr Val
            1130                1135                1140
        Asp Val  Asn Asn Val Gly Ile  Arg Gly Tyr Met Tyr  Leu Lys Gly
            1145                1150                1155
        Pro Arg  Gly Ser Val Met Thr  Thr Asn Ile Tyr Leu  Asn Ser Ser
            1160                1165                1170
        Leu Tyr  Arg Gly Thr Lys Phe  Ile Ile Lys Lys Tyr  Ala Ser Gly
            1175                1180                1185
        Asn Lys  Asp Asn Ile Val Arg  Asn Asn Asp Arg Val  Tyr Ile Asn
            1190                1195                1200
        Val Val  Val Lys Asn Lys Glu  Tyr Arg Leu Ala Thr  Asn Ala Ser
            1205                1210                1215
        Gln Ala  Gly Val Glu Lys Ile  Leu Ser Ala Leu Glu  Ile Pro Asp
            1220                1225                1230
        Val Gly  Asn Leu Ser Gln Val  Val Val Met Lys Ser  Lys Asn Asp
            1235                1240                1245
        Gln Gly  Ile Thr Asn Lys Cys  Lys Met Asn Leu Gln  Asp Asn Asn
            1250                1255                1260
        Gly Asn  Asp Ile Gly Phe Ile  Gly Phe His Gln Phe  Asn Asn Ile
            1265                1270                1275
```

```
Ala Lys Leu Val Ala Ser Asn Trp Tyr Asn Arg Gln Ile Glu Arg
    1280                1285                1290

Ser Ser Arg Thr Leu Gly Cys Ser Trp Glu Phe Ile Pro Val Asp
1295                1300                1305

Asp Gly Trp Gly Glu Arg Pro Leu
    1310                1315

<210> SEQ ID NO 26
<211> LENGTH: 1324
<212> TYPE: PRT
<213> ORGANISM: Artificial Sequence
<220> FEATURE:
<223> OTHER INFORMATION: Synthetic Polypeptide

<400> SEQUENCE: 26

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320
```

Val Gln Gly Arg Leu Gly Asn Phe Lys Leu Asp Thr Ala Glu Phe Glu
            325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
            370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
            405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Ser Ser Leu Leu
            450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
            485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
            530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
            565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
            610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
            645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
            690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
            725                 730                 735

```
Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
            755                 760                 765

Ala Asn Tyr Lys Gly Asn Ile Asp Asp Lys Ala Lys Ile Lys Asn Ala
770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
            805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
            835                 840                 845

Leu Gly Thr Asn Leu Ser Ser Ser Leu Arg Arg Lys Val Ser Ile Arg
            850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Ile Leu Asn Asn
                    885                 890                 895

Ile Ile Leu Asn Leu Arg Tyr Lys Asp Asn Asn Leu Ile Asp Leu Ser
                    900                 905                 910

Gly Tyr Gly Ala Lys Val Glu Val Tyr Asp Gly Val Glu Leu Asn Asp
                    915                 920                 925

Lys Asn Gln Phe Lys Leu Thr Ser Ser Ala Asn Ser Lys Ile Arg Val
            930                 935                 940

Thr Gln Asn Gln Asn Ile Ile Phe Asn Ser Val Phe Leu Asp Phe Ser
945                 950                 955                 960

Val Ser Phe Trp Ile Arg Ile Pro Lys Tyr Lys Asn Asp Gly Ile Gln
                    965                 970                 975

Asn Tyr Ile His Asn Glu Tyr Thr Ile Ile Asn Cys Met Lys Asn Asn
                    980                 985                 990

Ser Gly Trp Lys Ile Ser Ile Arg Gly Asn Arg Ile Ile Trp Thr Leu
            995                 1000                1005

Ile Asp Ile Asn Gly Lys Thr Lys Ser Val Phe Phe Glu Tyr Asn
    1010                1015                1020

Ile Arg Glu Asp Ile Ser Glu Tyr Ile Asn Arg Trp Phe Phe Val
    1025                1030                1035

Thr Ile Thr Asn Asn Leu Asn Asn Ala Lys Ile Tyr Ile Asn Gly
    1040                1045                1050

Lys Leu Glu Ser Asn Thr Asp Ile Lys Asp Ile Arg Glu Val Ile
    1055                1060                1065

Ala Asn Gly Glu Ile Ile Phe Lys Leu Asp Gly Asp Ile Asp Arg
    1070                1075                1080

Thr Gln Phe Ile Trp Met Lys Tyr Phe Ser Ile Phe Asn Thr Glu
    1085                1090                1095

Leu Ser Gln Ser Asn Ile Glu Glu Arg Tyr Lys Ile Gln Ser Tyr
    1100                1105                1110

Ser Glu Tyr Leu Lys Asp Phe Trp Gly Asn Pro Leu Met Tyr Asn
    1115                1120                1125

Lys Glu Tyr Tyr Met Phe Asn Ala Gly Asn Lys Asn Ser Tyr Ile
    1130                1135                1140

Lys Leu Lys Lys Asp Ser Pro Val Gly Glu Ile Leu Thr Arg Ser
```

```
            1145                1150                1155

Lys Tyr Asn Gln Asn Ser Lys Tyr Ile Asn Tyr Arg Asp Leu Tyr
        1160                1165                1170

Ile Gly Glu Lys Phe Ile Ile Arg Arg Lys Ser Asn Ser Gln Ser
    1175                1180                1185

Ile Asn Asp Asp Ile Val Arg Lys Glu Asp Tyr Ile Tyr Leu Asp
    1190                1195                1200

Phe Phe Asn Leu Asn Gln Glu Trp Arg Val Tyr Thr Tyr Lys Tyr
    1205                1210                1215

Phe Lys Lys Glu Glu Lys Leu Phe Leu Ala Pro Ile Ser Asp
    1220                1225                1230

Ser Asp Glu Phe Tyr Asn Thr Ile Gln Ile Lys Glu Tyr Asp Glu
    1235                1240                1245

Gln Pro Thr Tyr Ser Cys Gln Leu Leu Phe Lys Lys Asp Glu Glu
    1250                1255                1260

Ser Thr Asp Glu Ile Gly Leu Ile Gly Ile His Arg Phe Tyr Glu
    1265                1270                1275

Ser Gly Ile Val Phe Glu Glu Tyr Lys Asp Tyr Phe Cys Ile Ser
    1280                1285                1290

Lys Trp Tyr Leu Lys Glu Val Lys Arg Lys Pro Tyr Asn Leu Lys
    1295                1300                1305

Leu Gly Cys Asn Trp Gln Phe Ile Pro Lys Asp Glu Gly Trp Thr
    1310                1315                1320

Glu

<210> SEQ ID NO 27
<211> LENGTH: 1316
<212> TYPE: PRT
<213> ORGANISM: Artificial Sequence
<220> FEATURE:
<223> OTHER INFORMATION: Synthetic Polypeptide

<400> SEQUENCE: 27

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175
```

```
Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
        435                 440                 445

Lys Lys Thr Thr Ser Lys Thr Asn Val Ser Tyr Pro Ser Ser Leu Leu
    450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Lys Leu Pro Pro Gln Asp Ile Thr
            500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590
```

```
Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
            645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
        690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
        770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Ile Asn Asp Ser
                885                 890                 895

Lys Ile Leu Ser Leu Gln Asn Arg Lys Asn Thr Leu Val Asp Thr Ser
            900                 905                 910

Gly Tyr Asn Ala Glu Val Ser Glu Glu Gly Asp Val Gln Leu Asn Pro
        915                 920                 925

Ile Phe Pro Phe Asp Phe Lys Leu Gly Ser Ser Gly Glu Asp Arg Gly
        930                 935                 940

Lys Val Ile Val Thr Gln Asn Glu Asn Ile Val Tyr Asn Ser Met Tyr
945                 950                 955                 960

Glu Ser Phe Ser Ile Ser Phe Trp Ile Arg Ile Asn Lys Trp Val Ser
                965                 970                 975

Asn Leu Pro Gly Tyr Thr Ile Ile Asp Ser Val Lys Asn Asn Ser Gly
            980                 985                 990

Trp Ser Ile Gly Ile Ile Ser Asn Phe Leu Val Phe Thr Leu Lys Gln
        995                 1000                1005

Asn Glu  Asp Ser Glu Gln Ser  Ile Asn Phe Ser Tyr  Asp Ile Ser
```

```
                    1010                1015                1020
Asn Asn Ala Pro Gly Tyr Asn Lys Trp Phe Phe Val Thr Val Thr
            1025                1030                1035

Asn Asn Met Met Gly Asn Met Lys Ile Tyr Ile Asn Gly Lys Leu
            1040                1045                1050

Ile Asp Thr Ile Lys Val Lys Glu Leu Thr Gly Ile Asn Phe Ser
            1055                1060                1065

Lys Thr Ile Thr Phe Glu Ile Asn Lys Ile Pro Asp Thr Gly Leu
            1070                1075                1080

Ile Thr Ser Asp Ser Asp Asn Ile Asn Met Trp Ile Arg Asp Phe
            1085                1090                1095

Tyr Ile Phe Ala Lys Glu Leu Asp Gly Lys Asp Ile Asn Ile Leu
            1100                1105                1110

Phe Asn Ser Leu Gln Tyr Thr Asn Val Val Lys Asp Tyr Trp Gly
            1115                1120                1125

Asn Asp Leu Arg Tyr Asn Lys Glu Tyr Tyr Met Val Asn Ile Asp
            1130                1135                1140

Tyr Leu Asn Arg Tyr Met Tyr Ala Asn Ser Arg Gln Ile Val Phe
            1145                1150                1155

Asn Thr Arg Arg Asn Asn Asn Asp Phe Asn Glu Gly Tyr Lys Ile
            1160                1165                1170

Ile Ile Lys Arg Ile Arg Gly Asn Thr Asn Asp Thr Arg Val Arg
            1175                1180                1185

Gly Gly Asp Ile Leu Tyr Phe Asp Met Thr Ile Asn Asn Lys Ala
            1190                1195                1200

Tyr Asn Leu Phe Met Lys Asn Glu Thr Met Tyr Ala Asp Asn His
            1205                1210                1215

Ser Thr Glu Asp Ile Tyr Ala Ile Gly Leu Arg Glu Gln Thr Lys
            1220                1225                1230

Asp Ile Asn Asp Asn Ile Ile Phe Gln Ile Gln Pro Met Asn Asn
            1235                1240                1245

Thr Tyr Tyr Tyr Ala Ser Gln Ile Phe Lys Ser Asn Phe Asn Gly
            1250                1255                1260

Glu Asn Ile Ser Gly Ile Cys Ser Ile Gly Thr Tyr Arg Phe Arg
            1265                1270                1275

Leu Gly Gly Asp Trp Tyr Arg His Asn Tyr Leu Val Pro Thr Val
            1280                1285                1290

Lys Gln Gly Asn Tyr Ala Ser Leu Leu Glu Ser Thr Ser Thr His
            1295                1300                1305

Trp Gly Phe Val Pro Val Ser Glu
            1310                1315

<210> SEQ ID NO 28
<211> LENGTH: 1316
<212> TYPE: PRT
<213> ORGANISM: Artificial Sequence
<220> FEATURE:
<223> OTHER INFORMATION: Synthetic Polypeptide

<400> SEQUENCE: 28

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
```

```
            35                  40                  45
Ile Val Pro Glu Arg Tyr Asn Phe Thr Asn Asn Thr Asn Asp Leu Asn
 50                  55                  60

Ile Pro Ser Glu Pro Ile Met Glu Ala Asp Ala Ile Tyr Asn Pro Asn
 65                  70                  75                  80

Tyr Leu Asn Thr Pro Ser Glu Lys Asp Glu Phe Leu Gln Gly Val Ile
                 85                  90                  95

Lys Val Leu Glu Arg Ile Lys Ser Lys Pro Glu Gly Glu Lys Leu Leu
                100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Ile Asp Leu Glu Asp
        435                 440                 445

Lys Lys Thr Thr Ser Lys Thr Asn Val Ser Tyr Pro Cys Ser Leu Leu
    450                 455                 460
```

```
Asn Gly Ser Ile Glu Val Glu Asn Lys Asp Leu Phe Leu Ile Ser Asn
465                 470                 475                 480

Lys Asp Ser Leu Asn Asp Ile Asn Leu Ser Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
                515                 520                 525

Gln Gln Asn Ile Leu Glu Arg Asn Glu Glu Leu Tyr Glu Pro Ile Arg
530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
        610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
                675                 680                 685

Thr Ile Pro Ile Leu Val Gly Leu Glu Val Ile Gly Gly Glu Leu Ala
        690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
        770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
                835                 840                 845

Leu Gly Thr Asn Leu Ser Ser Ser Leu Arg Arg Lys Val Ser Ile Arg
        850                 855                 860

Leu Asn Lys Asn Ile Ala Phe Asp Ile Asn Asp Ile Pro Phe Ser Glu
865                 870                 875                 880
```

```
Phe Asp Asp Leu Ile Asn Gln Tyr Lys Asn Glu Ile Ile Asn Thr
                885                 890                 895
Ser Ile Leu Asn Leu Arg Tyr Glu Ser Asn His Leu Ile Asp Leu Ser
        900                 905                 910
Arg Tyr Ala Ser Lys Ile Asn Ile Gly Ser Lys Val Asn Phe Asp Pro
    915                 920                 925
Ile Asp Lys Asn Gln Ile Gln Leu Phe Asn Leu Glu Ser Ser Lys Ile
930                 935                 940
Glu Val Ile Leu Lys Asn Ala Ile Val Tyr Asn Ser Met Tyr Glu Asn
945                 950                 955                 960
Phe Ser Thr Ser Phe Trp Ile Arg Ile Pro Lys Tyr Phe Asn Ser Ile
            965                 970                 975
Ser Leu Asn Asn Glu Tyr Thr Ile Ile Asn Cys Met Glu Asn Asn Ser
        980                 985                 990
Gly Trp Lys Val Ser Leu Asn Tyr Gly Glu Ile Ile Trp Thr Leu Gln
    995                 1000                1005
Asp Thr Gln Glu Ile Lys Gln Arg Val Val Phe Lys Tyr Ser Gln
    1010                1015                1020
Met Ile Asn Ile Ser Asp Tyr Ile Asn Arg Trp Ile Phe Val Thr
    1025                1030                1035
Ile Thr Asn Asn Arg Leu Asn Asn Ser Lys Ile Tyr Ile Asn Gly
    1040                1045                1050
Arg Leu Ile Asp Gln Lys Pro Ile Ser Asn Leu Gly Asn Ile His
    1055                1060                1065
Ala Ser Asn Asn Ile Met Phe Lys Leu Asp Gly Cys Arg Asp Thr
    1070                1075                1080
His Arg Tyr Ile Trp Ile Lys Tyr Phe Asn Leu Phe Asp Lys Glu
    1085                1090                1095
Leu Asn Glu Lys Glu Ile Lys Asp Leu Tyr Asp Asn Gln Ser Asn
    1100                1105                1110
Ser Gly Ile Leu Lys Asp Phe Trp Gly Asp Tyr Leu Gln Tyr Asp
    1115                1120                1125
Lys Pro Tyr Tyr Met Leu Asn Leu Tyr Asp Pro Asn Lys Tyr Val
    1130                1135                1140
Asp Val Asn Asn Val Gly Ile Arg Gly Tyr Met Tyr Leu Lys Gly
    1145                1150                1155
Pro Arg Gly Ser Val Met Thr Thr Asn Ile Tyr Leu Asn Ser Ser
    1160                1165                1170
Leu Tyr Arg Gly Thr Lys Phe Ile Ile Lys Lys Tyr Ala Ser Gly
    1175                1180                1185
Asn Lys Asp Asn Ile Val Arg Asn Asn Asp Arg Val Tyr Ile Asn
    1190                1195                1200
Val Val Val Lys Asn Lys Glu Tyr Arg Leu Ala Thr Asn Ala Ser
    1205                1210                1215
Gln Ala Gly Val Glu Lys Ile Leu Ser Ala Leu Glu Ile Pro Asp
    1220                1225                1230
Val Gly Asn Leu Ser Gln Val Val Val Met Lys Ser Lys Asn Asp
    1235                1240                1245
Gln Gly Ile Thr Asn Lys Cys Lys Met Asn Leu Gln Asp Asn Asn
    1250                1255                1260
Gly Asn Asp Ile Gly Phe Ile Gly Phe His Gln Phe Asn Asn Ile
    1265                1270                1275
Ala Lys Leu Val Ala Ser Asn Trp Tyr Asn Arg Gln Ile Glu Arg
```

```
                1280                1285                1290
Ser Ser Arg Thr Leu Gly Cys Ser Trp Glu Phe Ile Pro Val Asp
    1295                1300                1305

Asp Gly Trp Gly Glu Arg Pro Leu
    1310                1315

<210> SEQ ID NO 29
<211> LENGTH: 1324
<212> TYPE: PRT
<213> ORGANISM: Artificial Sequence
<220> FEATURE:
<223> OTHER INFORMATION: Synthetic Polypeptide

<400> SEQUENCE: 29

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
```

```
                          325                 330                 335
Lys Lys Leu Asn Thr Ile Leu Phe Val Leu Asn Glu Ser Asn Leu Ala
            340                 345                 350
Gln Arg Phe Ser Ile Leu Val Arg Lys His Tyr Leu Lys Glu Arg Pro
            355                 360                 365
Ile Asp Pro Ile Tyr Val Asn Ile Leu Asp Asp Asn Ser Tyr Ser Thr
            370                 375                 380
Leu Glu Gly Phe Asn Ile Ser Ser Gln Gly Ser Asn Asp Phe Gln Gly
385                 390                 395                 400
Gln Leu Leu Glu Ser Ser Tyr Phe Glu Lys Ile Glu Ser Asn Ala Leu
            405                 410                 415
Arg Ala Phe Ile Lys Ile Cys Pro Arg Asn Gly Leu Leu Tyr Asn Ala
            420                 425                 430
Ile Tyr Arg Asn Ser Lys Asn Tyr Leu Asn Asn Ile Asp Leu Glu Asp
            435                 440                 445
Lys Lys Thr Thr Ser Lys Thr Asn Val Ser Tyr Pro Cys Ser Leu Leu
            450                 455                 460
Asn Gly Ser Ile Glu Val Glu Asn Lys Asp Leu Phe Leu Ile Ser Asn
465                 470                 475                 480
Lys Asp Ser Leu Asn Asp Ile Asn Leu Ser Glu Glu Lys Ile Lys Pro
            485                 490                 495
Glu Thr Thr Val Phe Phe Lys Asp Lys Leu Pro Pro Gln Asp Ile Thr
            500                 505                 510
Leu Ser Asn Tyr Asp Phe Thr Glu Ala Asn Ser Ile Pro Ser Ile Ser
            515                 520                 525
Gln Gln Asn Ile Leu Glu Arg Asn Glu Glu Leu Tyr Glu Pro Ile Arg
            530                 535                 540
Asn Ser Leu Phe Glu Ile Lys Thr Ile Tyr Val Asp Lys Leu Thr Thr
545                 550                 555                 560
Phe His Phe Leu Glu Ala Gln Asn Ile Asp Glu Ser Ile Asp Ser Ser
            565                 570                 575
Lys Ile Arg Val Glu Leu Thr Asp Ser Val Asp Glu Ala Leu Ser Asn
            580                 585                 590
Pro Asn Lys Val Tyr Ser Pro Phe Lys Asn Met Ser Asn Thr Ile Asn
            595                 600                 605
Ser Ile Glu Thr Gly Ile Thr Ser Thr Tyr Ile Phe Tyr Gln Trp Leu
            610                 615                 620
Arg Ser Ile Val Lys Asp Phe Ser Asp Glu Thr Gly Lys Ile Asp Val
625                 630                 635                 640
Ile Asp Lys Ser Ser Asp Thr Leu Ala Ile Val Pro Tyr Ile Gly Pro
            645                 650                 655
Leu Leu Asn Ile Gly Asn Asp Ile Arg His Gly Asp Phe Val Gly Ala
            660                 665                 670
Ile Glu Leu Ala Gly Ile Thr Ala Leu Leu Glu Tyr Val Pro Glu Phe
            675                 680                 685
Thr Ile Pro Ile Leu Val Gly Leu Glu Val Ile Gly Gly Glu Leu Ala
            690                 695                 700
Arg Glu Gln Val Glu Ala Ile Val Asn Asn Ala Leu Asp Lys Arg Asp
705                 710                 715                 720
Gln Lys Trp Ala Glu Val Tyr Asn Ile Thr Lys Ala Gln Trp Trp Gly
            725                 730                 735
Thr Ile His Leu Gln Ile Asn Thr Arg Leu Ala His Thr Tyr Lys Ala
            740                 745                 750
```

-continued

```
Leu Ser Arg Gln Ala Asn Ala Ile Lys Met Asn Met Glu Phe Gln Leu
        755                 760                 765
Ala Asn Tyr Lys Gly Asn Ile Asp Asp Lys Ala Lys Ile Lys Asn Ala
    770                 775                 780
Ile Ser Glu Thr Glu Ile Leu Leu Asn Lys Ser Val Glu Gln Ala Met
785                 790                 795                 800
Lys Asn Thr Glu Lys Phe Met Ile Lys Leu Ser Asn Ser Tyr Leu Thr
                805                 810                 815
Lys Glu Met Ile Pro Lys Val Gln Asp Asn Leu Lys Asn Phe Asp Leu
                820                 825                 830
Glu Thr Lys Lys Thr Leu Asp Lys Phe Ile Lys Glu Lys Glu Asp Ile
                835                 840                 845
Leu Gly Thr Asn Leu Ser Ser Ser Leu Arg Arg Lys Val Ser Ile Arg
    850                 855                 860
Leu Asn Lys Asn Ile Ala Phe Asp Ile Asn Asp Ile Pro Phe Ser Glu
865                 870                 875                 880
Phe Asp Asp Leu Ile Asn Gln Tyr Lys Asn Glu Ile Ile Leu Asn Asn
                885                 890                 895
Ile Ile Leu Asn Leu Arg Tyr Lys Asp Asn Asn Leu Ile Asp Leu Ser
            900                 905                 910
Gly Tyr Gly Ala Lys Val Glu Val Tyr Asp Gly Val Glu Leu Asn Asp
        915                 920                 925
Lys Asn Gln Phe Lys Leu Thr Ser Ser Ala Asn Ser Lys Ile Arg Val
    930                 935                 940
Thr Gln Asn Gln Asn Ile Ile Phe Asn Ser Val Phe Leu Asp Phe Ser
945                 950                 955                 960
Val Ser Phe Trp Ile Arg Ile Pro Lys Tyr Lys Asn Asp Gly Ile Gln
                965                 970                 975
Asn Tyr Ile His Asn Glu Tyr Thr Ile Ile Asn Cys Met Lys Asn Asn
                980                 985                 990
Ser Gly Trp Lys Ile Ser Ile Arg Gly Asn Arg Ile Ile Trp Thr Leu
        995                 1000                1005
Ile Asp Ile Asn Gly Lys Thr Lys Ser Val Phe Phe Glu Tyr Asn
    1010                1015                1020
Ile Arg Glu Asp Ile Ser Glu Tyr Ile Asn Arg Trp Phe Phe Val
    1025                1030                1035
Thr Ile Thr Asn Asn Leu Asn Asn Ala Lys Ile Tyr Ile Asn Gly
    1040                1045                1050
Lys Leu Glu Ser Asn Thr Asp Ile Lys Asp Ile Arg Glu Val Ile
    1055                1060                1065
Ala Asn Gly Glu Ile Ile Phe Lys Leu Asp Gly Asp Ile Asp Arg
    1070                1075                1080
Thr Gln Phe Ile Trp Met Lys Tyr Phe Ser Ile Phe Asn Thr Glu
    1085                1090                1095
Leu Ser Gln Ser Asn Ile Glu Glu Arg Tyr Lys Ile Gln Ser Tyr
    1100                1105                1110
Ser Glu Tyr Leu Lys Asp Phe Trp Gly Asn Pro Leu Met Tyr Asn
    1115                1120                1125
Lys Glu Tyr Tyr Met Phe Asn Ala Gly Asn Lys Asn Ser Tyr Ile
    1130                1135                1140
Lys Leu Lys Lys Asp Ser Pro Val Gly Glu Ile Leu Thr Arg Ser
    1145                1150                1155
```

Lys Tyr Asn Gln Asn Ser Lys Tyr Ile Asn Tyr Arg Asp Leu Tyr
            1160                1165                1170

Ile Gly Glu Lys Phe Ile Ile Arg Arg Lys Ser Asn Ser Gln Ser
        1175                1180                1185

Ile Asn Asp Asp Ile Val Arg Lys Glu Asp Tyr Ile Tyr Leu Asp
        1190                1195                1200

Phe Phe Asn Leu Asn Gln Glu Trp Arg Val Tyr Thr Tyr Lys Tyr
        1205                1210                1215

Phe Lys Lys Glu Glu Lys Leu Phe Leu Ala Pro Ile Ser Asp
        1220                1225                1230

Ser Asp Glu Phe Tyr Asn Thr Ile Gln Ile Lys Glu Tyr Asp Glu
        1235                1240                1245

Gln Pro Thr Tyr Ser Cys Gln Leu Leu Phe Lys Lys Asp Glu Glu
        1250                1255                1260

Ser Thr Asp Glu Ile Gly Leu Ile Gly Ile His Arg Phe Tyr Glu
        1265                1270                1275

Ser Gly Ile Val Phe Glu Glu Tyr Lys Asp Tyr Phe Cys Ile Ser
        1280                1285                1290

Lys Trp Tyr Leu Lys Glu Val Lys Arg Lys Pro Tyr Asn Leu Lys
        1295                1300                1305

Leu Gly Cys Asn Trp Gln Phe Ile Pro Lys Asp Glu Gly Trp Thr
        1310                1315                1320

Glu

<210> SEQ ID NO 30
<211> LENGTH: 1316
<212> TYPE: PRT
<213> ORGANISM: Artificial Sequence
<220> FEATURE:
<223> OTHER INFORMATION: Synthetic Polypeptide

<400> SEQUENCE: 30

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Asn Gly Ala
        115                 120                 125

Leu Thr Leu Ser Asp Asn Glu Thr Ile Ala Tyr Gln Glu Asn Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu

-continued

```
            180                 185                 190
Lys Pro Phe Asp Glu Ser Tyr Gly Asn Tyr Arg Ser Leu Val Asn Ile
            195                 200                 205
Val Asn Lys Phe Val Lys Arg Glu Phe Ala Pro Asp Pro Ala Ser Thr
            210                 215                 220
Leu Met His Glu Leu Val His Val Thr His Asn Leu Tyr Gly Ile Ser
225                 230                 235                 240
Asn Arg Asn Phe Tyr Tyr Asn Phe Asp Thr Gly Lys Ile Glu Thr Ser
            245                 250                 255
Arg Gln Gln Asn Ser Leu Ile Phe Glu Glu Leu Leu Thr Phe Gly Gly
            260                 265                 270
Ile Asp Ser Lys Ala Ile Ser Ser Leu Ile Ile Lys Lys Ile Ile Glu
            275                 280                 285
Thr Ala Lys Asn Asn Tyr Thr Thr Leu Ile Ser Glu Arg Leu Asn Thr
            290                 295                 300
Val Thr Val Glu Asn Asp Leu Leu Lys Tyr Ile Lys Asn Lys Ile Pro
305                 310                 315                 320
Val Gln Gly Arg Leu Gly Asn Phe Lys Leu Asp Thr Ala Glu Phe Glu
            325                 330                 335
Lys Lys Leu Asn Thr Ile Leu Phe Val Leu Asn Glu Ser Asn Leu Ala
            340                 345                 350
Gln Arg Phe Ser Ile Leu Val Arg Lys His Tyr Leu Lys Glu Arg Pro
            355                 360                 365
Ile Asp Pro Ile Tyr Val Asn Ile Leu Asp Asp Asn Ser Tyr Ser Thr
            370                 375                 380
Leu Glu Gly Phe Asn Ile Ser Ser Gln Gly Ser Asn Asp Phe Gln Gly
385                 390                 395                 400
Gln Leu Leu Glu Ser Ser Tyr Phe Glu Lys Ile Glu Ser Asn Ala Leu
            405                 410                 415
Arg Ala Phe Ile Lys Ile Cys Pro Arg Asn Gly Leu Leu Tyr Asn Ala
            420                 425                 430
Ile Tyr Arg Asn Ser Lys Asn Tyr Leu Asn Asn Ile Asp Leu Glu Asp
            435                 440                 445
Lys Lys Thr Thr Ser Lys Thr Asn Val Ser Tyr Pro Cys Ser Leu Leu
450                 455                 460
Asn Gly Ser Ile Glu Val Glu Asn Lys Asp Leu Phe Leu Ile Ser Asn
465                 470                 475                 480
Lys Asp Ser Leu Asn Asp Ile Asn Leu Ser Glu Glu Lys Ile Lys Pro
            485                 490                 495
Glu Thr Thr Val Phe Phe Lys Asp Lys Leu Pro Pro Gln Asp Ile Thr
            500                 505                 510
Leu Ser Asn Tyr Asp Phe Thr Glu Ala Asn Ser Ile Pro Ser Ile Ser
            515                 520                 525
Gln Gln Asn Ile Leu Glu Arg Asn Glu Glu Leu Tyr Glu Pro Ile Arg
            530                 535                 540
Asn Ser Leu Phe Glu Ile Lys Thr Ile Tyr Val Asp Lys Leu Thr Thr
545                 550                 555                 560
Phe His Phe Leu Glu Ala Gln Asn Ile Asp Glu Ser Ile Asp Ser Ser
            565                 570                 575
Lys Ile Arg Val Glu Leu Thr Asp Ser Val Asp Glu Ala Leu Ser Asn
            580                 585                 590
Pro Asn Lys Val Tyr Ser Pro Phe Lys Asn Met Ser Asn Thr Ile Asn
            595                 600                 605
```

```
Ser Ile Glu Thr Gly Ile Thr Ser Thr Tyr Ile Phe Tyr Gln Trp Leu
    610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
    690                 695                 700

Arg Glu Gln Val Glu Ala Ile Val Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
    770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
    850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Ile Asn Asp Ser
                885                 890                 895

Lys Ile Leu Ser Leu Gln Asn Arg Lys Asn Thr Leu Val Asp Thr Ser
            900                 905                 910

Gly Tyr Asn Ala Glu Val Ser Glu Gly Asp Val Gln Leu Asn Pro
        915                 920                 925

Ile Phe Pro Phe Asp Phe Lys Leu Gly Ser Ser Gly Glu Asp Arg Gly
    930                 935                 940

Lys Val Ile Val Thr Gln Asn Glu Asn Ile Val Tyr Asn Ser Met Tyr
945                 950                 955                 960

Glu Ser Phe Ser Ile Ser Phe Trp Ile Arg Ile Asn Lys Trp Val Ser
                965                 970                 975

Asn Leu Pro Gly Tyr Thr Ile Ile Asp Ser Val Lys Asn Asn Ser Gly
            980                 985                 990

Trp Ser Ile Gly Ile Ile Ser Asn Phe Leu Val Phe Thr Leu Lys Gln
        995                 1000                1005

Asn Glu Asp Ser Glu Gln Ser Ile Asn Phe Ser Tyr Asp Ile Ser
       1010                1015                1020
```

Asn Asn Ala Pro Gly Tyr Asn Lys Trp Phe Phe Val Thr Val Thr
1025                1030                1035

Asn Asn Met Met Gly Asn Met Lys Ile Tyr Ile Asn Gly Lys Leu
1040                1045                1050

Ile Asp Thr Ile Lys Val Lys Glu Leu Thr Gly Ile Asn Phe Ser
1055                1060                1065

Lys Thr Ile Thr Phe Glu Ile Asn Lys Ile Pro Asp Thr Gly Leu
1070                1075                1080

Ile Thr Ser Asp Ser Asp Asn Ile Asn Met Trp Ile Arg Asp Phe
1085                1090                1095

Tyr Ile Phe Ala Lys Glu Leu Asp Gly Lys Asp Ile Asn Ile Leu
1100                1105                1110

Phe Asn Ser Leu Gln Tyr Thr Asn Val Val Lys Asp Tyr Trp Gly
1115                1120                1125

Asn Asp Leu Arg Tyr Asn Lys Glu Tyr Tyr Met Val Asn Ile Asp
1130                1135                1140

Tyr Leu Asn Arg Tyr Met Tyr Ala Asn Ser Arg Gln Ile Val Phe
1145                1150                1155

Asn Thr Arg Arg Asn Asn Asn Asp Phe Asn Glu Gly Tyr Lys Ile
1160                1165                1170

Ile Ile Lys Arg Ile Arg Gly Asn Thr Asn Asp Thr Arg Val Arg
1175                1180                1185

Gly Gly Asp Ile Leu Tyr Phe Asp Met Thr Ile Asn Asn Lys Ala
1190                1195                1200

Tyr Asn Leu Phe Met Lys Asn Glu Thr Met Tyr Ala Asp Asn His
1205                1210                1215

Ser Thr Glu Asp Ile Tyr Ala Ile Gly Leu Arg Glu Gln Thr Lys
1220                1225                1230

Asp Ile Asn Asp Asn Ile Ile Phe Gln Ile Gln Pro Met Asn Asn
1235                1240                1245

Thr Tyr Tyr Tyr Ala Ser Gln Ile Phe Lys Ser Asn Phe Asn Gly
1250                1255                1260

Glu Asn Ile Ser Gly Ile Cys Ser Ile Gly Thr Tyr Arg Phe Arg
1265                1270                1275

Leu Gly Gly Asp Trp Tyr Arg His Asn Tyr Leu Val Pro Thr Val
1280                1285                1290

Lys Gln Gly Asn Tyr Ala Ser Leu Leu Glu Ser Thr Ser Thr His
1295                1300                1305

Trp Gly Phe Val Pro Val Ser Glu
1310                1315

<210> SEQ ID NO 31
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 31

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
        35                  40                  45

```
Ile Val Pro Glu Arg Tyr Asn Phe Thr Asn Asn Thr Asn Asp Leu Asn
 50                  55                  60

Ile Pro Ser Glu Pro Ile Met Glu Ala Asp Ala Ile Tyr Asn Pro Asn
 65                  70                  75                  80

Tyr Leu Asn Thr Pro Ser Glu Lys Asp Glu Phe Leu Gln Gly Val Ile
                 85                  90                  95

Lys Val Leu Glu Arg Ile Lys Ser Lys Pro Glu Gly Glu Lys Leu Leu
                100                 105                 110

Glu Leu Ile Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Ala Lys His Phe Leu Lys Glu Arg Pro
            355                 360                 365

Ile Asp Pro Ile Tyr Val Asn Ile Leu Asp Asp Asn Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
450                 455                 460

Asn Gly Cys Ile Glu Val Glu Asn Lys Asp Leu Phe Leu Ile Ser Asn
```

-continued

```
            465                 470                 475                 480
        Lys Asp Ser Leu Asn Asp Ile Asn Leu Ser Glu Glu Lys Ile Lys Pro
                            485                 490                 495
        Glu Thr Thr Val Phe Lys Asp Lys Leu Pro Pro Gln Asp Ile Thr
                        500                 505                 510
        Leu Ser Asn Tyr Asp Phe Thr Glu Ala Asn Ser Ile Pro Ser Ile Ser
                        515                 520                 525
        Gln Gln Asn Ile Leu Glu Arg Asn Glu Glu Leu Tyr Glu Pro Ile Arg
                    530                 535                 540
        Asn Ser Leu Phe Glu Ile Lys Thr Ile Tyr Val Asp Lys Leu Thr Thr
        545                 550                 555                 560
        Phe His Phe Leu Glu Ala Gln Asn Ile Asp Glu Ser Ile Asp Ser Ser
                            565                 570                 575
        Lys Ile Arg Val Glu Leu Thr Asp Ser Val Asp Glu Ala Leu Ser Asn
                        580                 585                 590
        Pro Asn Lys Val Tyr Ser Pro Phe Lys Asn Met Ser Asn Thr Ile Asn
                    595                 600                 605
        Ser Ile Glu Thr Gly Ile Thr Ser Thr Tyr Ile Phe Tyr Gln Trp Leu
        610                 615                 620
        Arg Ser Ile Val Lys Asp Phe Ser Asp Glu Thr Gly Lys Ile Asp Val
        625                 630                 635                 640
        Ile Asp Lys Ser Ser Asp Thr Leu Ala Ile Val Pro Tyr Ile Gly Pro
                            645                 650                 655
        Leu Leu Asn Ile Gly Asn Asp Ile Arg His Gly Asp Phe Val Gly Ala
                        660                 665                 670
        Ile Glu Leu Ala Gly Ile Thr Ala Leu Leu Glu Tyr Val Pro Glu Phe
                    675                 680                 685
        Thr Ile Pro Ile Leu Val Gly Leu Glu Val Ile Gly Gly Glu Leu Ala
                690                 695                 700
        Arg Glu Gln Val Glu Ala Ile Val Asn Ala Leu Asp Lys Arg Asp
        705                 710                 715                 720
        Gln Lys Trp Ala Glu Val Tyr Asn Ile Thr Lys Ala Gln Trp Trp Gly
                        725                 730                 735
        Thr Ile His Leu Gln Ile Asn Thr Arg Leu Ala His Thr Tyr Lys Ala
                    740                 745                 750
        Leu Ser Arg Gln Ala Asn Ala Ile Lys Met Asn Met Glu Phe Gln Leu
                755                 760                 765
        Ala Asn Tyr Lys Gly Asn Ile Asp Asp Lys Ala Lys Ile Lys Asn Ala
            770                 775                 780
        Ile Ser Glu Thr Glu Ile Leu Leu Asn Lys Ser Val Glu Gln Ala Met
        785                 790                 795                 800
        Lys Asn Thr Glu Lys Phe Met Ile Lys Leu Ser Asn Ser Tyr Leu Thr
                        805                 810                 815
        Lys Glu Met Ile Pro Lys Val Gln Asp Asn Leu Lys Asn Phe Asp Leu
                    820                 825                 830
        Glu Thr Lys Lys Thr Leu Asp Lys Phe Ile Lys Glu Lys Glu Asp Ile
                835                 840                 845
        Leu Gly Thr Asn Leu Ser Ser Ser Leu Arg Arg Lys Val Ser Ile Arg
        850                 855                 860
        Leu Asn Lys Asn Ile Ala Phe Asp Ile Asn Asp Ile Pro Phe Ser Glu
        865                 870                 875                 880
        Phe Asp Asp Leu Ile Asn Gln Tyr Lys Asn Glu Ile Glu Asp Tyr Glu
                            885                 890                 895
```

```
Val Leu Asn Leu Gly Ala Glu Asp Gly Lys Ile Lys Asp Leu Ser Gly
            900                 905                 910

Thr Thr Ser Asp Ile Asn Ile Gly Ser Asp Ile Glu Leu Ala Asp Gly
            915                 920                 925

Arg Glu Asn Lys Ala Ile Lys Ile Lys Gly Ser Glu Asn Ser Thr Ile
        930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
            980                 985                 990

Lys Ile Ser Ile Gln Asp Ser Lys Leu Ile Trp Tyr Leu Arg Asp His
            995                 1000                1005

Asn Asn Ser Ile Lys Ile Val Thr Pro Asp Tyr Ile Ala Phe Asn
    1010                1015                1020

Gly Trp Asn Leu Ile Thr Ile Thr Asn Asn Arg Ser Lys Gly Ser
    1025                1030                1035

Ile Val Tyr Val Asn Gly Ser Lys Ile Glu Glu Lys Asp Ile Ser
    1040                1045                1050

Ser Ile Trp Asn Thr Glu Val Asp Asp Pro Ile Ile Phe Arg Leu
    1055                1060                1065

Lys Asn Asn Arg Asp Thr Gln Ala Phe Thr Leu Leu Asp Gln Phe
    1070                1075                1080

Ser Ile Tyr Arg Lys Glu Leu Asn Gln Asn Glu Val Val Lys Leu
    1085                1090                1095

Tyr Asn Tyr Tyr Phe Asn Ser Asn Tyr Ile Arg Asp Ile Trp Gly
    1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Cys Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290
```

```
Trp Tyr Phe Ile Pro Lys Asp Glu Gly Trp Asp Glu Asp
    1295                1300                1305
```

<210> SEQ ID NO 32
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 32

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met Tyr Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350
```

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
            530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
            755                 760                 765

Ala Asn Tyr Lys Gly Asn Ile Asp Asp Lys Ala Lys Ile Lys Asn Ala

```
            770             775             780
Ile Ser Glu Thr Glu Ile Leu Leu Asn Lys Ser Val Glu Gln Ala Met
785             790             795             800
Lys Asn Thr Glu Lys Phe Met Ile Lys Leu Ser Asn Ser Tyr Leu Thr
                805             810             815
Lys Glu Met Ile Pro Lys Val Gln Asp Asn Leu Lys Asn Phe Asp Leu
                820             825             830
Glu Thr Lys Lys Thr Leu Asp Lys Phe Ile Lys Glu Lys Glu Asp Ile
                835             840             845
Leu Gly Thr Asn Leu Ser Ser Ser Leu Arg Arg Lys Val Ser Ile Arg
        850             855             860
Leu Asn Lys Asn Ile Ala Phe Asp Ile Asn Asp Ile Pro Phe Ser Glu
865             870             875             880
Phe Asp Asp Leu Ile Asn Gln Tyr Lys Asn Gly Ile Glu Asp Tyr Glu
                885             890             895
Val Leu Asn Leu Gly Ala Glu Asp Gly Lys Ile Lys Asp Leu Ser Gly
                900             905             910
Thr Thr Ser Asp Ile Asn Ile Gly Ser Asp Ile Glu Leu Ala Asp Gly
                915             920             925
Arg Glu Asn Lys Ala Ile Lys Ile Lys Gly Ser Glu Asn Ser Thr Ile
                930             935             940
Lys Ile Ala Met Asn Lys Tyr Leu Arg Phe Ser Ala Thr Asp Asn Phe
945             950             955             960
Ser Ile Ser Phe Trp Ile Lys His Pro Lys Pro Thr Asn Leu Leu Asn
                965             970             975
Asn Gly Ile Glu Tyr Thr Leu Val Glu Asn Phe Asn Gln Arg Gly Trp
                980             985             990
Lys Ile Ser Ile Gln Asp Ser Lys Leu Ile Trp Tyr Leu Arg Asp His
                995             1000            1005
Asn Asn Ser Ile Lys Ile Val Thr Pro Asp Tyr Ile Ala Phe Asn
        1010            1015            1020
Gly Trp Asn Leu Ile Thr Ile Thr Asn Asn Arg Ser Lys Gly Ser
        1025            1030            1035
Ile Val Tyr Val Asn Gly Ser Lys Ile Glu Glu Lys Asp Ile Ser
        1040            1045            1050
Ser Ile Trp Asn Thr Glu Val Asp Asp Pro Ile Ile Phe Arg Leu
        1055            1060            1065
Lys Asn Asn Arg Asp Thr Gln Ala Phe Thr Leu Leu Asp Gln Phe
        1070            1075            1080
Ser Ile Tyr Arg Lys Glu Leu Asn Gln Asn Glu Val Val Lys Leu
        1085            1090            1095
Tyr Asn Tyr Tyr Phe Asn Ser Asn Tyr Ile Arg Asp Ile Trp Gly
        1100            1105            1110
Asn Pro Leu Gln Tyr Asn Lys Lys Tyr Tyr Leu Gln Thr Gln Asp
        1115            1120            1125
Lys Pro Gly Lys Gly Leu Ile Arg Glu Tyr Trp Ser Ser Phe Gly
        1130            1135            1140
Tyr Asp Tyr Val Ile Leu Ser Asp Ser Lys Thr Ile Thr Phe Pro
        1145            1150            1155
Asn Asn Ile Arg Tyr Gly Ala Leu Tyr Asn Gly Ser Lys Val Leu
        1160            1165            1170
Ile Lys Asn Ser Lys Lys Leu Asp Gly Leu Val Arg Asn Lys Asp
        1175            1180            1185
```

```
Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Cys Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Asp Glu Gly Trp Asp Glu Asp
    1295                1300                1305

<210> SEQ ID NO 33
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 33

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Gln Leu Val His Val Thr His Asn Leu Tyr Gly Ile Ser
225                 230                 235                 240
```

-continued

```
Asn Arg Asn Phe Tyr Tyr Asn Phe Asp Thr Gly Lys Ile Glu Thr Ser
            245                 250                 255

Arg Gln Gln Asn Ser Leu Ile Phe Glu Leu Leu Thr Phe Gly Gly
        260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
                340                 345                 350

Gln Arg Phe Ser Ile Leu Val Arg Lys His Tyr Leu Lys Glu Arg Pro
                355                 360                 365

Ile Asp Pro Ile Tyr Val Asn Ile Leu Asp Asp Asn Ser Tyr Ser Thr
        370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Arg Asn Ser Lys Asn Tyr Leu Asn Asn Ile Asp Leu Glu Asp
                435                 440                 445

Lys Lys Thr Thr Ser Lys Thr Asn Val Ser Tyr Pro Cys Ser Leu Leu
        450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
                515                 520                 525

Gln Gln Asn Ile Leu Glu Arg Asn Glu Glu Leu Tyr Glu Pro Ile Arg
        530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
    610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655
```

```
Leu Leu Asn Ile Gly Asn Asp Ile Arg His Gly Asp Phe Val Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Leu Ala
    690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
        740                 745                 750

Leu Ser Arg Gln Ala Asn Ala Ile Lys Met Asn Met Glu Phe Gln Leu
    755                 760                 765

Ala Asn Tyr Lys Gly Asn Ile Asp Asp Lys Ala Lys Ile Lys Asn Ala
770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
        820                 825                 830

Glu Thr Lys Lys Thr Leu Asp Lys Phe Ile Lys Glu Lys Glu Asp Ile
    835                 840                 845

Leu Gly Thr Asn Leu Ser Ser Ser Leu Arg Arg Lys Val Ser Ile Arg
850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
        900                 905                 910

Thr Thr Ser Asp Ile Asn Ile Gly Ser Asp Ile Glu Leu Ala Asp Gly
    915                 920                 925

Arg Glu Asn Lys Ala Ile Lys Ile Lys Gly Ser Glu Asn Ser Thr Ile
930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
        980                 985                 990

Lys Ile Ser Ile Gln Asp Ser Lys  Leu Ile Trp Tyr Leu Arg Asp His
    995                 1000                1005

Asn Asn  Ser Ile Lys Ile Val  Thr Pro Asp Tyr Ile  Ala Phe Asn
        1010                1015                1020

Gly Trp  Asn Leu Ile Thr Ile  Thr Asn Asn Arg Ser  Lys Gly Ser
        1025                1030                1035

Ile Val  Tyr Val Asn Gly Ser  Lys Ile Glu Glu Lys  Asp Ile Ser
        1040                1045                1050

Ser Ile  Trp Asn Thr Glu Val  Asp Asp Pro Ile Ile  Phe Arg Leu
        1055                1060                1065

Lys Asn  Asn Arg Asp Thr Gln  Ala Phe Thr Leu Leu  Asp Gln Phe
```

```
                1070                1075                1080
Ser Ile Tyr Arg Lys Glu Leu Asn Gln Asn Val Val Lys Leu
    1085                1090                1095

Tyr Asn Tyr Phe Asn Ser Asn Tyr Ile Arg Asp Ile Trp Gly
1100                1105                1110

Asn Pro Leu Gln Tyr Asn Lys Lys Tyr Tyr Leu Gln Thr Gln Asp
    1115                1120                1125

Lys Pro Gly Lys Gly Leu Ile Arg Glu Tyr Trp Ser Ser Phe Gly
    1130                1135                1140

Tyr Asp Tyr Val Ile Leu Ser Asp Ser Lys Thr Ile Thr Phe Pro
    1145                1150                1155

Asn Asn Ile Arg Tyr Gly Ala Leu Tyr Asn Gly Ser Lys Val Leu
    1160                1165                1170

Ile Lys Asn Ser Lys Lys Leu Asp Gly Leu Val Arg Asn Lys Asp
    1175                1180                1185

Phe Ile Gln Leu Glu Ile Asp Gly Tyr Asn Met Gly Ile Ser Ala
    1190                1195                1200

Asp Arg Phe Asn Glu Asp Thr Asn Tyr Ile Gly Thr Thr Tyr Gly
    1205                1210                1215

Thr Thr His Asp Leu Thr Thr Asp Phe Glu Ile Ile Gln Arg Gln
    1220                1225                1230

Glu Lys Tyr Arg Asn Tyr Cys Gln Leu Lys Thr Pro Tyr Asn Ile
    1235                1240                1245

Phe His Lys Ser Gly Leu Met Ser Thr Glu Thr Ser Lys Pro Thr
    1250                1255                1260

Phe His Asp Tyr Arg Asp Trp Val Tyr Ser Ser Ala Trp Tyr Phe
    1265                1270                1275

Gln Asn Tyr Glu Asn Leu Asn Leu Arg Lys His Thr Lys Thr Asn
    1280                1285                1290

Trp Tyr Phe Ile Pro Lys Glu Gly Trp Asp Glu Asp
    1295                1300                1305

<210> SEQ ID NO 34
<211> LENGTH: 1306
<212> TYPE: PRT
<213> ORGANISM: Artificial Sequence
<220> FEATURE:
<223> OTHER INFORMATION: Synthetic Polypeptide

<400> SEQUENCE: 34

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
```

-continued

```
            115                 120                 125
Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
                195                 200                 205

Val Asn Lys Phe Val Lys Arg Glu Phe Ala Pro Asp Pro Ala Ser Thr
        210                 215                 220

Leu Met His Glu Leu Val Tyr Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
                275                 280                 285

Thr Ala Lys Asn Asn Tyr Thr Thr Leu Ile Ser Glu Arg Leu Asn Thr
        290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
                355                 360                 365

Ile Asp Pro Ile Tyr Val Asn Ile Leu Asp Asp Asn Ser Tyr Ser Thr
        370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
        435                 440                 445

Lys Lys Thr Thr Ser Lys Thr Asn Val Ser Tyr Pro Cys Ser Leu Leu
450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Lys Ile Lys Pro
                485                 490                 495

Glu Thr Thr Val Phe Lys Asp Lys Leu Pro Pro Gln Asp Ile Thr
                500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
        530                 535                 540
```

-continued

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
                675                 680                 685

Thr Ile Pro Ile Leu Val Gly Leu Glu Val Ile Gly Gly Glu Leu Ala
                690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
                755                 760                 765

Ala Asn Tyr Lys Gly Asn Ile Asp Asp Lys Ala Lys Ile Lys Asn Ala
                770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
                835                 840                 845

Leu Gly Thr Asn Leu Ser Ser Ser Leu Arg Arg Lys Val Ser Ile Arg
                850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
                900                 905                 910

Thr Thr Ser Asp Ile Asn Ile Gly Ser Asp Ile Glu Leu Ala Asp Gly
                915                 920                 925

Arg Glu Asn Lys Ala Ile Lys Ile Lys Gly Ser Glu Asn Ser Thr Ile
                930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
        965                 970                 975

Asn Gly Ile Glu Tyr Thr Leu Val Glu Asn Phe Asn Gln Arg Gly Trp
        980                 985                 990

Lys Ile Ser Ile Gln Asp Ser Lys Leu Ile Trp Tyr Leu Arg Asp His
        995                 1000                1005

Asn Asn Ser Ile Lys Ile Val Thr Pro Asp Tyr Ile Ala Phe Asn
    1010            1015                1020

Gly Trp Asn Leu Ile Thr Ile Thr Asn Arg Ser Lys Gly Ser
    1025            1030                1035

Ile Val Tyr Val Asn Gly Ser Lys Ile Glu Glu Lys Asp Ile Ser
    1040            1045                1050

Ser Ile Trp Asn Thr Glu Val Asp Asp Pro Ile Ile Phe Arg Leu
    1055            1060                1065

Lys Asn Asn Arg Asp Thr Gln Ala Phe Thr Leu Leu Asp Gln Phe
    1070            1075                1080

Ser Ile Tyr Arg Lys Glu Leu Asn Gln Asn Glu Val Val Lys Leu
    1085            1090                1095

Tyr Asn Tyr Tyr Phe Asn Ser Asn Tyr Ile Arg Asp Ile Trp Gly
    1100            1105                1110

Asn Pro Leu Gln Tyr Asn Lys Lys Tyr Leu Gln Thr Gln Asp
    1115            1120                1125

Lys Pro Gly Lys Gly Leu Ile Arg Glu Tyr Trp Ser Ser Phe Gly
    1130            1135                1140

Tyr Asp Tyr Val Ile Leu Ser Asp Ser Lys Thr Ile Thr Phe Pro
    1145            1150                1155

Asn Asn Ile Arg Tyr Gly Ala Leu Tyr Asn Gly Ser Lys Val Leu
    1160            1165                1170

Ile Lys Asn Ser Lys Lys Leu Asp Gly Leu Val Arg Asn Lys Asp
    1175            1180                1185

Phe Ile Gln Leu Glu Ile Asp Gly Tyr Asn Met Gly Ile Ser Ala
    1190            1195                1200

Asp Arg Phe Asn Glu Asp Thr Asn Tyr Ile Gly Thr Thr Tyr Gly
    1205            1210                1215

Thr Thr His Asp Leu Thr Thr Asp Phe Glu Ile Ile Gln Arg Gln
    1220            1225                1230

Glu Lys Tyr Arg Asn Tyr Cys Gln Leu Lys Thr Pro Tyr Asn Ile
    1235            1240                1245

Phe His Lys Ser Gly Leu Met Ser Thr Glu Thr Ser Lys Pro Thr
    1250            1255                1260

Phe His Asp Tyr Arg Asp Trp Val Tyr Ser Ser Ala Trp Tyr Phe
    1265            1270                1275

Gln Asn Tyr Glu Asn Leu Asn Leu Arg Lys His Thr Lys Thr Asn
    1280            1285                1290

Trp Tyr Phe Ile Pro Lys Asp Glu Gly Trp Asp Glu Asp
    1295            1300                1305

<210> SEQ ID NO 35
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 35

```
Met Lys Leu Glu Ile Asn Lys Phe Asn Tyr Asn Asp Pro Ile Asp Gly
 1               5                  10                  15

Ile Asn Val Ile Thr Met Arg Pro Pro Arg His Ser Asp Lys Ile Asn
             20                  25                  30

Lys Gly Lys Gly Pro Phe Lys Ala Phe Gln Val Ile Lys Asn Ile Trp
             35                  40                  45

Ile Val Pro Glu Arg Tyr Asn Phe Thr Asn Asn Thr Asn Asp Leu Asn
 50                  55                  60

Ile Pro Ser Glu Pro Ile Met Glu Ala Asp Ala Ile Tyr Asn Pro Asn
 65                  70                  75                  80

Tyr Leu Asn Thr Pro Ser Glu Lys Asp Glu Phe Leu Gln Gly Val Ile
             85                  90                  95

Lys Val Leu Glu Arg Ile Lys Ser Lys Pro Glu Gly Glu Lys Leu Leu
             100                 105                 110

Glu Leu Ile Ser Ser Ile Pro Leu Pro Leu Val Ser Asn Gly Ala
             115                 120                 125

Leu Thr Leu Ser Asp Asn Glu Thr Ile Ala Tyr Gln Glu Asn Asn Asn
             130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                 165                 170                 175

Asn Gly Glu Gly Thr Leu Ser Glu Val Ser Phe Ser Pro Phe Tyr Leu
             180                 185                 190

Lys Pro Phe Asp Glu Ser Tyr Gly Asn Tyr Arg Ser Leu Val Asn Ile
             195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                 245                 250                 255

Arg Gln Gln Asn Ser Leu Ile Phe Glu Glu Leu Leu Thr Phe Gly Gly
             260                 265                 270

Ile Asp Ser Lys Ala Ile Ser Ser Leu Ile Ile Lys Lys Ile Ile Glu
             275                 280                 285

Thr Ala Lys Asn Asn Tyr Thr Thr Leu Ile Ser Glu Arg Leu Asn Thr
             290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                 325                 330                 335

Lys Lys Leu Asn Thr Ile Leu Phe Val Leu Asn Glu Ser Asn Leu Ala
             340                 345                 350

Gln Arg Phe Ser Ile Leu Val Ala Lys His Phe Leu Lys Glu Arg Pro
             355                 360                 365

Ile Asp Pro Ile Tyr Val Asn Ile Leu Asp Asp Asn Ser Tyr Ser Thr
 370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                 405                 410                 415

Arg Ala Phe Ile Lys Ile Cys Pro Arg Asn Gly Leu Leu Tyr Asn Ala
```

```
                420             425             430
Ile Tyr Arg Asn Ser Lys Asn Tyr Leu Asn Asn Ile Asp Leu Glu Asp
                435             440             445
Lys Lys Thr Thr Ser Lys Thr Asn Val Ser Tyr Pro Cys Ser Leu Leu
    450             455             460
Asn Gly Cys Ile Glu Val Glu Asn Lys Asp Leu Phe Leu Ile Ser Asn
465             470             475             480
Lys Asp Ser Leu Asn Asp Ile Asn Leu Ser Glu Glu Lys Ile Lys Pro
            485             490             495
Glu Thr Thr Val Phe Phe Lys Asp Lys Leu Pro Pro Gln Asp Ile Thr
                500             505             510
Leu Ser Asn Tyr Asp Phe Thr Glu Ala Asn Ser Ile Pro Ser Ile Ser
        515             520             525
Gln Gln Asn Ile Leu Glu Arg Asn Glu Glu Leu Tyr Glu Pro Ile Arg
    530             535             540
Asn Ser Leu Phe Glu Ile Lys Thr Ile Tyr Val Asp Lys Leu Thr Thr
545             550             555             560
Phe His Phe Leu Glu Ala Gln Asn Ile Asp Glu Ser Ile Asp Ser Ser
            565             570             575
Lys Ile Arg Val Glu Leu Thr Asp Ser Val Asp Glu Ala Leu Ser Asn
                580             585             590
Pro Asn Lys Val Tyr Ser Pro Phe Lys Asn Met Ser Asn Thr Ile Asn
        595             600             605
Ser Ile Glu Thr Gly Ile Thr Ser Thr Tyr Ile Phe Tyr Gln Trp Leu
    610             615             620
Arg Ser Ile Val Lys Asp Phe Ser Asp Glu Thr Gly Lys Ile Asp Val
625             630             635             640
Ile Asp Lys Ser Ser Asp Thr Leu Ala Ile Val Pro Tyr Ile Gly Pro
            645             650             655
Leu Leu Asn Ile Gly Asn Asp Ile Arg His Gly Asp Phe Val Gly Ala
                660             665             670
Ile Glu Leu Ala Gly Ile Thr Ala Leu Leu Glu Tyr Val Pro Glu Phe
        675             680             685
Thr Ile Pro Ile Leu Val Gly Leu Glu Val Ile Gly Gly Glu Leu Ala
    690             695             700
Arg Glu Gln Val Glu Ala Ile Val Asn Asn Ala Leu Asp Lys Arg Asp
705             710             715             720
Gln Lys Trp Ala Glu Val Tyr Asn Ile Thr Lys Ala Gln Trp Trp Gly
            725             730             735
Thr Ile His Leu Gln Ile Asn Thr Arg Leu Ala His Thr Tyr Lys Ala
                740             745             750
Leu Ser Arg Gln Ala Asn Ala Ile Lys Met Asn Met Glu Phe Gln Leu
        755             760             765
Ala Asn Tyr Lys Gly Asn Ile Asp Asp Lys Ala Lys Ile Lys Asn Ala
    770             775             780
Ile Ser Glu Thr Glu Ile Leu Leu Asn Lys Ser Val Glu Gln Ala Met
785             790             795             800
Lys Asn Thr Glu Lys Phe Met Ile Lys Leu Ser Asn Ser Tyr Leu Thr
            805             810             815
Lys Glu Met Ile Pro Lys Val Gln Asp Asn Leu Lys Asn Phe Asp Leu
                820             825             830
Glu Thr Lys Lys Thr Leu Asp Lys Phe Ile Lys Glu Lys Glu Asp Ile
        835             840             845
```

```
Leu Gly Thr Asn Leu Ser Ser Ser Leu Arg Arg Lys Val Ser Ile Arg
            850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile
                885                 890
```

<210> SEQ ID NO 36
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 36

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
210                 215                 220

Leu Met Tyr Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
290                 295                 300

Val Thr Val Glu Asn Asp Leu Leu Lys Tyr Ile Lys Asn Lys Ile Pro
305                 310                 315                 320
```

```
Val Gln Gly Arg Leu Gly Asn Phe Lys Leu Asp Thr Ala Glu Phe Glu
            325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
            370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
            405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
            485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
            530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
            565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
            595                 600                 605

Ser Ile Glu Thr Gly Ile Thr Ser Thr Tyr Ile Phe Tyr Gln Trp Leu
            610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
            645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
            675                 680                 685

Thr Ile Pro Ile Leu Val Gly Leu Glu Val Ile Gly Gly Glu Leu Ala
            690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
            725                 730                 735
```

```
Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
        770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
        820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
        850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile
                885                 890

<210> SEQ ID NO 37
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 37

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
                100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
                180                 185                 190

Lys Pro Phe Asp Glu Ser Tyr Gly Asn Tyr Arg Ser Leu Val Asn Ile
        195                 200                 205
```

```
Val Asn Lys Phe Val Lys Arg Glu Phe Ala Pro Asp Pro Ala Ser Thr
210                 215                 220

Leu Met His Gln Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
            245                 250                 255

Arg Gln Gln Asn Ser Leu Ile Phe Glu Glu Leu Leu Thr Phe Gly Gly
        260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
        435                 440                 445

Lys Lys Thr Thr Ser Lys Thr Asn Val Ser Tyr Pro Cys Ser Leu Leu
        450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
            485                 490                 495

Glu Thr Thr Val Phe Phe Lys Asp Lys Leu Pro Pro Gln Asp Ile Thr
        500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Glu Leu Tyr Glu Pro Ile Arg
530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
```

```
                625                 630                 635                 640
Ile Asp Lys Ser Ser Asp Thr Leu Ala Ile Val Pro Tyr Ile Gly Pro
                645                 650                 655
Leu Leu Asn Ile Gly Asn Asp Ile Arg His Gly Asp Phe Val Gly Ala
                660                 665                 670
Ile Glu Leu Ala Gly Ile Thr Ala Leu Leu Glu Tyr Val Pro Glu Phe
                675                 680                 685
Thr Ile Pro Ile Leu Val Gly Leu Glu Val Ile Gly Gly Glu Leu Ala
                690                 695                 700
Arg Glu Gln Val Glu Ala Ile Val Asn Asn Ala Leu Asp Lys Arg Asp
705                 710                 715                 720
Gln Lys Trp Ala Glu Val Tyr Asn Ile Thr Lys Ala Gln Trp Trp Gly
                725                 730                 735
Thr Ile His Leu Gln Ile Asn Thr Arg Leu Ala His Thr Tyr Lys Ala
                740                 745                 750
Leu Ser Arg Gln Ala Asn Ala Ile Lys Met Asn Met Glu Phe Gln Leu
                755                 760                 765
Ala Asn Tyr Lys Gly Asn Ile Asp Asp Lys Ala Lys Ile Lys Asn Ala
                770                 775                 780
Ile Ser Glu Thr Glu Ile Leu Leu Asn Lys Ser Val Glu Gln Ala Met
785                 790                 795                 800
Lys Asn Thr Glu Lys Phe Met Ile Lys Leu Ser Asn Ser Tyr Leu Thr
                805                 810                 815
Lys Glu Met Ile Pro Lys Val Gln Asp Asn Leu Lys Asn Phe Asp Leu
                820                 825                 830
Glu Thr Lys Lys Thr Leu Asp Lys Phe Ile Lys Glu Lys Glu Asp Ile
                835                 840                 845
Leu Gly Thr Asn Leu Ser Ser Ser Leu Arg Arg Lys Val Ser Ile Arg
                850                 855                 860
Leu Asn Lys Asn Ile Ala Phe Asp Ile Asn Asp Ile Pro Phe Ser Glu
865                 870                 875                 880
Phe Asp Asp Leu Ile Asn Gln Tyr Lys Asn Glu Ile
                885                 890

<210> SEQ ID NO 38
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 38

Met Lys Leu Glu Ile Asn Lys Phe Asn Tyr Asn Asp Pro Ile Asp Gly
1               5                   10                  15
Ile Asn Val Ile Thr Met Arg Pro Pro Arg His Ser Asp Lys Ile Asn
                20                  25                  30
Lys Gly Lys Gly Pro Phe Lys Ala Phe Gln Val Ile Lys Asn Ile Trp
            35                  40                  45
Ile Val Pro Glu Arg Tyr Asn Phe Thr Asn Asn Thr Asn Asp Leu Asn
        50                  55                  60
Ile Pro Ser Glu Pro Ile Met Glu Ala Asp Ala Ile Tyr Asn Pro Asn
65                  70                  75                  80
Tyr Leu Asn Thr Pro Ser Glu Lys Asp Glu Phe Leu Gln Gly Val Ile
                85                  90                  95
Lys Val Leu Glu Arg Ile Lys Ser Lys Pro Glu Gly Glu Lys Leu Leu
```

100              105              110
Glu Leu Ile Ser Ser Ile Pro Leu Pro Leu Val Ser Asn Gly Ala
         115              120              125
Leu Thr Leu Ser Asp Asn Glu Thr Ile Ala Tyr Gln Glu Asn Asn
         130              135              140
Ile Val Ser Asn Leu Gln Ala Asn Leu Val Ile Tyr Gly Pro Gly
145              150              155              160
Asp Ile Ala Asn Asn Ala Thr Tyr Gly Leu Tyr Ser Thr Pro Ile Ser
                 165              170              175
Asn Gly Glu Gly Thr Leu Ser Glu Val Ser Phe Ser Pro Phe Tyr Leu
             180              185              190
Lys Pro Phe Asp Glu Ser Tyr Gly Asn Tyr Arg Ser Leu Val Asn Ile
         195              200              205
Val Asn Lys Phe Val Lys Arg Glu Phe Ala Pro Asp Pro Ala Ser Thr
210              215              220
Leu Met His Glu Leu Val Tyr Val Thr His Asn Leu Tyr Gly Ile Ser
225              230              235              240
Asn Arg Asn Phe Tyr Tyr Asn Phe Asp Thr Gly Lys Ile Glu Thr Ser
             245              250              255
Arg Gln Gln Asn Ser Leu Ile Phe Glu Glu Leu Leu Thr Phe Gly Gly
             260              265              270
Ile Asp Ser Lys Ala Ile Ser Ser Leu Ile Ile Lys Lys Ile Ile Glu
         275              280              285
Thr Ala Lys Asn Asn Tyr Thr Thr Leu Ile Ser Glu Arg Leu Asn Thr
         290              295              300
Val Thr Val Glu Asn Asp Leu Leu Lys Tyr Ile Lys Asn Lys Ile Pro
305              310              315              320
Val Gln Gly Arg Leu Gly Asn Phe Lys Leu Asp Thr Ala Glu Phe Glu
             325              330              335
Lys Lys Leu Asn Thr Ile Leu Phe Val Leu Asn Glu Ser Asn Leu Ala
             340              345              350
Gln Arg Phe Ser Ile Leu Val Arg Lys His Tyr Leu Lys Glu Arg Pro
         355              360              365
Ile Asp Pro Ile Tyr Val Asn Ile Leu Asp Asp Asn Ser Tyr Ser Thr
         370              375              380
Leu Glu Gly Phe Asn Ile Ser Ser Gln Gly Ser Asn Asp Phe Gln Gly
385              390              395              400
Gln Leu Leu Glu Ser Ser Tyr Phe Glu Lys Ile Glu Ser Asn Ala Leu
             405              410              415
Arg Ala Phe Ile Lys Ile Cys Pro Arg Asn Gly Leu Leu Tyr Asn Ala
             420              425              430
Ile Tyr Arg Asn Ser Lys Asn Tyr Leu Asn Asn Ile Asp Leu Glu Asp
         435              440              445
Lys Lys Thr Thr Ser Lys Thr Asn Val Ser Tyr Pro Cys Ser Leu Leu
         450              455              460
Asn Gly Cys Ile Glu Val Glu Asn Lys Asp Leu Phe Leu Ile Ser Asn
465              470              475              480
Lys Asp Ser Leu Asn Asp Ile Asn Leu Ser Glu Glu Lys Ile Lys Pro
             485              490              495
Glu Thr Thr Val Phe Phe Lys Asp Lys Leu Pro Pro Gln Asp Ile Thr
             500              505              510
Leu Ser Asn Tyr Asp Phe Thr Glu Ala Asn Ser Ile Pro Ser Ile Ser
         515              520              525

Gln Gln Asn Ile Leu Glu Arg Asn Glu Glu Leu Tyr Glu Pro Ile Arg
530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
                580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
                660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
                740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
                820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile
                885                 890

<210> SEQ ID NO 39
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 39

```
Met Ser Ala Pro Ala Gln Pro Ala Glu Gly Thr Glu Gly Thr Ala
1               5                   10                  15

Pro Gly Gly Gly Pro Pro Gly Pro Pro Asn Met Thr Ser Asn Arg
                20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Phe Phe Thr
            115

<210> SEQ ID NO 40
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 40

Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Ser
            115

<210> SEQ ID NO 41
<211> LENGTH: 103
<212> TYPE: PRT
<213> ORGANISM: Artificial Sequence
<220> FEATURE:
<223> OTHER INFORMATION: Synthetic Polypeptide

<400> SEQUENCE: 41

Met Ser Thr Gly Val Pro Ser Gly Ser Ser Ala Ala Thr Gly Ser Asn
1               5                   10                  15

Arg Arg Leu Gln Gln Thr Gln Asn Gln Val Asp Glu Val Val Asp Ile
                20                  25                  30

Met Arg Val Asn Val Asp Lys Val Leu Glu Arg Asp Gln Lys Leu Ser
            35                  40                  45

Glu Leu Asp Asp Arg Ala Asp Ala Leu Gln Ala Gly Ala Ser Gln Phe
```

```
                    50                  55                  60
Glu Thr Ser Ala Ala Lys Leu Lys Arg Lys Tyr Trp Trp Lys Asn Cys
 65                  70                  75                  80

Lys Met Trp Ala Ile Gly Ile Ser Val Leu Val Ile Val Ile Ile
                     85                  90                  95

Ile Ile Val Trp Cys Val Ser
                100

<210> SEQ ID NO 42
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 42

Met Pro Pro Lys Phe Lys Arg His Leu Asn Asp Asp Val Thr Gly
 1               5                  10                  15

Ser Val Lys Ser Glu Arg Arg Asn Leu Leu Glu Asp Asp Ser Asp Glu
                 20                  25                  30

Glu Glu Asp Phe Phe Leu Arg Gly Pro Ser Gly Pro Arg Phe Gly Pro
                 35                  40                  45

Arg Asn Asp Lys Ile Lys His Val Gln Asn Gln Val Asp Glu Val Ile
 50                  55                  60

Asp Val Met Gln Glu Asn Ile Thr Lys Val Ile Glu Arg Gly Glu Arg
 65                  70                  75                  80

Leu Asp Glu Leu Gln Asp Lys Ser Glu Ser Leu Ser Asp Asn Ala Thr
                 85                  90                  95

Ala Phe Ser Asn Arg Ser Lys Gln Leu Arg Arg Gln Met Trp Trp Arg
                100                 105                 110

Gly Cys Lys Ile Lys Ala Ile Met Ala Leu Val Ala Ala Ile Leu Leu
                115                 120                 125

Leu Val Ile Ile Ile Leu Ile Val Met Lys Tyr Arg Thr
                130                 135                 140

<210> SEQ ID NO 43
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 43

Met Ala Gly Ile Glu Leu Glu Arg Cys Gln Gln Gln Ala Asn Glu Val
 1               5                  10                  15

Thr Glu Ile Met Arg Asn Asn Phe Gly Lys Val Leu Glu Arg Gly Val
                 20                  25                  30

Lys Leu Ala Glu Leu Gln Gln Arg Ser Asp Gln Leu Leu Asp Met Ser
                 35                  40                  45

Ser Thr Phe Asn Lys Thr Thr Gln Asn Leu Ala Gln Lys Lys Cys Trp
 50                  55                  60

Glu Asn Ile Arg Tyr Arg Ile Cys Val Gly Leu Val Val Gly Val
 65                  70                  75                  80

Leu Leu Ile Ile Leu Ile Val Leu Leu Val Val Phe Leu Pro Gln Ser
                 85                  90                  95

Ser Asp Ser Ser Ser Ala Pro Thr Gln Asp Ala Gly Ile Ala Ser
                100                 105                 110
```

Gly Pro Gly Asn
        115

<210> SEQ ID NO 44
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 44

Met Lys Leu Tyr Ser Leu Ser Val Leu Tyr Lys Gly Glu Ala Lys Val
1               5                   10                  15

Val Leu Leu Lys Ala Ala Tyr Asp Val Ser Ser Phe Ser Phe Phe Gln
                20                  25                  30

Arg Ser Ser Val Gln Glu Phe Met Thr Phe Thr Ser Gln Leu Ile Val
            35                  40                  45

Glu Arg Ser Ser Lys Gly Thr Arg Ala Ser Val Lys Glu Gln Asp Tyr
50                  55                  60

Leu Cys His Val Tyr Val Arg Asn Asp Ser Leu Ala Gly Val Val Ile
65                  70                  75                  80

Ala Asp Asn Glu Tyr Pro Ser Arg Val Ala Phe Thr Leu Leu Glu Lys
                85                  90                  95

Val Leu Asp Glu Phe Ser Lys Gln Val Asp Arg Ile Asp Trp Pro Val
            100                 105                 110

Gly Ser Pro Ala Thr Ile His Tyr Pro Ala Leu Asp Gly His Leu Ser
        115                 120                 125

Arg Tyr Gln Asn Pro Arg Glu Ala Asp Pro Met Thr Lys Val Gln Ala
    130                 135                 140

Glu Leu Asp Glu Thr Lys Ile Ile Leu His Asn Thr Met Glu Ser Leu
145                 150                 155                 160

Leu Glu Arg Gly Glu Lys Leu Asp Asp Leu Val Ser Lys Ser Glu Val
                165                 170                 175

Leu Gly Thr Gln Ser Lys Ala Phe Tyr Lys Thr Ala Arg Lys Gln Asn
            180                 185                 190

Ser Cys Cys Ala Ile Ile
        195

<210> SEQ ID NO 45
<211> LENGTH: 898
<212> TYPE: PRT
<213> ORGANISM: Artificial Sequence
<220> FEATURE:
<223> OTHER INFORMATION: Synthetic Polypeptide

<400> SEQUENCE: 45

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

```
Lys Val Leu Glu Arg Ile Lys Ser Lys Pro Glu Gly Glu Lys Leu Leu
            100                 105                 110

Glu Leu Ile Ser Ser Ile Pro Leu Pro Val Ser Asn Gly Ala
            115                 120                 125

Leu Thr Leu Ser Asp Asn Glu Thr Ile Ala Tyr Gln Glu Asn Asn
130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
            290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
            325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365

Ile Asp Pro Ile Tyr Val Asn Ile Leu Asp Asp Asn Ser Tyr Ser Thr
            370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
            435                 440                 445

Lys Lys Thr Thr Ser Lys Thr Asn Val Ser Tyr Pro Cys Ser Leu Leu
            450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
            500                 505                 510
```

-continued

```
Leu Ser Asn Tyr Asp Phe Thr Glu Ala Asn Ser Ile Pro Ser Ile Ser
            515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560

Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
    595                 600                 605

Ser Ile Glu Thr Gly Ile Thr Ser Thr Tyr Ile Phe Tyr Gln Trp Leu
610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
    675                 680                 685

Thr Ile Pro Ile Leu Val Gly Leu Glu Val Ile Gly Gly Glu Leu Ala
690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
    755                 760                 765

Ala Asn Tyr Lys Gly Asn Ile Asp Asp Lys Ala Lys Ile Lys Asn Ala
770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
    835                 840                 845

Leu Gly Thr Asn Leu Ser Ser Ser Leu Arg Arg Lys Val Ser Ile Arg
850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Leu Pro Glu Thr
                885                 890                 895

Gly Gly

<210> SEQ ID NO 46
<211> LENGTH: 415
<212> TYPE: PRT
<213> ORGANISM: Artificial Sequence
```

<220> FEATURE:
<223> OTHER INFORMATION: Synthetic Polypeptide

<400> SEQUENCE: 46

```
Gly Glu Asp Tyr Glu Val Leu Asn Leu Gly Ala Glu Asp Gly Lys Ile
1               5                   10                  15

Lys Asp Leu Ser Gly Thr Thr Ser Asp Ile Asn Ile Gly Ser Asp Ile
            20                  25                  30

Glu Leu Ala Asp Gly Arg Glu Asn Lys Ala Ile Lys Ile Lys Gly Ser
        35                  40                  45

Glu Asn Ser Thr Ile Lys Ile Ala Met Asn Lys Tyr Leu Arg Phe Ser
    50                  55                  60

Ala Thr Asp Asn Phe Ser Ile Ser Phe Trp Ile Lys His Pro Lys Pro
65                  70                  75                  80

Thr Asn Leu Leu Asn Asn Gly Ile Glu Tyr Thr Leu Val Glu Asn Phe
                85                  90                  95

Asn Gln Arg Gly Trp Lys Ile Ser Ile Gln Asp Ser Lys Leu Ile Trp
            100                 105                 110

Tyr Leu Arg Asp His Asn Asn Ser Ile Lys Ile Val Thr Pro Asp Tyr
        115                 120                 125

Ile Ala Phe Asn Gly Trp Asn Leu Ile Thr Ile Thr Asn Asn Arg Ser
    130                 135                 140

Lys Gly Ser Ile Val Tyr Val Asn Gly Ser Lys Ile Glu Glu Lys Asp
145                 150                 155                 160

Ile Ser Ser Ile Trp Asn Thr Glu Val Asp Asp Pro Ile Ile Phe Arg
                165                 170                 175

Leu Lys Asn Asn Arg Asp Thr Gln Ala Phe Thr Leu Leu Asp Gln Phe
            180                 185                 190

Ser Ile Tyr Arg Lys Glu Leu Asn Gln Asn Glu Val Val Lys Leu Tyr
        195                 200                 205

Asn Tyr Tyr Phe Asn Ser Asn Tyr Ile Arg Asp Ile Trp Gly Asn Pro
    210                 215                 220

Leu Gln Tyr Asn Lys Lys Tyr Tyr Leu Gln Thr Gln Asp Lys Pro Gly
225                 230                 235                 240

Lys Gly Leu Ile Arg Glu Tyr Trp Ser Ser Phe Gly Tyr Asp Tyr Val
                245                 250                 255

Ile Leu Ser Asp Ser Lys Thr Ile Thr Phe Pro Asn Asn Ile Arg Tyr
            260                 265                 270

Gly Ala Leu Tyr Asn Gly Ser Lys Val Leu Ile Lys Asn Ser Lys Lys
        275                 280                 285

Leu Asp Gly Leu Val Arg Asn Lys Asp Phe Ile Gln Leu Glu Ile Asp
    290                 295                 300

Gly Tyr Asn Met Gly Ile Ser Ala Asp Arg Phe Asn Glu Asp Thr Asn
305                 310                 315                 320

Tyr Ile Gly Thr Thr Tyr Gly Thr Thr His Asp Leu Thr Thr Asp Phe
                325                 330                 335

Glu Ile Ile Gln Arg Gln Glu Lys Tyr Arg Asn Tyr Cys Gln Leu Lys
            340                 345                 350

Thr Pro Tyr Asn Ile Phe His Lys Ser Gly Leu Met Ser Thr Glu Thr
        355                 360                 365

Ser Lys Pro Thr Phe His Asp Tyr Arg Asp Trp Val Tyr Ser Ser Ala
    370                 375                 380

Trp Tyr Phe Gln Asn Tyr Glu Asn Leu Asn Leu Arg Lys His Thr Lys
385                 390                 395                 400
```

Thr Asn Trp Tyr Phe Ile Pro Lys Asp Glu Gly Trp Asp Glu Asp
                405                 410                 415

<210> SEQ ID NO 47
<211> LENGTH: 424
<212> TYPE: PRT
<213> ORGANISM: Artificial Sequence
<220> FEATURE:
<223> OTHER INFORMATION: Synthetic Polypeptide

<400> SEQUENCE: 47

Ile Ile Asn Thr Ser Ile Leu Asn Leu Arg Tyr Glu Ser Asn His Leu
1               5                   10                  15

Ile Asp Leu Ser Arg Tyr Ala Ser Lys Ile Asn Ile Gly Ser Lys Val
            20                  25                  30

Asn Phe Asp Pro Ile Asp Lys Asn Gln Ile Gln Leu Phe Asn Leu Glu
        35                  40                  45

Ser Ser Lys Ile Glu Val Ile Leu Lys Asn Ala Ile Val Tyr Asn Ser
    50                  55                  60

Met Tyr Glu Asn Phe Ser Thr Ser Phe Trp Ile Arg Ile Pro Lys Tyr
65                  70                  75                  80

Phe Asn Ser Ile Ser Leu Asn Asn Glu Tyr Thr Ile Ile Asn Cys Met
                85                  90                  95

Glu Asn Asn Ser Gly Trp Lys Val Ser Leu Asn Tyr Gly Glu Ile Ile
            100                 105                 110

Trp Thr Leu Gln Asp Thr Gln Glu Ile Lys Gln Arg Val Val Phe Lys
        115                 120                 125

Tyr Ser Gln Met Ile Asn Ile Ser Asp Tyr Ile Asn Arg Trp Ile Phe
    130                 135                 140

Val Thr Ile Thr Asn Asn Arg Leu Asn Asn Ser Lys Ile Tyr Ile Asn
145                 150                 155                 160

Gly Arg Leu Ile Asp Gln Lys Pro Ile Ser Asn Leu Gly Asn Ile His
                165                 170                 175

Ala Ser Asn Asn Ile Met Phe Lys Leu Asp Gly Cys Arg Asp Thr His
            180                 185                 190

Arg Tyr Ile Trp Ile Lys Tyr Phe Asn Leu Phe Asp Lys Glu Leu Asn
        195                 200                 205

Glu Lys Glu Ile Lys Asp Leu Tyr Asp Asn Gln Ser Asn Ser Gly Ile
    210                 215                 220

Leu Lys Asp Phe Trp Gly Asp Tyr Leu Gln Tyr Asp Lys Pro Tyr Tyr
225                 230                 235                 240

Met Leu Asn Leu Tyr Asp Pro Asn Lys Tyr Val Asp Val Asn Asn Val
                245                 250                 255

Gly Ile Arg Gly Tyr Met Tyr Leu Lys Gly Pro Arg Gly Ser Val Met
            260                 265                 270

Thr Thr Asn Ile Tyr Leu Asn Ser Ser Leu Tyr Arg Gly Thr Lys Phe
        275                 280                 285

Ile Ile Lys Lys Tyr Ala Ser Gly Asn Lys Asp Asn Ile Val Arg Asn
    290                 295                 300

Asn Asp Arg Val Tyr Ile Asn Val Val Lys Asn Lys Glu Tyr Arg
305                 310                 315                 320

Leu Ala Thr Asn Ala Ser Gln Ala Gly Val Glu Lys Ile Leu Ser Ala
                325                 330                 335

Leu Glu Ile Pro Asp Val Gly Asn Leu Ser Gln Val Val Val Met Lys
            340                 345                 350

```
Ser Lys Asn Asp Gln Gly Ile Thr Asn Lys Cys Lys Met Asn Leu Gln
        355                 360                 365

Asp Asn Asn Gly Asn Asp Ile Gly Phe Ile Gly Phe His Gln Phe Asn
370                 375                 380

Asn Ile Ala Lys Leu Val Ala Ser Asn Trp Tyr Asn Arg Gln Ile Glu
385                 390                 395                 400

Arg Ser Ser Arg Thr Leu Gly Cys Ser Trp Glu Phe Ile Pro Val Asp
                405                 410                 415

Asp Gly Trp Gly Glu Arg Pro Leu
                420

<210> SEQ ID NO 48
<211> LENGTH: 432
<212> TYPE: PRT
<213> ORGANISM: Artificial Sequence
<220> FEATURE:
<223> OTHER INFORMATION: Synthetic Polypeptide

<400> SEQUENCE: 48

Ile Leu Asn Asn Ile Ile Leu Asn Leu Arg Tyr Lys Asp Asn Asn Leu
1               5                   10                  15

Ile Asp Leu Ser Gly Tyr Gly Ala Lys Val Glu Val Tyr Asp Gly Val
                20                  25                  30

Glu Leu Asn Asp Lys Asn Gln Phe Lys Leu Thr Ser Ser Ala Asn Ser
            35                  40                  45

Lys Ile Arg Val Thr Gln Asn Gln Asn Ile Ile Phe Asn Ser Val Phe
        50                  55                  60

Leu Asp Phe Ser Val Ser Phe Trp Ile Arg Ile Pro Lys Tyr Lys Asn
65                  70                  75                  80

Asp Gly Ile Gln Asn Tyr Ile His Asn Glu Tyr Thr Ile Ile Asn Cys
                85                  90                  95

Met Lys Asn Asn Ser Gly Trp Lys Ile Ser Ile Arg Gly Asn Arg Ile
                100                 105                 110

Ile Trp Thr Leu Ile Asp Ile Asn Gly Lys Thr Lys Ser Val Phe Phe
            115                 120                 125

Glu Tyr Asn Ile Arg Glu Asp Ile Ser Glu Tyr Ile Asn Arg Trp Phe
        130                 135                 140

Phe Val Thr Ile Thr Asn Asn Leu Asn Asn Ala Lys Ile Tyr Ile Asn
145                 150                 155                 160

Gly Lys Leu Glu Ser Asn Thr Asp Ile Lys Asp Ile Arg Glu Val Ile
                165                 170                 175

Ala Asn Gly Glu Ile Ile Phe Lys Leu Asp Gly Asp Ile Asp Arg Thr
            180                 185                 190

Gln Phe Ile Trp Met Lys Tyr Phe Ser Ile Phe Asn Thr Glu Leu Ser
        195                 200                 205

Gln Ser Asn Ile Glu Glu Arg Tyr Lys Ile Gln Ser Tyr Ser Glu Tyr
    210                 215                 220

Leu Lys Asp Phe Trp Gly Asn Pro Leu Met Tyr Asn Lys Glu Tyr Tyr
225                 230                 235                 240

Met Phe Asn Ala Gly Asn Lys Asn Ser Tyr Ile Lys Leu Lys Lys Asp
                245                 250                 255

Ser Pro Val Gly Glu Ile Leu Thr Arg Ser Lys Tyr Asn Gln Asn Ser
            260                 265                 270

Lys Tyr Ile Asn Tyr Arg Asp Leu Tyr Ile Gly Glu Lys Phe Ile Ile
        275                 280                 285
```

```
Arg Arg Lys Ser Asn Ser Gln Ser Ile Asn Asp Asp Ile Val Arg Lys
    290                 295                 300

Glu Asp Tyr Ile Tyr Leu Asp Phe Phe Asn Leu Asn Gln Glu Trp Arg
305                 310                 315                 320

Val Tyr Thr Tyr Lys Tyr Phe Lys Lys Glu Glu Lys Leu Phe Leu
                325                 330                 335

Ala Pro Ile Ser Asp Ser Asp Glu Phe Tyr Asn Thr Ile Gln Ile Lys
                340                 345                 350

Glu Tyr Asp Glu Gln Pro Thr Tyr Ser Cys Gln Leu Leu Phe Lys Lys
                355                 360                 365

Asp Glu Glu Ser Thr Asp Glu Ile Gly Leu Ile Gly Ile His Arg Phe
                370                 375                 380

Tyr Glu Ser Gly Ile Val Phe Glu Glu Tyr Lys Asp Tyr Phe Cys Ile
385                 390                 395                 400

Ser Lys Trp Tyr Leu Lys Glu Val Lys Arg Lys Pro Tyr Asn Leu Lys
                405                 410                 415

Leu Gly Cys Asn Trp Gln Phe Ile Pro Lys Asp Glu Gly Trp Thr Glu
                420                 425                 430

<210> SEQ ID NO 49
<211> LENGTH: 424
<212> TYPE: PRT
<213> ORGANISM: Artificial Sequence
<220> FEATURE:
<223> OTHER INFORMATION: Synthetic Polypeptide

<400> SEQUENCE: 49

Ile Asn Asp Ser Lys Ile Leu Ser Leu Gln Asn Arg Lys Asn Thr Leu
1               5                   10                  15

Val Asp Thr Ser Gly Tyr Asn Ala Glu Val Ser Glu Glu Gly Asp Val
                20                  25                  30

Gln Leu Asn Pro Ile Phe Pro Phe Asp Phe Lys Leu Gly Ser Ser Gly
                35                  40                  45

Glu Asp Arg Gly Lys Val Ile Val Thr Gln Asn Glu Asn Ile Val Tyr
50                  55                  60

Asn Ser Met Tyr Glu Ser Phe Ser Ile Ser Phe Trp Ile Arg Ile Asn
65                  70                  75                  80

Lys Trp Val Ser Asn Leu Pro Gly Tyr Thr Ile Ile Asp Ser Val Lys
                85                  90                  95

Asn Asn Ser Gly Trp Ser Ile Gly Ile Ile Ser Asn Phe Leu Val Phe
                100                 105                 110

Thr Leu Lys Gln Asn Glu Asp Ser Glu Gln Ser Ile Asn Phe Ser Tyr
                115                 120                 125

Asp Ile Ser Asn Asn Ala Pro Gly Tyr Asn Lys Trp Phe Phe Val Thr
                130                 135                 140

Val Thr Asn Asn Met Met Gly Asn Met Lys Ile Tyr Ile Asn Gly Lys
145                 150                 155                 160

Leu Ile Asp Thr Ile Lys Val Lys Glu Leu Thr Gly Ile Asn Phe Ser
                165                 170                 175

Lys Thr Ile Thr Phe Glu Ile Asn Lys Ile Pro Asp Thr Gly Leu Ile
                180                 185                 190

Thr Ser Asp Ser Asp Asn Ile Asn Met Trp Ile Arg Asp Phe Tyr Ile
                195                 200                 205

Phe Ala Lys Glu Leu Asp Gly Lys Asp Ile Asn Ile Leu Phe Asn Ser
                210                 215                 220
```

```
Leu Gln Tyr Thr Asn Val Val Lys Asp Tyr Trp Gly Asn Asp Leu Arg
225                 230                 235                 240

Tyr Asn Lys Glu Tyr Tyr Met Val Asn Ile Asp Tyr Leu Asn Arg Tyr
                245                 250                 255

Met Tyr Ala Asn Ser Arg Gln Ile Val Phe Asn Thr Arg Arg Asn Asn
            260                 265                 270

Asn Asp Phe Asn Glu Gly Tyr Lys Ile Ile Lys Arg Ile Arg Gly
        275                 280                 285

Asn Thr Asn Asp Thr Arg Val Arg Gly Gly Asp Ile Leu Tyr Phe Asp
        290                 295                 300

Met Thr Ile Asn Asn Lys Ala Tyr Asn Leu Phe Met Lys Asn Glu Thr
305                 310                 315                 320

Met Tyr Ala Asp Asn His Ser Thr Glu Asp Ile Tyr Ala Ile Gly Leu
                325                 330                 335

Arg Glu Gln Thr Lys Asp Ile Asn Asp Asn Ile Ile Phe Gln Ile Gln
                340                 345                 350

Pro Met Asn Asn Thr Tyr Tyr Tyr Ala Ser Gln Ile Phe Lys Ser Asn
            355                 360                 365

Phe Asn Gly Glu Asn Ile Ser Gly Ile Cys Ser Ile Gly Thr Tyr Arg
        370                 375                 380

Phe Arg Leu Gly Gly Asp Trp Tyr Arg His Asn Tyr Leu Val Pro Thr
385                 390                 395                 400

Val Lys Gln Gly Asn Tyr Ala Ser Leu Leu Glu Ser Thr Ser Thr His
                405                 410                 415

Trp Gly Phe Val Pro Val Ser Glu
            420

<210> SEQ ID NO 50
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 50

Leu Val Pro Arg Gly Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 51

Glu Asn Leu Tyr Phe Gln Gly
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 52

Leu Glu Val Leu Phe Gln Gly Pro
1               5
```

```
<210> SEQ ID NO 53
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 53

Ile Glu Gly Arg
1

<210> SEQ ID NO 54
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 54

Ile Asp Gly Arg
1

<210> SEQ ID NO 55
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 55

Asp Asp Asp Asp Lys
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 56

Ala His Arg Glu Gln Ile Gly Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 57

Leu Pro Xaa Thr Gly
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 58
```

-continued

```
Leu Pro Glu Thr Gly Gly
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 59

Leu Pro Glu Thr Gly Ser
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 60

Leu Pro Xaa Thr Gly Gly
1               5

<210> SEQ ID NO 61
<211> LENGTH: 101
<212> TYPE: PRT
<213> ORGANISM: Artificial Sequence
<220> FEATURE:
<223> OTHER INFORMATION: Synthetic Polypeptide

<400> SEQUENCE: 61

Gly Gly Ser His His His His His Gly Met Ala Ser Met Thr Gly
1               5                   10                  15

Gly Gln Gln Met Gly Arg Asp Leu Tyr Asp Asp Asp Lys Asp Arg
                20                  25                  30

Trp Gly Ser Met Ser Ala Thr Ala Ala Thr Val Pro Pro Ala Ala Pro
                35                  40                  45

Ala Gly Glu Gly Gly Pro Pro Ala Pro Pro Pro Asn Leu Thr Ser Asn
            50                  55                      60

Arg Arg Leu Gln Gln Thr Gln Ala Gln Val Asp Glu Val Val Asp Ile
65                  70                  75                  80

Met Arg Val Asn Val Asp Lys Val Leu Glu Arg Asp Gln Lys Leu Ser
                85                  90                      95

Glu Leu Asp Asp Arg
            100

<210> SEQ ID NO 62
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 62

Ala Asp Ala Leu Gln Ala Gly Ala Ser Gln Phe Glu Thr Ser Ala Ala
1               5                   10                  15

Lys Leu Lys Arg Lys Tyr Trp Trp Lys Asn Leu
                20                  25
```

```
<210> SEQ ID NO 63
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 63

Gln Gln Thr Gln Ala Gln Val Asp Glu Val Val Asp Ile Met Arg Val
1               5                   10                  15

Asn Val Asp Lys Val Leu Glu Arg Asp Gln Lys Leu Ser Glu Leu Asp
            20                  25                  30

Asp Arg Ala Asp Ala Leu Gln Ala Gly Ala Ser Gln Phe Glu Thr Ser
        35                  40                  45

Ala Ala Lys Leu Lys Arg
    50

<210> SEQ ID NO 64
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 64

Gln Gln Thr Gln Ala Gln Val Glu Glu Val Val Asp Ile Met Arg Val
1               5                   10                  15

Asn Val Asp Lys Val Leu Glu Arg Asp Gln Lys Leu Ser Glu Leu Asp
            20                  25                  30

Asp Arg Ala Asp Ala Leu Gln Ala Gly Ala Ser Gln Phe Glu Ser Ser
        35                  40                  45

Ala Ala Lys Leu Lys Arg
    50

<210> SEQ ID NO 65
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 65

Gln Gln Thr Gln Asn Gln Val Asp Glu Val Val Asp Ile Met Arg Val
1               5                   10                  15

Asn Val Asp Lys Val Leu Glu Arg Asp Gln Lys Leu Ser Glu Leu Asp
            20                  25                  30

Asp Arg Ala Asp Ala Leu Gln Ala Gly Ala Ser Gln Phe Glu Thr Ser
        35                  40                  45

Ala Ala Lys Leu Lys Arg
    50

<210> SEQ ID NO 66
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 66

Lys His Val Gln Asn Gln Val Asp Glu Val Ile Asp Val Met Gln Glu
1               5                   10                  15
```

```
Asn Ile Thr Lys Val Ile Glu Arg Gly Glu Arg Leu Asp Glu Leu Gln
            20                  25                  30

Asp Lys Ser Glu Ser Leu Ser Asp Asn Ala Thr Ala Phe Ser Asn Arg
        35                  40                  45

Ser Lys Gln Leu Arg Arg
    50
```

<210> SEQ ID NO 67
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 67

```
Glu Arg Cys Gln Gln Gln Ala Asn Glu Val Thr Glu Ile Met Arg Asn
1               5                   10                  15

Asn Phe Gly Lys Val Leu Glu Arg Gly Val Lys Leu Ala Glu Leu Gln
            20                  25                  30

Gln Arg Ser Asp Gln Leu Leu Asp Met Ser Ser Thr Phe Asn Lys Thr
        35                  40                  45

Thr Gln Asn Leu Ala Gln
    50
```

<210> SEQ ID NO 68
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 68

```
Thr Glu Thr Gln Ala Gln Val Asp Glu Leu Lys Gly Ile Met Val Arg
1               5                   10                  15

Asn Ile Asp Leu Val Ala Gln Arg Gly Glu Arg Leu Glu Leu Leu Ile
            20                  25                  30

Asp Lys Thr Glu Asn Leu Val Asp Ser Ser Val Thr Phe Lys Thr Thr
        35                  40                  45

Ser Arg Asn Leu Ala Arg
    50
```

<210> SEQ ID NO 69
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 69

```
Arg Asn Leu Gln Ser Glu Val Glu Gly Val Lys Asn Ile Met Thr Gln
1               5                   10                  15

Asn Val Glu Arg Ile Leu Ala Arg Gly Glu Asn Leu Asp His Leu Arg
            20                  25                  30

Asn Lys Thr Glu Asp Leu Glu Ala Thr Ser Glu His Phe Lys Thr Thr
        35                  40                  45

Ser Gln Lys Val Ala Arg
    50
```

<210> SEQ ID NO 70
<211> LENGTH: 54

```
<212> TYPE: PRT
<213> ORGANISM: Artificial Sequence
<220> FEATURE:
<223> OTHER INFORMATION: Synthetic Polypeptide

<400> SEQUENCE: 70

Gly Ser Ile Asn Thr Glu Leu Gln Asp Val Gln Arg Ile Met Val Ala
1               5                   10                  15

Asn Ile Glu Glu Val Leu Gln Arg Gly Glu Ala Leu Ser Ala Leu Asp
            20                  25                  30

Ser Lys Ala Asn Asn Leu Ser Ser Leu Ser Lys Lys Tyr Arg Gln Asp
        35                  40                  45

Ala Lys Tyr Leu Asn Met
    50

<210> SEQ ID NO 71
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 71

Ser Lys Val Gln Ala Glu Leu Asp Glu Thr Lys Ile Ile Leu His Asn
1               5                   10                  15

Thr Met Glu Ser Leu Leu Glu Arg Gly Glu Lys Leu Asp Asp Leu Val
            20                  25                  30

Ser Lys Ser Glu Val Leu Gly Thr Gln Ser Lys Ala Phe Tyr Lys Thr
        35                  40                  45

Ala Arg
    50

<210> SEQ ID NO 72
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 72

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 73
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 73

Cys Lys Ser Val Lys Ala Pro Gly Ile Cys
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 74
```

```
Cys His Lys Ala Ile Asp Gly Arg Ser Leu Tyr Asn Lys Thr Leu Asp
1               5                   10                  15

Cys
```

<210> SEQ ID NO 75
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 75

```
Cys Leu Arg Leu Thr Lys Asn Ser Arg Asp Asp Ser Thr Cys
1               5                   10
```

<210> SEQ ID NO 76
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 76

```
Cys Lys Asn Ile Val Ser Val Lys Gly Ile Arg Lys Ser Ile Cys
1               5                   10                  15
```

<210> SEQ ID NO 77
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 77

```
Cys Lys Ser Val Ile Pro Arg Lys Gly Thr Lys Ala Pro Pro Arg Leu
1               5                   10                  15

Cys
```

<210> SEQ ID NO 78
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 78

```
Cys Lys Pro Val Met Tyr Lys Asn Thr Gly Lys Ser Glu Gln Cys
1               5                   10                  15
```

<210> SEQ ID NO 79
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 79

```
Cys Pro Arg Asn Gly Leu Leu Tyr Asn Ala Ile Tyr Arg Asn Ser Lys
1               5                   10                  15

Asn Tyr Leu Asn Asn Ile Asp Leu Glu Asp Lys Lys Thr Thr Ser Lys
                20                  25                  30

Thr Asn Val Ser Tyr Pro Cys Ser Leu Leu Asn Gly Cys
            35                  40                  45
```

<210> SEQ ID NO 80
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by GST

<400> SEQUENCE: 80

Leu Val Pro Arg Gly Ser
1               5

<210> SEQ ID NO 81
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 81

Leu Pro Glu Thr Gly Gly His His His His His His
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 82

Gly Gly His His His His His His
1               5

<210> SEQ ID NO 83
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 83

Gly Gly Ser His His His His His Gly Met Ala Ser Met Thr Gly
1               5                   10                  15

Gly Gln Gln Met Gly Arg Asp Leu Tyr Asp Asp Asp Lys Asp Arg
            20                  25                  30

Trp Gly Ser Met Ser Ala Thr Ala Ala Thr Val Pro Pro Ala Ala Pro
        35                  40                  45

Ala Gly Glu Gly Gly Pro Pro Ala Pro Pro Pro Asn Leu Thr Ser Asn
        50                  55                  60

Arg Arg Leu Gln Gln Thr Gln Ala Gln Val Asp Glu Val Val Asp Ile
65                  70                  75                  80

Met Arg Val Asn Val Asp Lys Val Leu Glu Arg Asp Gln Lys Leu Ser
                85                  90                  95

Glu Leu Asp Asp Arg Ala Asp Ala Leu Gln Ala Gly Ala Ser Gln Phe
            100                 105                 110

Glu Thr Ser Ala Ala Lys Leu Lys Arg Lys Tyr Trp Trp Lys Asn Leu
        115                 120                 125

<210> SEQ ID NO 84

```
<211> LENGTH: 280
<212> TYPE: PRT
<213> ORGANISM: Artificial Sequence
<220> FEATURE:
<223> OTHER INFORMATION: Synthetic Polypeptide

<400> SEQUENCE: 84

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Gln Gln Thr Gln Ala Gln Val Asp Glu Val Val Asp Ile Met
225                 230                 235                 240

Arg Val Asn Val Asp Lys Val Leu Glu Arg Asp Gln Lys Leu Ser Glu
                245                 250                 255

Leu Asp Asp Arg Ala Asp Ala Leu Gln Ala Gly Ala Ser Gln Phe Glu
            260                 265                 270

Thr Ser Ala Ala Lys Leu Lys Arg
        275                 280

<210> SEQ ID NO 85
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 85

Ala Asp Ala Leu Gln Ala Gly Ala Ser Gln Phe Glu Thr Ser Ala Ala
1               5                   10                  15

Lys Leu Lys Arg
            20
```

```
<210> SEQ ID NO 86
<211> LENGTH: 260
<212> TYPE: PRT
<213> ORGANISM: Artificial Sequence
<220> FEATURE:
<223> OTHER INFORMATION: Synthetic Polypeptide

<400> SEQUENCE: 86
```

Met Ser Pro Ile Leu Gly Tyr Trp Lys Ile Lys Gly Leu Val Gln Pro
1               5                   10                  15

Thr Arg Leu Leu Leu Glu Tyr Leu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Gln Gln Thr Gln Ala Gln Val Asp Glu Val Val Asp Ile Met
225                 230                 235                 240

Arg Val Asn Val Asp Lys Val Leu Glu Arg Asp Gln Lys Leu Ser Glu
                245                 250                 255

Leu Asp Asp Arg
            260

```
<210> SEQ ID NO 87
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 87
```

Glu Ser Leu Leu Glu Arg Gly Glu Lys Leu Asp Asp Leu Val Ser Lys
1               5                   10                  15

```
<210> SEQ ID NO 88
<211> LENGTH: 6
<212> TYPE: PRT
<213> ORGANISM: Artificial Sequence
<220> FEATURE:
```

<223> OTHER INFORMATION: Synthetic Polypeptide

<400> SEQUENCE: 88

Asp Glu Leu Gln Asp Lys
1               5

<210> SEQ ID NO 89
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 89

Ser Glu Ser Leu Ser Asp Asn Ala Thr Ala Phe
1               5                   10

<210> SEQ ID NO 90
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 90

Ala Glu Leu Gln Gln Arg
1               5

<210> SEQ ID NO 91
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 91

Ser Asp Gln Leu Leu Asp Met Ser Ser Thr Phe
1               5                   10

<210> SEQ ID NO 92
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 92

His Glu Leu Val His
1               5

<210> SEQ ID NO 93
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 93

Ser Ala Trp Tyr
1

<210> SEQ ID NO 94
<211> LENGTH: 8
<212> TYPE: PRT
<213> ORGANISM: Artificial Sequence
<220> FEATURE:
<223> OTHER INFORMATION: Synthetic Polypeptide

```
<400> SEQUENCE: 94

Lys Leu Glu Ile Asn Lys Phe Asn
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 95

Lys Leu Glu Ile Asn Lys Phe Asn
1               5

<210> SEQ ID NO 96
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 96

Phe Asn Tyr Asn Asp Pro Ile Asp Gly Ile Asn Val Ile Thr Met Arg
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 97

Phe Asn Tyr Asn Asp Pro Ile Asp Gly Ile Asn Val Ile Thr Met Arg
1               5                   10                  15

<210> SEQ ID NO 98
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 98

Phe Asn Tyr Asn Asp Pro Ile Asp Gly Ile Asn Val Ile Thr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 99

Phe Asn Tyr Asn Asp Pro Ile Asp Gly Ile Asn Val
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic Polypeptide
```

```
<400> SEQUENCE: 100

Phe Asn Tyr Asn Asp Pro Ile Asp Gly Ile Asn Val
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 101

Asp Pro Ile Asp Gly Ile Asn Val Ile Thr
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 102

Asp Pro Ile Asp Gly Ile Asn Val Ile Thr
1               5                   10

<210> SEQ ID NO 103
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 103

Tyr Asn Pro Asn Tyr Leu Asn Thr Pro Ser Glu Lys Asp Glu Phe Leu
1               5                   10                  15

Gln Gly Val Ile Lys Val Leu Glu
            20

<210> SEQ ID NO 104
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 104

Tyr Asn Pro Asn Tyr Leu Asn Thr Pro Ser Glu Lys Asp Glu Phe Leu
1               5                   10                  15

Gln Gly Val Ile Lys Val Leu Glu
            20

<210> SEQ ID NO 105
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 105

Tyr Asn Pro Asn Tyr Leu Asn Thr Pro Ser Glu Lys Asp Glu Phe Leu
1               5                   10                  15

Gln Gly Val Ile Lys Val Leu Glu
            20
```

<210> SEQ ID NO 106
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 106

Tyr Asn Pro Asn Tyr Leu Asn Thr Pro Ser Glu Lys Asp Glu Phe Leu
1               5                   10                  15

Gln Gly Val Ile Lys Val Leu Glu
            20

<210> SEQ ID NO 107
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 107

Leu Leu Glu Leu Ile Ser Ser Ser Ile Pro Leu Pro Leu Val
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 108

Leu Glu Leu Ile Ser Ser Ser Ile Pro Leu Pro Leu Val
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 109

Leu Glu Leu Ile Ser Ser Ser Ile Pro Leu Pro Leu Val
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 110

Leu Glu Leu Ile Ser Ser Ser Ile Pro Leu Pro Leu Val
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 111

Leu Ile Ser Ser Ser Ile Pro Leu Pro Leu Val

```
1               5                   10
```

<210> SEQ ID NO 112
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 112

```
Leu Ile Ser Ser Ser Ile Pro Leu Pro Leu Val
1               5                   10
```

<210> SEQ ID NO 113
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 113

```
Leu Ile Ser Ser Ser Ile Pro Leu Pro Leu Val
1               5                   10
```

<210> SEQ ID NO 114
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 114

```
Leu Ile Ser Ser Ser Ile Pro Leu Pro Leu Val
1               5                   10
```

<210> SEQ ID NO 115
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 115

```
Leu Val Ser Asn Gly Ala Leu Thr Leu Ser Asp Asn Glu Thr Ile Ala
1               5                   10                  15

Tyr Gln
```

<210> SEQ ID NO 116
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 116

```
Leu Val Ser Asn Gly Ala Leu Thr Leu Ser Asp Asn Glu Thr Ile Ala
1               5                   10                  15

Tyr Gln
```

<210> SEQ ID NO 117
<211> LENGTH: 8
<212> TYPE: PRT
<213> ORGANISM: Artificial Sequence
<220> FEATURE:
<223> OTHER INFORMATION: Synthetic Polypeptide

```
<400> SEQUENCE: 117

Leu Val Ser Asn Gly Ala Leu Thr
1               5

<210> SEQ ID NO 118
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 118

Leu Thr Leu Ser Asp Asn Glu Thr Ile Ala Tyr Gln
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 119

Leu Thr Leu Ser Asp Asn Glu Thr Ile Ala Tyr Gln
1               5                   10

<210> SEQ ID NO 120
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 120

Leu Gln Ala Asn Leu Val Ile Tyr Gly Pro Gly Pro Asp Ile Ala Asn
1               5                   10                  15

Asn Ala Thr Tyr Gly
            20

<210> SEQ ID NO 121
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 121

Leu Gln Ala Asn Leu Val Ile Tyr Gly Pro Gly Pro Asp Ile Ala Asn
1               5                   10                  15

Asn Ala Thr Tyr Gly
            20

<210> SEQ ID NO 122
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 122

Leu Val Ile Tyr Gly Pro Gly Pro Asp Ile Ala Asn Asn Ala
1               5                   10

<210> SEQ ID NO 123
<211> LENGTH: 17
```

```
<212> TYPE: PRT
<213> ORGANISM: Artificial Sequence
<220> FEATURE:
<223> OTHER INFORMATION: Synthetic Polypeptide

<400> SEQUENCE: 123

Leu Val Ile Tyr Gly Pro Gly Pro Asp Ile Ala Asn Asn Ala Thr Tyr
1               5                   10                  15

Gly

<210> SEQ ID NO 124
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 124

Tyr Gly Pro Gly Pro Asp Ile Ala Asn Asn Ala Thr Tyr Gly
1               5                   10

<210> SEQ ID NO 125
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 125

Asn Ala Thr Tyr Gly Leu Tyr Ser
1               5

<210> SEQ ID NO 126
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 126

Tyr Gly Leu Tyr Ser Thr Pro Ile Ser Asn Gly Glu Gly Thr Leu Ser
1               5                   10                  15

Glu Val Ser Phe Ser
            20

<210> SEQ ID NO 127
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 127

Tyr Gly Leu Tyr Ser Thr Pro Ile Ser Asn Gly Glu Gly Thr Leu Ser
1               5                   10                  15

Glu Val Ser Phe Ser
            20

<210> SEQ ID NO 128
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 128
```

```
Tyr Gly Leu Tyr Ser Thr Pro Ile Ser Asn Gly Glu Gly Thr Leu Ser
1               5                   10                  15

Glu Val Ser Phe Ser Pro Phe Tyr
            20

<210> SEQ ID NO 129
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 129

Tyr Gly Leu Tyr Ser Thr Pro Ile Ser Asn Gly Glu Gly Thr Leu Ser
1               5                   10                  15

Glu Val Ser Phe Ser Pro Phe Tyr
            20

<210> SEQ ID NO 130
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 130

Tyr Gly Leu Tyr Ser Thr Pro Ile Ser Asn Gly Glu Gly Thr Leu Ser
1               5                   10                  15

Glu

<210> SEQ ID NO 131
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 131

Tyr Gly Leu Tyr Ser Thr Pro Ile Ser Asn Gly Glu Gly Thr Leu Ser
1               5                   10                  15

Glu

<210> SEQ ID NO 132
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 132

Tyr Gly Leu Tyr Ser Thr Pro Ile Ser Asn Gly Glu Gly Thr Leu Ser
1               5                   10                  15

Glu Val Ser Phe Ser Pro Phe Tyr
            20

<210> SEQ ID NO 133
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 133
```

```
Tyr Ser Thr Pro Ile Ser Asn Gly Glu Gly Thr Leu Ser Glu Val Ser
1               5                   10                  15

Phe

<210> SEQ ID NO 134
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 134

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 135
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 135

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 136
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 136

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 137
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 137

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 138
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 138
```

Tyr Ser Thr Pro Ile Ser Asn Gly Glu Gly Thr Leu Ser Glu Val Ser
1               5                   10                  15

Phe Ser

<210> SEQ ID NO 139
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 139

Tyr Ser Thr Pro Ile Ser Asn Gly Glu Gly Thr Leu Ser Glu Val Ser
1               5                   10                  15

Phe Ser

<210> SEQ ID NO 140
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 140

Tyr Ser Thr Pro Ile Ser Asn Gly Glu Gly Thr Leu Ser Glu Val Ser
1               5                   10                  15

Phe Ser

<210> SEQ ID NO 141
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 141

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 142
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 142

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 143
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 143

Tyr Ser Thr Pro Ile Ser Asn Gly Glu Gly Thr Leu Ser Glu Val Ser
1               5                   10                  15

Phe Ser

<210> SEQ ID NO 144
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 144

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 145
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 145

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 146
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 146

Tyr Ser Thr Pro Ile Ser Asn Gly Glu Gly Thr Leu Ser Glu Val Ser
1               5                   10                  15

Phe Ser

<210> SEQ ID NO 147
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 147

Tyr Ser Thr Pro Ile Ser Asn Gly Glu Gly Thr Leu Ser Glu Val Ser
1               5                   10                  15

Phe Ser

<210> SEQ ID NO 148
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 148

Tyr Ser Thr Pro Ile Ser Asn Gly Glu Gly Thr Leu Ser Glu
1               5                   10

```
<210> SEQ ID NO 149
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 149

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 150
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 150

Tyr Ser Thr Pro Ile Ser Asn Gly Glu Gly Thr Leu Ser Glu Val Ser
1               5                   10                  15

Phe Ser Pro Phe Tyr
            20

<210> SEQ ID NO 151
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 151

Tyr Ser Thr Pro Ile Ser Asn Gly Glu Gly Thr Leu Ser Glu
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 152

Leu Ser Glu Val Ser Phe Ser Pro Phe Tyr
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 153

Leu Ser Glu Val Ser Phe Ser Pro Phe Tyr
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 154
```

```
Phe Tyr Leu Lys Pro Phe Asp Glu Ser Tyr Gly Asn Tyr Arg
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 155

Phe Tyr Leu Lys Pro Phe Asp Glu Ser Tyr Gly
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 156

Phe Asp Glu Ser Tyr Gly Asn Tyr Arg
1               5

<210> SEQ ID NO 157
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 157

Tyr Gly Asn Tyr Arg Ser Leu Val Asn Ile Val Asn Lys Phe Val
1               5                   10                  15

<210> SEQ ID NO 158
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 158

His Asn Leu Tyr Gly Ile Ser Asn Arg Asn Phe Tyr
1               5                   10

<210> SEQ ID NO 159
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 159

Phe Tyr Tyr Asn Phe Asp Thr Gly Lys Ile Glu Thr Ser Arg Gln Gln
1               5                   10                  15

Asn Ser

<210> SEQ ID NO 160
<211> LENGTH: 18
<212> TYPE: PRT
<213> ORGANISM: Artificial Sequence
<220> FEATURE:
<223> OTHER INFORMATION: Synthetic Polypeptide
```

```
<400> SEQUENCE: 160

Phe Tyr Tyr Asn Phe Asp Thr Gly Lys Ile Glu Thr Ser Arg Gln Gln
1               5                   10                  15

Asn Ser

<210> SEQ ID NO 161
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 161

Tyr Tyr Asn Phe Asp Thr Gly Lys Ile Glu Thr Ser Arg Gln Gln Asn
1               5                   10                  15

Ser Leu Ile

<210> SEQ ID NO 162
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 162

Leu Ile Ser Glu Arg Leu Asn Thr Val Thr Val Glu Asn Asp Leu Leu
1               5                   10                  15

Lys Tyr Ile

<210> SEQ ID NO 163
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 163

Leu Asn Thr Val Thr Val Glu Asn Asp Leu Leu Lys Tyr Ile
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 164

Phe Val Leu Asn Glu Ser Asn Leu Ala Gln Arg Phe Ser
1               5                   10

<210> SEQ ID NO 165
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 165

His Tyr Leu Lys Glu Arg Pro Ile Asp Pro Ile Tyr Val Asn Ile Leu
1               5                   10                  15

Asp Asp Asn Ser Tyr Ser
            20
```

```
<210> SEQ ID NO 166
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 166

Asp Pro Ile Tyr Val Asn Ile Leu Asp Asp Asn Ser Tyr Ser
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 167

Asp Pro Ile Tyr Val Asn Ile Leu Asp Asp Asn Ser Tyr Ser
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 168

Asn Ile Leu Asp Asp Asn Ser Tyr Ser Thr Leu Glu
1               5                   10

<210> SEQ ID NO 169
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 169

Tyr Ser Thr Leu Glu Gly Phe Asn
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 170

Tyr Ser Thr Leu Glu Gly Phe Asn
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 171

Tyr Ser Thr Leu Glu Gly Phe Asn
1               5
```

<210> SEQ ID NO 172
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 172

Tyr Ser Thr Leu Glu Gly Phe Asn
1               5

<210> SEQ ID NO 173
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 173

Phe Asn Ile Ser Ser Gln Gly Ser Asn Asp Phe Gln Gly Gln Leu Leu
1               5                   10                  15

Glu

<210> SEQ ID NO 174
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 174

Phe Asn Ile Ser Ser Gln Gly Ser Asn Asp Phe Gln Gly Gln Leu Leu
1               5                   10                  15

Glu Ser Ser Tyr Phe Glu
            20

<210> SEQ ID NO 175
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 175

Phe Asn Ile Ser Ser Gln Gly Ser Asn Asp Phe Gln Gly Gln Leu
1               5                   10                  15

<210> SEQ ID NO 176
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 176

Leu Leu Tyr Asn Ala Ile Tyr Arg
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 177

```
Leu Leu Tyr Asn Ala Ile Tyr Arg
1               5
```

<210> SEQ ID NO 178
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 178

```
Lys Asn Tyr Leu Asn Asn Ile Asp Leu Glu Asp Lys Lys Thr Thr
1               5                   10                  15
```

<210> SEQ ID NO 179
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 179

```
Lys Asn Tyr Leu Asn Asn Ile Asp Leu Glu Asp Lys Lys Thr Thr Ser
1               5                   10                  15

Lys Thr Asn Val
            20
```

<210> SEQ ID NO 180
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 180

```
Lys Asn Tyr Leu Asn Asn Ile Asp Leu Glu Asp Lys Lys Thr Thr Ser
1               5                   10                  15

Lys Thr Asn Val
            20
```

<210> SEQ ID NO 181
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 181

```
Lys Asn Tyr Leu Asn Asn Ile Asp Leu Glu Asp Lys Lys Thr Thr Ser
1               5                   10                  15
```

<210> SEQ ID NO 182
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 182

```
Lys Asn Tyr Leu Asn Asn Ile Asp Leu Glu Asp Lys Lys Thr Thr Ser
1               5                   10                  15

Lys Thr Asn
```

<210> SEQ ID NO 183
<211> LENGTH: 15

```
<212> TYPE: PRT
<213> ORGANISM: Artificial Sequence
<220> FEATURE:
<223> OTHER INFORMATION: Synthetic Polypeptide

<400> SEQUENCE: 183

Asn Tyr Leu Asn Asn Ile Asp Leu Glu Asp Lys Lys Thr Thr Ser
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 184

Asn Tyr Leu Asn Asn Ile Asp Leu Glu Asp Lys Lys Thr Thr Ser
1               5                   10                  15

<210> SEQ ID NO 185
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 185

Gly Cys Ile Glu Val Glu Asn Lys Asp Leu Phe Leu
1               5                   10

<210> SEQ ID NO 186
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 186

Phe Leu Ile Ser Asn Lys Asp Ser Leu Asn Asp Ile Asn Leu Ser Glu
1               5                   10                  15

Glu Lys Ile Lys Pro Glu Thr Thr Val Phe Phe
            20                  25

<210> SEQ ID NO 187
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 187

Phe Leu Ile Ser Asn Lys Asp Ser Leu Asn Asp Ile Asn Leu Ser Glu
1               5                   10                  15

Glu Lys Ile Lys Pro Glu Thr Thr Val Phe Phe
            20                  25

<210> SEQ ID NO 188
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 188

Lys Asp Ser Leu Asn Asp Ile Asn Leu Ser Glu Glu Lys Ile Lys Pro
```

```
                1               5                  10                 15
Glu Thr Thr Val Phe Phe
            20

<210> SEQ ID NO 189
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 189

Asp Ser Leu Asn Asp Ile Asn Leu Ser Glu Glu Lys Ile Lys Pro Glu
1               5                   10                  15

Thr Thr Val Phe Phe
            20

<210> SEQ ID NO 190
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 190

Leu Ser Asn Tyr Asp Phe Thr Glu Ala Asn Ser Ile Pro Ser Ile
1               5                   10                  15

<210> SEQ ID NO 191
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 191

Leu Ser Asn Tyr Asp Phe Thr Glu Ala Asn Ser Ile Pro Ser Ile Ser
1               5                   10                  15

Gln Gln Asn

<210> SEQ ID NO 192
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 192

Leu Ser Asn Tyr Asp Phe Thr Glu Ala Asn Ser
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 193

Leu Ser Asn Tyr Asp Phe Thr Glu Ala Asn Ser
1               5                   10

<210> SEQ ID NO 194
<211> LENGTH: 19
<212> TYPE: PRT
```

<213> ORGANISM: Artificial Sequence
<220> FEATURE:
<223> OTHER INFORMATION: Synthetic Polypeptide

<400> SEQUENCE: 194

Tyr Asp Phe Thr Glu Ala Asn Ser Ile Pro Ser Ile Ser Gln Gln Asn
1               5                   10                  15

Ile Leu Glu

<210> SEQ ID NO 195
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 195

Tyr Asp Phe Thr Glu Ala Asn Ser Ile Pro Ser Ile Ser Gln Gln Asn
1               5                   10                  15

Ile Leu Glu

<210> SEQ ID NO 196
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 196

Tyr Asp Phe Thr Glu Ala Asn Ser Ile Pro Ser Ile Ser Gln Gln Asn
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 197

Tyr Asp Phe Thr Glu Ala Asn Ser Ile Pro Ser Ile Ser Gln Gln Asn
1               5                   10                  15

<210> SEQ ID NO 198
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 198

Tyr Asp Phe Thr Glu Ala Asn Ser Ile Pro Ser Ile Ser Gln Gln Asn
1               5                   10                  15

Ile Leu Glu Arg Asn Glu Glu Leu Tyr Glu Pro Ile Arg Asn Ser
            20                  25                  30

<210> SEQ ID NO 199
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 199

Tyr Asp Phe Thr Glu Ala Asn Ser Ile Pro Ser Ile Ser Gln Gln Asn

```
1               5                   10                  15

Ile

<210> SEQ ID NO 200
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 200

Tyr Asp Phe Thr Glu Ala Asn Ser Ile Pro Ser Ile Ser Gln Gln Asn
1               5                   10                  15

Ile

<210> SEQ ID NO 201
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 201

Asn Ser Ile Pro Ser Ile Ser Gln Gln Asn Ile Leu Glu Arg Asn Glu
1               5                   10                  15

Glu Leu Tyr Glu Pro Ile Arg Asn Ser Leu Phe Glu
            20                  25

<210> SEQ ID NO 202
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 202

Leu Thr Asp Ser Val Asp Glu Ala Leu Ser Asn Pro Asn Lys Val Tyr
1               5                   10                  15

Ser

<210> SEQ ID NO 203
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 203

Leu Thr Asp Ser Val Asp Glu Ala Leu Ser Asn Pro Asn Lys Val Tyr
1               5                   10                  15

Ser

<210> SEQ ID NO 204
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 204

Leu Thr Asp Ser Val Asp Glu Ala Leu Ser Asn Pro Asn Lys Val Tyr
1               5                   10                  15

Ser
```

<210> SEQ ID NO 205
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 205

Leu Ser Asn Pro Asn Lys Val Tyr Ser
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 206

Leu Ser Asn Pro Asn Lys Val Tyr Ser
1               5

<210> SEQ ID NO 207
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 207

Tyr Ser Pro Phe Lys Asn Met Ser Asn Thr Ile Asn Ser Ile Glu Thr
1               5                   10                  15

Gly Ile Thr Ser Thr Tyr Ile
            20

<210> SEQ ID NO 208
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 208

Tyr Ser Pro Phe Lys Asn Met Ser Asn Thr Ile Asn Ser Ile Glu Thr
1               5                   10                  15

Gly Ile Thr Ser Thr Tyr Ile
            20

<210> SEQ ID NO 209
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 209

Phe Lys Asn Met Ser Asn Thr Ile Asn Ser Ile Glu Thr Gly Ile Thr
1               5                   10                  15

Ser Thr Tyr Ile
            20

<210> SEQ ID NO 210
<211> LENGTH: 20
<212> TYPE: PRT

<213> ORGANISM: Artificial Sequence
<220> FEATURE:
<223> OTHER INFORMATION: Synthetic Polypeptide

<400> SEQUENCE: 210

Phe Lys Asn Met Ser Asn Thr Ile Asn Ser Ile Glu Thr Gly Ile Thr
1               5                   10                  15

Ser Thr Tyr Ile
            20

<210> SEQ ID NO 211
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 211

Phe Lys Asn Met Ser Asn Thr Ile Asn Ser Ile Glu Thr Gly Ile Thr
1               5                   10                  15

Ser Thr Tyr Ile
            20

<210> SEQ ID NO 212
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 212

Met Ser Asn Thr Ile Asn Ser Ile Glu Thr Gly Ile Thr Ser Thr Tyr
1               5                   10                  15

Ile

<210> SEQ ID NO 213
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 213

Met Ser Asn Thr Ile Asn Ser Ile Glu Thr Gly Ile Thr Ser Thr Tyr
1               5                   10                  15

Ile

<210> SEQ ID NO 214
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 214

Asn Thr Ile Asn Ser Ile Glu Thr Gly Ile Thr Ser Thr Tyr Ile
1               5                   10                  15

<210> SEQ ID NO 215
<211> LENGTH: 19
<212> TYPE: PRT
<213> ORGANISM: Artificial Sequence
<220> FEATURE:
<223> OTHER INFORMATION: Synthetic Polypeptide

```
<400> SEQUENCE: 215

Phe Ser Asp Glu Thr Gly Lys Ile Asp Val Ile Asp Lys Ser Ser Asp
1               5                   10                  15

Thr Leu Ala

<210> SEQ ID NO 216
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 216

Leu Ala Ile Val Pro Tyr Ile Gly Pro Leu Leu
1               5                   10

<210> SEQ ID NO 217
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 217

Val Pro Tyr Ile Gly Pro Leu Leu
1               5

<210> SEQ ID NO 218
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 218

Val Ile Gly Gly Glu Leu Ala Arg Glu Gln Val Glu Ala
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 219

Leu Ser Arg Gln Ala Asn Ala Ile Lys Met Asn
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 220

Leu Ser Arg Gln Ala Asn Ala Ile Lys Met Asn
1               5                   10

<210> SEQ ID NO 221
<211> LENGTH: 12
<212> TYPE: PRT
<213> ORGANISM: Artificial Sequence
<220> FEATURE:
<223> OTHER INFORMATION: Synthetic Polypeptide
```

<400> SEQUENCE: 221

Phe Ser Glu Phe Asp Asp Leu Ile Asn Gln Tyr Lys
1               5                   10

<210> SEQ ID NO 222
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 222

Phe Asp Asp Leu Ile Asn Gln Tyr Lys Asn Glu Gly Ser Ile Leu Pro
1               5                   10                  15

Glu Thr Gly Gly Leu Glu His His His
            20                  25

<210> SEQ ID NO 223
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 223

Tyr Lys Asn Glu Gly Ser Ile Leu Pro Glu Thr Gly Gly Leu Glu His
1               5                   10                  15

His His His His His
            20

<210> SEQ ID NO 224
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 224

Tyr Lys Asn Glu Gly Ser Ile Leu Pro Glu Thr Gly Gly Leu Glu
1               5                   10                  15

<210> SEQ ID NO 225
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 225

Tyr Lys Asn Glu Gly Ser Ile Leu Pro Glu Thr Gly Gly Leu Glu His
1               5                   10                  15

His

<210> SEQ ID NO 226
<211> LENGTH: 18
<212> TYPE: PRT
<213> ORGANISM: Artificial Sequence
<220> FEATURE:
<223> OTHER INFORMATION: Synthetic Polypeptide

```
<400> SEQUENCE: 226

Tyr Lys Asn Glu Gly Ser Ile Leu Pro Glu Thr Gly Gly Leu Glu His
1               5                   10                  15

His His
```